US007202269B2

(12) United States Patent
Barclay et al.

(10) Patent No.: US 7,202,269 B2
(45) Date of Patent: Apr. 10, 2007

(54) GLYT2 MODULATORS

(75) Inventors: Tristin K. Barclay, Denver, CO (US); Alejandro Santillán, Jr., San Diego, CA (US); Liu Y. Tang, San Diego, CA (US); Hariharan Venkatesan, San Diego, CA (US); Ronald L. Wolin, San Diego, CA (US)

(73) Assignee: Janssen Pharmaceutica N.V. (BE)

( * ) Notice: Subject to any disclaimer, the term of this patent is extended or adjusted under 35 U.S.C. 154(b) by 23 days.

(21) Appl. No.: 10/976,067

(22) Filed: Oct. 28, 2004

(65) Prior Publication Data

US 2005/0119245 A1 Jun. 2, 2005

Related U.S. Application Data

(60) Provisional application No. 60/515,949, filed on Oct. 30, 2003.

(51) Int. Cl.
*A61K 31/40* (2006.01)
*A61K 31/17* (2006.01)
*C07D 207/06* (2006.01)
*C07C 335/18* (2006.01)

(52) U.S. Cl. ............... 514/428; 514/586; 548/568; 564/27

(58) Field of Classification Search ........... 548/568; 564/104, 27
See application file for complete search history.

(56) References Cited

U.S. PATENT DOCUMENTS 6,057,338 A   5/2000   Yang et al.
6,063,796 A   5/2000   Yang et al.

FOREIGN PATENT DOCUMENTS

FR   2 838 739 A1   10/2003
WO   WO 99/34790 A1   7/1999
WO   WO 00/71507   11/2000
WO   WO 02/64135 A1   8/2002

OTHER PUBLICATIONS

Berk, S.C. et al. A Combinatorial Approach toward the Discovery of Non-Peptide Subtype-Selective Somatostatin Receptor Ligans. J. Comb. Chem. 1999, 1(5):388-396.
Evans, J. et al. Cloning, Functional Characterization and Population Analysis of a Variant Form of the Human Glycine Type 2 Transporter. FEBS Lett. 1999, 463(3):301-306.
Friauf, E. et al. Developmental Expression of the Glycine Transporter GLYT2 in the Auditory System of Rats Suggests Involvement in Synapse Maturation. J. Comp. Neurol. 1999, 412(1):17-37.
Gallagher, M.J. et al. Characterization of Multiple Forms of the Human Glycine Transporter Type-2. Mol. Brain Res. 1999, 70(1):101-115.
Geerlings, A. et al. Characterization of the Interactions Between the Glycine Transporters GLYT1 and GLYT2 and the SNARE protein syntaxin 1A. FEBS Letters 2000, 470:51-54.
Grenningloh, G. et al. The Strychnine-binding Subunit of the Glycine Receptor Shows Homology with Nicotinic Acetylcholine Receptors. Nature (London) 1987, 328(16):215-220.
Guastella, J. et al. Cloning, Expression, and Localization of a Rat Brain High-Affinity Glycine Transporter. Proc. Natl. Acad. Sci. U.S.A. 1992, 89(15):7189-7193.
Huang, W. and R.K. Simpson. Long-term Intrathecal Administration of Glycine Prevents Mechanical Hyperalgesia in a Rat Model of Neuropathic Pain. Neurol. Res. 2000, 22:160-164.
Isaac, M. Synthesis and Structure Activity Relationship of Novel Chiral Ligans for the Glycine-Reuptake Transporter Type-2 (GlyT-2). Abstracts of Papers, 228th ACS National Meeting, Philadelphia, PA, U.S., Aug. 22-26, 2004.
Iversen, L.L. Role of Transmitter Uptake Mechanism in Synaptic Neurotransmission. Br. J. Pharmacol. 1971, 41(4):571-591.
Krnjevic, K. Chemical Nature of Synaptic Transmission in Vertebrates. Physiol. Rev. 1974, 54(2):418-540.
Liu, Q-R. et al. Cloning and Expression of a Spinal Cord- and Brian-Specific Glycine Transporter with Novel Structural Features. J. Biol. Chem. 1993, 268(30):22802-22808.
Lopez-Corcuera, B. et al. Differential Properties of Two Stably Expressed Brain-Specific Glycine Transporters. J. Neurochem. 1998, 71(5):2211-2219.
Luque, J.M. et al. Cellular Expression of Glycine Transporter 2 Messenger RNA Exclusively in Rat Hindbrain and Spinal Cord. Neuroscience 1995, 64(2):525-535.
Ponce, J. et al. Transmembrane Domain III Plays an Important Role in Ion Binging and Permeation in the Glycine Tranporter GLYT2. J. Biol. Chem. 2000, 275(18):13856-13862.
Probst, A. et al. The Distribution of Glycine Receptors in the Human Brain. A Light Microscopic Autoradiographic Study Using [3H]Strychnine. Neuroscience 1986, 17(1):11-35.
Raiteri, L. et al. Glycine Taken Up Through GLYT1 and GLYT2 Heterotransporters into Glutamatergic Axon Terminals of Mouse Spinal Cord Elicits Release of Glutamate by Homo-Transporter Reversal and Through Anion Channels. Biochem. Pharm. 2005, 69(1):159-168.
Rajendra, S. and P.R. Schofield. Molecular Mechanisms of Inherited Startle Syndromes. Trends Neurosci. 1995, 18(2):80-82.
Simpson, R.K., Jr. et al. Reduction in the Mechanonociceptive Response by Intrathecal Administration of Glycine and Related Compounds. Neurochem. Res. 1996, 21(10):1221-1226.
Young, A.B. and S.H. Snyder. Strychnine Binding Associated with Glycine Receptors of the Central Nervous System. Proc. Natl. Acad. Sci. U.S.A. 1973, 70(10):2832-2836.
Zarbin, M.A. et al. Glycine Receptor: Light Microscopic Autoradiographic Localization with [3H]Strychnine. J. Neurosci. 1981, 1(5):532-547.
Wolin, R.L. et al. Inhibitors of the Glycine Transporter Type-2 (GlyT-2): Synthesis and Biological Activity of Benzoylpiperidine Derivatives. Bioorg. Med. Chem. 2004, 12(16):4511-4532.
Wolin, R.L. et al. Novel Glycine Transporter Type-2 Reuptake Inhibitors. Part 2: b- and g-Amino Acid Derivatives. Bioorg. Med. Chem. 2004, 12(16):4493-4509.
International Search Report dated Mar. 31, 2005, for corresponding application PCT/US2004/036009.

*Primary Examiner*—Joseph K. McKane
*Assistant Examiner*—Jason M. Nolan
(74) *Attorney, Agent, or Firm*—John Harbour

(57) ABSTRACT

Certain α-, β-, and γ-amino acid derivatives are disclosed as selective GlyT2 inhibitors for the treatment of central nervous system (CNS) conditions such as muscle spasticity, tinnitus, epilepsy and neuropathic pain.

23 Claims, No Drawings

GLYT2 MODULATORS

This application claims priority to provisional application, which is U.S. Ser. No. 60/515,949, filed Oct. 30, 2003. The complete disclosures of the aforementioned related U.S. patent applications are hereby incorporated herein by reference for all purposes.

This invention relates to modulators of the type 2 glycine transporter (GlyT2). More particularly, this invention relates to certain α-, β-, and γ-amino acid derivatives useful as selective GlyT2 inhibitors for the treatment of central nervous system (CNS) conditions such as muscle spasticity, tinnitus, epilepsy and neuropathic pain.

BACKGROUND OF THE INVENTION

Glycine, along with γ-aminobutyric acid (GABA), is primarily responsible for inhibiting neurotransmission in the CNS. Additionally, glycine is an essential co-agonist at the N-methyl-D-aspartate (NMDA) receptor, where it acts to attenuate the excitatory actions of glutamate (L. L. Iverson, *Br. J. Pharmacol.* 1971, 41(4):571–591).

Radio-labeled strychnine binding studies (A. B. Young and S. H. Snyder, *Proc. Natl. Acad. Sci. U.S.A.* 1973, 70(10):2832–2836; M. A. Zarbin et al., *J. Neurosci.* 1981, 1(5):532–547; A. Probst et al., *Neuroscience* 1986, 17(1):11–35; H. Betz, *Nature* 1987, 328(16):215–220) provide strong evidence that glycine is the major inhibitory amino acid operating in the brainstem and spinal cord of vertebrates, and exerts its effects post-synaptically at the strychnine-sensitive glycinergic receptor (K. Krnjevic, *Physiol. Rev.* 1974, 54(2):418–540).

The binding of glycine to its specific receptor induces the opening of a ligand-gated chloride channel, which results in an influx of chloride ion into the post-synaptic neuron. This process causes the neuron to become hyperpolarized, and ultimately raises the threshold for neuronal signaling. The physiological effects of glycine are regulated by glycine transporters, which provide a mechanism for the re-uptake of glycine from the synaptic cleft back into the pre-synaptic neuron and surrounding glial cells.

Currently there are two known glycine transporters expressed in the CNS: GlyT1 and GlyT2 (J. Guastella et al., *Proc. Natl. Acad. Sci. USA* 1992, 89(15):7189–7193; Q.-R. Liu et al., *J. Biol. Chem.* 1993, 268(30):22802–22808; B. Lopez-Corcuera et al., *J. Neurochem.* 1998, 71(5):2211–2219). Separate genes encode each transporter, and the transporters have distinctly different pharmacologies as evidenced by their sensitivities to sarcosine (N-methylglycine) (B. López-Corcuera et al., *J. Neurochem.* 1998, 71(5):2211–2219). Both the rat and human GlyT2 transporters have been cloned and share ~93% sequence homology at the amino acid level (M. J. Gallagher et al., *Mol. Brain Res.* 1999, 70(1):101–115; J. Evans et al., *FEBS Lett.* 1999, 463(3):301–306). Biochemical evidence gathered thus far suggests that the GlyT2 transporter is closely associated with the strychnine-sensitive glycine receptors in the brainstem and spinal cord.

GlyT2 inhibitors should prevent glycine reuptake and accentuate the post-synaptic inhibitory activity of the glycineric receptor, and may thus be useful in the treatment of CNS conditions associated with glycinergic receptor malfunction, such as muscle spasticity, tinnitus, epilepsy and neuropathic pain (E. Friauf et al., *J. Comp. Neurol.* 1999, 412(1):17–37; R. K. Simpson et al., *Neurochem. Res.* 1996, 21(10):1221–1226; W. Huang and R. K. Simpson, *Neurological Res.* 2000, 22:160–164).

SUMMARY OF THE INVENTION

The invention features a compound of formula (I):

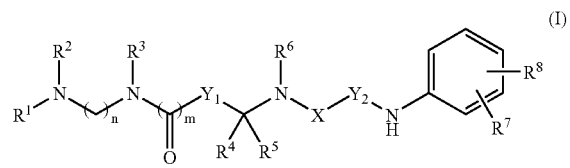

wherein, $R^1$ and $R^2$ are independently selected from the group consisting of H, $C_{1-6}$ alkyl, $C_{2-6}$ alkenyl, $C_{3-7}$ cycloalkyl and benzyl, or alternatively $R^1$ and $R^2$ taken together with the nitrogen atom to which they are attached form a saturated or partially unsaturated 4- to 7-membered heterocyclyl optionally having one carbon replaced with >O, >S, =N—, >NH or >N($C_{1-4}$ alkyl), wherein the heterocyclyl is optionally substituted with 1–3 independently selected $C_{1-6}$ alkyl substituents;

$R^3$ is H or $C_{1-6}$ alkyl, optionally substituted with $NH_2$;

n is 2, 3, 4 or 5;

m is 0 or 1;

$Y_1$ is a covalent bond, $C_{1-4}$ alkane-diyl, or cis or trans $C_{2-4}$ alkene-diyl, optionally substituted with 1 or 2 independently selected $C_{1-4}$ alkyl substituents;

$R^4$ is H, $C_{1-4}$ alkyl or phenyl;

$R^5$ is selected from the group consisting of $C_{1-6}$ alkyl, $C_{2-6}$ alkenyl, $C_{3-7}$ cycloalkyl, phenyl, thienyl, benzhydryl and —$Y_3$—$R^a$, where $Y_3$ is $C_{1-3}$ alkane-diyl or $C_{2-3}$ alkene-diyl, and $R^a$ is selected from the group consisting of $C_{3-7}$ cycloalkyl, phenyl, naphthyl, biphenyl, benzylsulfanyl, benzyloxy, thienyl, furyl, thiazolyl, oxazolyl, imidazolyl, 1H-indol-2-yl, 1H-indol-3-yl and pyridyl;

or alternatively $R^4$ and $R^5$ taken together with the carbon atom to which they are attached form a saturated or partially unsaturated 3- to 7-membered monocyclic carbocyclyl, optionally benzofused;

where $R^5$ is substituted at any stable position except $Y_3$ with 0, 1 or 2 substituents independently selected from the group consisting of hydroxy, sulfanyl, halo, $C_{1-4}$ alkyl, $C_{1-4}$ haloalkyl, $C_{1-4}$ alkoxy, $C_{1-4}$ alkylsulfanyl, carboxy, amino and carbamoyl, and $Y_3$ is substituted with 0, 1 or 2 substituents independently selected from the group consisting of fluoro, $C_{1-4}$ alkyl, $C_{1-4}$ haloalkyl, $C_{1-4}$ alkoxy and amino; or alternatively $R^4$ and $R^5$ taken together is substituted with 0, 1 or 2 substituents independently selected from the group consisting of hydroxy, halo, $C_{1-4}$ alkyl, $C_{1-4}$ haloalkyl, $C_{1-4}$ alkoxy and amino;

$R^6$ is H or $C_{1-4}$ alkyl;

X is selected from the group consisting of >C=O, >C=S, >C=N—CN and >C=CHNO$_2$;

$Y_2$ is a covalent bond or methylene;

$R^7$ is H, halo or $C_{1-4}$ alkyl;

$R^8$ is selected from the group consisting of H, phenyl, —O-phenyl, —O-tetrahydronaphthyl, —$SO_{0-2}$-phenyl, thienyl, and pyridyl;

or alternatively $R^7$ and $R^8$ taken together with the phenyl to which they are attached form fluorenyl or tetrahydronaphthyl;

where $R^8$, or $R^7$ and $R^8$ taken together, is substituted with 0, 1 or 2 substituents independently selected from the group consisting of hydroxy, cyano, nitro, amino, dimethylamino, halo, $C_{1-4}$ alkyl, $C_{1-4}$ haloalkyl, $C_{1-4}$ alkoxy, —(CO)—$C_{1-4}$ alkyl and —(SO$_2$)—$C_{1-4}$ alkyl;

and stereoisomers, solvates, pharmaceutically acceptable salts and polymorphs, thereof.

The invention also features pharmaceutical compositions containing such compounds and methods of using such compounds or compositions in the treatment or prevention of disease states mediated by GlyT2 receptor activity, including but not limited to neuropathic pain, tinnitus, muscle spasticity, and epilepsy.

DETAILED DESCRIPTION OF THE INVENTION

Preferred $R^1$ and $R^2$ are independently selected from the group consisting of H, methyl, ethyl, propyl, i-propyl, ethenyl, allyl, cyclopropyl, cyclobutyl, cyclopentyl, cyclohexyl, and benzyl. Preferred, optionally substituted, $R^1$ and $R^2$ taken together with the nitrogen atom to which they are attached is selected from the group consisting of 2-pyrrolin-1-yl, 3-pyrrolin-1-yl, pyrrolidin-1-yl, 2-imidazolin-1-yl, imidazolidin-1-yl, 2-pyrazolin-1-yl, pyrazolidin-1-yl, piperidin-1-yl, morpholin-4-yl, thiomorpholin-4-yl and piperazin-1-yl.

Preferred, optionally substituted, $R^3$ is independently selected from the group consisting of H, methyl, ethyl and propyl.

Preferably, n is 2 or 3.

Preferrably, m is 1.

Preferred, optionally substituted, $Y_1$ is independently selected from the group consisting of a covalent bond, methdiyl, eth-1,2-diyl, prop-1,3-diyl, but-1,4-diyl, cis-ethen-1,2-diyl and trans-ethen-1,2-diyl.

Preferred $R^4$ is independently selected from the group consisting of H, methyl, ethyl, propyl and phenyl.

Preferred, optionally substituted, $R^5$ is independently selected from the group consisting of methyl, ethyl, propyl, i-propyl, butyl, t-butyl, i-butyl, ethenyl, allyl, cyclopropyl, cyclobutyl, cyclopentyl, cyclohexyl, phenyl, thienyl, benzhydryl, cyclopropylmethyl, cyclobutylmethyl, cyclopentylmethyl, cyclohexylmethyl, benzyl, naphthylmethyl, biphenylmethyl, benzylsulfanylmethyl, benzyloxymethyl, thienylmethyl, furylmethyl, thiazolylmethyl, oxazolylmethyl, imidazolylmethyl, 1H-indol-2-ylmethyl, 1H-indol-3-ylmethyl, pyridylmethyl and phenylethyl.

Preferred $R^4$ and $R^5$ taken together with the carbon atom to which they are attached is selected from the group consisting of cyclobutan-1,1-diyl, cyclopentan-1,1-diyl, cyclohexan-1,1-diyl and indan-2,2-diyl.

Preferred $R^6$ is selected from the group consisting of H, methyl, ethyl and propyl.

Preferrably, $Y_2$ is a covalent bond.

Preferred $R^7$ is selected from the group consisting of H, bromo, chloro, fluoro, iodo, methyl, ethyl, propyl, and t-butyl.

Preferred, optionally substituted, $R^8$ is selected from the group consisting of phenyl and —O-phenyl.

Preferred, optionally substituted, $R^7$ and $R^8$ taken together with the phenyl to which they are attached is fluorenyl.

Embodiments of this invention where, in formula (I), n is 1, X is >C=N—CN and $Y_2$ is a covalent bond are made according to the synthetic methods outlined in Schemes A–D and F–H, have demonstrated GlyT2 inhibitory activity, and are selected from the group consisting of:

Ex Compound Name
1   (S)-2-(N'-Biphenyl-4-yl-N'''-cyano-guanidino)-3-phenyl-N-(3-pyrrolidin-1-yl-propyl)-propionamide;
4   (S)-2-{N'-[4-(4-Fluoro-phenoxy)-phenyl]-N'''-cyano-guanidino}-3-phenyl-N-(3-pyrrolidin-1-yl-propyl)-propionamide;
8   (R)-3-(N'-Biphenyl-4-yl-N'''-cyano-guanidino)-3-phenyl-N-(2-pyrrolidin-1-yl-ethyl)-propionamide;
10  3-{N'-[4-(3,4-Dichloro-phenoxy)-phenyl]-N'''-cyano-guanidino}-3-phenyl-N-(2-pyrrolidin-1-yl-ethyl)-propionamide;
32  3-{N'-[4-(4-Chloro-phenoxy)-phenyl]-N'''-cyano-guanidino}-3-phenyl-N-(2-pyrrolidin-1-yl-ethyl)-propionamide;
33  3-[N'-Methyl-N'''-(4-p-tolyloxy-phenyl)-guanidino]-3-phenyl-N-(2-pyrrolidin-1-yl-ethyl)-propionamide;
34  (S)-2-{N'-[4-(4-Chloro-phenoxy)-phenyl]-N'''-cyano-guanidino}-3-phenyl-N-(3-pyrrolidin-1-yl-propyl)-propionamide;
35  3-{N'-[4-(4-Fluoro-phenoxy)-phenyl]-N'''-cyano-guanidino}-3-phenyl-N-(2-pyrrolidin-1-yl-ethyl)-propionamide;
36  (S)-2-{N'-[4-(4-Chloro-phenoxy)-phenyl]-N'''-cyano-guanidino}-N-(2-diisopropylamino-ethyl)-3-phenyl-propionamide;
37  (R)-2-{N'-[4-(4-Chloro-phenoxy)-phenyl]-N'''-cyano-guanidino}-3-phenyl-N-(2-pyrrolidin-1-yl-ethyl)-propionamide;
38  (R)-4-{N'-[4-(4-Chloro-phenoxy)-phenyl]-N'''-cyano-guanidino}-5-phenyl-pentanoic acid (2-pyrrolidin-1-yl-ethyl)-amide;
39  (R)-4-(N'-Biphenyl-4-yl-N'''-cyano-guanidino)-5-phenyl-pentanoic acid (2-isopropylamino-ethyl)-amide;
40  3-(N'-Biphenyl-4-yl-N'''-cyano-guanidino)-N-(2-diisopropylamino-ethyl)-3-phenyl-propionamide;
41  3-[N'-(9H-Fluoren-2-yl)-N'''-cyano-guanidino]-3-phenyl-N-(2-pyrrolidin-1-yl-ethyl)-propionamide;
42  (R)-4-(N'-Biphenyl-4-yl-N'''-cyano-guanidino)-5-phenyl-pentanoic acid (2-pyrrolidin-1-yl-ethyl)-amide;
43  (S)-2-{N'-[4-(4-Chloro-phenoxy)-phenyl]-N'''-cyano-guanidino}-3-phenyl-N-(2-pyrrolidin-1-yl-ethyl)-propionamide;
44  (R)-4-(N'-Biphenyl-4-yl-N'''-cyano-guanidino)-5-phenyl-pentanoic acid (2-diethylamino-ethyl)-amide;
45  (R)-4-(N'-Biphenyl-4-yl-N'''-cyano-guanidino)-5-phenyl-pentanoic acid (2-dimethylamino-ethyl)-amide;
46  (R)-4-{N'-[4-(4-Fluoro-phenoxy)-phenyl]-N'''-cyano-guanidino}-5-phenyl-pentanoic acid (2-pyrrolidin-1-yl-ethyl)-amide;
47  (R)-4-{N'-[4-(3,4-Dichloro-phenoxy)-phenyl]-N'''-cyano-guanidino}-5-phenyl-pentanoic acid (2-pyrrolidin-1-yl-ethyl)-amide;
48  (R)-4-[N'-Cyano-N'''-(4-p-tolyloxy-phenyl)-guanidino]-5-phenyl-pentanoic acid (2-pyrrolidin-1-yl-ethyl)-amide;
49  3-(N'-Biphenyl-4-yl-N'''-cyano-guanidino)-3-phenyl-N-(2-pyrrolidin-1-yl-ethyl)-propionamide;
50  (S)-3-{N'-[4-(4-Chloro-phenoxy)-phenyl]-N'''-cyano-guanidino}-4-phenyl-N-(2-pyrrolidin-1-yl-ethyl)-butyramide;
51  (S)-2-{N'-[4-(4-Chloro-phenoxy)-phenyl]-N'''-cyano-guanidino}-N-(2-dimethylamino-ethyl)-3-phenyl-propionamide;
52  (S)-3-(N'-Biphenyl-4-yl-N'''-cyano-guanidino)-5-methyl-hexanoic acid (2-pyrrolidin-1-yl-ethyl)-amide;
53  (S)-3-(N'-Biphenyl-4-yl-N'''-cyano-guanidino)-4-phenyl-N-(2-pyrrolidin-1-yl-ethyl)-butyramide;

54 (S)-4-(N'-Biphenyl-4-yl-N''-cyano-guanidino)-5-phenyl-pentanoic acid (2-pyrrolidin-1-yl-ethyl)-amide;
55 3-[N'-Cyano-N''-(4-phenoxy-phenyl)-guanidino]-3-phenyl-N-(2-pyrrolidin-1-yl-ethyl)-propionamide;
56 (R)-4-[N'-Cyano-N''-(4-phenoxy-phenyl)-guanidino]-5-phenyl-pentanoic acid (2-pyrrolidin-1-yl-ethyl)-amide; and
57 (R)-2-(N'-Biphenyl-4-yl-N''-cyano-guanidino)-3-phenyl-N-(3-pyrrolidin-1-yl-propyl)-propionamide;

and stereoisomers, solvates, pharmaceutically acceptable salts and polymorphs, thereof.

Embodiments of this invention where, in formula (I), X is >C=O are made according to the synthetic methods outlined in Schemes A–D and F–J, have demonstrated GlyT2 inhibitory activity, and are selected from the group consisting of:

Ex Compound Name
2 1-[(R)-1-Benzyl-4-(2-pyrrolidin-1-yl-ethylamino)-butyl]-3-biphenyl-4-yl-urea;
3 (S)-2-{3-[4-(4-Chloro-phenoxy)-phenyl]-ureido}-N-(2-diisopropylamino-ethyl)-3-phenyl-propionamide;
5 (S)-2-{3-[4-(4-Chloro-phenoxy)-phenyl]-ureido}-N-(2-dimethylamino-ethyl)-3-phenyl-propionamide;
6 (R)-3-(3-Biphenyl-4-yl-ureido)-N-(2-pyrrolidin-1-yl-ethyl)-3-p-tolyl-propionamide;
7 (S)-N-(2-Diisopropylamino-ethyl)-2-[3-(4-phenoxy-phenyl)-ureido]-3-phenyl-propionamide;
11 (E)-(S)-4-{3-[4-(4-Fluoro-phenoxy)-phenyl]-ureido}-5-phenyl-pent-2-enoic acid (2-pyrrolidin-1-yl-ethyl)-amide;
12 (S)-2-(3-Biphenyl-4-yl-ureido)-3-phenyl-N-(3-pyrrolidin-1-yl-propyl)-propionamide;
13 (S)-2-(3-Biphenyl-4-yl-ureido)-N-(3-diethylamino-propyl)-3-phenyl-propionamide;
14 (S)-2-(3-Biphenyl-4-yl-ureido)-N-(2-isopropylamino-ethyl)-3-phenyl-propionamide;
15 (R)-3-(3-Biphenyl-4-yl-ureido)-4-methyl-pentanoic acid (2-pyrrolidin-1-yl-ethyl)-amide;
16 (S)-2-{3-[4-(4-Chloro-phenoxy)-phenyl]-ureido}-N-(2-methylamino-ethyl)-3-phenyl-propionamide;
17 (S)-2-(3-Biphenyl-4-yl-ureido)-N-(3-pyrrolidin-1-yl-propyl)-3-thiophen-2-yl-propionamide;
18 (E)-(S)-4-[3-(4-Phenoxy-phenyl)-ureido]-5-phenyl-pent-2-enoic acid (2-methylamino-ethyl)-amide;
19 (E)-(S)-4-(3-Biphenyl-4-yl-ureido)-5-phenyl-pent-2-enoic acid (2-diethylamino-ethyl)-amide;
21 (E)-(S)-4-(3-Biphenyl-4-yl-ureido)-5-phenyl-pent-2-enoic acid (2-isopropylamino-ethyl)-amide;
22 (E)-(S)-4-[3-(4-Phenoxy-phenyl)-ureido]-5-phenyl-pent-2-enoic acid (2-ethylamino-ethyl)-amide;
23 3-(3-Biphenyl-4-yl-ureido)-3-phenyl-N-(2-pyrrolidin-1-yl-ethyl)-propionamide;
24 3-(3-Biphenyl-4-yl-ureido)-3-(4-methoxy-phenyl)-N-(2-pyrrolidin-1-yl-ethyl)-propionamide;
25 (E)-(S)-4-(3-Biphenyl-4-yl-ureido)-5-(3-chloro-phenyl)-pent-2-enoic acid (2-pyrrolidin-1-yl-ethyl)-amide;
26 (R)-4-(3-Biphenyl-4-yl-ureido)-5-phenyl-pentanoic acid (2-isopropylamino-ethyl)-amide;
27 (S)-2-{2-[4-(4-Chloro-phenoxy)-phenylamino]-acetylamino}-3-phenyl-N-(2-pyrrolidin-1-yl-ethyl)-propionamide;
28 (S)-3-{2-[4-(4-Chloro-phenoxy)-phenylamino]-acetylamino}-4-phenyl-N-(2-pyrrolidin-1-yl-ethyl)-butyramide;
29 3-(3-Biphenyl-4-yl-ureido)-N-(2-isopropylamino-ethyl)-3-phenyl-propionamide;
30 (S)-2-(3-Biphenyl-4-yl-ureido)-N-(2-diisopropylamino-ethyl)-3-phenyl-propionamide;
58 (E)-(S)-4-(3-Biphenyl-4-yl-ureido)-5-phenyl-pent-2-enoic acid (2-propylamino-ethyl)-amide;
59 (S)-2-{3-[4-(4-Fluoro-phenoxy)-phenyl]-ureido}-3-phenyl-N-(2-pyrrolidin-1-yl-ethyl)-propionamide;
60 (S)-2-{3-[4-(4-Methoxy-phenoxy)-phenyl]-ureido}-3-phenyl-N-(2-pyrrolidin-1-yl-ethyl)-propionamide;
61 2-(3-Biphenyl-4-yl-ureido)-N-(2-dimethylamino-ethyl)-N-methyl-3-phenyl-propionamide;
62 (R)-2-(3-Biphenyl-4-yl-1-methyl-ureido)-N-(2-dimethylamino-ethyl)-3-phenyl-propionamide;
63 (S)-2-(3-Biphenyl-4-yl-1-methyl-ureido)-3-phenyl-N-(2-pyrrolidin-1-yl-ethyl)-propionamide;
64 (S)-3-Phenyl-N-(2-pyrrolidin-1-yl-ethyl)-2-{3-[4-(5,6,7,8-tetrahydro-naphthalen-2-yloxy)-phenyl]-ureido}-propionamide;
65 (S)-N-(2-Diisopropylamino-ethyl)-3-phenyl-2-[3-(4-thiophen-2-yl-phenyl)-ureido]-propionamide;
66 (S)-2-[3-(4-Iodo-phenyl)-ureido]-3-phenyl-N-(2-pyrrolidin-1-yl-ethyl)-propionamide;
67 (S)-3-Biphenyl-4-yl-2-(3-biphenyl-4-yl-ureido)-N-(3-pyrrolidin-1-yl-propyl)-propionamide;
68 2-[3-(4-Phenoxy-phenyl)-ureido]-2-propyl-pentanoic acid (2-pyrrolidin-1-yl-ethyl)-amide;
69 (S)-N-(2-Amino-ethyl)-2-(3-biphenyl-4-yl-ureido)-3-cyclohexyl-propionamide;
70 (S)-2-(3-Biphenyl-4-yl-ureido)-3-phenyl-N-(2-piperazin-1-yl-ethyl)-propionamide;
71 (S)-N,N-Bis-(3-amino-propyl)-2-(3-biphenyl-4-yl-ureido)-3-phenyl-propionamide;
72 1-[3-(4-Phenoxy-phenyl)-ureido]-cyclopentanecarboxylic acid (2-pyrrolidin-1-yl-ethyl)-amide;
73 (S)-2-[3-(9H-Fluoren-2-yl)-ureido]-3-phenyl-N-(3-pyrrolidin-1-yl-propyl)-propionamide;
74 (S)-2-[3-(4-Phenoxy-phenyl)-ureido]-N-(2-pyrrolidin-1-yl-ethyl)-3-thiazol-4-yl-propionamide;
75 (S)-3,3-Dimethyl-2-[3-(4-phenoxy-phenyl)-ureido]-N-(3-pyrrolidin-1-yl-propyl)-butyramide;
76 (S)-2-[3-(4-Phenoxy-phenyl)-ureido]-3,3-diphenyl-N-(2-pyrrolidin-1-yl-ethyl)-propionamide;
77 (R)-3-Benzylsulfanyl-2-[3-(4-phenoxy-phenyl)-ureido]-N-(2-pyrrolidin-1-yl-ethyl)-propionamide;
78 (S)-2-(3-Biphenyl-4-yl-ureido)-3-pyridin-4-yl-N-(3-pyrrolidin-1-yl-propyl)-propionamide;
79 (S)-3-Methyl-2-[3-(4-phenoxy-phenyl)-ureido]-N-(2-pyrrolidin-1-yl-ethyl)-butyramide;
80 (S)-2-(3-Biphenyl-4-yl-ureido)-2-phenyl-N-(3-pyrrolidin-1-yl-propyl)-acetamide;
81 (S)-2-(3-Biphenyl-4-yl-ureido)-4-phenyl-N-(3-pyrrolidin-1-yl-propyl)-butyramide;
82 (S)-3-Naphthalen-2-yl-2-[3-(4-phenoxy-phenyl)-ureido]-N-(3-pyrrolidin-1-yl-propyl)-propionamide;
83 2-[3-(4-Phenoxy-phenyl)-ureido]-2,2-diphenyl-N-(2-pyrrolidin-1-yl-ethyl)-acetamide;
84 2-(3-Biphenyl-4-yl-ureido)-indan-2-carboxylic acid (2-pyrrolidin-1-yl-ethyl)-amide;
85 (S)-2-{3-[4-(4-Chloro-benzenesulfonyl)-phenyl]-ureido}-3-phenyl-N-(2-pyrrolidin-1-yl-ethyl)-propionamide;
86 (E)-(S)-4-(3-Biphenyl-4-yl-ureido)-5-phenyl-pent-2-enoic acid (3-diethylamino-propyl)-amide;
87 (R)-4-(3-Biphenyl-4-yl-ureido)-5-phenyl-pentanoic acid (2-propylamino-ethyl)-amide;
88 (E)-(S)-4-(3-Biphenyl-4-yl-ureido)-5-(4-methoxy-phenyl)-pent-2-enoic acid (2-pyrrolidin-1-yl-ethyl)-amide;
89 3-(3-Biphenyl-4-yl-ureido)-N-(2-diethylamino-ethyl)-3-phenyl-propionamide;

90 (S)-3-[3-(9H-Fluoren-2-yl)-ureido]-5-methyl-hexanoic acid (2-pyrrolidin-1-yl-ethyl)-amide;
91 N-(2-Amino-ethyl)-2-(3-biphenyl-4-yl-ureido)-3-phenyl-propionamide;
92 (R)-4-(3-Biphenyl-4-yl-ureido)-5-phenyl-pentanoic acid (2-amino-ethyl)-amide;
93 (E)-(R)-4-(3-Biphenyl-4-yl-ureido)-5-phenyl-pent-2-enoic acid (2-amino-ethyl)-amide;
94 2-(3-Biphenyl-4-yl-ureido)-N-(2-morpholin-4-yl-ethyl)-3-phenyl-propionamide;
95 (S)-4-(3-Biphenyl-4-yl-ureido)-5-phenyl-pentanoic acid (2-amino-ethyl)-amide;
96 (R)-4-(3-Biphenyl-4-yl-ureido)-5-phenyl-pentanoic acid (3-amino-propyl)-amide;
97 (S)-N-(2-Amino-ethyl)-3-phenyl-2-(3-phenyl-ureido)-propionamide;
98 (S)-N-(2-Amino-ethyl)-2-[3-(4-phenoxy-phenyl)-ureido]-3-phenyl-propionamide;
99 2-(3-Biphenyl-4-yl-ureido)-3-phenyl-N-(2-pyrrolidin-1-yl-ethyl)-propionamide;
100 2-(3-Biphenyl-4-yl-ureido)-3-phenyl-N-(2-piperidin-1-yl-ethyl)-propionamide;
101 (E)-(S)-4-(3-Biphenyl-4-yl-ureido)-5-phenyl-pent-2-enoic acid (2-pyrrolidin-1-yl-ethyl)-amide;
102 (S)-2-{3-[4-(4-Chloro-phenoxy)-phenyl]-ureido}-3-phenyl-N-(2-pyrrolidin-1-yl-ethyl)-propionamide;
103 (R)-4-(3-Biphenyl-4-yl-ureido)-5-phenyl-pentanoic acid (2-pyrrolidin-1-yl-ethyl)-amide;
104 (E)-(S)-4-[3-(4-Phenoxy-phenyl)-ureido]-5-phenyl-pent-2-enoic acid (2-pyrrolidin-1-yl-ethyl)-amide;
105 (S)-2-[3-(4-tert-Butyl-phenyl)-ureido]-3-phenyl-N-(2-pyrrolidin-1-yl-ethyl)-propionamide;
106 2-(3-Biphenyl-4-yl-ureido)-N-(2-dimethylamino-ethyl)-3-phenyl-propionamide;
107 1-(3-Biphenyl-4-yl-ureido)-cyclopentanecarboxylic acid (2-pyrrolidin-1-yl-ethyl)-amide;
108 (R)-4-[3-(4-Phenoxy-phenyl)-ureido]-5-phenyl-pentanoic acid (2-pyrrolidin-1-yl-ethyl)-amide;
109 (S)-2-{3-[4-(3,4-Dichloro-phenoxy)-phenyl]-ureido}-3-phenyl-N-(2-pyrrolidin-1-yl-ethyl)-propionamide;
110 (E)-(S)-4-[3-(4-Phenoxy-phenyl)-ureido]-5-phenyl-pent-2-enoic acid (2-amino-ethyl)-amide;
111 (R)-4-[3-(4-Phenoxy-phenyl)-ureido]-5-phenyl-pentanoic acid (2-amino-ethyl)-amide;
112 (E)-(S)-4-[3-(4-Phenoxy-phenyl)-ureido]-5-phenyl-pent-2-enoic acid (3-pyrrolidin-1-yl-propyl)-amide;
113 (E)-(S)-4-(3-Biphenyl-4-yl-ureido)-5-phenyl-pent-2-enoic acid (3-pyrrolidin-1-yl-propyl)-amide;
114 (S)-2-[3-(4-Phenoxy-phenyl)-ureido]-3-phenyl-N-(3-pyrrolidin-1-yl-propyl)-propionamide;
115 (E)-(S)-4-(3-Biphenyl-4-yl-ureido)-5-phenyl-pent-2-enoic acid (2-methylamino-ethyl)-amide;
116 (E)-(S)-4-(3-Biphenyl-4-yl-ureido)-5-phenyl-pent-2-enoic acid (2-dimethylamino-ethyl)-amide;
117 (E)-(S)-4-[3-(4-Phenoxy-phenyl)-ureido]-5-phenyl-pent-2-enoic acid (2-dimethylamino-ethyl)-amide;
118 (E)-(S)-4-(3-Biphenyl-4-yl-ureido)-5-phenyl-pent-2-enoic acid (3-methylamino-propyl)-amide;
119 (E)-(S)-4-(3-Biphenyl-4-yl-ureido)-5-phenyl-pent-2-enoic acid (3-dimethylamino-propyl)-amide;
120 (R)-4-(3-Biphenyl-4-yl-ureido)-5-phenyl-pentanoic acid (3-dimethylamino-propyl)-amide;
121 (Z)-(S)-4-(3-Biphenyl-4-yl-ureido)-5-phenyl-pent-2-enoic acid (2-pyrrolidin-1-yl-ethyl)-amide;
122 (S)-2-[3-(3-Phenoxy-phenyl)-ureido]-3-phenyl-N-(3-pyrrolidin-1-yl-propyl)-propionamide;
123 (S)-2-(3-Biphenyl-4-yl-ureido)-N-(2-diethylamino-ethyl)-3-phenyl-propionamide;
124 2-(3-Biphenyl-4-yl-ureido)-2-propyl-pentanoic acid (2-pyrrolidin-1-yl-ethyl)-amide;
125 (R)-4-(3-Biphenyl-4-yl-ureido)-5-phenyl-pentanoic acid (2-methylamino-ethyl)-amide;
126 (S)-3-(3-Biphenyl-4-yl-ureido)-4-phenyl-N-(2-pyrrolidin-1-yl-ethyl)-butyramide;
127 (S)-3-[3-(4-Phenoxy-phenyl)-ureido]-4-phenyl-N-(2-pyrrolidin-1-yl-ethyl)-butyramide;
128 (S)-3-(3-Biphenyl-4-yl-ureido)-5-methyl-hexanoic acid (2-pyrrolidin-1-yl-ethyl)-amide;
129 (S)-5-Methyl-3-[3-(4-phenoxy-phenyl)-ureido]-hexanoic acid (2-pyrrolidin-1-yl-ethyl)-amide;
130 (S)-2-[3-(2-Phenoxy-phenyl)-ureido]-3-phenyl-N-(3-pyrrolidin-1-yl-propyl)-propionamide;
131 (S)-3-(3-Biphenyl-4-yl-ureido)-3-phenyl-N-(2-pyrrolidin-1-yl-ethyl)-propionamide;
132 (R)-3-(3-Biphenyl-4-yl-ureido)-3-phenyl-N-(2-pyrrolidin-1-yl-ethyl)-propionamide;
133 N-(2-Amino-ethyl)-3-(3-biphenyl-4-yl-ureido)-3-phenyl-propionamide;
134 (R)-4-(3-Biphenyl-4-yl-ureido)-5-phenyl-pentanoic acid (2-diethylamino-ethyl)-amide;
135 3-(3-Biphenyl-4-yl-ureido)-N-(2-dimethylamino-ethyl)-3-phenyl-propionamide;
136 (E)-(R)-4-(3-Biphenyl-4-yl-ureido)-5-phenyl-pent-2-enoic acid (3-pyrrolidin-1-yl-propyl)-amide;
137 (S)-N-(2-Dimethylamino-ethyl)-2-[3-(4-phenoxy-phenyl)-ureido]-3-phenyl-propionamide;
138 3-(3-Biphenyl-4-yl-ureido)-3-phenyl-N-(3-pyrrolidin-1-yl-propyl)-propionamide;
139 (S)-3-(3-Biphenyl-4-yl-ureido)-N-(2-dimethylamino-ethyl)-4-phenyl-butyramide;
140 (S)-N-(2-Dimethylamino-ethyl)-3-[3-(4-phenoxy-phenyl)-ureido]-4-phenyl-butyramide;
141 (S)-2-(3-Biphenyl-4-yl-ureido)-N-(2-pyrrolidin-1-yl-ethyl)-3-thiophen-2-yl-propionamide;
142 (S)-2-(3-Biphenyl-4-yl-ureido)-3-pyridin-3-yl-N-(3-pyrrolidin-1-yl-propyl)-propionamide;
143 2-(3-Biphenyl-4-yl-ureido)-2,2-diphenyl-N-(2-pyrrolidin-1-yl-ethyl)-acetamide;
144 3-(3-Biphenyl-4-yl-ureido)-3-(4-chloro-phenyl)-N-(2-pyrrolidin-1-yl-ethyl)-propionamide;
145 (R)-4-Methyl-3-[3-(4-phenoxy-phenyl)-ureido]-pentanoic acid (2-pyrrolidin-1-yl-ethyl)-amide;
146 (R)-3-(3-Biphenyl-4-yl-ureido)-4-methyl-pentanoic acid (2-diisopropylamino-ethyl)-amide;
147 (R)-4-Methyl-3-[3-(4-phenoxy-phenyl)-ureido]-pentanoic acid (2-diisopropylamino-ethyl)-amide;
148 (E)-(R)-4-(3-Biphenyl-4-yl-ureido)-5-phenyl-pent-2-enoic acid (2-diisopropylamino-ethyl)-amide;
149 (S)-4-(3-Biphenyl-4-yl-ureido)-5-phenyl-pentanoic acid (2-diisopropylamino-ethyl)-amide;
150 (S)-2-(3-Biphenyl-3-yl-ureido)-3-phenyl-N-(3-pyrrolidin-1-yl-propyl)-propionamide;
151 (S)-3-(3-Biphenyl-4-yl-ureido)-N-(2-pyrrolidin-1-yl-ethyl)-3-p-tolyl-propionamide;
152 (E)-(S)-4-(3-Biphenyl-4-yl-ureido)-5-phenyl-pent-2-enoic acid (3-amino-propyl)-amide;
153 (E)-(R)-4-(3-Biphenyl-4-yl-ureido)-5-phenyl-pent-2-enoic acid (3-amino-propyl)-amide;
157 1-[(S)-1-Benzyl-2-(2-pyrrolidin-1-yl-ethylamino)-ethyl]-3-(4-phenoxy-phenyl)-urea; and
158 1-[(S)-1-Benzyl-4-(2-pyrrolidin-1-yl-ethylamino)-butyl]-3-biphenyl-4-yl-urea;

and stereoisomers, solvates, pharmaceutically acceptable salts and polymorphs, thereof.

Embodiments of this invention where, in formula (I), n is 1, X is >C=S and $Y_2$ is a covalent bond are made according to the synthetic methods outlined in Schemes A, C, D and F–H, have demonstrated GlyT2 inhibitory activity, and are selected from the group consisting of:

Ex Compound Name
9   (S)-2-{3-[4-(4-Chloro-phenoxy)-phenyl]-thioureido}-3-phenyl-N-(2-pyrrolidin-1-yl-ethyl)-propionamide;
20   (S)-N-(2-Diisopropylamino-ethyl)-2-{3-[4-(4-fluoro-phenoxy)-phenyl]-thioureido}-3-phenyl-propionamide;
31   (R)-4-(3-Biphenyl-4-yl-thioureido)-5-phenyl-pentanoic acid (2-pyrrolidin-1-yl-ethyl)-amide;
154   (S)-2-(3-Biphenyl-4-yl-thioureido)-3-phenyl-N-(3-pyrrolidin-1-yl-propyl)-propionamide;
155   (S)-2-{3-[4-(4-Chloro-phenoxy)-phenyl]-thioureido}-N-(2-diisopropylamino-ethyl)-3-phenyl-propionamide; and
156   (S)-N-(2-Diisopropylamino-ethyl)-3-phenyl-2-[3-(4-p-tolyloxy-phenyl)-thioureido]-propionamide;

and stereoisomers, solvates, pharmaceutically acceptable salts and polymorphs, thereof.

Compounds of the invention are effective in modulating or treating: anxiolytic disorders; a condition requiring treatment of injured mammalian nerve tissue; a condition amenable to treatment through administration of a neurotrophic factor; a neurological disorder; obesity; or an obesity-related disorder. These disorders or conditions are defined hereinafter. For example, in certain embodiments, compounds of the invention can be used as anticonvulsants, antiepileptics, neuroprotective agents, and muscle relaxants.

As used herein, the following terms have the following respective meanings. Other terms that are used to describe the present invention have the same definitions as those generally used by those skilled in the art. Specific examples recited in any definition are not intended to be limiting in any way.

"Hydrocarbon" refers to a substituted or unsubstituted organic compound.

"Acetal" refers to a compound in which two ether oxygens are bound to the same carbon. A "ketal" is an acetal derived from a ketone.

"Acyl" means a compound of the formula RCO, where R is aliphatic (characterized by a straight chain of carbon atoms), alicyclic (a saturated hydrocarbon containing at least one ring), or aromatic.

"Acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

"Alkyl" refers to a fully saturated monovalent hydrocarbon radical containing carbon and hydrogen that may be a straight chain, branched, or cyclic. Examples of alkyl groups are methyl, ethyl, n-butyl, n-heptyl, isopropyl, 2-methylpropyl, cyclopropyl, cyclopropylmethyl, cyclobutyl, cyclopentyl, cyclopentylethyl and cyclohexyl. "Cycloalkyl" groups refer to cyclic alkyl groups such as cyclopropyl, cyclobutyl, cyclopentyl and cyclohexyl. $C_1$–$C_7$ alkyl groups are preferably used in the present invention.

"Substituted alkyl" refers to alkyls as just described that include one or more functional groups such an alkyl containing from 1 to 6 carbon atoms, preferably a lower alkyl containing 1–3 carbon atoms, aryl, substituted aryl, acyl, halogen (i.e., alkyl halos, e.g., $CF_3$), hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like. The term "substituted cycloalkyl" has essentially the same definition as and is subsumed under the term "substituted alkyl" for purposes of describing the present invention.

"Amine" refers to aliphatic amines, aromatic amines (e.g., aniline), saturated heterocyclic amines (e.g., piperidine), and substituted derivatives such as an alkly morpholine. "Amine" as used herein includes nitrogen-containing aromatic heterocyclic compounds such as pyridine or purine.

"Aralkyl" refers to an alkyl group with an aryl substituent, and the term "aralkylene" refers to an alkenyl group with an aryl substituent. The term "alkaryl" refers to an aryl group that has an alkyl substituent, and the term "alkarylene" refers to an arylene group with an alkyl substituent. The term "arylene" refers to the diradical derived from aryl (including substituted aryl) as exemplified by 1,2-phenylene, 1,3-phenylene, 1,4-phenylene, 1,2-naphthylene and the like.

"Alkenyl" refers to a branched or unbranched hydrocarbon group typically although not necessarily containing 2 to about 24 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, preferably two to four carbon atoms.

"Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

"Aryl" refers to a substituted or unsubstituted monovalent aromatic radical having a single ring (e.g., phenyl) or multiple condensed rings (e.g., naphthyl). Other examples include heterocyclic aromatic ring groups having one or more nitrogen, oxygen, or sulfur atoms in the ring, such as imidazolyl, furyl, pyrrolyl, pyridyl, thienyl and indolyl, among others. Therefore, "aryl" as used herein includes "heteroaryls" having a mono- or polycyclic ring system that contains 1 to 15 carbon atoms and 1 to 4 heteroatoms, and in which at least one ring of the ring system is aromatic. Heteroatoms are sulfur, nitrogen or oxygen.

"Substituted aryl" refers to an aryl as just described that contains one or more functional groups such as lower alkyl, acyl, aryl, halogen, alkylhalos (e.g., $CF_3$), hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like.

"Alkynyl" as used herein refers to a branched or unbranched hydrocarbon group typically although not necessarily containing 2 to about 24 carbon atoms and at least one triple bond, such as ethynyl, n-propynyl, isopropynyl, n-butynyl, isobutynyl, octynyl, decynyl, and the like. Generally, although again not necessarily, alkynyl groups herein contain 2 to about 12 carbon atoms. The term "lower alkynyl" intends an alkynyl group of two to six carbon atoms, preferably three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

"Alkoxy" as used herein refers to an alkyl group bound through an ether linkage; that is, an "alkoxy" group may be represented as —O-alkyl where alkyl is as defined above. A "lower alkoxy" group intends an alkoxy group containing one to six, more preferably one to four, carbon atoms.

"Allenyl" is used herein in the conventional sense to refer to a molecular segment having the structure —CH=C=CH$_2$. An "allenyl" group may be unsubstituted or substituted with one or more non-hydrogen substituents.

"Anomer" as used herein means one of a pair of isomers of a cyclic carbohydrate resulting from creation of a new point of symmetry when a rearrangement of atoms occurs at an aldehyde or ketone position.

"Halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refer to an alkyl, alkenyl or alkynyl group, respectively, in which at least one of the hydrogen atoms in the group has been replaced with a halogen atom.

"Heterocycle" or "heterocyclic" refers to a carbocylic ring wherein one or more carbon atoms have been replaced with one or more heteroatoms such as nitrogen, oxygen or sulfur. A substitutable nitrogen on an aromatic or non-aromatic heterocyclic ring may be optionally substituted. The heteroatoms N or S may also exist in oxidized form such as NO, SO and SO$_2$. Examples of heterocycles include, but are not limited to, piperidine, pyrrolidine, morpholine, thiomorpholine, piperazine, tetrahydrofuran, tetrahydropyran, 2-pyrrolidinone, δ-valerolactam, δ-valerolactone and 2-ketopiperazine, among numerous others.

"Heteroatom-containing" refers to a molecule or molecular fragment in which one or more carbon atoms is replaced with an atom other carbon, e.g., nitrogen, oxygen, sulfur, phosphorus or silicon. "Substituted heterocycle" refers to a heterocycle as just described that contains one or more functional groups such as lower alkyl, acyl, aryl, cyano, halogen, hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like. In other instances where the term "substituted" is used, the substituents that fall under this definition may be readily gleaned from the other definitions of substituents that are presented in the specification as well the circumstances under which such substituents occur in a given chemical compound. One having ordinary skill in the art will recognize that the maximum number of heteroatoms in a stable, chemically feasible heterocyclic ring, whether it is aromatic or non-aromatic, is determined by the size of the ring, degree of unsaturation, and valence of the heteroatoms. In general, a heterocyclic ring may have one to four heteroatoms so long as the heterocyclic ring is chemically feasible and stable.

"Isostere" refers to compounds that have substantially similar physical properties as a result of having substantially similar electron arrangements.

"Substituted", as in "substituted alkyl" or "substituted alkenyl", means that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, amino, halo, silyl, and the like. When the term "substituted" appears prior to a list of possible substituted groups, it is intended that the term apply to every member of that group.

"Effective amount" refers to the amount of a selected compound, intermediate or reactant that is used to produce an intended result. The precise amount of a compound, intermediate or reactant used will vary depending upon the particular compound selected and its intended use, the age and weight of the subject, route of administration, and so forth, but may be easily determined by routine experimentation. In the case of the treatment of a condition or disease state, an effective amount is the amount used to effectively treat the particular condition or disease state.

The term "subjects" is used throughout the specification to describe an animal, preferably a human, to whom treatment, including prophylactic treatment, with the compositions according to the present invention is provided. For treatment of those infections, conditions or disease states that are specific for a specific animal such as a human patient, the term patient refers to that specific animal.

The present invention includes the pharmaceutically acceptable acid-addition salts of compounds of formula (I). The acids that are used to prepare the pharmaceutically acceptable acid-addition salts of the aforementioned base compounds of this invention are those that form non-toxic acid-addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)] salts.

The invention also includes base-addition salts of formula (I). The chemical bases that may be used as reagents to prepare pharmaceutically acceptable base salts of those compounds of formula (I) that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines.

The compounds of this invention include all stereoisomers (i.e., cis and trans isomers) and all optical isomers of compounds of the formula (I) (e.g., R and S enantiomers), as well as racemic, diastereomeric and other mixtures of such isomers, as well as all polymorphs of the compounds.

As modulators of the GlyT2 receptor, the compounds of the instant invention are useful in an effective amount for treating central nervous system conditions in subjects suffering there from. Specific central nervous system conditions include conditions such as muscle spasticity, tinnitus, epilepsy and neuropathic pain.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and cornstarch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of a GlyT2 inhibitor of the instant invention that may be combined with the carrier materials to produce a single dosage form will vary depending upon the host treated, and the particular mode of administration. Preferably, the compositions should be formulated to contain between about 10 milligrams to about 500 milligrams of active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

General Synthetic Methods

Representative compounds of the present invention can be synthesized in accordance with the general synthetic methods described below and are illustrated more particularly in the schemes that follow. Since the schemes are illustrative, the invention should not be construed as being limited by the chemical reactions and conditions expressed. The preparation of the various starting materials used in the schemes is well within the skill of persons versed in the art.

Unless specified to the contrary, reactions herein occur at approximately atmospheric pressure and at a temperature of between about 0° C. and the boiling point of any organic solvent used in the reaction. Inert organic solvents such as dichloromethane, diethyl ether, dimethylformamide, chloroform or tetrahydrofuran are preferred solvents in the reactions disclosed herein. Reaction times can range from about one hour to about forty-eight hours, and reactants optionally are stirred, shaken, or agitated. Reactions can be done one pot or in steps, unless specified to the contrary.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (W. C. Still et al., *J. Org. Chem.* 1978, 43(14):2923–2925), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, diethyl ether, tetrahydrofuran and dioxane are common examples of an ethereal solvent; benzene, toluene, hexanes and cyclohexane are typical hydrocarbon solvents; and dichloromethane and dichloroethane are representative halohydrocarbon solvents. In those cases wherein the product is isolated as the acid addition salt, the free base may be obtained by techniques known to those skilled in the art. In those cases in which the product is isolated as an acid addition salt, the salt may contain one or more equivalents of the acid.

The following schemes illustrate the synthesis of the compounds of the present invention. The compound numbers used in the schemes do not correspond to the example numbers.

Examples of the described synthetic routes include Synthetic Examples 1 through 158. Compounds analogous to the target compounds of these examples can be, and in many cases, have been, made according to similar routes. The disclosed compounds are useful in basic research and as pharmaceutical agents as described in the next section.

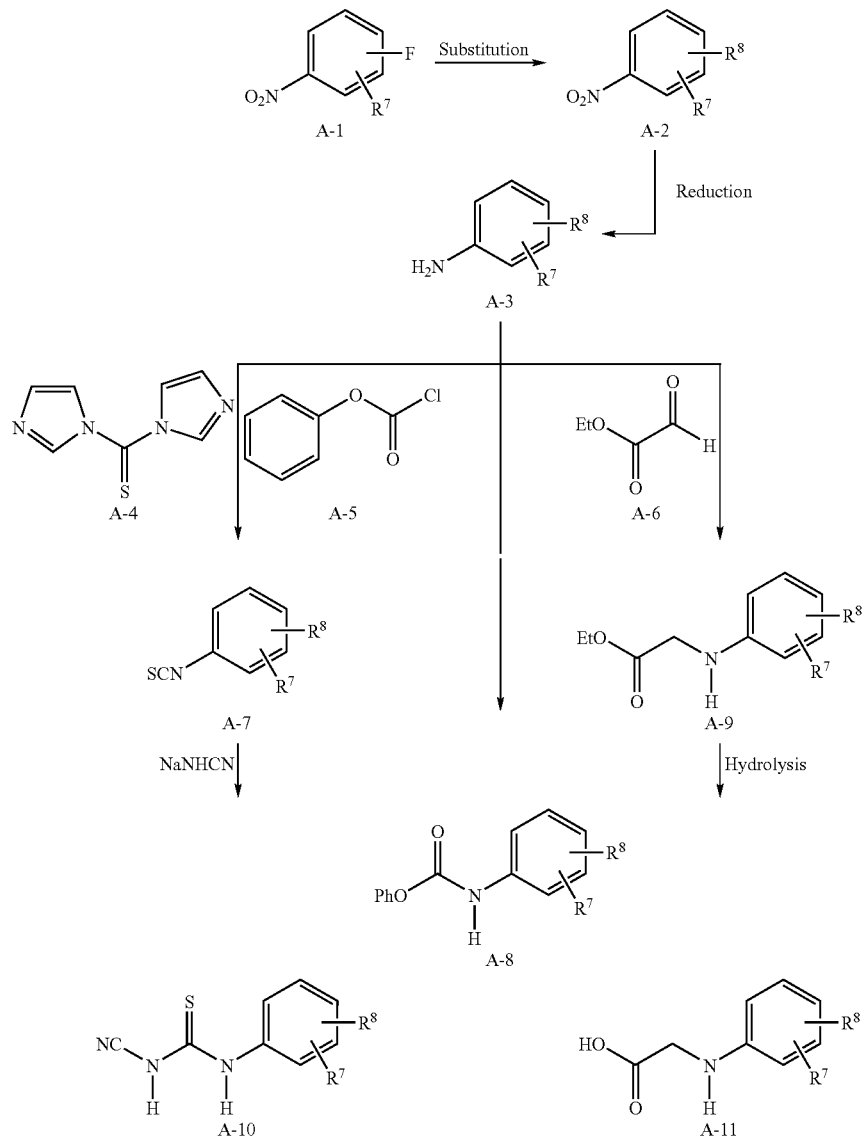

Referring to Scheme A, advanced intermediates of formulas A-7 through A-11 may be prepared from fluoro-nitrobenzene (A-1) via common intermediate A-3. Nucleophile $R^8H$ or $R^8H_2$ (e.g. a phenol or aniline, respectively) displaces fluorine on A-1 under standard conditions, such as Cs₂CO₃ in DMF, to provide A-2, the nitro group of which is subsequently reduced to an amine under standard conditions such as sodium hydrosulfite in EtOH under reflux. Aniline A-3 may be treated with thiocarbonyl diimidazole (A-4) in CH₂Cl₂ to provide isothiocyanate A-7. Treatment of A-7 with sodium hydrogen cyanamide in EtOH provides A-10.

Intermediate A-3 may also be treated with phenyl chloroformate (A-5) in THF in the presence of a base such as pyridine to provide compound A-8. Reductive amination of A-3 with oxo-acetic acid ethyl ester (A-6) and Na(OAc)₃BH in dichloroethane (DCE) provides ester A-9, which may be hydrolyzed with LiOH in THF/H₂O to acid A-11.

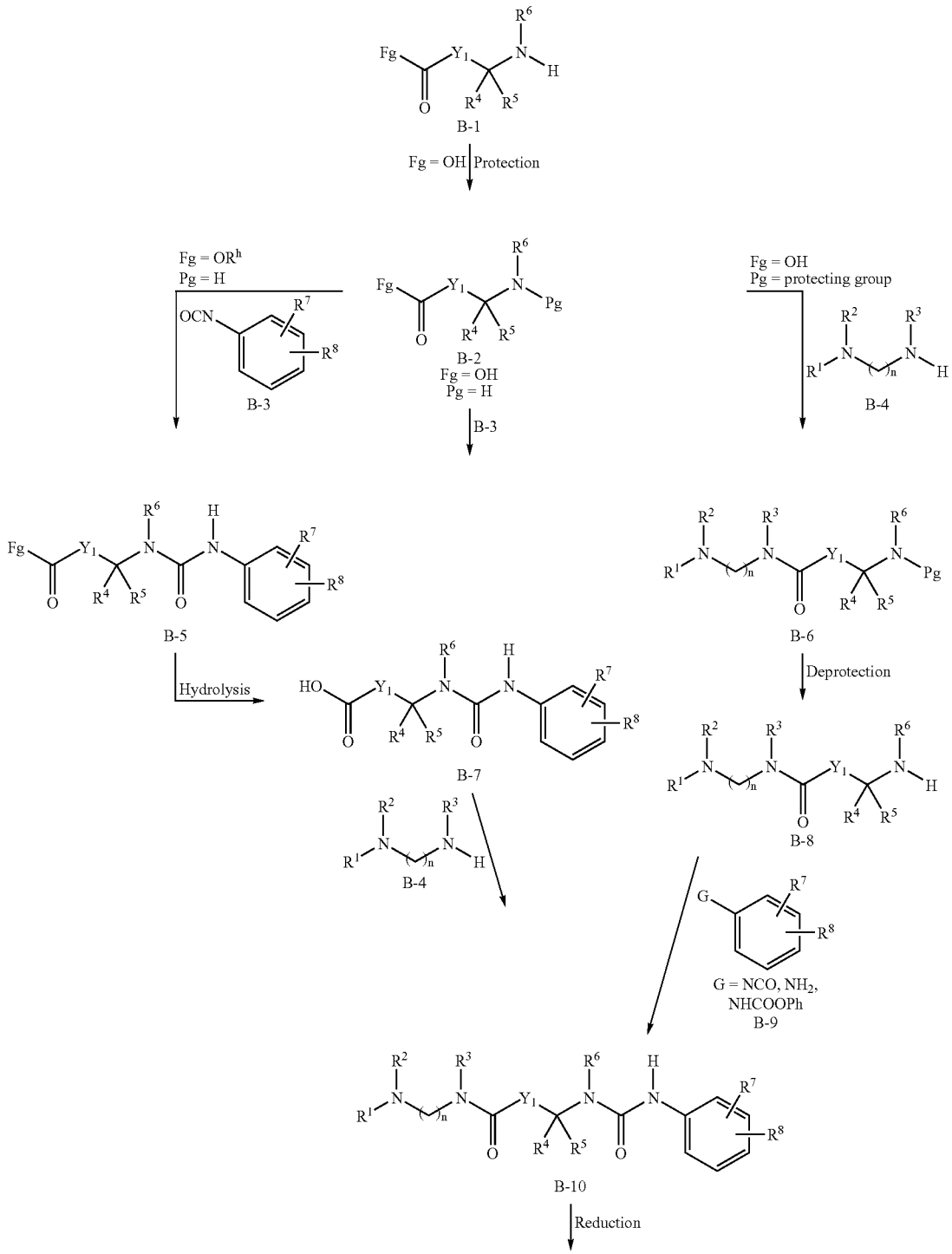

-continued

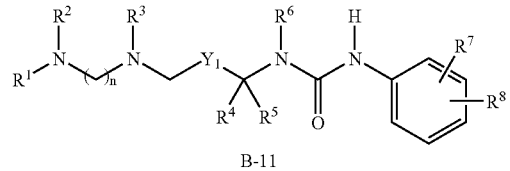

B-11

A compound of formula B-11 may be prepared from B-2 as shown in Scheme B. When a desired nitrogen-protected B-2 acid is not commercially available, the nitrogen of precursor B-1 can be protected using standard carbamoylating conditions such as treatment with di-tert-butyl dicarbonate in the presence of a base such as tetramethylammonium hydroxide in acetonitrile. Where Fg is an alkoxy group and Pg is hydrogen, B-2 is treated with isocyanate B-3 in the presence of a base such as triethylamine (TEA) in $CH_2Cl_2$ to provide B-5. Hydrolysis of the alkoxy group, for example using LiOH in $THF/H_2O$, provides B-7. Alternatively, where Fg is —OH and Pg is hydrogen, treatment of B-2 with isocyanate B-3 in THF in the presence of a base, such as TEA in acetone/$H_2O$, provides B-7 directly. Acid B-7 is reacted with di-amine B-4 under standard amide-bond forming conditions, such as treatment with 1-(3-dimethylaminopropyl)-3-ethylcarbodiimide hydrochloride/1-hydroxy-benzotriazole hydrate (EDCl/HOBT) in DMF, to provide B-10. Alternatively, B-10 can be synthesized from B-2 wherein Fg is —OH and Pg is a protecting group. Such a B-2 is reacted with di-amine B-4 under standard amide-bond forming conditions, such as EDCl/HOBT in DMF, to provide B-6, which is subsequently deprotected to provide B-8; for example, a t-BOC protecting group can be removed under standard conditions such as HCl in dioxane and $CH_2Cl_2$. Advanced intermediate B-8 is reacted with reagent B-9 to provide B-10. One skilled in the art will recognize that there are several ways to synthesize compounds of formula B-10 from B-8. In a preferred embodiment wherein G is isocyanate, B-9 is reacted with B-8 under standard urea-forming conditions, for example, treatment with a base such as TEA in $CH_2Cl_2$, to provide B-10. Alternatively, when G is an amino group, B-9 is reacted with B-8 in the presence of a coupling reagent such as 1,1'-carbonyldiimidazole (CDI) in THF to provide B-10. In yet another embodiment, when G is a phenyl carbamate, B-9 is reacted with B-8 in DMSO to provide B-10. Finally, amide B-10 is selectively reduced with borane dimethyl sulfide in THF to provide B-11.

Scheme C

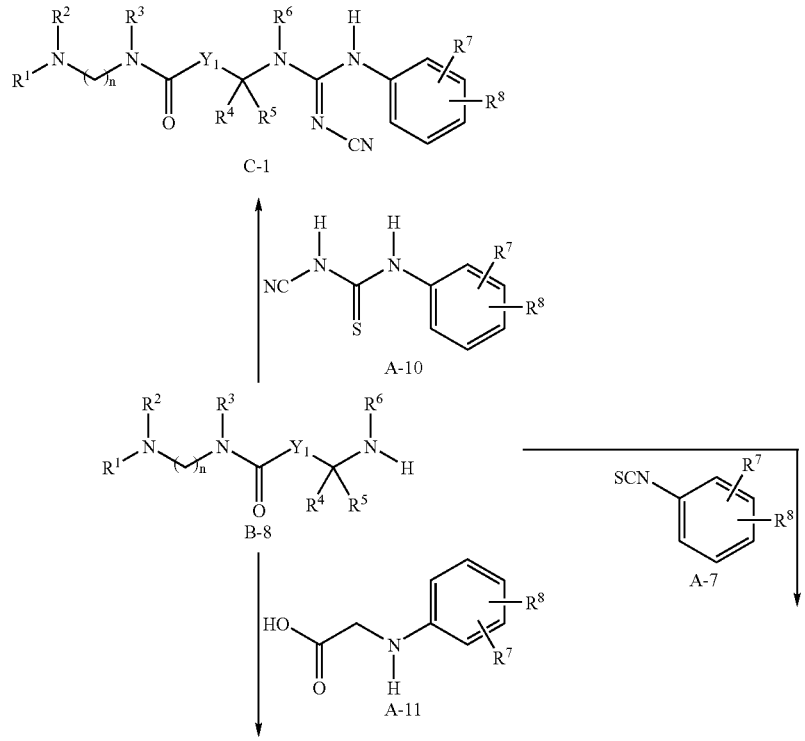

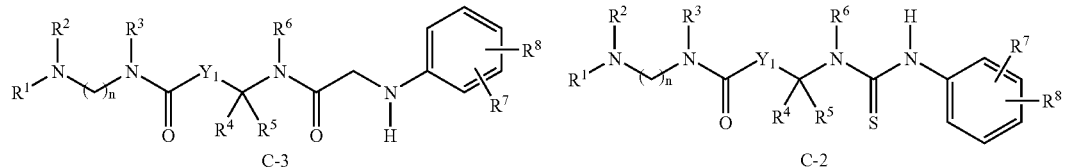

As shown in Scheme C, compounds of formulas C-1, C-2 and C-3 can be prepared from compounds of formula B-8 and advanced intermediates prepared according to Scheme A. B-8 is reacted with thiourea A-10 under standard conditions such as EDCl in DMF to provide C-1. B-8 is reacted with isothiocyanate A-7 under standard thio-urea forming conditions in $CH_2Cl_2$ to provide C-2. B-8 is reacted with acid A-11 under standard amide-bond forming conditions such as EDCl/HOBT in DMF to provide C-3.

different pathways. Removal of the D-1 t-BOC group followed by urea-bond formation, as described previously in Scheme B, provides compound D-2. Where $Y_1$ is ethenylene, the D-2 double bond may be selectively reduced under standard hydrogenation conditions such as Pd/C in EtOH. Reduction of the D-2 ester group with DIBAL-H provides D-3. Finally, D-4 is obtained upon reductive amination of D-3 with amine B-4 under standard conditions, such as $Na(OAc)_3BH$ in DCE. In an alternative route, the

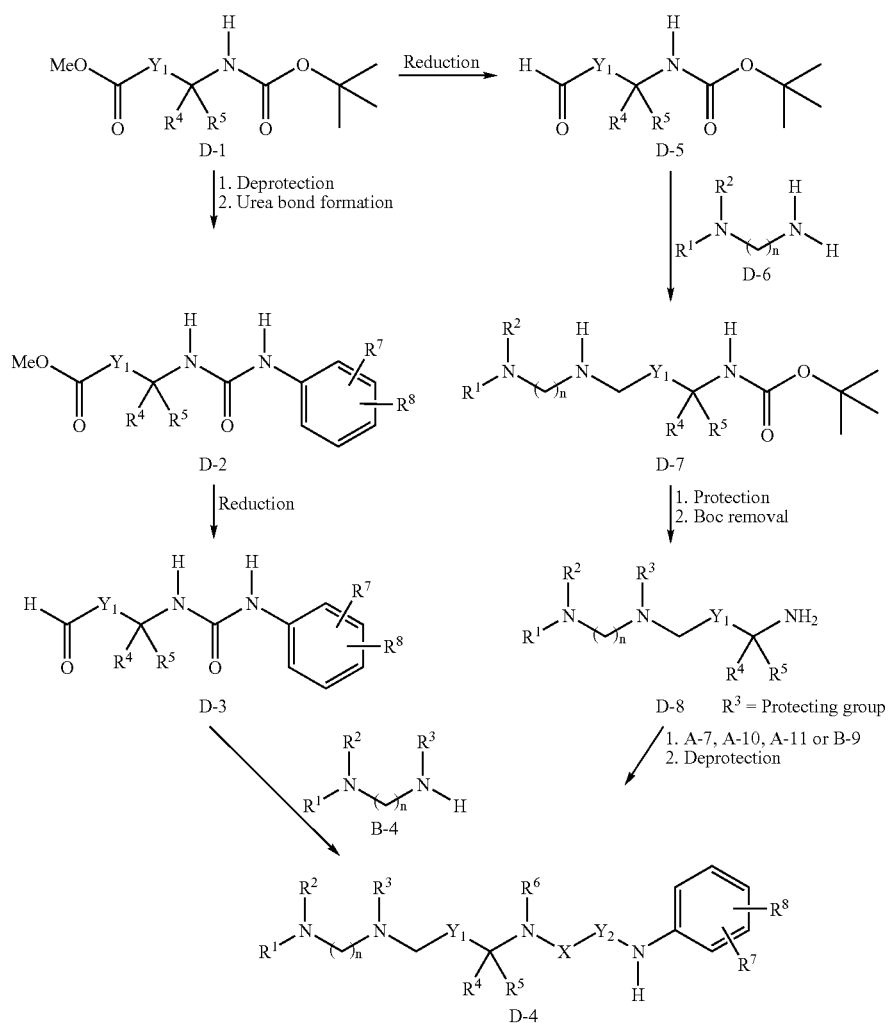

Compounds of formula D-4 may be synthesized from compounds of formula D-1 as shown in Scheme D using two ester group of D-1 is reduced using DIBAL-H to provide D-5. (As above, where $Y_1$ is ethenylene, the double bond may be selectively reduced under standard hydrogenation conditions such as Pd/C in EtOH.) D-5 is subjected to reductive amination with primary amine D-6 under standard conditions, such as Na(OAc)$_3$BH in DCE, to provide D-7. One D-7 amine is protected under standard conditions, such as Cbz chloride in the presence of NaOH in THF, and then another is deprotected when the t-BOC group is removed under standard conditions, as described previously, to provide D-8. D-4 is obtained from D-8 in a two-step sequence of urea bond formation using, for example, an isocyanate followed by removal of the Cbz protecting group under standard conditions, such as treatment with Pd/C in EtOH. D-8 can also be reacted with one of advanced intermediates A-7, A-10, A-11 and B-9, and subsequently deprotected, to provide compounds of formula D-4. In addition, where X=CO and Y$_2$=-CH$_2$—, D-4 can be reacted with Lawesson's reagent under standard conditions, such as refluxing in toluene, to provide D-4 where X=CS and Y$_2$=-CH$_2$—.

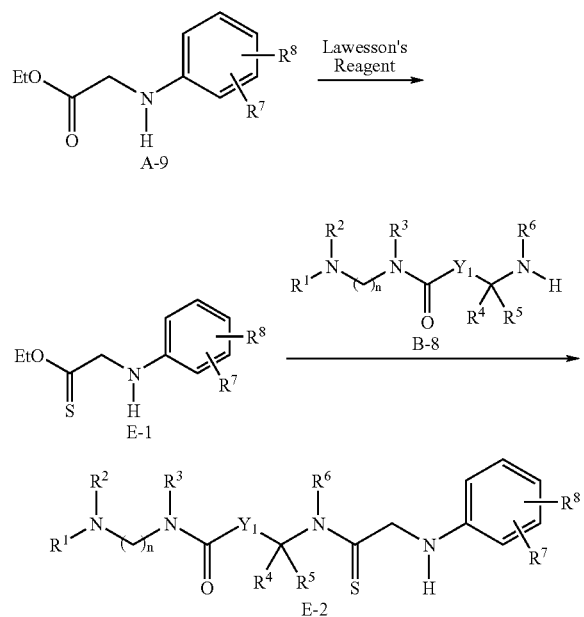

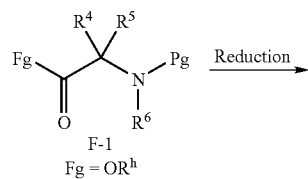

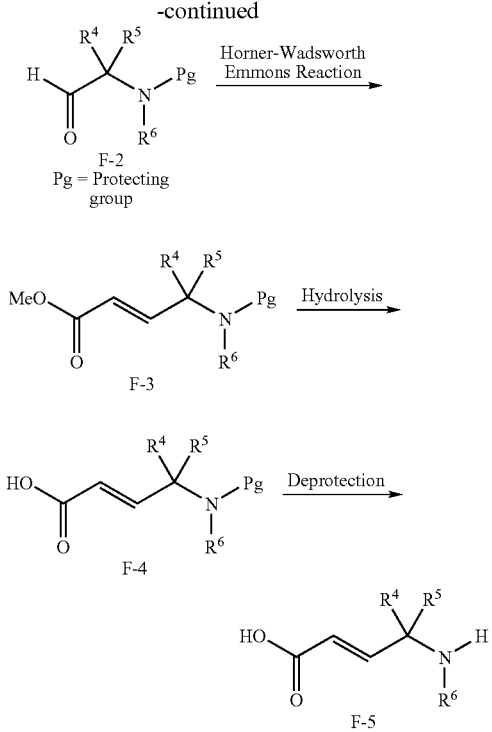

Intermediates of formula F-5, corresponding to formula (I) where Y$_1$ is ethenylene, can be synthesized from compounds of formula F-1 as shown in Scheme F. Reduction of the F-1 carboxy group using DIBAL-H in CH$_2$Cl$_2$ provides aldehyde F-2. F-2 is reacted with methyl (triphenylphosphoranylidene)acetate in CH$_2$Cl$_2$ to provide F-3. Hydrolysis of the F-3 methyl ester using LiOH in THF/H$_2$O, and subsequent deprotection of product F-4, under standard conditions, provide F-5. For example, a t-BOC protecting group can be removed using HCl in dioxane and CH$_2$Cl$_2$. Compounds of formulas F-4 and F-5 may be subjected to reaction sequences analogous to those described in Scheme B for a B-2 acid, to provide compounds of formula B-10 where Y$_1$ is ethenylene.

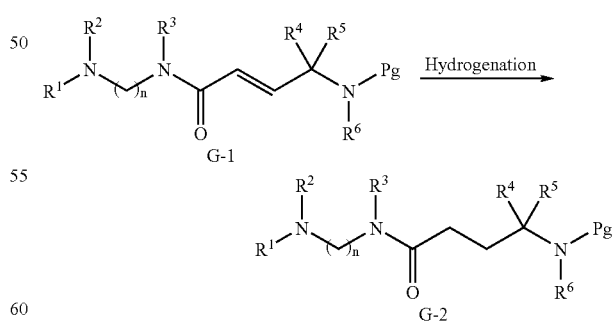

In Scheme G, the G-1 double bond is hydrogenated under standard conditions, such as Pd/C in EtOH, to provide G-2. Compounds of formulas G-1 and G-2 may be subjected to the same reactions described for B-6 in Scheme B and for B-8 in Scheme C.

As shown in Scheme E, compounds of formula E-2 can be prepared from compounds of formula B-8 and advanced intermediates such as E-1. A-9 is reacted with Lawesson's reagent under standard conditions, such as refluxing in toluene, to provide E-1, which is reacted with B-8 under standard conditions, such as Na$_2$CO$_3$ in THF/H$_2$O, to provided E-2.

Scheme H

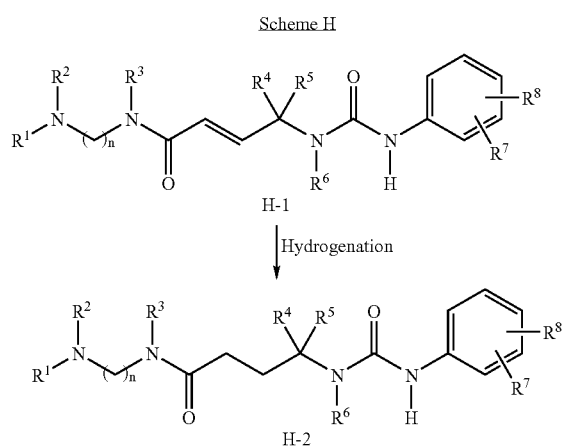

In Scheme H, hydrogenation of the H-1 double bond under standard conditions, such as Pd/C in EtOH, provides H-2.

Compounds of formula I-9 may be prepared using the solid-phase route outlined in Scheme I. Treatment of solid support resin I-1 with CDI in THF provides I-2. Subsequently, I-2 is reacted with compounds of formula I-3 in the presence of a base such as N,N-diisopropylethylamine (DIPEA) in $CH_2Cl_2$ to provide I-4. I-4 is treated with a compound of formula I-5 under standard amide-bond forming reactions, such as treatment with 1,3-diisopropylcarbodiimide and 4-(dimethylamino)pyridine (DIC/DMAP) in DMF/$CH_2Cl_2$, to provide I-6. Removal of the 9-fluorenylmethoxycarbonyl (FMOC) protecting group under standard conditions, such as treatment with piperidine in DMF, provides I-7. I-7 is treated with isocyanate B-3 in DMF to provide I-8. Final product I-9 is cleaved from the solid support under acidic conditions such as TFA in $CH_2Cl_2$.

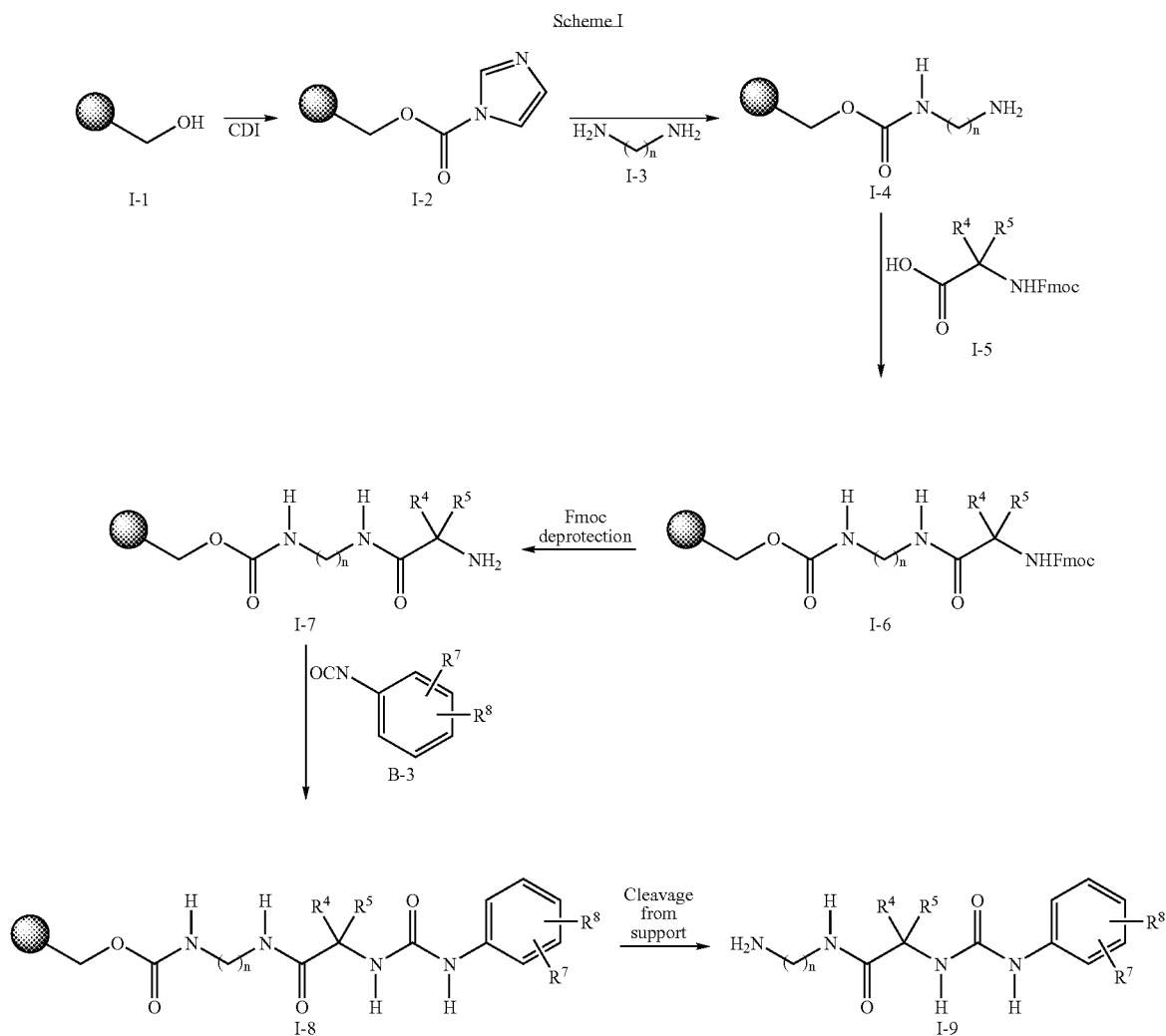

Scheme I

Scheme J

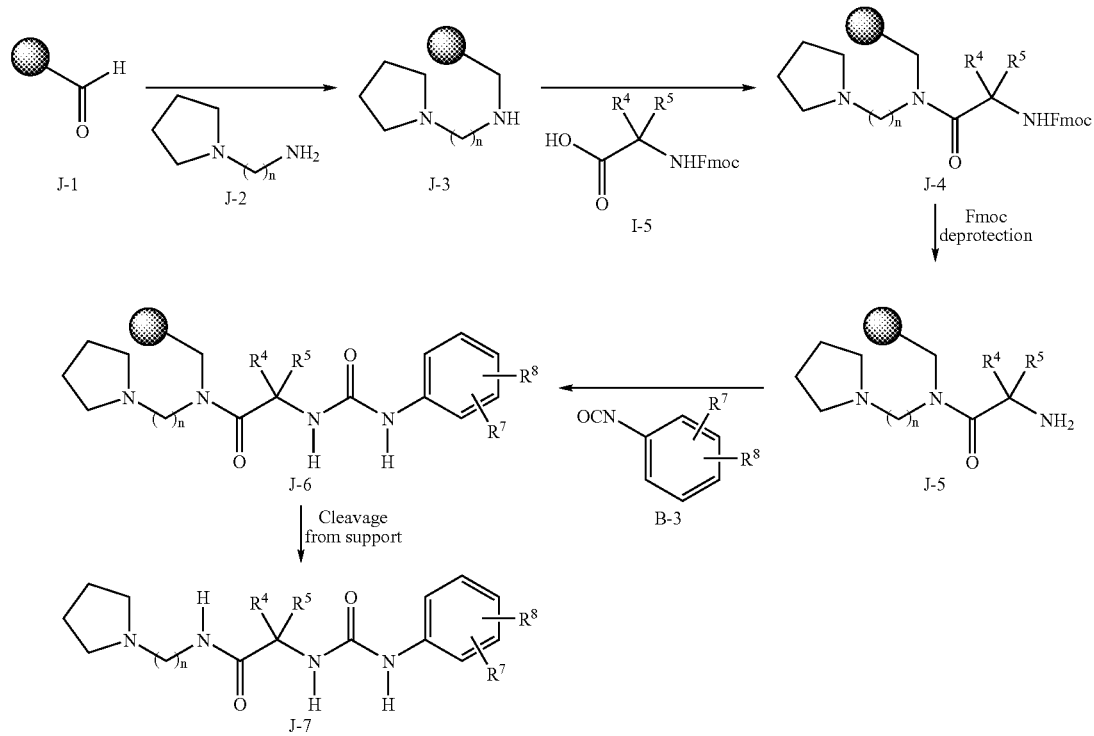

Compounds of formula J-7 may be prepared using the solid-phase processes outlined in Scheme J. Pyrrolidin-1-yl-alkylamine J-2 reacts with aldehyde-functionalized solid support resin J-1 under standard reductive amination conditions, such as Ti(iPrO)$_4$ in THF, after which treatment with NaBH$_4$ in EtOH, provides J-3. J-3 is reacted with compounds of formula 1–5 under standard amide-bond forming conditions such as treatment with DIC/DMAP in DMF/CH$_2$Cl$_2$ to provide J-4. Removal of the FMOC protecting group under standard conditions such as treatment with piperidine in DMF provides J-5. J-5 is treated with isocyanate B-3 in DMF to provide J-6. Final product J-7 is cleaved from the solid support under acidic conditions such as TFA in CH$_2$Cl$_2$.

GlyT2 antagonist activity of representative compounds of the invention was determined in accordance with the assay described in the Examples and by measuring the ability of compounds to inhibit the uptake of [$^{14}$C]-glycine in COS-7 cells transfected with the human glycine transporter-2 (GlyT2). The GlyT2 antagonist activities of these representative compounds are set forth hereinafter in Table 1.

The following examples describe the invention in greater detail and are intended to illustrate the invention, but not to limit it. All compounds were identified by a variety of methods including nuclear magnetic resonance spectroscopy, mass spectrometry and, in some cases, infrared spectroscopy and elemental analysis. Unless otherwise noted, the materials used in the examples were obtained from readily available commercial sources or synthesized by standard methods known to those skilled in the art.

EXAMPLES

General Experimental Details

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration). $^{13}$C NMR data is shown in ppm.

Mass spectra were obtained on an Agilent series 1100 MSD using electrospray ionization (ESI) in either positive or negative mode as indicated. The "mass calculated" for a molecular formula is the monoisotopic mass of the compound.

Flash column chromatography was accomplished using the ISCO Foxy 200 system and one of the following commercially-available, prepacked columns: Biotage 40S (SiO$_2$; 40 g), Biotage 40M (SiO$_2$; 90 g), Biotage 40L (SiO$_2$; 120 g), Biotage 65M (SiO$_2$; 300 g) or ISCO Redisep (SiO$_2$; 10, 12, 35, 40, or 120 g).

Preparative TLC was accomplished using PLC plates (20×20 cm silica gel 60 F$_{254}$, 0.5 mm).

Example 1

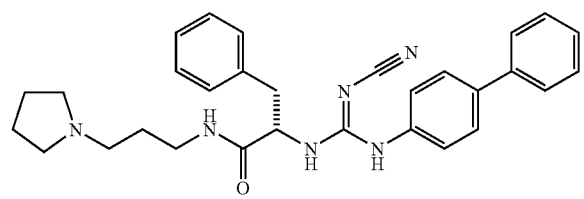

(S)-2-(N'-Biphenyl-4-yl-N''-cyano-guanidino)-3-phenyl-N-(3-pyrrolidin-1-yl-propyl)-propionamide A. [(S)-2-Phenyl-1-(3-pyrrolidin-1-yl-propylcarbamoyl)-ethyl]-carbamic acid tert-butyl ester. To a mixture of EDCl (5.75 g, 30 mmol), HOBT (4.05 g, 30 mmol) and (S)-2-tert-butoxycarbonylamino-3-phenyl-propionic acid (5.3 g, 20 mmol) in DMF (80 mL), was added 3-pyrrolidin-1-yl-propylamine (3.85 g, 30 mmol) in DMF (10 mL) followed by N-methylmorpholine (4.05 g, 40 mmol) in 10 mL of DMF at rt. The solution was stirred for 14 h and was diluted with ethyl acetate (500 mL). The organic layer was washed with saturated $NaHCO_3$ (2×100 mL), brine (3×100 mL) and dried ($Na_2SO_4$). The solvent was removed, and the crude residue was stirred in a mixture of 10% EtOAc/hexanes for 1 h to afford 6.5 g (87%) of the desired product as a white solid. MS (electrospray): mass calculated for $C_{21}H_{33}N_3O_3$, 375.25, m/z found, 376.2 [M+H]$^+$, 398.2 [M+Na]$^+$. $^1$H NMR (400 MHz, $CD_3OD$): 7.25–7.18 (m, 5H), 4.22 (t, J=3.6 Hz, 1H), 3.18–3.14 (m, 2H), 3.04 (dd, J=22.0, 6.5 Hz, 1H), 2.83 (dd, J=22.0, 8.3 Hz, 1H), 2.53–2.49 (m, 4H), 2.42 (t, J=7.9 Hz, 1H), 1.81–1.76 (m, 4H), 1.65–1.61 (m, 2H), 1.37 (s, 9H).

B. 4-Isothiocyanato-biphenyl. To a cooled solution (0° C.) of biphenyl-4-ylamine (0.67 g, 3.96 mmol) in anhydrous $CH_2Cl_2$ (70 mL) was added dropwise over a 2 h period a solution of 1,1'-thiocarbonyldiimidazole (2.0 g, 11.2 mmol) in $CH_2Cl_2$ (100 mL). The resulting solution was stirred (0° C., 0.5 h) and then warmed (25° C., 0.5 h). The solution was washed with saturated aqueous sodium bicarbonate (100 mL), brine (100 mL) and water (100 mL). The organic layer was dried ($Na_2SO_4$), filtered and concentrated in vacuo. The yellow residue was purified by column chromatography using a gradient of 0-25% EtOAc/hexanes to provide the desired product as a tan solid (0.78 g, 93%): $R_f$=0.72 (25%, EtOAc/hexanes). MS (electrospray): mass calculated for $C_{13}H_9NS$, 211.05; m/z found, 212.0 [M+H]$^+$. $^1$H NMR ($CDCl_3$, 400 MHz): 7.45–7.49 (m, 4H), 7.34–7.39 (m, 2H), 7.26–7.30 (m, 1H), 7.16–7.22 (m, 2H); $^{13}$C NMR ($CDCl_3$, 100 MHz) 140.7, 140.1, 136.0, 130.7, 129.4, 128.6, 128.3, 124.4, 126.5.

C. 1-Biphenyl-4-yl-3-cyano-thiourea. To a suspension of 4-isothiocyanato-biphenyl (0.72 g, 3.4 mmol) in EtOH (34 mL) was added sodium hydrogen cyanamide (0.22 g, 3.4 mmol), and the resulting suspension was stirred (70° C., 1.5 h). During the course of the reaction a white solid precipitated. The precipitate was collected, washed with EtOH (100 mL), and dried in vacuo to provide the desired product (0.8 g, 93%). MS (electrospray): mass calculated for $C_{14}H_{11}N_3S$, 253.07; m/z found, 254.1 [M+H]$^+$, 276.0 [M+Na]$^+$; 252.1 [M−H]$^−$. $^1$H NMR ($CDCl_3$, 400 MHz): 7.57–7.62 (m, 4H), 7.50–7.53 (m, 2H), 7.37–7.41 (m, 2H), 7.21–7.30 (m, 1H). $^{13}$C NMR ($CDCl_3$, 100 MHz): 186.5, 140.6, 139.3, 135.7, 128.3, 126.4, 126.1, 121.9, 121.1, 121.0.

D. (S)-2-(N'-Biphenyl-4-yl-N''-cyano-guanidino)-3-phenyl-N-(3-pyrrolidin-1-yl-propyl)-propionamide. To a solution of [(S)-2-phenyl-1-(3-pyrrolidin-1-yl-propylcarbamoyl)-ethyl]-carbamic acid tert-butyl ester (1.35 g, 3.6 mmol) in $CH_2Cl_2$ (20 mL), a 4 M solution of HCl in dioxane (2.5 mL, 10 mmol) was added, and the mixture was stirred for 3 h at rt. The solvents were removed, and the residue was treated with $CH_2Cl_2$. The solvents were removed again. The residue was dissolved in MeOH and treated with strongly basic ion exchange resin. After the mixture was stirred for 10 min, the resin was filtered off, and the solvents were removed. The residue was dissolved in DMF (18 mL), and 1-biphenyl-4-yl-3-cyano-thiourea (1.1 g, 4.36 mmol) was added followed by EDC (1.04 g, 5.45 mmol). The reaction mixture was stirred for 14 h, diluted with ethyl acetate (250 mL) and washed sequentially with saturated $NaHCO_3$ (2×50 mL) and brine (2×50 mL). After drying the mixture with $Na_2SO_4$, the solvents were removed. Purification of the residue by flash column chromatography using 0–20% MeOH (1% $NH_4OH$)/$CH_2Cl_2$ afforded 1.03 g (57%) of the desired product. MS (electrospray): mass calculated for $C_{30}H_{34}N_6O$, 494.28, m/z found, 495.3 [M+H]$^+$, 517.3 [M+Na]$^+$. $^1$H NMR (400 MHz, $CD_3OD$): 7.61–7.55 (m, 4H), 7.45–7.42 (m, 2H), 7.36–7.18 (m, 6H), 7.09–7.06 (m, 2H), 4.6 (dd, J=8.5, 6.2 Hz, 1H), 3.3–3.16 (m, 2H), 3.10 (dd, J=14.0, 6.2 Hz, 1H), 2.94 (dd, J=14.0, 8.5 Hz 1H), 2.53 (br m, 4H), 2.47 (m, 2H), 1.78 (br m, 4H), 1.71–1.65 (m, 2H).

Example 2

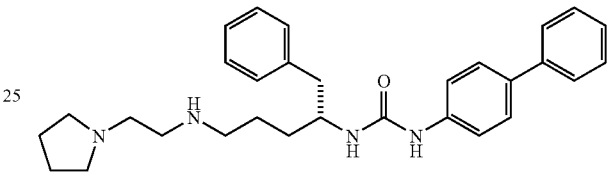

1-[(R)-1-Benzyl-4-(2-pyrrolidin-1-yl-ethylamino)-butyl]-3-biphenyl-4-yl-urea

Method 1

A. (E)-(S)-4-tert-Butoxycarbonylamino-5-phenyl-pent-2-enoic acid methyl ester. To a solution of ((S)-1-benzyl-2-oxo-ethyl)-carbamic acid tert-butyl ester (0.27 g, 1.1 mmol) in $CH_2Cl_2$ (11 mL) was added methyltriphenyl-phosphoranylidine acetate (0.36 g, 1.1 mmol), and the solution was stirred (25° C., 2 h). The solvent was removed in vacuo, and the resulting residue was purified by column chromatography using 0–40% EtOAc/hexanes to provide the desired product as a white solid (0.26 g, 80%): $R_f$=0.50 (25% EtOAc/hexanes). MS (electrospray): mass calculated for $C_{17}H_{23}NO_4$, 305.37; m/z found, 328.1 [M+Na]$^+$. $^1$H NMR ($CDCl_3$, 400 MHz): 7.18–7.34 (m, 5H), 6.93 (dd, J=15.7, 4.8 Hz, 1H), 5.88 (d, J=15.7 Hz, 1H), 4.62 (br s, 1H), 4.59 (br s, 1H), 3.74 (s, 3H), 2.88–2.94 (m, 2H), 1.41 (s, 9H). $^{13}$C NMR ($CDCl_3$, 100 MHz): 167.0, 155.6, 148.3, 136.7, 129.8, 128.9, 127.3, 121.1, 80.3, 52.7, 52.0, 41.2, 28.7 ppm.

B. (E)-(S)-4-(3-Biphenyl-4-yl-ureido)-5-phenyl-pent-2-enoic acid methyl ester. To a solution of (E)-(S)-4-tert-butoxycarbonylamino-5-phenyl-pent-2-enoic acid methyl ester (0.42 g, 1.4 mmol) in anhydrous $CH_2Cl_2$ (14 mL) was added HCl-dioxane (4 M, 4.1 mL), and the resulting suspension was stirred (25° C., 45 min). The solvent was removed in vacuo, and the resulting salt was suspended in toluene (14 mL), treated with TEA (0.14 g, 1.4 mmol) and 4-biphenyl-isocyanate (0.27 g, 1.4 mmol), and stirred (25° C., 4 h). The solution was diluted with $CH_2Cl_2$ (200 mL), washed with $H_2O$ (2×200 mL), dried ($Na_2SO_4$), filtered, and concentrated in vacuo. The residue was recrystallized (EtOAc/hexanes) to afford the desired product as a white solid (0.20 g, 36%): $R_f$=0.55 (3% MeOH/$CH_2Cl_2$). MS (electrospray): mass calculated for $C_{25}H_{24}N_2O_3$, 400.47; m/z found, 401.2 [M+H]$^+$, 423.1 [M+Na]$^+$. $^1$H NMR (DMSO-d$_6$, 400 MHz): 8.60 (br s, 1H), 7.53–7.66 (m, 5H), 7.40–7.46 (m, 4H), 7.20–7.34 (m, 6H), 6.89 (dd, J=15.7, 5.1 Hz, 1H), 6.42 (d, J=8.4 Hz, 1H), 5.87 (dd, J=15.7, 1.4 Hz, 1H), 4.64–4.69 (m, 1H), 3.65 (s, 3H), 2.96 (dd, J=13.7, 6.0 Hz, 1H), 2.86 (dd, J=13.7, 8.0 Hz, 1H). $^{13}$C NMR (DMSO-d$_6$, 100 MHz): 165.9, 154.2, 149.7, 139.8, 139.6, 137.6, 132.8, 129.2, 128.7, 128.2, 126.8, 126.6, 126.3, 125.9, 119.4, 117.9, 51.3; the remaining two peaks were not detected and are believed to overlapping with the solvent peak at 39 ppm.

C. (R)-4-(3-Biphenyl-4-yl-ureido)-5-phenyl-pentanoic acid methyl ester. To a solution of (E)-(S)-4-(3-biphenyl-4-yl-ureido)-5-phenyl-pent-2-enoic acid methyl ester (0.25 g, 0.63 mmol) in EtOH (6 mL) was added 10% Pd/C (0.09 g). The resulting suspension was stirred under H$_2$ (1 atm, 25° C., 4 h). The suspension was filtered, and the solid washed with EtOH (30 mL). The solvent was removed in vacuo to provide the desired product as a white solid (0.09 g, 36%): R$_f$=0.55 (3% MeOH/CH$_2$Cl$_2$). MS (electrospray): mass calculated for C$_{25}$H$_{26}$N$_2$O$_3$, 402.49; m/z found, 403.2 [M+H]$^+$, 425.2 [M+Na]$^+$. $^1$H NMR (CDCl$_3$, 400 MHz): 7.49–7.55 (m, 5H), 7.42 (t, J=7.5 Hz, 2H), 7.18–7.35 (m, 9H), 5.44 (d, J=8.8 Hz, 1H), 4.07–4.13 (m, 1H), 3.62 (s, 3H), 2.85 (dd, J=13.6, 6.2 Hz, 1H), 2.77 (dd, J=13.6, 6.8 Hz, 1H), 2.34–2.47 (m, 2H), 1.87–1.94 (m, 1H), 1.61–1.73 (m, 1H). $^{13}$C NMR (CDCl$_3$, 100 MHz): 174.9, 156.3, 140.9, 138.6, 138.3, 136.5, 129.8, 129.2, 128.9, 128.1, 127.3, 127.1, 126.9, 121.0, 52.1, 51.9, 42.2, 31.4, 29.8.

D. 1-((R)-1-Benzyl-4-oxo-butyl)-3-biphenyl-4-yl-urea. To a cooled solution (−78° C.) of (R)-4-(3-biphenyl-4-yl-ureido)-5-phenyl-pentanoic acid methyl ester (0.15 g, 0.37 mmol) in anhydrous CH$_2$Cl$_2$ (4 mL) was added DIBAL-H (0.17 g, 1.13 mmol), and the resulting solution was stirred (−78° C., 2 h). The solution was treated with 1 M NaOH (50 mL) and extracted with CH$_2$Cl$_2$ (50 mL). The organic layer was dried (Na$_2$SO$_4$), filtered and concentrated in vacuo. The resulting residue was purified by column chromatography using a gradient of 0–75% EtOAc/hexanes to provide the desired product as a clear oil (0.06 g, 43%): R$_f$=0.42 (3%, MeOH/CH$_2$Cl$_2$). MS (electrospray): mass calculated for C$_{24}$H$_{24}$N$_2$O$_2$, 373.18; m/z found, 374.2 [M+H]$^+$.

E. 1-[(R)-1-Benzyl-4-(2-pyrrolidin-1-yl-ethylamino)-butyl]-3-biphenyl-4-yl-urea. To a solution of 1-((R)-1-benzyl-4-oxo-butyl)-3-biphenyl-4-yl-urea (0.06 g, 0.16 mmol) and 1-(2-aminoethyl)pyrrolidine (0.02 g, 0.19 mmol) in DCE (3.2 mL), was added NaBH(OAc)$_3$ (0.05 g, 0.24 mmol). The resulting suspension was stirred (25° C., 18 h). The solution was concentrated in vacuo and the residue was partitioned with 1 N NaOH (50 mL) and CH$_2$Cl$_2$ (50 mL). The organic layer was dried (Na$_2$SO$_4$), filtered, and concentrated in vacuo. The resulting residue was purified by column chromatography using a gradient of 0–20% 1% NH$_4$OH/MeOH in CH$_2$Cl$_2$ to provide the desired product as a clear oil (0.04 g, 47%): R$_f$=0.07 (10%, 1% NH$_4$OH/MeOH in CH$_2$Cl$_2$). MS (electrospray): mass calculated for C$_{30}$H$_{38}$N$_4$O, 470.30; m/z found, 471.3 [M+H]$^+$, 493.3 [M+Na]$^+$. $^1$H NMR (CDCl$_3$, 400 MHz): 7.74 (br s, 1H), 7.48–7.50 (m, 2H), 7.41–7.44 (m, 2H), 7.32–7.36 (m, 4H), 7.17–7.26 (m, 3H), 7.10–7.13 (m, 3H), 6.13 (br s, 1H), 3.89 (br s, 1H), 2.85 (dd, J=13.5, 8.1 Hz, 1H), 2.58–2.69 (m, 4H), 2.10–2.50 (m, 6H), 1.71–1.91 (m, 4H), 1.45–1.51 (m, 3H), 1.18–1.25 (m, 3H). $^{13}$C NMR (CDCl$_3$, 100 MHz): 154.4, 141.1, 139.4, 139.0, 135.8, 130.0, 129.1, 128.7, 127.9, 127.2, 127.1, 126.6, 120.5, 55.9, 54.8, 54.2, 51.7, 50.2, 48.9, 42.2, 32.0, 30.1, 26.4, 23.8.

Method 2

A. (R)-4-tert-Butoxycarbonylamino-5-phenyl-pentanoic acid methyl ester. To a solution of (E)-(S)-4-tert-butoxycarbonylamino-5-phenyl-pent-2-enoic acid methyl ester (Example 2, Method 1, Step A) (0.72 g, 3.4 mmol) in EtOH (34 mL) was added 10% Pd/C (0.19 g). The resulting suspension was stirred under H$_2$ (1 atm, 25° C., 4 h). The suspension was filtered, and the solid was washed with EtOH (50 mL). The solvent was removed in vacuo to provide the desired product as a white solid (0.54 g, 99%): R$_f$=0.50 (25% EtOAc/hexanes). MS (electrospray): mass calculated for C$_{17}$H$_{25}$NO$_4$, 307.18; m/z found, 330.1 [M+Na]$^+$. $^1$H NMR (CDCl$_3$, 400 MHz): 7.28–7.33 (m, 2H), 7.19–7.25 (m, 3H), 4.38 (br d, J=8.6 Hz, 1H), 3.77–3.85 (br s, 1H), 3.67 (s, 3H), 2.85 (dd, J=13.3, 5.7 Hz, 1H), 2.76 (dd, J=13.3, 6.9 Hz, 1H), 2.35–2.42 (m, 2H), 1.84–1.92 (m, 1H), 1.59–1.68 (m, 1H), 1.41 (s, 9H). $^{13}$C NMR (CDCl$_3$, 100 MHz): 28.7, 29.2, 31.4, 42.2, 51.8, 52.0, 79.6, 126.8, 128.8, 129.8, 138.2, 155.9, 174.4.

B. ((R)-4-tert-Butoxycarbonylamino-5-phenyl-pentyl)-(2-pyrrolidin-1-yl-ethyl)-carbamic acid benzyl ester. To a cooled solution (−78° C.) of (R)-4-tert-butoxycarbonylamino-5-phenyl-pentanoic acid methyl ester (1.0 g, 2.9 mmol) in anhydrous toluene (29 mL) was added DIBAL-H (0.81 g, 5.7 mmol), and the resulting solution was stirred (−78° C., 2 h). The solution was treated with 1 M HCl (10 mL), and the resulting suspension was warmed (25° C.). The suspension was filtered (diatomaceous earth), and the solution was partitioned with EtOAc and brine (50 mL each). The organic layer was washed with brine (2×30 mL), dried (Na$_2$SO$_4$), filtered, and concentrated in vacuo to provide the desired product as a clear oil (0.7 g, 88%). To the clear oil (0.7 g, 2.5 mmol) in 1,2-dichloroethane (50 mL) was added 1-(2-aminoethyl)pyrrolidine (0.36 g, 3.0 mmol), and the resulting solution was stirred (25° C., 30 min). The solution was treated with Na(OAc)$_3$BH (0.8 g, 2.8 mmol), and the resulting suspension was stirred (25° C., 14 h). The solvent was removed in vacuo, and the residue was partitioned with CH$_2$Cl$_2$ and 1 M NaOH (100 mL each). The organic layer was washed with brine (100 mL), dried (Na$_2$SO$_4$), filtered, and concentrated in vacuo to provide the desired product as a clear oil (0.52 g, 55%). To a cooled solution (0° C.) of the clear oil (0.52 g, 1.4 mmol) in THF (14 mL) was simultaneously added 1 N NaOH (1.5 mL, 0.06 g, 1.5 mmol) and CBz-Cl (0.26 g, 1.5 mmol), and the resulting solution was stirred while warming (25° C., 4 h). The solvent was removed in vacuo, and the resulting residue was partitioned with 1 N NaOH and EtOAc (50 mL each), washed with brine (100 mL), dried (Na$_2$SO$_4$), filtered, and concentrated in vacuo to provide the desired product as an amber oil (0.37 g, 52%). MS (electrospray): mass calculated for C$_{30}$H$_{43}$N$_3$O$_4$, 509.68; m/z found, 510.3 [M+H]$^+$. $^1$H NMR (CDCl$_3$, 400 MHz): 7.02–7.31 (m, 11H), 5.04 (s, 2H), 3.72 (br s, 1H), 3.24–3.30 (m, 2H), 3.13–3.18 (m, 2H), 2.39–2.67 (m, 8H), 1.67 (br s, 4H), 1.39 (br s, 4H), 1.32 (s, 9H).

C. [(R)-4-(3-Biphenyl-4-yl-ureido)-5-phenyl-pentyl]-(2-pyrrolidin-1-yl-ethyl)-carbamic acid benzyl ester. To a solution of ((R)-4-tert-butoxycarbonylamino-5-phenyl-pentyl)-(2-pyrrolidin-1-yl-ethyl)-carbamic acid benzyl ester (0.06 g, 0.16 mmol) in CH$_2$Cl$_2$ (1.7 mL) was added HCl in dioxane (3 M, 0.6 mL), and the solution was stirred (25° C., 1 h). The solution was concentrated in vacuo, and the residue was dissolved in MeOH (2 mL) and treated with basic resin, and the resulting suspension was stirred (25° C., 1 h). The suspension was filtered and concentrated in vacuo, and the residue was dissolved in CH$_2$Cl$_2$ (2.0 mL). The solution was treated with 4-biphenylisocyanate (0.033 g, 0.17 mmol), and the reaction mixture was stirred for 4 h (25° C.), during which time a precipitate, the desired product, formed. The product was collected as a clear semi-solid (0.064 g, 64%). MS (electrospray): mass calculated for $C_{38}H_{44}N_4O_3$, 604.79; m/z found, 605.3 [M+H]$^+$, 627.3 [M+Na]$^+$. $^1$H NMR (CDCl$_3$, 400 MHz): 7.09–7.49 (m, 21H), 5.01–5.04 (m, 2H), 3.41 (br s, 1H), 3.14–3.30 (m, 2H), 2.85–2.92 (m, 2H), 2.49–2.58 (m, 8H), 1.17–1.56 (m, 8H).

D. 1-[(R)-1-Benzyl-4-(2-pyrrolidin-1-yl-ethylamino)-butyl]-3-biphenyl-4-yl-urea. To a solution of [(R)-4-(3-biphenyl-4-yl-ureido)-5-phenyl-pentyl]-(2-pyrrolidin-1-yl-ethyl)-carbamic acid benzyl ester (0.09 g, 0.15 mmol) in EtOH (1.5 mL) was added Pd—C (10%, 0.03 g), and the suspension was purged with N$_2$ (g). The suspension was stirred under H$_2$ (1 atm, 25° C., 1 h). The suspension was filtered (diatomaceous earth) and concentrated in vacuo to provide the desired product as a white solid (0.041 g, 51%).

Example 3

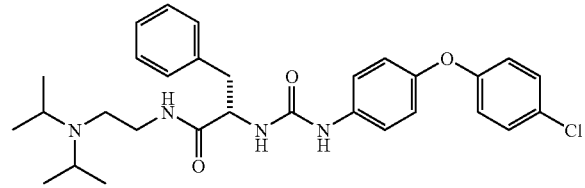

(S)-2-{3-[4-(4-Chloro-phenoxy)-phenyl]-ureido}-N-(2-diisopropylamino-ethyl)-3-phenyl-propionamide A. [4-(4-Chloro-phenoxy)-phenyl]-carbamic acid phenyl ester. To a solution of 4-(4-chloro-phenoxy)-phenylamine (2.2 g, 10 mmol) in THF (30 mL) at 0° C., was added pyridine (0.98 g, 12.5 mmol) followed by phenylchloroformate (1.61 g, 10.3 mmol). After the mixture was stirred for 10 min, the ice bath was removed. After further stirring for 2.5 h at rt, the mixture was diluted with EtOAc (150 mL) and washed sequentially with 10% HCl (40 mL), H$_2$O (40 mL), saturated NaHCO$_3$ (40 mL) and brine (40 mL). The organics were dried (Na$_2$SO$_4$), and the solvents were removed. The residue was recrystallized from CH$_2$Cl$_2$/hexanes to afford 2.8 g (85%) of the desired product. MS (electrospray): mass calculated for $C_{19}H_{14}ClNO_3$, 339.07; m/z found, 340.0 [M+H]$^+$, 362.0 [M+Na]$^+$. $^1$H NMR (400 MHz, DMSO-d$_6$): 10.32 (br s, 1H), 7.57–6.96 (m, 13H).

B. [(S)-1-(2-Diisopropylamino-ethylcarbamoyl)-2-phenyl-ethyl]-carbamic acid tert-butyl ester. HOBT (1.2 g, 8.49 mmol) and EDCI (1.6 g, 8.49 mmol) were added to a solution of (S)-2-tert-butoxycarbonylamino-3-phenyl-propionic acid in DMF (11 mL). Following the addition of a solution of N',N'-diisopropyl-ethane-1,2-diamine (0.978 g, 6.8 mmol) in DMF (2 mL), N-methyl-morpholine (1.1 g, 11.3 mmol) was added dropwise. The reaction mixture was stirred at rt overnight. Water (20 mL) and EtOAc (30 mL) were then added to the mixture. The aqueous layer was extracted with EtOAc (3×30 mL). The combined organic layers were washed sequentially with 1 N NaOH (2×20 mL) and brine (40 mL) and dried (MgSO$_4$). The solvents were removed. The crude product was purified by column chromatography [0–20% (1% NH$_4$OH/MeOH)/CH$_2$Cl$_2$] to afford 1.6 g (72%) of the desired product. MS (electrospray): mass calculated for $C_{22}H_{37}N_3O_3$, 391.55; m/z found, 392.3 [M+H]$^+$. $^1$H NMR (400 MHz, CDCl$_3$): 7.57 (s, 1H), 7.36–7.29 (m, 2H), 7.26–7.21 (m, 3H), 3.62–3.55 (m, 1H), 3.49 (d, J=5.5 Hz, 1H), 3.27 (dd, J=4.1, 13.6 Hz, 1H), 3.24 (d, J=6.2 Hz, 1H), 3.22 (d, J=6.1 Hz), 3.02–2.95 (m, 2H), 2.67 (dd, J=13.6, 9.4 Hz, 1H), 2.54 (t, J=6.3 Hz, 2H), 1.67 (s, 1H), 1.24 (d, J=5.6 Hz, 2H), 0.98 (d, J=6.6 Hz, 12H).

C. (S)-2-{3-[4-(4-Chloro-phenoxy)-phenyl]-ureido}-N-(2-diisopropylamino-ethyl)-3-phenyl-propionamide. To a solution of [(S)-1-(2-diisopropylamino-ethylcarbamoyl)-2-phenyl-ethyl]-carbamic acid tert-butyl ester (0.2 g, 0.5 mmol) in CH$_2$Cl$_2$ (5 mL) was added 4 M HCl solution in 1,4-dioxane (3 mL). The mixture was stirred at rt for 4 h. Upon completion of the reaction, the solvent was removed. The crude product was redissolved in MeOH (5 mL) and was treated with basic resin (Dowex 550A OH anion-exchange resin) for 2 h. The resin was filtered off, and the filtrate was concentrated to provide the crude product. To a stirred solution of the crude product in DMSO (1 mL) was added [4-(4-chloro-phenoxy)-phenyl]-carbamic acid phenyl ester (0.174 g, 0.5 mmol). The mixture was stirred at rt overnight. Excess EtOAc (50 mL) was then added, along with 0.1 N HCl (5 mL). The organic layers were washed sequentially with H$_2$O (10 mL), 1 N NaOH (10 mL) and brine (20 mL), and dried (MgSO$_4$). The solvent was removed. Purification by column chromatography [0–20% of (1% NH$_4$OH/MeOH)/CH$_2$Cl$_2$] afforded 0.222 g (80%) of the desired product. MS (electrospray): mass calculated for $C_{30}H_{37}ClN_4O_3$, 536.26; m/z found, 537.3 [M+H]$^+$. $^1$H NMR (400 MHz, CD$_3$OD): 7.32–7.24 (m, 9H), 6.91–6.88 (m, 4H), 4.47 (dd, J=7.5, 6.7 Hz, 1H), 3.21–3.3.16 (m, 1H), 3.13–2.96 (m, 5H), 2.46 (s, 2H), 1.02 (d, J=6.5 Hz, 12H).

Example 4

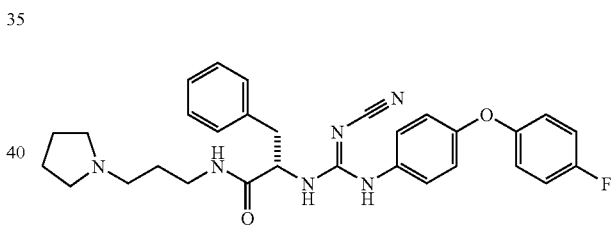

(S)-2-{N'-[4-(4-Fluoro-phenoxy)-phenyl]-N''-cyano-guanidino}-3-phenyl-N-(3-pyrrolidin-1-yl-propyl)-propionamide A. 4-(4-Fluoro-phenoxy)-nitrobenzene. Cesium carbonate (0.276 g, 0.85 mmol) and 4-fluorophenol (0.095 g, 0.85 mmol) were added to a solution of 4-fluoronitrobenzene (0.1 g, 0.7 mmol) in DMA (1.4 mL). After the reaction mixture was stirred at 90° C. overnight, H$_2$O (10 mL) and Et$_2$O (10 mL) were added. The aqueous layer was extracted with Et$_2$O (3×20 mL). The combined organic layers were washed with 1 N NaOH (20 mL) and brine (20 mL), and dried (MgSO$_4$). Removal of the solvent afforded 0.165 g (100%) of the desired product. $^1$H NMR (400 MHz, CDCl$_3$): 8.15–8.14 (m, 1H), 8.13–8.11 (m, 1H), 7.09–7.02 (m, 2H), 7.01–6.98 (m, 2H), 6.94–6.92 (m, 1H), 6.91–6.90 (m, 1H).

B. 4-(4-Fluoro-phenoxy)-phenylamine. To a solution of 4-(4-fluoro-phenoxy)-nitrobenzene (0.166 g, 0.71 mmol) in EtOH (7 mL) was added 10% Pd/C (0.06 g, 35 weight %). The reaction mixture was stirred under H$_2$ at rt for 5 h. Upon completion of the reaction, the mixture was filtered through a plug of silica gel, and the solvent was removed. The crude product was purified by column chromatography with 20–50% EtOAc/hexanes, giving 0.124 g (86%) of the desired product. MS (electrospray): mass calculated for $C_{12}H_{10}FNO$, 203.21; m/z found, 204.1 [M+H]$^+$. $^1$H NMR (400 MHz, CDCl$_3$): 6.94–6.88 (m, 2H), 6.85–6.81 (m, 2H), 6.80–6.76 (m, 2H), 6.63–6.62 (m, 1H), 6.61–6.59 (m, 1H).

C. 4-(4-Fluoro-Phenoxy)-phenylisothiocyanate. To a solution of 1,1'-thiocarbonylimidizole (4.4 g, 24.6 mmol) in CH$_2$Cl$_2$ (120 mL) cooled to 0° C. was added a solution of 4-(4-fluoro-phenoxy)-phenylamine (2.5 g, 12.3 mmol) in CH$_2$Cl$_2$ (120 mL) dropwise over 1.5 h. Upon completion of the addition, the solution was brought to rt and was stirred for 45 min. The solution was washed with aqueous saturated NaHCO$_3$ (2×60 mL), followed by brine (60 mL), dried (Na$_2$SO$_4$) and filtered, and the solvent was removed. The resulting brown oil was purified by column chromatography on silica gel using 5% EtOAc/hexanes to afford 3.01 g (99.8%) of the desired product as a yellow oil. R$_f$=0.94 (25% EtOAc/hexanes). $^1$H NMR (400 MHz, CDCl$_3$): 7.05–7.02 (m, 2H), 6.95–6.89 (m, 2H), 6.88–6.84 (m, 2H), 6.80–6.76 (m, 2H).

D. 1-[4-(4-Fluoro-phenoxy)-phenyl]-3-cyano-thiourea. To a solution of 4-(4-fluoro-phenoxy)-phenylisothiocyanate (2.06 g, 8.4 mmol) in EtOH (84 mL) was added sodium hydrogen cyanamide (0.54 g, 8.4 mmol), and the mixture was heated to 70° C. for 2 h. The solution was cooled, and the solvent was removed. The residue was recrystallized from MeOH/CH$_2$Cl$_2$ (3:70 mL) and was dried under vacuum to afford 2.32 g (96%) of the desired product as a white solid. $^1$H NMR (400 MHz, CD$_3$OD): 7.48–7.46 (m, 2H), 7.08–7.03 (m, 2H), 6.98–6.95 (m, 2H), 6.89–6.87 (m, 2H).

E. (S)-2-{N'-[4-(4-Fluoro-phenoxy)-phenyl]-N''-cyano-guanidino}-3-phenyl-N-(3-pyrrolidin-1-yl-propyl)-propionamide. To a solution of [(S)-2-phenyl-1-(3-pyrrolidin-1-yl-propylcarbamoyl)-ethyl]-carbamic acid tert-butyl ester (Example 1, step A) (0.14 g, 0.38 mmol) in CH$_2$Cl$_2$ (2 mL), a 4 M solution of HCl in dioxane (0.95 mL, 3.8 mmol) was added, and the mixture was stirred for 3 h at rt. The solvents were removed, and the residue was treated with CH$_2$Cl$_2$. The solvents were removed again. The crude product was dissolved in MeOH and was treated with strongly basic ion exchange resin. After the mixture was stirred for 10 min, the resin was filtered off, and the solvents were removed. The crude product was dissolved in DMF (2 mL), and 1-[4-(4-fluoro-phenoxy)-phenyl]-3-cyano-thiourea (0.131 g, 0.46 mmol) was added followed by EDC (0.088 g, 0.46 mmol). The mixture was stirred for 1 h, was diluted with EtOAc (50 mL), and was washed sequentially with saturated NaHCO$_3$ (2×10 mL) and brine (2×10 mL). After drying the mixture with Na$_2$SO$_4$, the solvents were removed. Purification by flash column chromatography using 0–20% MeOH (1% NH$_4$OH)/CH$_2$Cl$_2$ afforded 0.13 g (66%) of the desired product. MS (electrospray): mass calculated for $C_{30}H_{33}FN_6O_2$, 528.26; m/z found, 529.3 [M+H]$^+$. $^1$H NMR (400 MHz, CD$_3$OD): 7.3–6.9 (m, 13H), 4.57 (dd, J=8.5, 6.0 Hz, 1H), 3.2 (m, 2H), 3.10 (dd, J=13.8, 6.0 Hz 1H), 2.9 (dd, J=13.8, 8.6 Hz 1H), 2.55 (br m, 4H), 2.46 (m, 2H), 1.81 (br m, 4H), 1.68 (br m, 2H).

Example 5

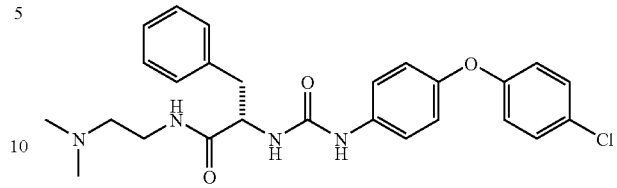

(S)-2-{3-[4-(4-Chloro-phenoxy)-phenyl]-ureido}-N-(2-dimethylamino-ethyl)-3-phenyl-propionamide A. [(S)-1-(2-Dimethylamino-ethylcarbamoyl)-2-phenyl-ethyl]-carbamic acid tert-butyl ester. HOBT (1.4 g, 10.7 mmol) and EDCl (2 g, 10.7 mmol) were added to a solution of (S)-2-tert-butoxycarbonylamino-3-phenyl-propionic acid (2 g, 7.2 mmol) in DMF (36 mL). Following the addition of a solution of N',N'-dimethyl-ethane-1,2-diamine (0.946 g, 10.7 mmol) in DMF (5 mL), N-methyl-morpholine (1.5 g, 14.4 mmol) was added dropwise. The reaction mixture was stirred at rt overnight. Water (50 mL) and EtOAc (70 mL) were then added to the mixture. The aqueous layer was extracted with EtOAc (3×70 mL). The combined organic layers were washed with 1 N NaOH (2×50 mL) and brine (50 mL), dried (MgSO$_4$), and concentrated. Purification by column chromatography [0–20% (1% NH$_4$OH/MeOH)/CH$_2$Cl$_2$] afforded 2.5 g (99%) of the desired product. MS (electrospray): mass calculated for $C_{18}H_{29}N_3O_3$, 335.22; m/z found, 336.1 [M+H]$^+$. $^1$H NMR (400 MHz, CDCl$_3$): 8.02 (s, 1H), 7.32–7.28 (m, 2H), 7.25–7.20 (m, 3H), 6.24 (s, 1H), 5.23 (d, J=6.5 Hz, 1H), 4.32–4.30 (m, 1H), 3.23–3.19 (m, 2H), 3.09 (dd, J=13.5, 6.3 Hz, 1H), 2.98 (dd, J=13.5, 6.3 Hz, 1H), 2.31–2.15 (m, 4H), 2.10 (s, 6H), 1.41 (s, 9H).

B. (S)-2-{3-[4-(4-Chloro-phenoxy)-phenyl]-ureido}-N-(2-dimethylamino-ethyl)-3-phenyl-Propionamide. To a solution of [(S)-1-(2-dimethylamino-ethylcarbamoyl)-2-phenyl-ethyl]-carbamic acid tert-butyl ester (0.15 g, 0.45 mmol) in CH$_2$Cl$_2$ (5 mL) was added 4 M HCl solution in 1,4-dioxane (2 mL). The mixture was stirred at rt for 4 h. Upon completion of the reaction, the solvent was removed. The residue was redissolved in MeOH (5 mL) and treated with basic resin (Dowex 550A OH anion-exchange resin) for 2 h. The resin was filtered off, and the solvents were removed again. To a stirred solution of the residue in DMSO (0.84 mL) was added [4-(4-chloro-phenoxy)-phenyl]-carbamic acid phenyl ester (0.144 g, 0.42 mmol). The mixture was stirred at rt overnight. Excess EtOAc (50 mL) was then added, along with 0.1 N HCl (5 mL). The organic layers were washed sequentially with H$_2$O (10 mL), 1 N NaOH (10 mL) and brine (20 mL), and were dried (MgSO$_4$). The solvent was removed. Purification by column chromatography [0–20% of (1% NH$_4$OH/MeOH)/CH$_2$Cl$_2$] afforded 0.115 g (76%) of the desired product. MS (electrospray): mass calculated for $C_{26}H_{29}ClN_4O_3$, 480.19; m/z found, 481.2 [M+H]$^+$. $^1$H NMR (400 MHz, CDCl$_3$): 8.19 (s, 1H), 7.33–7.28 (m, 3H), 7.25–7.21 (m, 3H), 7.18–7.12 (m, 3H), 6.82–6.78 (m, 4H), 4.82 (dd, J=15.4, 7.8 Hz, 1H), 3.27–3.22 (m, 2H), 3.16–3.08 (m, 2H), 2.35–2.26 (m, 1H), 2.21–2.15 (m, 1H), 2.10 (s, 6H).

Example 6

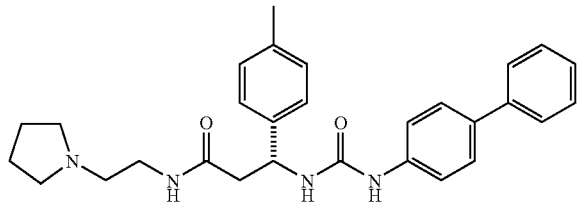

(R)-3-(3-Biphenyl-4-yl-ureido)-N-(2-pyrrolidin-1-yl-ethyl)-3-p-tolyl-propionamide A. 3-(3-Biphenyl-4-yl-ureido)-3-p-tolyl-propionic acid. To a solution of 3-amino-3-(p-tolyl)propionic acid (0.50 g, 2.79 mmol) and TEA (0.26 g, 2.56 mmol) in $CH_2Cl_2$ (28 mL) cooled to 0° C., was added 4-isocyanato-biphenyl (0.55 g, 2.79 mmol). The mixture was stirred at 0° C. for 30 min and was then brought to rt and stirred for an additional 3 h. The solvent was removed, water (20 mL) was added to the clear residue, and the mixture was then chilled to 0° C. and acidified using 1 N HCl. The resulting precipitate was collected by filtration, washed with copious amounts of $H_2O$, and dried under vacuum to afford 0.87 g (83%) of the desired product as a white solid. MS (electrospray): mass calculated for $C_{23}H_{22}N_2O_3$, 374.16; m/z found, 413.0 [M+Na]$^+$. $^1$H NMR (400 MHz, DMSO-d$_6$): 8.74 (s, 1H), 7.65–7.29 (m, 9H), 7.25 (d, J=8.1 Hz, 2H), 7.14 (d, J=7.9 Hz, 2H), 6.64 (d, J=8.5 Hz, 1H), 5.11–5.06 (m, 1H), 2.74–2.67 (m, 2H), 2.27 (s, 3H).

B. 3-(3-Biphenyl-4-yl-ureido)-N-(2-pyrrolidin-1-yl-ethyl)-3-tolyl-propionamide. To a solution of 3-(3-biphenyl-4-yl-ureido)-3-p-tolyl-propionic acid (0.15 g, 0.40 mmol), 2-pyrrolidin-1-yl-ethylamine (0.05 g, 0.40 mmol) and HOBt (0.081 g, 0.60 mmol) in DMF (4 mL), was added EDCI (0.12 g, 0.60 mmol). The resulting solution was stirred under $N_2$ at rt for 20 h. The solution was diluted with $H_2O$ (20 mL) and extracted with EtOAc (3×30 mL). The combined extracts were washed with brine (40 mL), dried ($Na_2SO_4$), and filtered, and the solvent was removed. The crude product was purified by column chromatography on silica gel using a gradient of 0–20% (MeOH(1% $NH_4OH$)/$CH_2Cl_2$) to afford 0.12 g (63%) of the desired product as a white solid. Racemic compound: $R_f$=0.11 (10% MeOH (1% $NH_4OH$)/$CH_2Cl_2$). MS (electrospray): mass calculated for $C_{29}H_{34}N_4O_2$, 470.27; m/z found, 471.3 [M+H]$^+$. $^1$H NMR (400 MHz, CD$_3$OD): 7.57–7.50 (m, 4H), 7.43–7.37 (m, 4H), 7.29–7.25 (m, 3H), 7.16 (d, J=7.9 Hz, 2H), 5.22 (t, J=6.9 Hz, 1H), 3.28–3.23 (m, 2H), 2.68 (d, J=6.4 Hz, 2H), 2.52–2.48 (m, 6H), 2.31 (s, 3H), 1.77–1.75 (m, 4H).

C. (R)-3-(3-Biphenyl-4-yl-ureido)-N-(2-pyrrolidin-1-yl-ethyl)-3-p-tolyl-propionamide. The enantiomers of the product obtained in step B were separated on a chiral O.D. (0.46 cm×25 cm) column using 0.1% DEA/MeOH at a flow rate of 0.5 mL/min. The (S) and (R) enantiomers had retention times of 10.3 min and 32.4 min, respectively. MS (electrospray): mass calculated for $C_{29}H_{34}N_4O_2$, 470.27; m/z found, 471.2 [M+H]$^+$.

Example 7

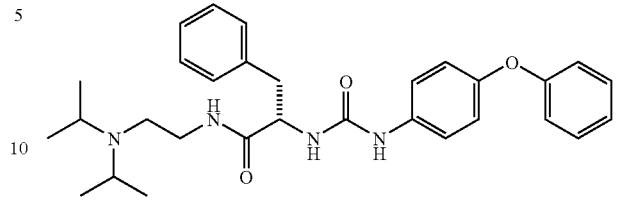

(S)-N-(2-Diisopropylamino-ethyl)-2-[3-(4-phenoxy-phenyl)-ureido]-3-phenyl-propionamide To a solution of [(S)-1-(2-diisopropylamino-ethylcarbamoyl)-2-phenyl-ethyl]-carbamic acid tert-butyl ester (Example 3, step B) (0.1 g, 0.258 mmol) in $CH_2Cl_2$ (3 mL), a 4 M solution of HCl in dioxane (0.64 mL, 2.56 mmol) was added, and the mixture was stirred for 3 h at rt. The solvents were removed, the residue was treated with $CH_2Cl_2$, and the solvent was removed again. The crude product was dissolved in $CH_2Cl_2$ (3 mL), and triethylamine (0.037 g, 0.365 mmol) was added at 0° C. followed by 4-phenoxyphenyl-isocyanate (0.059 g, 0.28 mmol). The mixture was warmed to rt over a period of 2 h and was then diluted with EtOAc (100 mL). The organic layer was washed with saturated $NaHCO_3$ (25 mL) and brine (25 mL), and dried ($Na_2SO_4$). The solvent was removed, and the residue was purified by flash column chromatography using 0–20% MeOH (1% $NH_4OH$)/$CH_2Cl_2$ to afford 0.07 g (55%) of the desired product. MS (electrospray): mass calculated for $C_{30}H_{38}N_4O_3$, 502.29; m/z found, 503.3 [M+H]$^+$. $^1$H NMR (400 MHz, CD$_3$OD): 7.3–7.19 (m, 9H), 7.04 (m, 1H), 6.91–6.85 (m, 4H), 4.47 (t, J=7.4 Hz, 1H), 3.19–2.95 (m, 6H), 2.42 (br s, 2H), 1.02 (d, J=6.4 Hz, 12H).

Example 8

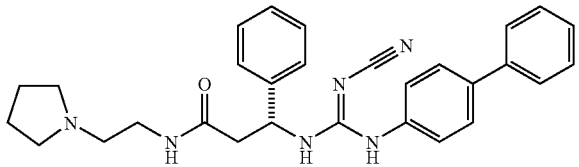

(R)-3-(N'-Biphenyl-4-yl-N''-cyano-guanidino)-3-phenyl-N-(2-pyrrolidin-1-yl-ethyl)-propionamide A. [(R)-1-Phenyl-2-(2-pyrrolidin-1-yl-ethylcarbamoyl)-ethyl]-carbamic acid tert-butyl ester. To a solution of (R)-3-tert-butoxycarbonylamino-3-phenyl-propionic acid (0.54 g, 2.04 mmol), 2-pyrrolidin-1-yl-ethylamine (0.35 g, 3.06 mmol), HOBt (0.41 g, 3.06 mmol) and 4-methylmorpholine (0.41 g, 4.08 mmol) in DMF (10 mL), was added EDCI (0.59 g, 3.06 mmol), and the resulting solution was stirred under $N_2$ at rt for 20 h. The solution was diluted with $H_2O$ (75 mL) and was extracted with EtOAc (3×75 mL). The combined extracts were washed with brine (100 mL), dried ($Na_2SO_4$) and filtered, and the solvent was removed. The crude product was purified by column chromatography on silica gel using a gradient of 2–30% (MeOH (1% $NH_4OH$)/$CH_2Cl_2$) to afford 0.65 g. (88%) of the desired product as a white solid.

$R_f$=0.34 (10% MeOH (1% NH$_4$OH)/CH$_2$Cl$_2$). MS (electrospray): mass calculated for C$_{20}$H$_{31}$N$_3$O$_3$, 361.24; m/z found, 362.2 [M+H]$^+$, 745.4 [2M+Na]$^+$. $^1$H NMR (400 MHz, CDCl$_3$): 7.32–7.28 (m, 4H), 7.24–7.20 (m, 1H), 6.37 (br s, 1H), 6.14 (br s, 1H), 5.01 (br s, 1H), 3.21 (dd, J=11.2, 5.7 Hz, 2H), 2.74–2.67 (m, 1H), 2.59 (dd, J=14, 5.9 Hz, 1H), 2.49–2.38 (m, 6H), 1.76–1.67 (m, 4H), 1.41 (s, 9H).

B. (R)-3-(N'-Biphenyl-4-yl-N''-cyano-guanidino)-3-phenyl-N-(2-pyrrolidin-1-yl-ethyl)-propionamide. To a solution of [(R)-1-phenyl-2-(2-pyrrolidin-1-yl-ethylcarbamoyl)-ethyl]-carbamic acid tert-butyl ester (0.25 g, 0.69 mmol) in CH$_2$Cl$_2$ (6.9 mL) was added 4 M HCl in 1,4-dioxane (2.4 mL), and the resulting solution was stirred at rt for 1.5 h. The solvent was removed, and the resulting residue was dissolved in MeOH (7 mL) and treated with basic resin (Dowex 550A OH anion-exchange resin). The resulting suspension was stirred at rt for 30 min. The resin was filtered off and washed with MeOH (7 mL). The filtrate and washings were concentrated, and the resulting free amine was dried under vacuum. To a solution of the free amine and 1-biphenyl-4-yl-3-cyano-thiourea (0.21 g, 0.83 mmol) in DMF (3.5 mL), was added EDCl (0.2 g, 1.04 mmol). The resulting solution was stirred under N$_2$ at rt for 2 h. The solution was diluted with EtOAc (70 mL) and washed with 1 N NaOH (2×50 mL). The organic layer was dried (Na$_2$SO$_4$) and filtered, and the solvent was removed. The crude product was purified by column chromatography on silica gel using a gradient of 5–10% (MeOH (1% NH$_4$OH)/CH$_2$Cl$_2$) to afford 0.23 g (69%) of the desired product as a white solid. $R_f$=0.39 (10% MeOH (1% NH$_4$OH)/CH$_2$Cl$_2$). MS (electrospray): mass calculated for C$_{29}$H$_{32}$N$_6$O, 480.26; m/z found, 481.2 [M+H]$^+$. $^1$H NMR (400 MHz, CD$_3$OD): 7.67–7.16 (m, 4H), 7.45–7.41 (m, 2H), 7.35–7.24 (m, 8H), 5.38 (t, J=6.4 Hz, 1H), 3.23 (t, J=6.8 Hz, 2H), 2.71 (d, J=6.4 Hz, 2H), 2.47–2.42 (m, 6H), 1.77–1.69 (m, 4H).

Example 9

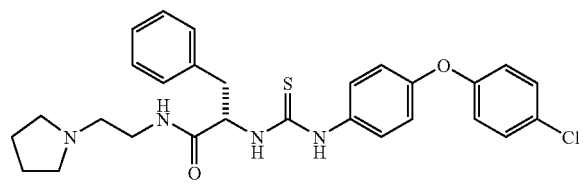

(S)-2-{3-[4-(4-Chloro-phenoxy)-phenyl]-thioureido}-3-phenyl-N-(2-pyrrolidin-1-yl-ethyl)-propionamide A. [(S)-2-Phenyl-1-(2-pyrrolidin-1-yl-ethylcarbamoyl)-ethyl]-carbamic acid tert-butyl ester. HOBT (3.8 g, 28.3 mmol) and EDCl (5.4 g, 28.3 mmol) were added to a solution of (S)-2-tert-butoxycarbonylamino-3-phenyl-propionic acid in DMF (100 mL). Following the addition of a solution of 2-pyrrolidin-1-yl-ethylamine (3.23 g, 28.3 mmol) in DMF (5 mL), N-methyl-morpholine (3.8 g, 37.7 mmol) was added dropwise. The reaction mixture was stirred at rt overnight. H$_2$O (100 mL) and EtOAc (50 mL) were then added to the mixture. The aqueous layer was extracted with EtOAc (3×100 mL). The combined organic layers were washed sequentially with 1 N NaOH (2×50 mL) and brine (50 mL), and dried (MgSO$_4$). The solvents were removed. Purification by column chromatography [0–20% (1% NH$_4$OH/MeOH)/CH$_2$Cl$_2$] afforded 5.5 g (81%) of the desired product. MS (electrospray): mass calculated for C$_{20}$H$_{31}$N$_3$O$_3$, 361.24; m/z found, 362.2 [M+H]$^+$. $^1$H NMR (400 MHz, CDCl$_3$): 7.31–7.20 (m, 5H), 6.15 (s, 1H), 5.20 (d, J=4.1 Hz, 1H), 4.30 (d, J=6.5 Hz, 1H), 3.29–3.20 (m, 2H), 3.09 (dd, J=13.3, 5.7 Hz, 1H), 2.97 (dd, J=8.2 Hz, 1H), 2.50–2.44 (m, 1H), 2.40–2.35 (m, 5H), 1.75–1.70 (m, 4H), 1.42 (s, 9H).

B. 4-(4-Chloro-Phenoxy)-phenylisothiocyanate. To a solution of 1,1'-thiocarbonyldiimidazole (4.99 g, 28 mmol) in CH$_2$Cl$_2$ (100 mL) was added a solution of 4-(4-chlorophenoxy)-phenylamine (2.19 g, 10 mmol) in CH$_2$Cl$_2$ (100 mL) dropwise over 1 h at 0° C. The ice bath was removed, and the reaction mixture was stirred for 30 min at rt. The mixture was then washed with NaHCO$_3$ (50 mL) and brine (50 mL). The organics were dried (Na$_2$SO$_4$), concentrated, passed through a plug of silica gel, and then washed with 20% EtOAc/hexanes to afford 2.6 g (99%) of the desired product. $^1$H NMR (400 MHz, CDCl$_3$): 7.25–7.23 (m, 2H), 7.13–7.10 (m, 2H), 6.89–6.84 (m, 4H).

C. (S)-2-{3-[4-(4-Chloro-Phenoxy)-phenyl]-thioureido}-3-phenyl-N-(2-pyrrolidin-1-yl-ethyl)-propionamide. To a solution of [(S)-2-phenyl-1-(2-pyrrolidin-1-yl-ethylcarbamoyl)-ethyl]-carbamic acid tert-butyl ester (0.138 g, 0.38 mmol) in CH$_2$Cl$_2$ (3 mL), a 4 M solution of HCl in dioxane (0.95 mL, 3.8 mmol) was added, and the mixture was stirred for 3 h at rt. The solvents were removed, and the residue was treated with CH$_2$Cl$_2$. The solvents were removed again under reduced pressure. The residue was dissolved in MeOH and treated with strongly basic ion exchange resin. After the mixture was stirred for 10 min, the resin was filtered off, and the solvents were removed. The residue, (S)-2-amino-3-phenyl-N-(2-pyrrolidin-1-yl-ethyl)-propionamide, was dissolved in CH$_2$Cl$_2$ (3 mL), and 4-(4-chloro-phenoxy)-phenylisothiocyanate (0.11 g, 0.42 mmol) was added. The crude product was purified by flash column chromatography on silica gel using 0–20% MeOH (1% NH$_4$OH)/CH$_2$Cl$_2$ afforded 0.09 g (45%) of the desired product. MS (electrospray): mass calculated for C$_{28}$H$_{31}$ClN$_4$O$_2$S, 522.19; m/z found, 523.2 [M+H]$^+$. $^1$H NMR (400 MHz, CD$_3$OD): 7.35–7.2 (m, 9H), 6.99–6.94 (m, 4H), 5.18 (t, J=6.9 Hz, 1H), 3.3 (m, 2H), 3.19 (dd, J=6.5 Hz, 13.8 Hz, 1H), 3.06 (dd, J=7.4 Hz, 13.8 Hz, 1H), 2.53 (br m, 6H), 1.79 (br m, 4H).

Example 10

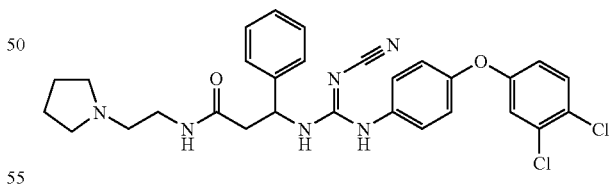

3-{N'-[4-(3,4-Dichloro-phenoxy)-phenyl]-N''-cyano-guanidino}-3-phenyl-N-(2-pyrrolidin-1-yl-ethyl)-propionamide A. 3-tert-Butoxycarbonylamino-3-phenyl-propionic acid. To a solution of 3-amino-3-phenylpropionic acid (1.98 g, 12.0 mmol) in THF/H$_2$O (1:1, 40 mL), was added NaOH (1.06 g, 26.4 mmol), and the resulting solution was stirred at rt for 30 min. Di-tert-butyl dicarbonate (2.9 g, 13.2 mmol) was added, and the solution was stirred at rt for 20 h. The solution was concentrated under reduced pressure, diluted with H$_2$O (100 mL), and extracted with Et$_2$O (2×150 mL). The aqueous layer was acidified using 1 N HCl, and extracted with EtOAc (2×200 mL). The combined organic extracts were washed with brine (200 mL), dried (Na$_2$SO$_4$) and filtered, and the solvent was removed to afford 2.65 g (83%) of the desired product as a tan solid. MS (electrospray): mass calculated for C$_{14}$H$_{19}$NO$_4$, 265.13; m/z found, 553.3 [2M+Na]$^+$. $^1$H NMR (400 MHz, CD$_3$OD): 7.37–7.26 (m, 5H), 5.51 (br s, 1H), 5.05 (br m, 1H), 2.98–2.74 (m, 2H), 1.44 (s, 9H).

B. [1-Phenyl-2-(2-pyrrolidin-1-yl-ethylcarbamoyl)-ethyl]-carbamic acid tert-butyl ester. To a solution of 3-tert-butoxycarbonylamino-3-phenyl-propionic acid (1.0 g, 3.77 mmol), 2-pyrrolidin-1-yl-ethylamine (0.65 g, 5.66 mmol), HOBt (0.77 g, 5.66 mmol) and 4-methylmorpholine (0.76 g, 47.5 mmol) in DMF (19 mL), was added EDCI (1.09 g, 5.66 mmol). The resulting solution was stirred under N$_2$ at rt for 20 h. The solution was diluted with EtOAc (75 mL), and washed with aqueous saturated NaHCO$_3$ (2×30 mL) followed by brine (30 mL). The organic layer was dried (Na$_2$SO$_4$) and filtered, and the solvent was removed. The residue was purified by column chromatography on silica gel using a gradient of 2–20% (MeOH (1% NH$_4$OH)/CH$_2$Cl$_2$) to afford 0.88 g (65%) of the desired product as a white solid. R$_f$=0.25 (10% MeOH (1% NH$_4$OH)/CH$_2$Cl$_2$). MS (electrospray): mass calculated for C$_{20}$H$_{31}$N$_3$O$_3$, 361.24; m/z found, 362.2 [M+H]$^+$, 384.2 [M+Na]$^+$, 745.4 [2M+Na]$^+$. $^1$H NMR (400 MHz, CD$_3$OD): 7.29–7.24 (m, 4H), 7.22–7.16 (m, 1H), 6.39 (br s, 1H), 6.26 (br s, 1H), 4.99 (br s, 1H), 3.18 (dd, J=11.0, 5.4 Hz, 2H), 2.70–2.61 (m, 1H), 2.58 (dd, J=13.8, 6.2 Hz, 1H), 2.47–2.38 (m, 6H), 1.74–1.65 (m, 4H), 1.38 (s, 9H).

C. 4-(3,4-Dichloro-phenoxy)-nitrobenzene. Cesium carbonate (2.7 g, 8.5 mmol) and 3,4-dichlorophenol (1.4 g, 8.5 mmol) were added to a solution of 4-fluoronitrobenzene (1 g, 7.1 mmol) in DMA (14 mL). The reaction mixture was stirred at 90° C. overnight, and then H$_2$O (30 mL) and Et$_2$O (50 mL) were added. The aqueous layer was extracted with Et$_2$O (3×50 mL). The combined organic layers were washed with 1 N NaOH (50 mL) and brine (50 mL), and dried (MgSO$_4$). Removal of the solvent under reduced pressure afforded 1.86 g (100%) of the desired product. $^1$H NMR (400 MHz, CDCl$_3$): 8.18–8.15 (m, 2H), 7.42 (d, J=8.7 Hz, 1H), 7.14 (d, J=2.6 Hz, 1H), 6.99–6.96 (m, 2H), 6.89 (dd, J=8.7, 2.7 Hz, 1H).

D. 4-(3,4-Dichloro-phenoxy)-phenylamine. To a stirred solution of 4-(3,4-dichloro-phenoxy)-nitrobenzene (1.9 g, 6.7 mmol) in THF (16 mL) was added a solution of Na$_2$S$_2$O$_4$ (5.8 g, 33.4 mmol) in H$_2$O (80 mL). The reaction mixture was heated to 60° C. for 2 h and then diluted with EtOAc (50 mL), and the aqueous layer was extracted with EtOAc (3×50 mL). The combined organic layers were washed with brine (40 mL) and dried (MgSO$_4$), and the solvent was removed. Column chromatography (20–50% EtOAc/hexanes) afforded 0.55 g (33%) of the desired product. MS (electrospray): mass calculated for C$_{12}$H$_9$Cl$_2$NO, 253.01; m/z found, 254.0 [M+H]$^+$. $^1$H NMR (400 MHz, CDCl$_3$): 7.25 (d, J=8.9 Hz, 1H), 6.91 (d, J=2.8 Hz, 1H), 6.81–6.77 (m, 2H), 6.72 (dd, J=8.9, 2.8 Hz, 1H), 6.66–6.62 (m, 2H).

E. 4-(3,4-Dichloro-phenoxy)-phenylisothiocyanate. To a solution of 1,1'-thiocarbonyldiimidazole (5.5 g, 30.96 mmol) in CH$_2$Cl$_2$ (100 mL) was added a solution of 4-(3,4-dichloro-phenoxy)-phenylamine (2.8 g, 11.05 mmol) in CH$_2$Cl$_2$ (100 mL) dropwise over 1.5 h at 0° C. The ice bath was removed, and the mixture was stirred for 30 min at rt. The CH$_2$Cl$_2$ solution was then washed with NaHCO$_3$ (70 mL) and brine (70 mL). The organics were dried (Na$_2$SO$_4$), concentrated, passed through a plug of silica gel, and washed with 20% EtOAc/hexanes to afford 3.2 g (99%) of the desired product. $^1$H NMR (400 MHz, CDCl$_3$): 7.39 (d, J=8.8 Hz, 1H), 7.22 (m, 2H), 7.08 (d, J=2.8 Hz, 1H), 6.96 (m, 2H), 6.86 (dd, J=8.8, 2.8 Hz, 1H).

F. 1-[4-(3,4-Dichloro-Phenoxy)-phenyl]-3-cyano-thio-urea. To a solution of 4-(3,4-dichloro-phenoxy)-phenyl-isothiocyanate (2.3 g, 7.77 mmol) in EtOH (40 mL), NaN-HCN (0.5 g, 7.77 mmol) was added, and the mixture was heated to reflux for 2 h. The solution was cooled, and the solvents were removed. CH$_2$Cl$_2$ (75 mL) and MeOH (5 mL) were then added, and the mixture was stirred for 5 min. The resulting precipitate was filtered and washed with copious amount of hexanes and dried under vacuum to afford 2.4 g (92%) of the desired product. MS (electrospray): mass calculated for C$_{14}$H$_9$Cl$_2$N$_3$OS, 336.98; m/z found, 359.9 [M+Na]$^+$, 362.0 [M+Na]$^+$. $^1$H NMR (400 MHz, DMSO-d$_6$): 9.08 (s, 1H), 7.49 (d, J=8.8 Hz, 2H), 7.37 (d, J=8.8 Hz, 1H), 6.96 (d, J=2.4 Hz, 1H), 6.76–6.69 (m, 3H).

G. 3-{N'-[4-(3,4-Dichloro-phenoxy)-phenyl]-N"-cyano-guanidino}-3-phenyl-N-(2-pyrrolidin-1-yl-ethyl)-propiona-mide. To a solution of [1-phenyl-2-(2-pyrrolidin-1-yl-ethyl-carbamoyl)-ethyl]-carbamic acid tert-butyl ester (0.10 g, 0.28 mmol) in CH$_2$Cl$_2$ (2.8 mL) was added 4 M HCl in 1,4-dioxane (0.98 mL), and the resulting solution was stirred at rt for 1.5 h. The solvent was removed, and the resulting residue was dissolved in MeOH (3 mL) and treated with basic resin (Dowex 550A OH anion-exchange resin). The resulting suspension was stirred at rt for 30 min. The resin was filtered off and washed with MeOH (3 mL). The filtrate and washings were concentrated under reduced pressure, and the resulting free amine was dried under vacuum. To a solution of the free amine and 1-[4-(3,4-dichloro-phenoxy)-phenyl]-3-cyano-thiourea (0.12 g, 0.34 mmol) in DMF (1.4 mL), was added EDCI (0.08 g, 0.42 mmol). The resulting solution was stirred under N$_2$ at rt for 6 h. The solution was then diluted with EtOAc (30 mL) and washed with 1 N NaOH (2×25 mL). The organic layer was dried (Na$_2$SO$_4$) and filtered, and the solvent was removed. The residue was purified by column chromatography on silica gel using a gradient of 5–10% (MeOH (1% NH$_4$OH)/CH$_2$Cl$_2$) to afford 0.092 g (58%) of the desired product as a white solid. R$_f$=0.29 (10% MeOH (1% NH$_4$OH)/CH$_2$Cl$_2$). MS (electrospray): mass calculated for C$_{29}$H$_{30}$Cl$_2$N$_6$O$_2$, 564.18; m/z found, 565.2 [M+H]$^+$. $^1$H NMR (400 MHz, CD$_3$OD): 7.47 (d, J=8.9 Hz, 1H), 7.35–7.23 (m, 7H), 7.19 (d, J=2.8 Hz, 1H), 7.09 (d, J=1.8 Hz, 2H), 6.97 (dd, J=8.8, 2.8 Hz, 1H), 5.34 (t, J=6.1 Hz, 1H), 3.26 (t, J=6.8 Hz, 2H), 2.71 (d, J=6.8 Hz, 2H), 2.57–2.50 (m, 6H), 1.81–1.74 (m, 4H).

Example 11

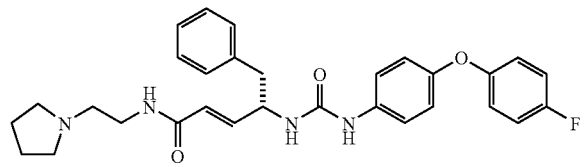

(E)-(S)-4-{3-[4-(4-Fluoro-phenoxy)-phenyl]-ure-ido}-5-phenyl-pent-2-enoic Acid (2-pyrrolidin-1-yl-ethyl)-amide A. (E)-(S)-4-tert-Butoxycarbonylamino-5-phenyl-pent-2-enoic acid. To a solution of (E)-(S)-4-tert-butoxycarbony-lamino-5-phenyl-pent-2-enoic acid methyl ester (Example 2, Method 1, step A) (0.4 g, 1.3 mmol) in THF/H$_2$O (3:1, 13 mL) was added aqueous LiOH (4 N, 0.04 g, 0.4 mL, 1.6 mmol), and the mixture was stirred (25° C., 15 h). The resulting suspension was partially concentrated in vacuo, and water (20 mL) was added to the residue. The solution was cooled (0° C.) and acidified (1 N HCl). The resulting precipitate was collected by filtration, washed with copious amounts of H$_2$O, and dried to provide the desired product as a white solid (0.35 g, 92%): MS (electrospray): mass calculated for C$_{16}$H$_{21}$NO$_4$, 291.34; m/z found, 290.1 [M−H]$^-$. $^1$H NMR (DMSO-d$_6$, 400 MHz): 12.44 (br s, 1H), 7.15–7.30 (m, 5H), 6.76 (dd, J=15.7, 5.6 Hz, 1H), 5.74 (d, J=15.7 Hz, 1H), 4.32–4.40 (m, 1H), 2.82 (dd, J=13.5, 6.0 Hz, 1H), 2.72 (dd, J=13.5, 4.0 Hz, 1H), 1.32 (s, 9H); $^{13}$C NMR (DMSO-d$_6$, 100 MHz): 166.9, 154.8, 148.4, 138.0, 129.1, 128.0, 126.1, 120.7, 77.8, 52.5, 28.0.

B. [(E)-(S)-1-Benzyl-3-(2-pyrrolidin-1-yl-ethylcarbamoyl)-allyl]-carbamic acid tert-butyl ester. To a solution of (E)-(S)-4-tert-butoxycarbonylamino-5-phenyl-pent-2-enoic acid (5.19 g, 17.8 mmol), 2-pyrrolidin-1-yl-ethylamine (3.05 g, 26.7 mmol), HOBt (3.61 g, 26.7 mmol) and 4-methylmorpholine (3.6 g, 35.6 mmol) in DMF (80 mL), was added EDCl (5.13 g, 26.7 mmol). The resulting solution was stirred under N$_2$ at rt for 20 h. The solution was diluted with EtOAc (300 mL) and washed with aqueous saturated NaHCO$_3$ (3×100 mL), followed by brine (100 mL). The organic layer was dried (Na$_2$SO$_4$) and filtered, and the solvent was removed. The crude product was purified by column chromatography on silica gel using a gradient of 2–30% (MeOH (1% NH$_4$OH)/CH$_2$Cl$_2$) to afford 3.77 g (55%) of the desired product as a light yellow solid. R$_f$=0.58 (10% MeOH (1% NH$_4$OH)/CH$_2$Cl$_2$). MS (electrospray): mass calculated for C$_{22}$H$_{33}$N$_3$O$_3$, 387.25; m/z found, 388.2 [M+H]$^+$, 410.2 [M+Na]$^+$. $^1$H NMR (400 MHz, CDCl$_3$): 7.25–7.21 (m, 2H), 7.17–7.14 (m, 3H). 6.81 (br t, J=5.0 Hz, 1H), 6.74 (dd, J=15.2, 4.8 Hz, 1H), 5.81 (d, J=15.2 Hz, 1H), 5.08 (d, J=8.9 Hz, 1H), 4.53 (br s, 1H), 3.52–3.44 (m, 1H), 3.31–3.22 (m, 1H), 2.87–2.77 (m, 2H), 2.69–2.63 (m, 1H), 2.57–2.50 (m, 5H), 1.79–1.69 (m, 4H), 1.33 (s, 9H).

C. (E)-(S)-4-{3-[4-(4-Fluoro-phenoxy)-phenyl]-ureido}-5-phenyl-pent-2-enoic acid (2-pyrrolidin-1-yl-ethyl)-amide. To a solution of [(E)-(S)-1-benzyl-3-(2-pyrrolidin-1-yl-ethylcarbamoyl)-allyl]-carbamic acid tert-butyl ester (0.25 g, 0.65 mmol) in CH$_2$Cl$_2$ (6.5 mL) was added 4 M HCl in 1,4-dioxane (2.3 mL), and the resulting solution was stirred at rt for 1 h. Additional CH$_2$Cl$_2$ (20 mL) was added, and the solution was washed with 1 N NaOH (2×15 mL). The aqueous layer was extracted with 3:1 EtOAc/iPrOH (2×25 mL), and the combined organic layers were dried (Na$_2$SO$_4$) and filtered. The solvent was removed. The resulting free amine was kept under vacuum until needed. To a solution of CDI (0.082 g, 0.51 mmol) and DMAP (0.61 g, 0.005 mmol) in DMF (1.53 mL), was added 4-(4-fluoro-phenoxy)-phenylamine (0.1 g, 0.49 mmol) in portions over 10 min. The resulting solution was stirred under N$_2$ at rt for 20 h, and a solution of the previously-formed free amine (0.14 g, 0.49 mmol) in DMF (0.3 mL) was added. The solution was heated to 100° C. and stirred under N$_2$ for 24 h. The solution was diluted with EtOAc (20 mL) and washed with H$_2$O (3×10 mL), followed by brine (10 mL). The organic layer was dried (Na$_2$SO$_4$), filtered, and concentrated under reduced pressure. The crude product was purified by preparative TLC (10% MeOH (1% NH$_4$OH)/CH$_2$Cl$_2$) to afford the desired product. R$_f$=0.43 (10% MeOH (1% NH$_4$OH)/CH$_2$Cl$_2$). MS (electrospray): mass calculated for C$_{30}$H$_{33}$FN$_4$O$_3$, 516.25; m/z found, 517.2 [M+H]$^+$, 539.2 [M+Na]$^+$. $^1$H NMR (400 MHz, CDCl$_3$): 7.46 (br s, 1H), 7.26–7.11 (m, 7H), 6.94–6.89 (m, 2H), 6.86–6.78 (m, 4H) 6.67 (dd, J=15.3, 5.2 Hz, 1H), 5.83 (dd, J=15.3, 1.6 Hz, 1H), 5.52 (br s, 1H), 4.78–4.69 (m, 1H), 3.54–3.46 (m, 1H), 3.18–3.11 (m, 1H), 2.87 (dd, J=13.7, 7.1 Hz, 1H), 2.78 (dd, J=13.7, 7.4 Hz, 1H), 2.64–2.58 (m, 1H), 2.48–2.38 (m, 5H), 1.86 (br s, 1H), 1.71–1.62 (m, 4H).

Example 12

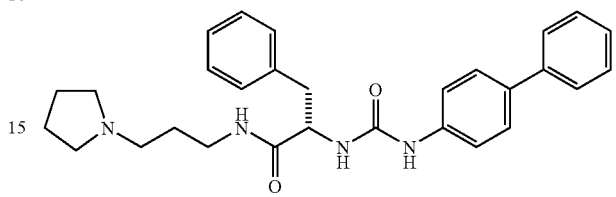

(S)-2-(3-Biphenyl-4-yl-ureido)-3-phenyl-N-(3-pyrrolidin-1-yl-propyl)-propionamide To a solution of [(S)-2-phenyl-1-(3-pyrrolidin-1-yl-propylcarbamoyl)-ethyl]-carbamic acid tert-butyl ester (Example 1, step A) (0.083 g, 0.22 mmol) in CH$_2$Cl$_2$ (3 mL), a 4 M solution of HCl in dioxane (0.55 mL, 2.2 mmol) was added, and the mixture was stirred for 3 h at rt. The solvents were removed. The residue was treated with CH$_2$Cl$_2$, and the solvent was removed again under reduced pressure. The residue was dissolved in CH$_2$Cl$_2$ (3 mL), and at 0° C., TEA (0.56 g, 0.55 mmol) was added followed by 4-isocyanatobiphenyl (0.052 g, 0.264 mmol). The mixture was warmed to rt over a period of 2 h and was then diluted with EtOAc (100 mL). The organic layer was washed with saturated NaHCO$_3$ (25 mL) and brine (25 mL), and was dried (Na$_2$SO$_4$). The solvent was removed, and the residue was purified by flash column chromatography using 0–20% MeOH (1% NH$_4$OH)/CH$_2$Cl$_2$ to afford 0.08 g (77%) of the desired product. MS (electrospray): mass calculated for C$_{29}$H$_{34}$N$_4$O$_2$, 470.27; m/z found, 471.3 [M+H]$^+$. $^1$H NMR (400 MHz, CD$_3$OD): 7.56–7.48 (m, 4H), 7.42–7.36 (m, 4H), 7.33–7.22 (m, 6H), 4.47 (t, J=7.1 Hz, 1H), 3.20–3.16 (m, 2H), 3.07 (dd, J=13.6, 7.1 Hz, 1H), 2.99 (dd, J=13.6, 7.1 Hz 1H), 2.51 (br m, 4H), 2.42 (m, 2H), 1.77 (br m, 4H), 1.65 (m, 2H).

Example 13

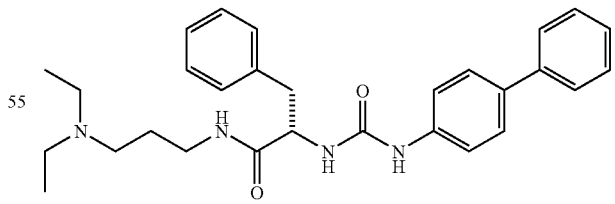

(S)-2-(3-Biphenyl-4-yl-ureido)-N-(3-diethylaminopropyl)-3-phenyl-propionamide

A. (S)-2-(3-Biphenyl-4-yl-ureido)-3-phenyl-Propionic acid. To a suspension of (S)-2-amino-3-phenyl-propionic acid (0.99 g, 6 mmol) in acetone/H$_2$O (1:1, 36 mL) was added TEA (0.91 g, 9 mmol), and the mixture was stirred for 5 min. A solution of 4-isocyanato-biphenyl in THF (8 mL) was added, and the reaction mixture was stirred for 7 h. The volume of the mixture was reduced in vacuo, and the pH of the solution was adjusted to approximately 2 using 10% HCl. The resulting white precipitate was filtered, washed with water and 10% $CH_2Cl_2$/hexanes, and dried under vacuum to afford 1.7 g (81%) of the desired product. MS (electrospray): mass calculated for $C_{22}H_{20}N_2O_3$, 360.15; m/z found, 361.1 [M+H]$^+$, 383.1 [M+Na]$^+$. $^1$H NMR (400 MHz, DMSO-$d_6$): 12.85 (br s, 1H), 8.81 (s, 1H), 7.66–7.21 (m, 14H), 6.37 (d, J=8 Hz, 1H), 4.47 (m, 1H), 3.11 (dd, J=13.8, 5 Hz, 1H), 2.97 (dd, J=13.8, 7.6 Hz, 1H).

B. (S)-2-(3-Biphenyl-4-yl-ureido)-N-(3-diethylamino-propyl)-3-phenyl-propionamide. To a mixture of EDC (0.08 g, 0.42 mmol), HOBT (0.056 g, 0.42 mmol) and (S)-2-(3-biphenyl-4-yl-ureido)-3-phenyl-propionic acid (0.1 g, 0.28 mmol) in DMF (3 mL), N',N'-diethyl-propane-1,3-diamine (0.054 g, 0.42 mmol) was added followed by N-methyl morpholine (0.056 g, 0.55 mmol) at rt. The solution was stirred for 6 h, diluted with EtOAc (100 mL), washed with saturated NaHCO$_3$ (2×20 mL) and brine (2×20 mL), and dried (Na$_2$SO$_4$). The solvent was removed, and the residue was purified by flash column chromatography using 0–20% MeOH (1% NH$_4$OH)/CH$_2$Cl$_2$ to afford 0.1 g (76%) of the desired product. MS (electrospray): mass calculated for $C_{29}H_{36}N_4O_2$, 472.28; m/z found, 473.3 [M+H]$^+$. $^1$H NMR (400 MHz, CD$_3$OD): 8.81 (s, 1H), 8.09 (t, J=5.4 Hz, 1H), 7.61–7.2 (m, 14H), 6.42 (d, J=8.3 Hz, 1H), 4.43 (m, 1H), 3.10–3.03 (m, 2H), 2.98 (dd, J=5.8 Hz, 13.7 Hz, 1H), 2.84 (dd, J=13.7, 7.8 Hz, 1H), 2.46–2.4 (q, J=7.0 Hz, 4H), 2.35 (t, J=7.2 Hz, 2H), 1.47 (m, 2H), 0.92 (t, J=7.0 Hz, 6H).

Example 14

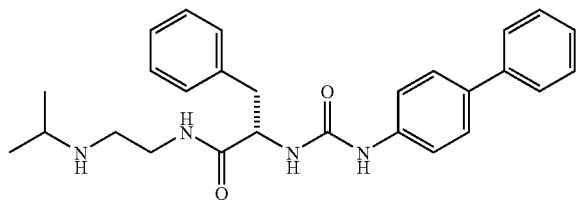

(S)-2-(3-Biphenyl-4-yl-ureido)-N-(2-isopropylamino-ethyl)-3-phenyl-propionamide

To a mixture of EDC (0.08 g, 0.42 mmol), HOBT (0.056 g, 0.42 mmol) and (S)-2-(3-biphenyl-4-yl-ureido)-3-phenyl-propionic acid (Example 13, step A)(0.1 g, 0.28 mmol) in DMF (3 mL), N'-isopropyl-ethane-1,2-diamine (0.054 g, 0.42 mmol) was added at rt followed by N-methyl morpholine (0.056 g, 0.55 mmol). The solution was stirred for 6 h, diluted with EtOAc (100 mL), washed with saturated NaHCO$_3$ (2×20 mL) and brine (2×20 mL), and dried (Na$_2$SO$_4$). The solvent was removed, and the residue was purified by flash column chromatography using 0–20% MeOH (1% NH$_4$OH)/CH$_2$Cl$_2$ to afford 0.07 g (57%) of the desired product. MS (electrospray): mass calculated for $C_{27}H_{32}N_4O_2$, 444.25; m/z found, 445.2 [M+H]$^+$. $^1$H NMR (400 MHz, DMSO-$d_6$): 8.89 (s, 1H), 8.18 (t, J=5 Hz, 1H), 7.61–7.2 (m, 14H), 6.53 (d, J=8 Hz, 1H), 4.46 (m, 1H), 3.16 (m, 2H), 2.9 (dd, J=13.7, 5.8 Hz, 1H), 2.86 (dd, J=13.7, 7.72 Hz, 1H), 2.79 (m, 1H), 2.58 (m, 2H), 0.98 (d, J=6.2 Hz, 6H).

Example 15

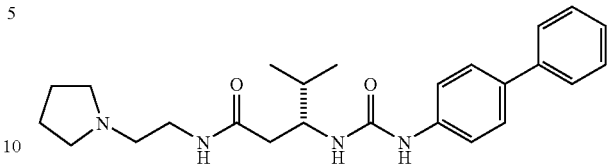

(R)-3-(3-Biphenyl-4-yl-ureido)-4-methyl-pentanoic Acid (2-pyrrolidin-1-yl-ethyl)-amide A. {(R)-2-Methyl-1-[(2-pyrrolidin-1-yl-ethylcarbamoyl)-methyl]-propyl}-carbamic acid tert-butyl ester. HOBT (0.351 g, 2.6 mmol) and EDCl (0.5 g, 2.6 mmol) were added to a solution of (R)-3-tert-butoxycarbonylamino-4-methyl-pentanoic acid (0.4 g, 1.7 mmol) in DMF (8.5 mL). Following the addition of a solution of 2-pyrrolidin-1-yl-ethylamine (0.3 g, 2.6 mmol) in DMF (2 mL), N-methyl-morpholine (0.26 g, 2.6 mmol) was added dropwise. The reaction mixture was stirred at rt overnight. Water (20 mL) and EtOAc (30 mL) were then added to the mixture. The aqueous layer was extracted with EtOAc (3×40 mL). The combined organic layers were washed with 1 N NaOH (2×20 mL) and brine (40 mL), dried (MgSO$_4$), and concentrated. Purification by column chromatography [0–20% (1% NH$_4$OH/MeOH)/CH$_2$Cl$_2$] afforded 0.44 g (78%) of the desired product. MS (electrospray): mass calculated for $C_{17}H_{33}N_3O_3$, 327.25; m/z found, 328.3 [M+H]$^+$. $^1$H NMR (400 MHz, CDCl$_3$): 6.22 (s, 1H), 5.30 (d, J=6.7 Hz, 1H), 3.66–3.59 (m, 1H), 3.44–3.36 (m, 1H), 3.35–3.27 (m, 1H), 2.59–2.56 (m, 2H), 2.52 (m, 4H), 2.42–2.40 (m, 2H), 1.87–1.74 (m, 8H), 1.43 (s, 9H), 0.93 (t, J=6.3 Hz, 6H).

B. (R)-3-(3-Biphenyl-4-yl-ureido)-4-methyl-Pentanoic acid (2-pyrrolidin-1-yl-ethyl)-amide. To a solution of {(R)-2-methyl-1-[(2-pyrrolidin-1-yl-ethylcarbamoyl)-methyl]-propyl}-carbamic acid tert-butyl ester (0.12 g, 0.37 mmol) in CH$_2$Cl$_2$ (4 mL) was added 4 M HCl solution in 1,4-dioxane (2 mL). The reaction mixture was stirred at rt for 4 h, and then the solvent was removed. The residue was redissolved in MeOH (5 mL) and treated with basic resin (Dowex 550A OH anion-exchange resin) for 2 h. The resin was filtered off, and the solvents were removed. 4-Isocyanato-biphenyl (0.134 g, 0.68 mmol) was then added to a solution of the residue in CH$_2$Cl$_2$ (3 mL). The reaction mixture was stirred at rt overnight, after which EtOAc (10 mL) and H$_2$O (10 mL) were added. The aqueous layer was extracted with EtOAc (3×10 mL). The combined organic layers were washed with brine (20 mL), and dried (MgSO$_4$). The solvent was removed. The residue was purified by column chromatography [0–20% (1% NH$_4$OH/MeOH)/CH$_2$Cl$_2$] to afford 0.124 g (86%) of the desired product. MS (electrospray): mass calculated for $C_{25}H_{34}N_4O_2$, 422.27; m/z found, 423.3 [M+H]$^+$. $^1$H NMR (400 MHz, CDCl$_3$): 7.47–7.30 (m, 8H), 7.24–7.22 (1H), 6.57 (s, 1H), 3.89–3.82 (m, 1H), 3.36–3.25 (m, 2H), 2.53 (t, J=6.2 Hz, 2H), 2.47 (d, J=3.8 Hz, 1H), 2.44 (s, 3H), 2.33 (dd, J=14.8, 8.6, Hz, 1H), 1.86–1.78 (m, 4H), 1.71–1.66 (m, 4H), 0.92 (d, J=4.4 Hz, 3H), 0.90 (d, J=4.3 Hz, 3H).

Example 16

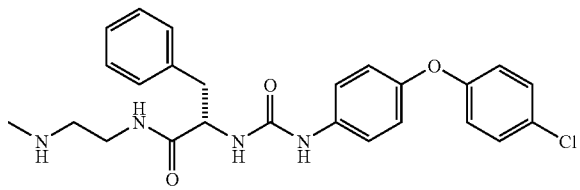

(S)-2-{3-[4-(4-Chloro-phenoxy)-phenyl]-ureido}-N-(2-methylamino-ethyl)-3-phenyl-propionamide A. (S)-2-{3-[4-(4-Chloro-phenoxy)-phenyl]-ureido}-3-phenyl-propionic acid tert-butyl ester. To a stirred solution of (S)-2-amino-3-phenyl-propionic acid tert-butyl ester (0.2 g, 0.9 mmol) in DMSO (2 mL) was added [4-(4-chloro-phenoxy)-phenyl]-carbamic acid phenyl ester (0.3 g, 0.9 mmol). The mixture was stirred at rt overnight. EtOAc (80 mL) was then added, along with 0.1 N HCl (5 mL). The organic layer was washed sequentially with $H_2O$ (10 mL), 1 N NaOH (10 mL) and brine (20 mL), and dried ($MgSO_4$). The solvent was removed. Purification by column chromatography [0–20% of (1% $NH_4OH$/MeOH)/$CH_2Cl_2$] afforded 0.35 g (83%) of the desired product. MS (electrospray): mass calculated for $C_{26}H_{27}ClN_2O_4$, 466.17; m/z found, 411.1 [M−tBu+H]$^+$. $^1$H NMR (400 MHz, $CDCl_3$): 7.22–7.13 (m, 5H), 7.10–7.07 (m, 4H), 6.82–6.78 (m, 4H), 6.70 (s, 1H), 4.66 (s, 1H), 3.03 (dd, J=13.9, 6.06 Hz, 1H), 2.94 (dd, J=13.8, 6.07 Hz, 1H), 1.37 (s, 9H).

B. (S)-2-{3-[4-(4-Chloro-phenoxy)-phenyl]-ureido}-3-phenyl-propionic acid. (S)-2-{3-[4-(4-Chloro-phenoxy)-phenyl]-ureido}-3-phenyl-propionic acid tert-butyl ester (0.35 g, 1.6 mmol) was dissolved in $HCO_2H$ (5 mL) and stirred at rt for 3 h. Then $H_2O$ (10 mL) was added to the reaction mixture at 0° C. The aqueous solution was extracted with EtOAc (3×20 mL). The combined organic layers were washed with brine (30 mL), and dried ($MgSO_4$). Removal of solvent under reduced pressure afforded 0.297 g (97%) of the desired product. MS (electrospray): mass calculated for $C_{22}H_{19}ClN_2O_4$, 410.2; m/z found, 409.25 [M−H]$^-$. $^1$H NMR (400 MHz, DMSO-$d_6$): 9.04 (s, 1H), 7.44–7.35 (m, 4H), 7.28–7.17 (m, 5H), 6.95–6.91 (m, 4H), 6.52 (d, J=7.4 Hz, 1H), 4.35 (dd, J=12.3, 6.9 Hz, 1H), 3.09 (dd, J=13.6, 5.1 Hz, 1H), 2.98 (dd, J=13.6, 6.9 Hz, 1H).

C. (S)-2-{3-[4-(4-Chloro-phenoxy)-phenyl]-ureido}-N-(2-methylamino-ethyl)-3-phenyl-propionamide. HOBT (0.04 g, 0.34 mmol) and EDCl (0.06 g, 0.34 mmol) were added to a solution of (S)-2-{3-[4-(4-chloro-phenoxy)-phenyl]-ureido}-3-phenyl-propionic acid in DMF (2.2 mL). Following the addition of a solution of N'-methyl-ethane-1,2-diamine (0.025 g, 0.34 mmol) in DMF (1 mL), N-methyl-morpholine (0.045 g, 0.44 mmol) was added dropwise. The reaction mixture was stirred at rt overnight. $H_2O$ (10 mL) and EtOAc (20 mL) were then added to the mixture. The aqueous layer was extracted with EtOAc (3×20 mL). The combined organic layers were washed with 1 N NaOH (2×10 mL) and brine (20 mL), dried ($MgSO_4$), and concentrated. Purification by column chromatography [0–20% (1% $NH_4OH$/MeOH)/$CH_2Cl_2$] afforded 0.05 g (47%) of the desired product. MS (electrospray): mass calculated for $C_{25}H_{27}ClN_4O_3$, 466.18; m/z found, 467.2 [M+H]$^+$. $^1$H NMR (400 MHz, $CDCl_3$): 7.34–7.22 (m, 9H), 6.94–6.86 (m, 4H), 4.36 (t, J=7.3 Hz, 1H), 3.08 (dd, J=13.6, 6.75 Hz, 1H), 2.98 (dd, J=13.6, 7.8 Hz, 1H), 2.68 (td, J=6.0, 1.41 Hz, 2H), 2.39 (s, 3H).

Example 17

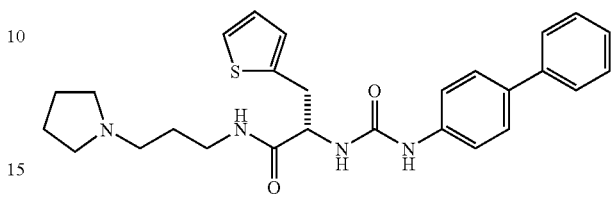

(S)-2-(3-Biphenyl-4-yl-ureido)-N-(3-pyrrolidin-1-yl-propyl)-3-thiophen-2-yl-propionamide A. [(S)-1-(3-Pyrrolidin-1-yl-propylcarbamoyl)-2-thiophen-2-yl-ethyl]-carbamic acid tert-butyl ester. To a mixture of EDC (0.53 g, 2.77 mmol), HOBT (0.37 g, 2.77 mmol) and (S)-2-tert-butoxycarbonylamino-3-thiophen-2-yl-propionic acid (0.5 g, 1.85 mmol) in DMF (10 mL), 3-pyrrolidin-1-yl-propylamine (3.85 g, 30 mmol) was added followed by N-methyl morpholine (0.37 g, 3.69 mmol) at rt. The solution was stirred for 15 h, diluted with EtOAc (150 mL), washed with saturated $NaHCO_3$ (2×50 mL) and brine (2×50 mL), and dried ($Na_2SO_4$). The solvent was removed, and the residue was stirred in a mixture of 10% EtOAc/hexanes at 0° C. for 0.5 h to afford 0.45 g (64%) of the desired product as a white solid. MS (electrospray): mass calculated for $C_{19}H_{14}N_3O_3S$, 381.21; m/z found, 382.2 [M+H]$^+$, 404.2 [M+Na]$^+$. $^1$H NMR (400 MHz, $CD_3OD$): 7.22 (d, J=4.9 Hz, 1H), 6.93–6.87 (m, $^2$H), 4.22 (t, J=7.2 Hz, 1H), 3.31–3.09 (m, 4H), 2.54 (br m, 4H), 2.46 (t, J=7.6 Hz, 2H), 1.8 (br m, 4H), 1.67 (m, 2H), 1.41 (s, 9H).

B. (S)-2-(3-Biphenyl-4-yl-ureido)-N-(3-pyrrolidin-1-yl-propyl)-3-thiophen-2-yl-propionamide. To a solution of [(S)-1-(3-pyrrolidin-1-yl-propylcarbamoyl)-2-thiophen-2-yl-ethyl]-carbamic acid tert-butyl ester (0.4 g, 1.05 mmol) in $CH_2Cl_2$ (6 mL), a 4 M solution of HCl in dioxane (2.63 mL, 10.5 mmol) was added, and the mixture was stirred for 3 h at rt. The solvents were removed, and the residue was treated with $CH_2Cl_2$. The solvents were removed again under reduced pressure. The residue was dissolved in $CH_2Cl_2$ (6 mL), and TEA (0.318 g, 3.15 mmol) was added at 0° C. followed by 4-isocyanato-biphenyl (0.23 g, 1.16 mmol). The mixture was warmed to rt over a period of 3.5 h and was then diluted with EtOAc (100 mL). The organic layer was washed with saturated $NaHCO_3$ (25 mL) and brine (25 mL), and dried ($Na_2SO_4$). The solvent was removed and was purified by flash column chromatography using 0–20% MeOH(1% $NH_4OH$)/$CH_2Cl_2$ to afford 0.41 g (82%) of the desired product. MS (electrospray): mass calculated for $C_{27}H_{32}N_4O_2S$, 476.22; m/z found, 477.2 [M+H]$^+$. $^1$H NMR (400 MHz, $CDCl_3$): 8.30 (t, J=4.7 Hz, 1H), 8.19 (s, 1H), 7.44–7.13 (m, 10H), 7.00 (d, J=8.4 Hz, 1H), 6.92 (m, 2H), 4.72–4.66 (m, 1H), 3.37–3.32 (m, 4H), 2.47–2.35 (m, 6H), 1.74–1.61 (6H).

Example 18

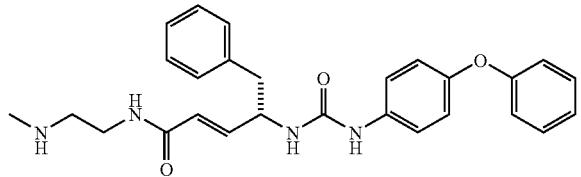

(E)-(S)-4-[3-(4-Phenoxy-phenyl)-ureido]-5-phenyl-pent-2-enoic acid (2-methylamino-ethyl)-amide A. (E)-(S)-4-[3-(4-Phenoxy-phenyl)-ureido]-5-phenyl-pent-2-enoic acid. To a solution of (E)-(S)-4-tert-butoxycarbonylamino-5-phenyl-pent-2-enoic acid (Example 11, step A) (2.12 g, 7.26 mmol) in $CH_2Cl_2$ (73 mL) was added 4 M HCl in 1,4-dioxane (25 mL), and the resulting solution was stirred at rt for 15 min. The solvent was removed. To a solution of the resulting residue and TEA (0.74 g, 7.26 mmol) in THF (73 mL) cooled to 0° C., was added 4-phenoxy phenyl isocyanate (1.53 g, 7.26 mmol), and the mixture was stirred for 30 min. The solution was brought to rt and was stirred for an additional 3 h. The solvent was removed, and the resulting yellow oil was purified by column chromatography on silica gel using a gradient of 0–35% (MeOH (10% acetic acid)/$CH_2Cl_2$). The purified product was recrystallized from $CH_2Cl_2$ and was washed with hexanes to afford 1.45 g (50%) of the desired product as a grey solid. $R_f$=0.47 (5% MeOH (1% $NH_4OH$)/$CH_2Cl_2$). MS (electrospray): mass calculated for $C_{24}H_{22}N_2O_4$, 402.16; m/z found, 403.1 $[M+H]^+$, 425.1 $[M+Na]^+$, 827.3 $[2M+Na]^+$. $^1H$ NMR (400 MHz, DMSO-$d_6$): 12.34 (br s, 1H), 8.51 (s, 1H), 7.40–7.20 (m, 9H), 7.08–7.05 (m, 1H), 6.93–6.91 (m, 4H), 6.86 (d, J=5.0 Hz, 1H), 6.35 (d, J=8.5 Hz, 1H), 5.77 (dd, J=15.6, 1.6 Hz, 1H), 4.70–4.61 (m, 1H), 2.93 (dd, J=13.7, 6.1 Hz, 1H), 2.84 (dd, J=13.7, 7.9 Hz, 1H).

B. (E)-(S)-4-[3-(4-Phenoxy-phenyl)-ureido]-5-phenyl-pent-2-enoic acid (2-methylamino-ethyl)-amide. To a solution of (E)-(S)-4-[3-(4-phenoxy-phenyl)-ureido]-5-phenyl-pent-2-enoic acid (0.20 g, 0.49 mmol), N'-methyl-ethane-1,2-diamine (0.04 g, 0.54 mmol) and HOBt (0.01 g, 0.732 mmol) in DMF (4.9 mL), was added EDCl (0.14 g, 0.732 mmol). The resulting solution was stirred under $N_2$ at rt for 20 h. The solution was diluted with $H_2O$ (30 mL) and extracted with 3:1 EtOAc/iPrOH (3×40 mL). The combined organic extracts were washed with 1 N NaOH (1×30 mL), dried ($Na_2SO_4$) and filtered, and the solvent was removed. The residue was purified by column chromatography on silica gel using a gradient of 0–15% (MeOH (1% $NH_4OH$)/$CH_2Cl_2$) to obtain 0.04 g (18%) of the desired product as a clear oil. $R_f$=0.20 (10% MeOH (1% $NH_4OH$)/$CH_2Cl_2$). MS (electrospray): mass calculated for $C_{27}H_{30}N_4O_3$, 458.23; m/z found, 459.3 $[M+H]^+$, 481.2 $[M+Na]^+$, 917.4 $[2M+H]^+$. $^1H$ NMR (400 MHz, $CDCl_3$): 8.10 (br s, 1H), 7.45 (br t, J=5.6 Hz, 1H), 7.23–7.06 (m, 9H), 6.98–6.94 (m, 1H), 6.84–6.78 (m, 4H), 6.64 (dd, J=15.4, 5.5 Hz, 1H), 6.05 (br d, J=6.4 Hz, 1H), 5.82 (dd, J=15.4, 1.2 Hz, 1H), 4.67–4.61 (m, 1H), 3.37–2.28 (m, 1H), 3.20–3.14 (m, 1H), 2.79–2.70 (m, 2H), 2.64–2.54 (m, 3H), 2.25 (s, 3H).

Example 19

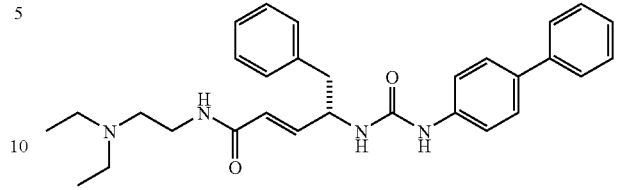

(E)-(S)-4-(3-Biphenyl-4-yl-ureido)-5-phenyl-pent-2-enoic Acid (2-diethylamino-ethyl)-amide A. (E)-(S)-4-(3-Biphenyl-4-yl-ureido)-5-phenyl-pent-2-enoic acid. To a solution of (E)-(S)-4-tert-butoxycarbonylamino-5-phenyl-pent-2-enoic acid (Example 11, step A) (1.2 g, 0.69 mmol) in anhydrous $CH_2Cl_2$ (7 mL) was added HCl-dioxane (4 M, 2.4 mL), and the resulting suspension was stirred (25° C., 45 min). The solvent was removed in vacuo, and the resulting salt was dissolved in toluene (7 mL), treated with TEA (0.08 g, 0.76 mmol) and 4-biphenylisocyanate (0.15 g, 0.76 mmol), and stirred (25° C., 3 h). The solvent was removed in vacuo, and the residue was suspended in $H_2O$ (50 mL) and acidified (1 N HCl). A white solid was collected by filtration to provide the desired product (0.22 g, 83%). MS (electrospray): mass calculated for $C_{24}H_{22}N_2O_3$, 386.45; m/z found, 387.1 $[M+H]^+$, 409.1 $[M+Na]^+$. $^1H$ NMR (DMSO-$d_6$, 400 MHz): 12.32 (br s, 1H), 8.55 (s, 1H), 7.53–7.64 (m, 5H), 7.40–7.48 (m, 4H), 7.16–7.34 (m, 5H), 6.86 (dd, J=15.6, 5.1 Hz, 1H), 6.41 (d, J=8.4 Hz, 1H), 5.78 (dd, J=15.6, 1.5 Hz, 1H), 4.63–4.69 (m, 1H), 2.94 (dd, J=13.7, 6.2 Hz, 1H), 2.86 (dd, J=13.7, 7.8 Hz, 1H). $^{13}C$ NMR (DMSO-$d_6$, 100 MHz): 166.9, 154.2, 148.7, 138.8, 139.6, 137.6, 132.8, 129.2, 128.9, 128.2, 128.3, 128.0, 126.9, 126.1, 120.7, 118.4, 51.6, 51.2.

B. (E)-(S)-4-(3-Biphenyl-4-yl-ureido)-5-phenyl-pent-2-enoic acid (2-diethylamino-ethyl)-amide. Prepared by a method similar to Example 18, step B, substituting (E)-(S)-4-(3-biphenyl-4-yl-ureido)-5-phenyl-pent-2-enoic acid for (E)-(S)-4-[3-(4-phenoxy-phenyl)-ureido]-5-phenyl-pent-2-enoic acid, and N',N'-diethyl-ethane-1,2-diamine for N'-methyl-ethane-1,2-diamine. MS (electrospray): mass calculated for $C_{30}H_{36}N_4O_2$, 484.64; m/z found, 485.3 $[M+H]^+$, 507.2 $[M+Na]^+$. $^1H$ NMR (400 MHz, $CD_3OD$): 8.39 (br s, 1H), 7.36–7.50 (m, 8H), 7.18–7.31 (m, 6H), 7.03 (br t, J=5.0 Hz, 1H), 6.75 (dd, J=15.4, 6.3 Hz, 1H), 6.51 (d, J=8.2 Hz, 1H), 6.03 (dd, J=15.4, 0.9 Hz, 1H), 4.78–4.85 (m, 1H), 3.28–3.44 (m, 2H), 2.81–2.95 (m, 2H), 2.53–2.65 (m, 6H), 1.00 (t, J=8.2 Hz, 6H).

Example 20

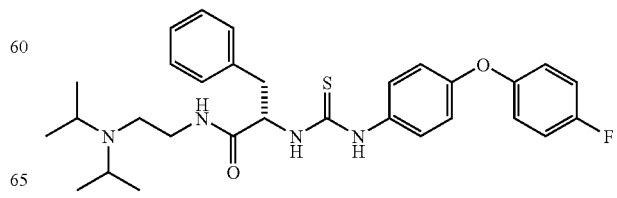

(S)-N-(2-Diisopropylamino-ethyl)-2-{3-[4-(4-fluoro-phenoxy)-phenyl]-thioureido}-3-phenyl-propionamide To a solution of [(S)-1-(2-diisopropylamino-ethylcarbamoyl)-2-phenyl-ethyl]-carbamic acid tert-butyl ester (Example 3, step B) (0.093 g, 0.24 mmol) in CH$_2$Cl$_2$ (2 mL) a 4 M solution of HCl in dioxane (0.6 mL, 2.4 mmol) was added, and the mixture was stirred for 3 h at rt. The solvents were removed, and the residue was treated with CH$_2$Cl$_2$. The solvents were removed again under reduced pressure. The residue was dissolved in MeOH and treated with strongly basic ion exchange resin. After 10 min of stirring, the resin was filtered off and the solvents were removed. The residue was dissolved in CH$_2$Cl$_2$ (2 mL), and 4-(4-fluoro-phenoxy)phenylisothiocyanate (0.064 g, 0.26 mmol) was added. After the mixture was stirred for 4 h, a small amount of 4-(4-fluoro-phenoxy)-phenylisothiocyanate (0.02 g) was added, and the mixture was stirred for 12 h. The crude mixture was purified by flash column chromatography using 0–20% MeOH(1% NH$_4$OH)/CH$_2$Cl$_2$ afforded 0.07 g (55%) of the desired product. MS (electrospray): mass calculated for C$_{30}$H$_{37}$FN$_4$O$_2$S, 536.26; m/z found, 537.3 [M+H]$^+$. $^1$H NMR (400 MHz, CD$_3$OD): 7.26–6.89 (m, 13H), 5.17 (t, J=7 Hz, 1H), 3.17–2.96 (m, 6H), 2.44 (m, 2H), 1.02 (d, J=6.5 Hz, 12H).

Example 21

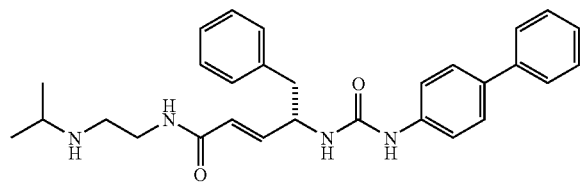

(E)-(S)-4-(3-Biphenyl-4-yl-ureido)-5-phenyl-pent-2-enoic Acid (2-isopropylamino-ethyl)-amide To a solution of (E)-(S)-4-(3-biphenyl-4-yl-ureido)-5-phenyl-pent-2-enoic acid (Example 19, step A) (0.30 g, 0.78 mmol), N-isopropyl-ethane-1,2-diamine (0.087 g, 0.85 mmol) and HOBt (0.16 g, 1.16 mmol) in DMF (7.8 mL), was added EDCl (0.22 g, 1.16 mmol). The resulting solution was stirred under N$_2$ at rt for 20 h. The solution was diluted with H$_2$O (50 mL) and extracted with 3:1 EtOAc/iPrOH (3×60 mL). The combined organic extracts were washed with 1 N NaOH (1×50 mL) and brine (75 mL), dried (Na$_2$SO$_4$) and filtered, and the solvent was removed. The residue was purified by column chromatography on silica gel using a gradient of 2–10% (MeOH (1% NH$_4$OH)/CH$_2$Cl$_2$ to afford 0.18 g (51%) of the desired product as a white solid. R$_f$=0.26 (10% MeOH (1% NH$_4$OH)/CH$_2$Cl$_2$). MS (electrospray): mass calculated for C$_{29}$H$_{34}$N$_4$O$_2$, 470.27; m/z found, 471.3 [M+H]$^+$, 493.2 [M+Na]$^+$, 941.5 [2M+H]$^+$. $^1$H NMR (400 MHz, CDCl$_3$): 8.10 (s, 1H), 7.48 (d, J=7.5 Hz, 2H), 7.43 (d, J=8.5 Hz, 2H), 7.39–7.33 (m, 5H), 7.31–7.25 (m, 3H), 7.21 (d, J=7.24 Hz, 2H), 6.76 (dd, J=15.3, 5.7 Hz, 1H), 6.25 (d, J=8.3 Hz, 1H), 6.00 (d, J=15.3 Hz, 1H), 4.86–4.79 (m, 1H), 3.46–3.41 (m, 1H), 3.31–3.27 (m, 1H), 2.95–2.85 (m, 2H), 2.77–2.67 (m, 3H), 1.01 (d, J=6.0 Hz, 6H).

Example 22

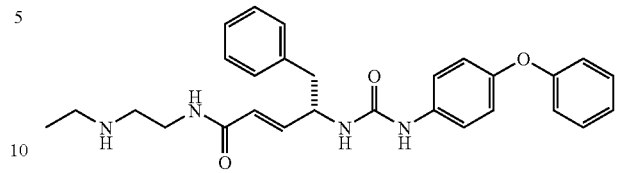

(E)-(S)-4-[3-(4-Phenoxy-phenyl)-ureido]-5-phenyl-pent-2-enoic Acid (2-ethylamino-ethyl)-amide Prepared as in Example 18 substituting N'-ethyl-ethane-1,2-diamine for IV-methyl-ethane-1,2-diamine in step B. MS (electrospray): mass calculated for C$_{28}$H$_{32}$N$_4$O$_2$, 456.25; m/z found, 457.3 [M+H]$^+$, 479.2 [M+Na]$^+$, 913.5 [2M+H]$^+$. $^1$H NMR (400 MHz, CD$_3$OD): 7.58–7.50 (m, 4H), 7.42–7.39 (m, 4H), 7.31–7.20 (m, 6H), 6.82 (dd, J=5.5, 15.4 Hz, 1H), 6.02 (dd, J=1.5, 15.4 Hz, 1H), 4.77–4.72 (m, 1H), 3.38 (t, J=6.4 Hz, 2H), 2.99 (dd, J=6.6, 13.7 Hz, 1H), 2.92 (dd, J=7.6, 13.7 Hz, 1H), 2.71 (t, J=6.4 Hz, 2H), 2.63 (q, J=7.2 Hz, 2H), 1.11 (t, J=7.2 Hz, 3H).

Example 23

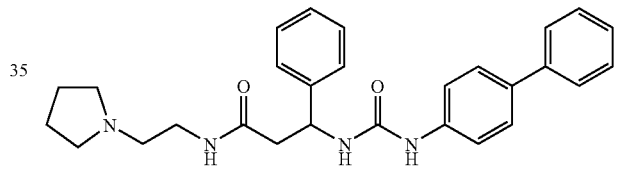

3-(3-Biphenyl-4-yl-ureido)-3-phenyl-N-(2-pyrrolidin-1-yl-ethyl)-propionamide Prepared as in Example 6, steps A and B, substituting 3-amino-3-phenylpropionic acid for 3-amino-3-(p-tolyl)propionic acid in step A. MS (electrospray): mass calculated for C$_{28}$H$_{32}$N$_4$O$_2$, 456.58; m/z found, 457.3 [M+H]$^+$, 479.3 [M+Na]$^+$. $^1$H NMR (400 MHz, CD$_3$OD): 7.49–7.56 (m, 4H), 7.32–7.43 (m, 8H), 7.23–7.29 (m, 2H), 5.27 (t, J=6.9 Hz, 1H), 3.29–3.32 (m, 4H), 2.70 (d, J=6.6 Hz, 2H), 2.57–2.62 (m, 6H), 1.76–1.79 (m, 4H).

Example 24

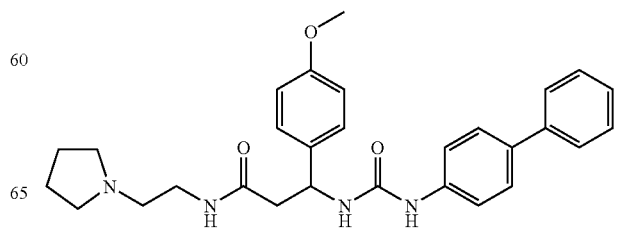

3-(3-Biphenyl-4-yl-ureido)-3-(4-methoxy-phenyl)-N-(2-pyrrolidin-1-yl-ethyl)-propionamide To a cooled solution (0° C.) of 3-amino-3-(4-methoxy-phenyl)-propionic acid (0.5 g, 2.56 mmol) in $CH_2Cl_2$ (26 mL) was added triethylamine (0.26 g, 2.56 mmol), and the solution was stirred (0° C., 0.5 h). The solution was treated with 4-isocyanato-biphenyl (0.5 g, 2.56 mmol), stirred (0° C., 0.5 h), and then allowed to warm to rt over 3 h. The solvent was removed in vacuo, and water (50 mL) was added to the resulting residue. The mixture was cooled to 0° C. and acidified (HCl). The resulting precipitate was collected by filtration, washed ($H_2O$), and dried in vacuo to provide the desired product as a white solid (0.67 g, 67%). To a solution of the white solid (0.15 g, 0.38 mmol) in DMF (3.8 mL) was added 2-pyrrolidin-1-yl-ethylamine (0.048 g, 0.42 mmol), and the solution was stirred (25° C., 15 min). The solution was treated with HOBt (0.077 g, 0.57 mmol) and EDCl (0.109 g, 0.57 mmol), sequentially, and the resulting solution was stirred (25° C., 15 h). The solution was partitioned with 1 M NaOH and EtOAc (40 mL each), and the organic layer was washed with 1 M HCl (40 mL), brine (40 mL) and water (40 mL). The organic layer was dried ($Na_2SO_4$), filtered and concentrated in vacuo. The resulting residue was purified by column chromatography (0–20% EtOAc/hexanes) to provide the desired product as a white solid (0.051 g, 27%): MS (electrospray): mass calculated for $C_{29}H_{34}N_4O_3$, 486.26; m/z found, 487.3 $[M+H]^+$, 509.3 $[M+Na]^+$. $^1H$ NMR (400 MHz, $CDCl_3$): 7.85 (br s, 1H), 7.49–7.30 (m, 8H), 7.25–7.19 (m, 5H), 6.80–6.74 (m, 2H), 5.24–5.19 (m, 1H), 3.68 (s, 3H), 3.20–3.12 (m, 2H), 2.73–2.60 (m, 8H), 1.81–1.73 (m, 4H).

Example 25

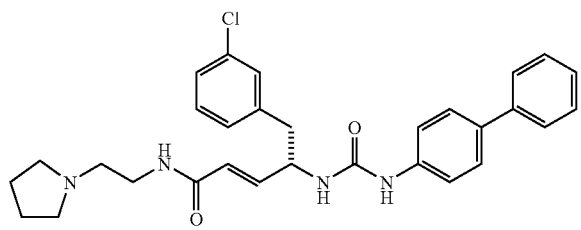

(E)-(S)-4-(3-Biphenyl-4-yl-ureido)-5-(3-chloro-phenyl)-pent-2-enoic Acid (2-pyrrolidin-1-yl-ethyl)-amide A. (S)-2-tert-Butoxycarbonylamino-3-(3-chloro-phenyl)-propionic acid methyl ester. To a cooled solution (0° C.) of (S)-2-tert-butoxycarbonylamino-3-(3-chloro-phenyl)-propionic acid (2.0 g, 1.0 mmol) in MeOH (8 mL) was added a solution of TMS-diazomethane (2 M in hexanes, 12.8 mL) in benzene (8 mL) over 30 min. The solution was allowed to warm and was stirred (25° C., 24 h). The solvent was removed in vacuo, and the resulting residue was purified by column chromatography using 0–55% (EtOAc/hexanes) to provide the desired product as a clear oil (1.96 g, 94%). MS (electrospray): mass calculated for $C_{15}H_{20}ClNO_4$, 313.78; m/z found, 336.1 $[M+Na]^+$. $^1H$ NMR ($CDCl_3$, 400 MHz): 7.07 (d, J=4.5 Hz, 2H), 6.97 (br s, 1H), 6.87 (t, J=3.7 Hz, 1H), 4.87 (br s, 1H), 4.42 (dd, J=14.0, 6.4 Hz, 1H), 3.57 (s, 3H), 2.96 (dd, J=14.0, 5.6 Hz, 1H), 2.85 (dd, J=14.0, 6.4 Hz, 1H), 1.27 (s, 9H).

B. (E)-(S)-4-tert-Butoxycarbonylamino-5-(3-chloro-phenyl)-pent-2-enoic acid methyl ester. To a cooled solution (−78° C.) of (S)-2-tert-butoxycarbonylamino-3-(3-chloro-phenyl)-propionic acid methyl ester (1.75 g, 5.6 mmol) in toluene (56 mL) was added DIBAL-H (1.5 M toluene, 1.6 g, 7.5 mL, 11.2 mmol), and the solution was stirred (−78° C., 2 h). The solution was quenched with 1 M HCl (12 mL) and allowed to warm (25° C.). A precipitate was filtered, and the filtrate was diluted with water (30 mL) and extracted with $CH_2Cl_2$ (50 mL). The organic layer was dried ($Na_2SO_4$), filtered and concentrated in vacuo to provide a white solid (1.6 g, 100%). To the white solid (1.6 g, 5.7 mmol) in $CH_2Cl_2$ (57 mL) was added methyltriphenyl-phosphoranylidine acetate (2.0 g, 6.2 mmol), and the resulting solution was stirred (25° C., 2 h). The solvent was removed in vacuo, and the residue was purified by column chromatography using 0–75% (EtOAc/hexanes) to provide the desired product as a white solid (1.2 g, 63%). MS (electrospray): mass calculated for $C_{17}H_{22}ClNO_4$, 339.81; m/z found, 362.1 $[M+Na]^+$; 338.0 $[M-H]^-$. $^1H$ NMR ($CDCl_3$, 400 MHz): 7.23–7.26 (m, 2H), 7.19 (br s, 1H), 7.06–7.09 (m, 1H), 6.91 (dd, J=15.9, 5.2 Hz, 1H), 5.90 (d, J=15.9 Hz, 1H), 4.60 (br s, 1H), 4.54 (br s, 1H), 3.75 (s, 3H), 2.80–2.94 (m, 2H), 1.42 (s, 9H).

C. (E)-(S)-4-tert-Butoxycarbonylamino-5-(3-chloro-phenyl)-pent-2-enoic acid. Prepared by a method similar to Example 11, step A. MS (electrospray): mass calculated for $C_{16}H_{20}ClNO_4$, 325.79; m/z found, 324.0 $[M-H]^-$. $^1H$ NMR (DMSO-$d_6$, 400 MHz): 12.38 (br s, 1H), 7.16–7.33 (m, 5H), 6.79 (dd, J=15.6, 5.6 Hz, 1H), 5.78 (d, J=15.6 Hz, 1H), 4.34 (br s, 1H), 2.89 (dd, J=13.8, 4.9 Hz, 1H), 2.66 (dd, J=13.8, 10.6 Hz, 1H), 1.30 (s, 9H).

D. [(E)-(S)-1-(3-Chloro-benzyl)-3-(2-pyrrolidin-1-yl-ethylcarbamoyl)-allyl]-carbamic acid tert-butyl ester. Prepared by a method similar to Example 11, step B. MS (electrospray): mass calculated for $C_{22}H_{32}ClN_3O_3$, 421.21; m/z found, 421.2 $[M+H]^+$, 444.2 $[M+Na]^+$. $^1H$ NMR ($CDCl_3$, 400 MHz): 7.19–7.25 (m, 3H), 7.06–7.11 (m, 1H), 6.76 (dd, J=15.0, 5.1 Hz, 1H), 6.31 (br s, 1H), 5.86 (d, J=15.0 Hz, 1H), 4.65 (br s, 1H), 4.57 (br s, 1H), 3.34–3.50 (m, 2H), 2.79–2.92 (m, 2H), 2.56–2.68 (m, 2H), 5.54 (br s, 4H), 1.79 (br s, 4H), 1.41 (s, 9H).

E. (E)-(S)-4-(3-Biphenyl-4-yl-ureido)-5-(3-chloro-phenyl)-pent-2-enoic acid (2-pyrrolidin-1-yl-ethyl)-amide. Prepared by a method similar to Example 2, Method 1, step B. MS (electrospray): mass calculated for $C_{30}H_{33}ClN_4O_2$, 516.23; m/z found, 517.2 $[M+H]^+$. $^1H$ NMR ($CDCl_3$, 400 MHz): 8.03 (br s, 1H), 7.29–7.48 (m, 9H), 7.18–7.23 (m, 1H), 7.09–7.13 (m, 3H), 6.98–7.02 (m, 1H), 6.52 (dd, J=15.4, 5.3 Hz, 1H), 6.03 (d, J=8.6 Hz, 1H), 5.88 (dd, J=15.4, 1.5 Hz, 1H), 4.65–4.75 (m, 1H), 3.44–3.53 (m, 1H), 3.16–3.25 (m, 1H), 2.80 (dd, J=13.8, 7.2 Hz, 1H), 2.71 (dd, J=13.8, 7.5 Hz, 1H), 2.62–2.67 (m, 1H), 2.45–2.57 (m, 5H), 1.69 (br s, 4H).

Example 26

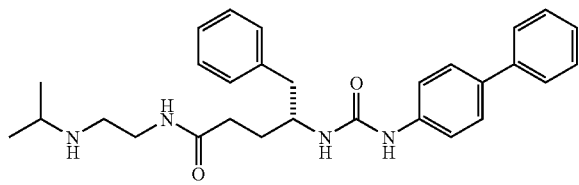

(R)-4-(3-Biphenyl-4-yl-ureido)-5-phenyl-pentanoic
Acid (2-isopropylamino-ethyl)-amide To a solution of (E)-(S)-4-(3-biphenyl-4-yl-ureido)-5-phenyl-pent-2-enoic acid (2-isopropylamino-ethyl)-amide (Example 21) (0.03 g, 0.06 mmol) in EtOH (0.64 mL) was added Pd/C (10%, 0.011 g). The reaction vessel was sealed, flushed with $N_2$ followed by evacuation (3×), and was then placed under $H_2$ (1 atm), and the contents were stirred at rt for 3 h. The suspension was filtered through diatomaceous earth, which was washed with copious amounts of MeOH. The filtrate was concentrated under reduced pressure to afford 0.03 g (99%) of the desired product as a white solid. MS (electrospray): mass calculated for $C_{29}H_{36}N_4O_2$, 472.28; m/z found, 473.3 $[M+H]^+$, 495.2 $[M+Na]^+$. $^1H$ NMR (400 MHz, $CDCl_3$): 7.85 (br s, 1H), 7.50–7.09 (m, 14H), 6.84 (br s, 1H), 5.72 (br d, J=7.8 Hz, 1H), 4.12–4.00 (m, 1H), 3.32–3.23 (m, H), 3.20–3.12 (m, 1H), 2.80 (dd, J=13.6, 6.3 Hz, 1H), 2.70–2.56 (m, 5H), 2.20 (br t, J=6.8 Hz, 2H), 1.79–1.72 (m, 1H), 1.69–1.60 (m, 1H), 0.89 (d, J=6.3 Hz, 6H).

Example 27

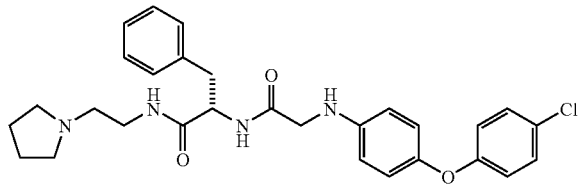

(S)-2-{2-[4-(4-Chloro-phenoxy)-phenylamino]-acetylamino}-3-phenyl-N-(2-pyrrolidin-1-yl-ethyl)-propionamide A. [(S)-1-Benzyl-2-(2-pyrrolidin-1-yl-ethylcarbamoyl)-ethyl]-carbamic acid tert-butyl ester. HOBT (0.318 g, 2.36 mmol) and EDCl (0.452 g, 2.36 mmol) were added to a solution of (S)-3-tert-butoxycarbonylamino-4-phenyl-butyric acid (0.27 g, 2.36 mmol) in DMF (16 mL). Following the addition of a solution of 2-pyrrolidin-1-yl-ethylamine (0.44 g, 1.6 mmol) in DMF (2 mL), N-methyl-morpholine (0.32 g, 3.16 mmol) was added dropwise. The reaction mixture was stirred at rt overnight. Water (30 mL) and EtOAc (50 mL) were then added to the mixture. The aqueous layer was extracted with EtOAc (3×50 mL). The combined organic layers were washed with 1 N NaOH (2×40 mL) and brine (50 mL), dried ($MgSO_4$), and concentrated. Purification by column chromatography [0–20% (1% $NH_4OH/MeOH)/CH_2Cl_2$] afforded 0.5 g (84%) of the desired product. MS (electrospray): mass calculated for $C_{21}H_{33}N_3O_3$, 375.25; m/z found, 376.2 $[M+H]^+$. $^1H$ NMR (400 MHz, $CDCl_3$): 7.32–7.21 (m, 5H), 6.22 (s, 1H), 5.78 (s, 1H), 4.14–4.06 (m, 1H), 3.40 (d, J=5.3 Hz, 2H), 3.02–3.00 (m, 1H), 2.83–2.77 (m, 1H), 2.63 (s, 2H), 2.57 (s, 3H), 2.41 (dd, J=14.5, 4.3 Hz, 1H), 2.27 (dd, J=14.5, 5.03 Hz, 1H), 1.82 (s, 4H), 1.43 (s, 9H).

B. [4-(4-Chloro-phenoxy)-phenylamino]-acetic acid ethyl ester. Oxo-acetic acid ethyl ester (0.243 g, 2.38 mmol) was added to a solution of 4-(4-chloro-phenoxy)-phenylamine (0.5 g, 2.27 mmol) in DCE (48 mL). The mixture was stirred at rt for 15–20 min, before the addition of $Na(OAc)_3BH$ (0.625 g, 2.95 mmol) and AcOH (0.24 mL). The mixture was stirred at rt for 5 h. More oxo-acetic acid ethyl ester (0.08 g) and AcOH (0.03 mL) were added, and the mixture was stirred at rt overnight. Saturated $NaHCO_3$ (50 mL) and excess $CH_2Cl_2$ (50 mL) were then added to the reaction mixture. The aqueous layer was extracted with $CH_2Cl_2$ (3×50 mL). The combined organic layers were washed with brine (40 mL) and dried ($MgSO_4$), and the solvent was removed. Purification by column chromatography with 20–50% EtOAc/hexanes afforded 0.4 g (61%) of the desired product. MS (electrospray): mass calculated for $C_{14}H_{12}ClNO_3$, 305.76; m/z found, 306.1 $[M+H]^+$. $^1H$ NMR (400 MHz, $CDCl_3$): 7.25–7.23. (m, 2H), 6.93–6.86 (m, 4H), 6.64–6.62 (m, 2H), 4.28 (dd, J=14.3, 7.1 Hz, 2H), 3.92 (s, 2H), 1.33 (t, J=7.1 Hz, 3H).

C. [4-(4-Chloro-phenoxy)-phenylamino]-acetic acid. To a solution of [4-(4-chloro-phenoxy)-phenylamino]-acetic acid ethyl ester (0.4 g, 1.44 mmol) in THF (10 mL) was added 4 N LiOH (5 mL). After stirring at rt for 2 h, the reaction mixture was diluted with $Et_2O$ (20 mL) and $H_2O$ (20 mL). The aqueous layer was first extracted with $Et_2O$ (2×20 mL), then acidified with the addition of 1 N HCl (10 mL). The acidified aqueous layer was extracted with EtOAc (3×20 mL). The combined EtOAc layers were washed with brine (30 mL), and dried ($MgSO_4$). Removal of the solvent under reduced pressure afforded 0.43 g (95%) of the desired product. MS (electrospray): mass calculated for $C_{14}H_{12}ClNO_3$, 277.05; m/z found, 276.0 $[M–H]^-$. $^1H$ NMR (400 MHz, $CD_3OD$): 7.26–7.22 (m, 2H), 6.85–6.83 (m, 4H), 6.65–6.63 (d, J=7.8 Hz, 2H), 3.82 (s, 2H).

D. (S)-2-{2-[4-(4-Chloro-phenoxy)-phenylamino]-acetylamino}-3-phenyl-N-(2-pyrrolidin-1-yl-ethyl)-propionamide. To a solution of [(S)-1-benzyl-2-(2-pyrrolidin-1-yl-ethylcarbamoyl)-ethyl]-carbamic acid tert-butyl ester (0.95 g, 2.6 mmol) was added 4 M HCl solution in 1,4-dioxane (5 mL). The mixture was stirred at rt for 4 h. The solvent was removed, and the residue was redissolved in MeOH (10 mL) and treated with basic ion exchange resin (Dowex 550A OH anion-exchange resin). The resin was filtered off, and the solvents were removed again under reduced pressure. The residue was then dissolved in DMF (2 mL), and added to a solution of HOBT (0.35 g, 2.6 mmol), EDCl (0.5 g, 2.6 mmol) and [4-(4-chloro-phenoxy)-phenylamino]-acetic acid in DMF (10 mL). N-Methyl-morpholine (0.35 g, 3.5 mmol) was added dropwise. The reaction mixture was stirred at rt overnight. $H_2O$ (20 mL) and EtOAc (20 mL) were then added to the mixture. The aqueous layer was extracted with EtOAc (3×20 mL). The combined organic layers were washed with 1 N NaOH (2×10 mL) and brine (20 mL), dried ($MgSO_4$), and concentrated. Purification by column chromatography [0–20% (1% $NH_4OH/MeOH)/CH_2Cl_2$] afforded 0.64 g (72%) of the desired product. MS (electrospray): mass calculated for $C_{29}H_{33}ClN_4O_3$, 520.22; m/z found, 521.16 $[M+H]^+$. $^1H$ NMR (400 MHz, $CDCl_3$): 7.33 (d, J=8.1 Hz, 1H), 7.28–7.24 (m, 6H), 7.15 (d, J=6.1 Hz, 2H), 6.91–6.87 (m, 4H), 6.57–6.54 (m, 2H), 6.19 (s, 1H), 4.69 (dd, J=14.6, 8.0 Hz, 1H), 4.24 (t, J=5.3 Hz, 1H), 3.83 (dd, J=6.11, 17.3

Hz, 1H), 3.75 (dd, J=17.3, 5.1 Hz, 1H), 3.50 (s, 1H), 3.26–3.19 (m, 2H), 3.10 (dd, J=13.5, 6.28 Hz, 1H), 2.95 (dd, J=8.0, 6.7 Hz, 1H), 2.50–2.45 (m, 1H), 2.42–2.34 (m, 5H), 1.73 (s, 4H).

Example 28

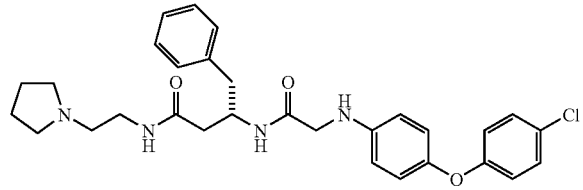

(S)-3-{2-[4-(4-Chloro-phenoxy)-phenylamino]-acetylamino}-4-phenyl-N-(2-pyrrolidin-1-yl-ethyl)-butyramide To a solution of [(S)-1-benzyl-2-(2-pyrrolidin-1-yl-ethylcarbamoyl)-ethyl]-carbamic acid tert-butyl ester (Example 27, step A, 0.26 g, 2.6 mmol) in CH$_2$Cl$_2$ (5 mL) was added 4 M HCl solution in 1,4-dioxane (2 mL). The mixture was stirred at rt for 4 h, and then the solvent was removed. The residue was redissolved in MeOH (10 mL) and treated with basic resin (Dowex 550A OH anion-exchange resin) for 2 h. The resin was filtered off, and the solvents were removed from the filtrate under reduced pressure. The residue was dissolved in DMF (1 mL) and added to a solution of HOBT (0.095 g, 0.7 mmol), EDCl (0.134 g, 0.7 mmol) and [4-(4-chloro-phenoxy)-phenylamino]-acetic acid (0.13 g, 0.47 mmol) in DMF (5 mL). N-Methyl-morpholine (0.095 g, 0.94 mmol) was then added dropwise. The reaction mixture was stirred at rt overnight, and H$_2$O (10 mL) was then added. The aqueous layer was extracted with EtOAc (3×30 mL). The combined organic layers were washed with 1 N NaOH (2×10 mL) and brine (30 mL), dried (MgSO$_4$), and concentrated. Purification by column chromatography [0–20% (1% NH$_4$OH/MeOH)/CH$_2$Cl$_2$] afforded 0.104 g (42%) of the desired product. MS (electrospray): mass calculated for C$_{30}$H$_{35}$ClN$_4$O$_3$, 534.24; m/z found, 535.24 [M+H]$^+$. $^1$H NMR (400 MHz, CDCl$_3$): 7.63 (d, J=8.6 Hz, 1H), 7.19–7.13 (m, 6H), 7.10–7.08 (m, 2H), 6.80–6.76 (m, 4H), 6.58–6.45 (m, 2H), 6.13 (s, 1H), 4.43–4.40 (m, 1H), 4.18 (s, 1H), 3.72–3.65 (m, 2H), 3.34–3.27 (m, 1H), 3.25–3.16 (m, 1H), 2.92 (dd, J=13.6, 6.5 Hz, 1H), 2.71 (dd, J=13.6, 8.1 Hz, 1H), 2.51 (t, J=6.0 Hz, 2H), 2.44 (s, 4H), 2.33 (dd, J=15.0, 4.87 Hz, 1H), 2.21 (dd, J=15.1, 5.37 Hz, 1H), 1.81 (s, 2H), 1.71 (s, 4H).

Example 29

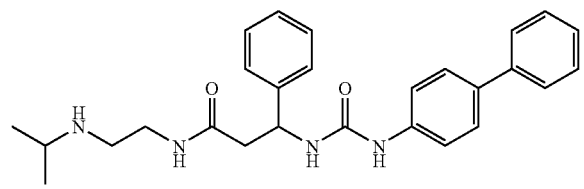

3-(3-Biphenyl-4-yl-ureido)-N-(2-isopropylamino-ethyl)-3-phenyl-propionamide

A. 3-(3-Biphenyl-4-yl-ureido)-3-phenyl-propionic acid. Prepared as in Example 6, step A, substituting 3-amino-3-phenylpropionic acid for 3-amino-3-(p-tolyl)propionic acid. MS (electrospray): mass calculated for C$_{22}$H$_{20}$N$_2$O$_3$, 360.41; m/z found, 361.2 [M+H]$^+$, 383.2 [M+Na]$^+$. $^1$H NMR (400 MHz, DMSO-d$_6$): 12.08 (br s, 1H), 8.73 (br s, 1H), 7.24–7.65 (m, 14H), 6.80 (d, J=8.4 Hz, 1H), 5.10–5.17 (m, 1H), 2.73–2.79 (m, 2H).

B. 3-(3-Biphenyl-4-yl-ureido)-N-(2-isopropylamino-ethyl)-3-phenyl-propionamide. Prepared as in Example 6, step B, substituting N'-isopropyl-ethane-1,2-diamine for 2-pyrrolidin-1-yl-ethylamine. MS (electrospray): mass calculated for C$_{27}$H$_{32}$N$_4$O$_2$, 444.25; m/z found, 445.2 [M+H]$^+$, 467.2 [M+Na]$^+$, 911.5 [2M+Na]$^+$. $^1$H NMR (400 MHz, CDCl$_3$): 8.70 (br s, 1H), 8.49 (br s, 1H), 7.45–7.43 (m, 3H), 7.39–7.22 (m, 11H), 5.69–5.61 (m, 1H), 3.41–3.30 (m, 2H), 3.10–3.01 (m, 1H), 2.91–2.82 (m, 1H), 2.67–2.58 (m, 3H), 0.92 (d, J=2.3 Hz, 3H), 0.90 (d, J=2.3 Hz, 3H).

Example 30

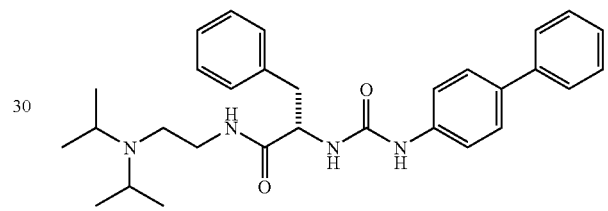

(S)-2-(3-Biphenyl-4-yl-ureido)-N-(2-diisopropylamino-ethyl)-3-phenyl-propionamide Prepared as in Example 7, substituting 4-isocyanato-biphenyl for 4-phenoxyphenyl isocyanate. MS (electrospray): mass calculated for C$_{30}$H$_{38}$N$_4$O$_2$, 486.30; m/z found, 487.3 [M+H]$^+$. $^1$H NMR (400 MHz, CD$_3$OD): 7.56–7.2 (m, 14H), 4.48 (t, J=7.4 Hz, 1H), 3.47–2.99 (m, 6H), 2.44 (br s, 2H), 1.00 (d, J=6.4 Hz, 12H).

Example 31

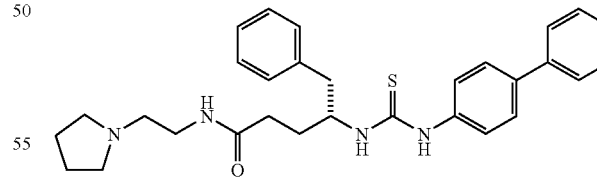

(R)-4-(3-Biphenyl-4-yl-thioureido)-5-phenyl-pentanoic Acid (2-pyrrolidin-1-yl-ethyl)-amide A. [(R)-1-Benzyl-3-(2-pyrrolidin-1-yl-ethylcarbamoyl)-propyl]-carbamic acid tert-butyl ester. To a solution of [(E)-(S)-1-benzyl-3-(2-pyrrolidin-1-yl-ethylcarbamoyl)-allyl]-carbamic acid tert-butyl ester (Example 11, step B, 2.11 g, 5.45 mmol) in EtOH (54 mL) was added Pd/C (10%, 0.739 g). The reaction vessel was sealed, flushed with N$_2$ and evacuated (3×), and then charged with H$_2$ (1 atm). The reaction mixture was stirred at rt for 2 h. The suspension was filtered through a diatomaceous earth pad, which was washed with copious amounts of MeOH. The filtrate and washings were concentrated under reduced pressure to afford 2.06 g (97%) of the desired product as a white solid. MS (electrospray): mass calculated for C$_{22}$H$_{35}$N$_3$O$_3$, 389.27; m/z found, 390.3 [M+H]$^+$, 412.3 [M+Na]$^+$, 801.5 [2M+Na]$^+$. $^1$H NMR (400 MHz, CD$_3$OD): 7.26–7.22 (m, 2H), 7.20–7.14 (m, 3H), 3.71–3.64 (m, 1H), 3.39–3.26 (m, 2H), 2.72 (d, J=7.0 Hz, 2H), 2.64–2.60 (m, 6H), 2.30–2.14 (m, 2H), 1.83–1.76 (m, 5H), 1.66–1.56 (m, 1H), 1.36 (s, 9H).

B. (R)-4-(3-Biphenyl-4-yl-thioureido)-5-phenyl-pentanoic acid (2-pyrrolidin-1-yl-ethyl)-amide. To a solution of [(R)-1-benzyl-3-(2-pyrrolidin-1-yl-ethylcarbamoyl)-propyl]-carbamic acid tert-butyl ester (0.39 g, 1.03 mmol) in CH$_2$Cl$_2$ (10.3 mL) was added 4 M HCl in 1,4-dioxane (3.6 mL), and the resulting solution was stirred at rt for 2 h. The solvent was removed, and the resulting residue was dissolved in MeOH (10 mL) and treated with basic resin (Dowex 550A OH anion-exchange resin). The resulting suspension was stirred at rt for 30 min. The resin was filtered off and washed with MeOH (10 mL). The filtrate and washings were concentrated under reduced pressure, and the resulting free amine was dried under vacuum. To a solution of the free amine in CH$_2$Cl$_2$ (5.2 mL) was added 4-isothiocyanato-biphenyl (0.23 g, 1.08 mmol). The resulting solution was stirred under N$_2$ at rt for 4 h. The solvent was removed, and the resulting residue was dissolved in EtOAc (50 mL). The solution was washed with aqueous saturated NaHCO$_3$ (2×40 mL) and brine (40 mL), dried (Na$_2$SO$_4$) and filtered, and the solvent was removed. The residue was purified by column chromatography on silica gel using a gradient of 2–20% (MeOH (1% NH$_4$OH)/CH$_2$Cl$_2$) to afford 0.32 g (62%) of the desired product as a white solid. R$_f$=0.16 (10% MeOH (1% NH$_4$OH)/CH$_2$Cl$_2$). MS (electrospray): mass calculated for C$_{30}$H$_{36}$N$_4$OS, 500.26; m/z found, 501.3 [M+H]$^+$. $^1$H NMR (400 MHz, CD$_3$OD): 7.59 (t, J=8.4 Hz, 4H), 7.41 (t, J=7.56 Hz, 2H), 7.32–7.17 (m, 8H), 4.82 (br s, 1H), 3.31–3.27 (m, 2H), 2.94 (dd, J=13.5, 6.1 Hz, 1H), 2.83 (dd, J=13.5, 7.2 Hz, 1H), 2.60–2.54 (m, 6H), 2.30 (t, J=7.3 Hz, 2H), 1.91–1.75 (m, 6H).

Example 32

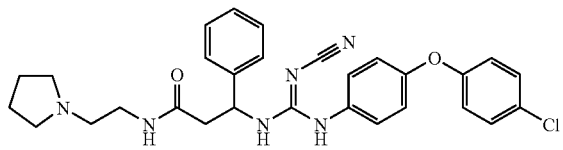

3-{N'-[4-(4-Chloro-phenoxy)-phenyl]-N"-cyano-guanidino}-3-phenyl-N-(2-pyrrolidin-1-yl-ethyl)-propionamide A. 1-[4-(4-Chloro-phenoxy)-phenyl]-3-cyano-thiourea. To a solution of 4-(4-chloro-phenoxy)-phenylisothiocyanate (1.6 g, 6.17 mmol) in EtOH (40 mL) was added NaNHCN (0.39 g, 6.17 mmol), and the mixture was heated to reflux for 1.5 h. The solution was cooled, and the solvents were removed. CH$_2$Cl$_2$ (70 mL) and MeOH (5 mL) were then added to the residue, and the resulting suspension was stirred for 5 min and then filtered. The solids were filtered, washed with copious amount of hexanes, and dried under vacuum to afford 1.8 g (98%) of the desired product. MS (electrospray): mass calculated for C$_{14}$H$_{10}$ClN$_3$OS, 303.02; m/z found, 304.0 [M+H]$^+$, 326.0 [M+Na]$^+$. $^1$H NMR (400 MHz, DMSO-d$_6$): 9.27 (s, 1H), 7.66 (d, J=8.6 Hz, 2H), 7.36 (d, J=8.6 Hz, 2H), 6.93 (d, J=9.0 Hz, 2H), 6.89 (d, J=9.0 Hz, 2H).

B. 3-{N'-[4-(4-Chloro-phenoxy)-phenyl]-N"-cyano-guanidino}-3-phenyl-N-(2-pyrrolidin-1-yl-ethyl)-propionamide. Prepared as in Example 8, step B, substituting 1-[4-(4-chloro-phenoxy)-phenyl]-3-cyano-thiourea for 1-biphenyl-4-yl-3-cyano-thiourea, and using racemic [1-phenyl-2-(2-pyrrolidin-1-yl-ethylcarbamoyl)-ethyl]-carbamic acid tert-butyl ester. MS (electrospray): mass calculated for C$_{29}$H$_{31}$ClN$_6$O$_2$, 530.22; m/z found, 531.2 [M+H]$^+$. $^1$H NMR (400 MHz, CDCl$_3$): 8.42 (br s, 1H), 7.41 (br s, 1H), 7.33–7.23 (m, 9H), 7.02–6.96 (m, 4H), 6.48 (br s, 1H), 5.36–5.32 (m, 1H), 3.19 (d, J=3.6 Hz, 2H), 2.72–2.68 (m, 2H), 2.50–2.36 (m, 6H), 1.73–1.67 (m, 4H).

Example 33

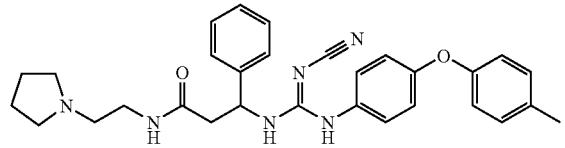

3-[N'-Methyl-N"-(4-p-tolyloxy-phenyl)-guanidino]-3-phenyl-N-(2-pyrrolidin-1-yl-ethyl)-propionamide A. 4-p-Tolyloxy-phenylisothiocyanate. Prepared as in Example 1, step B, substituting 4-p-tolyloxy-phenylamine for biphenyl-4-ylamine. $^1$H NMR (500 MHz, DMSO-d$_6$): 7.43–7.40 (m, 2H), 7.22 (d, J=8.0 Hz, 2H), 6.98–6.95 (m, 4H), 2.30 (s, 3H).

B. 1-Cyano-3-(4-tolyloxy-phenyl)-thiourea. Prepared as in Example 1, step C, from 4-p-tolyloxy-phenylisothiocyanate. MS (electrospray): mass calculated for C$_{15}$H$_{13}$N$_3$OS, 283.08; m/z found, 282.1 [M–H]$^-$. $^1$H NMR (500 MHz, DMSO-d$_6$): 9.18 (s, 1H), 7.61 (d, J=8.8 Hz, 2H), 7.13 (d, J=8.3 Hz, 2H), 6.83–6.81 (m, 4H), 2.26 (s, 3H).

C. 3-[N'-Methyl-N"-(4-p-tolyloxy-phenyl)-guanidino]-3-phenyl-N-(2-pyrrolidin-1-yl-ethyl)-Propionamide. Prepared as in Example 8, step B, substituting 1-cyano-3-(4-p-tolyloxy-phenyl)-thiourea for 1-biphenyl-4-yl-3-cyano-thiourea, and using racemic [1-phenyl-2-(2-pyrrolidin-1-yl-ethylcarbamoyl)-ethyl]-carbamic acid tert-butyl ester. MS (electrospray): mass calculated for C$_{30}$H$_{34}$N$_6$O$_2$, 510.27; m/z found, 511.3 [M+H]$^+$, 533.2 [M+Na]$^+$. $^1$H NMR (400 MHz, CDCl$_3$): 8.11 (br s, 1H), 7.34–7.23 (m, 7H), 7.16 (d, J=8.1 Hz, 2H), 7.01 (d, J=8.7 Hz, 2H), 6.96 (d, J=8.4 Hz, 2H), 6.46 (br s, 1H), 5.35–5.30 (m, 1H), 3.22–3.18 (m, 2H), 2.74–2.63 (m, 2H), 2.51–2.39 (m, 6H), 2.35 (s, 3H), 1.76–1.68 (m, 4H).

Example 34

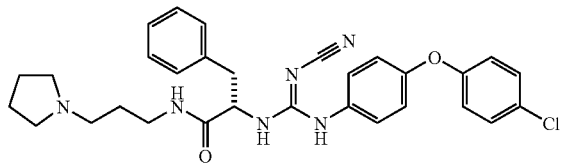

(S)-2-{N'-[4-(4-Chloro-phenoxy)-phenyl]-N''-cyano-guanidino}-3-phenyl-N-(3-pyrrolidin-1-yl-propyl)-propionamide Prepared as in Example 1, substituting (4-chloro-phenoxy)-4-phenylisothiocyanate for 4-isothiocyanato-biphenyl in step C. MS (electrospray): mass calculated for $C_{30}H_{33}ClN_6O_2$, 544.24; m/z found, 545.2 [M+H]$^+$. $^1$H NMR (400 MHz, CD$_3$OD): 7.37–6.8 (m, 13H), 4.57 (m, 1H), 3.18 (m, 2H), 3.12 (dd, J=13.7, 5.6 Hz, 1H), 2.93 (dd, J=13.7, 8.6 Hz, 1H), 2.54 (br s, 4H), 2.46 (t, J=7.9 Hz, 2H), 1.79 (br s, 4H), 1.68 (m, 2H).

Example 35

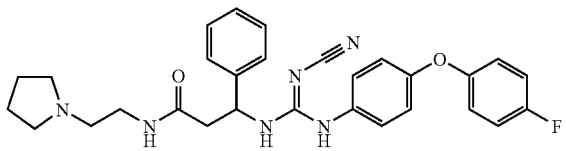

3-{N'-[4-(4-Fluoro-phenoxy)-phenyl]-N''-cyano-guanidino}-3-phenyl-N-(2-pyrrolidin-1-yl-ethyl)-propionamide Prepared as in Example 8, substituting 1-[4-(4-fluoro-phenoxy)-phenyl]-3-cyano-thiourea for 1-biphenyl-4-yl-3-cyano-thiourea in step B, and using racemic [1-phenyl-2-(2-pyrrolidin-1-yl-ethylcarbamoyl)-ethyl]-carbamic acid tert-butyl ester. MS (electrospray): mass calculated for $C_{29}H_{31}FN_6O_2$, 514.25; m/z found, 515.2 [M+H]$^+$. $^1$H NMR (400 MHz, CDCl$_3$): 7.33–7.24 (m, 7H), 7.06–6.98 (m, 6H), 6.46 (br s, 1H), 5.34–5.30 (m, 1H), 3.19 (d, J=4.0 Hz, 2H), 2.72–2.68 (m, 2H), 2.50–2.36 (m, 6H), 1.72–1.66 (m, 4H).

Example 36

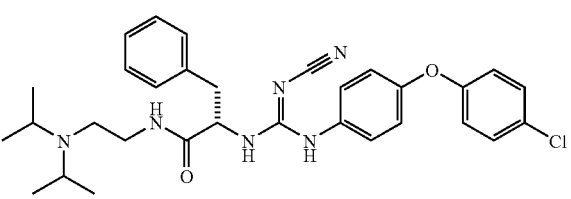

(S)-2-{N'-[4-(4-Chloro-phenoxy)-phenyl]-N''-cyano-guanidino}-N-(2-diisopropylamino-ethyl)-3-phenyl-propionamide Prepared as in Example 1, substituting N',N'-diisopropyl-ethane-1,2-diamine for 3-pyrrolidin-1-yl-propylamine in step A, and 4-(4-chloro-phenoxy)-phenylamine for biphenyl-4-ylamine in step B. MS (electrospray): mass calculated for $C_{31}H_{37}ClN_6O_2$, 560.27; m/z found, 561.3 [M+H]$^+$. $^1$H NMR (400 MHz, CDCl$_3$): 7.33–7.25 (m, 5H), 7.15–7.13 (m, 2H), 7.00–6.92 (m, 6H), 5.74 (d, J=5.1 Hz, 1H), 4.54 (dd, J=7.0, 14.0 Hz, 1H), 3.23–3.10 (m, 2H), 3.09–3.03 (m, 2H), 3.00–2.90 (m, 2H), 2.62–2.45 (m, 2H), 0.98 (d, J=6.38 Hz, 12H).

Example 37

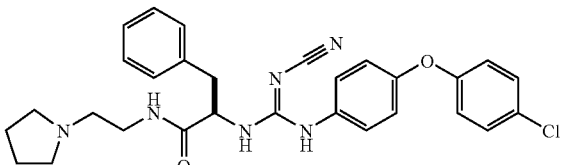

(R)-2-{N'-[4-(4-Chloro-phenoxy)-phenyl]-N''-cyano-guanidino}-3-phenyl-N-(2-pyrrolidin-1-yl-ethyl)-propionamide Prepared by a route similar to Example 1. MS (electrospray): mass calculated for $C_{29}H_{31}ClN_6O_2$, 530.22; m/z found, 531.2 [M+H]$^+$. $^1$H NMR (400 MHz, CD$_3$OD): 7.39–7.35 (m, 2H), 7.32–7.22 (m, 3H), 7.18–7.17 (m, 2H), 7.03–6.94 (m, 6H), 4.61 (dd, J=8.6, 5.9 Hz, 1H), 3.38–3.33 (m, 2H), 3.15 (dd, J=13.9, 5.9 Hz, 1H), 2.99–2.86 (m, 1H), 2.61–2.52 (m, 6H), 1.85–1.77 (m, 4H).

Example 38

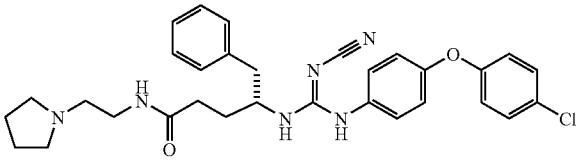

(R)-4-{N'-[4-(4-Chloro-phenoxy)-phenyl]-N''-cyano-guanidino}-5-phenyl-pentanoic Acid (2-pyrrolidin-1-yl-ethyl)-amide Prepared by a route similar to Example 1 steps A, C and D, substituting (R)-4-tert-butoxycarbonylamino-5-phenyl-pentanoic acid for (S)-2-tert-butoxycarbonylamino-3-phenyl-propionic acid and 2-pyrrolidin-1-yl-ethylamine for 3-pyrrolidin-1-yl-propylamine in step A, and (4-chloro-phenoxy)-4-phenylisothiocyanate for 4-isothiocyanato-biphenyl in step C. MS (electrospray): mass calculated for $C_{31}H_{35}ClN_6O_2$, 558.25; m/z found, 560.3 [M+H]$^+$. $^1$H NMR (400 MHz, CDCl$_3$): 7.23–7.10 (m, 9H), 6.88–6.82 (m, 4H), 6.39 (br s, 1H), 4.12–4.03 (m, 1H), 3.29–3.23 (m, 2H), 2.78 (d, J=5.6 Hz, 2H), 2.50 (t, J=6.0 Hz, 2H), 2.47–2.43 (m, 4H), 2.31–2.22 (m, 1H), 2.16–2.09 (m, 1H), 1.76–1.69 (m, 6H).

Example 39

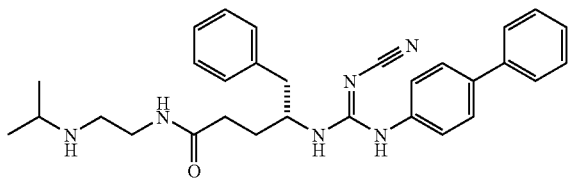

(R)-4-(N'-Biphenyl-4-yl-N''-cyano-guanidino)-5-phenyl-pentanoic Acid (2-isopropylamino-ethyl)-amide A. [(E)-(S)-1-Benzyl-3-(2-isopropylamino-ethylcarbamoyl)-allyl]-carbamic acid tert-butyl ester. Prepared by a route similar to Example 11, steps A and B. MS (electrospray): mass calculated for $C_{21}H_{33}N_3O_3$, 375.25; m/z found, 376.3 [M+H]$^+$, 398.3 [M+Na]$^+$. $^1$H NMR (400 MHz, CD$_3$OD): 7.16–7.27 (m, 5H), 6.74 (dd, J=15.3, 5.6 Hz, 1H), 5.97 (d, J=15.3 Hz, 1H), 4.43 (br s, 1H), 3.36 (t, J=6.7 Hz, 2H), 2.75–2.89 (m, 3H), 2.69 (t, J=6.7 Hz, 2H), 1.36 (s, 9H), 1.05 (d, J=6.3 Hz, 6H).

B. [(R)-1-Benzyl-3-(2-isopropylamino-ethylcarbamoyl)-propyl]-carbamic acid tert-butyl ester. Prepared by a route similar to Example 31, step A. MS (electrospray): mass calculated for $C_{21}H_{35}N_3O_3$, 377.27; m/z found, 376.3 [M–H]$^-$. $^1$H NMR (400 MHz, CDCl$_3$): 7.95 (s, 1H), 7.31–7.12 (m, 5H), 6.73 (dd, J=15.3, 5.6 Hz, 1H), 5.97 (d, J=15.3 Hz, 1H), 4.43 (m, 1H), 2.94 (s, 2H), 2.95–2.75 (m, 3H), 2.69 (t, J=6.4 Hz, 2H), 1.29 (s, 9H), 1.04 (d, J=6.4 Hz, 6H).

C. (R)-4-(N'-Biphenyl-4-yl-N''-cyano-guanidino)-5-phenyl-pentanoic acid (2-isopropylamino-ethyl)-amide. Prepared as in Example 1, step D, substituting [(R)-1-benzyl-3-(2-isopropylamino-ethylcarbamoyl)-propyl]-carbamic acid tert-butyl ester for [(S)-2-phenyl-1-(3-pyrrolidin-1-yl-propylcarbamoyl)-ethyl]-carbamic acid tert-butyl ester. MS (electrospray): mass calculated for $C_{30}H_{36}N_6O$, 496.66; m/z found, 497.2 [M+H]$^+$, 519.2 [M+Na]$^+$. $^1$H NMR (400 MHz, CDCl$_3$): 7.51–7.44 (m, 4H), 7.39–7.34 (m, 2H), 7.30–7.11 (m, 8H), 6.40 (br s, 1H), 5.29 (br s, 1H), 4.18–4.08 (m, 1H), 3.30–3.23 (m, 2H), 2.83–2.78 (m, 1H), 2.77–2.70 (m, 2H), 2.67 (t, J=5.8 Hz, 2H), 2.34–2.23 (m, 1H), 2.19–2.12 (m, 1H), 1.80–1.76 (m, 2H), 0.99 (d, J=6.4 Hz, 6H).

Example 40

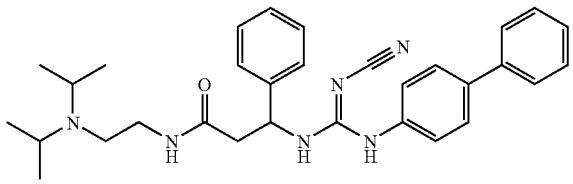

3-(N'-Biphenyl-4-yl-N''-cyano-guanidino)-N-(2-diisopropylamino-ethyl)-3-phenyl-propionamide A. [2-(2-Diisopropylamino-ethylcarbamoyl)-1-phenyl-ethyl]-carbamic acid tert-butyl ester. Prepared by a route similar to Example 10, steps A and B. MS (electrospray): mass calculated for $C_{22}H_{37}N_6O_3$, 391.28; m/z found, 392.3 [M+H]$^+$. $^1$H NMR (400 MHz, CDCl$_3$): 7.26–7.31 (m, 4H), 7.18–7.23 (m, 1H), 6.44 (br s, 1H), 6.13 (br s, 1H), 5.00 (br s, 1H), 3.04–3.13 (m, 2H), 2.85–2.95 (m, 2H), 2.65–2.74 (m, 1H), 2.54 (dd, J=14.3, 5.9 Hz, 2H), 2.33–2.48 (m, 2H), 1.41 (br s, 9H), 0.92 (d, J=6.2 Hz, 3H), 0.91 (d, J=6.2 Hz, 3H).

B. 3-(N'-Biphenyl-4-yl-N''-cyano-guanidino)-N-(2-diisopropylamino-ethyl)-3-phenyl-propionamide. Prepared as in Example 10, step G, from [2-(2-diisopropylamino-ethylcarbamoyl)-1-phenyl-ethyl]-carbamic acid tert-butyl ester, substituting 1-biphenyl-4-yl-3-cyano-thiourea (Example 1, step C) for 1-[4-(3,4-dichloro-phenoxy)-phenyl]-3-cyano-thiourea. MS (electrospray): mass calculated for $C_{31}H_{38}N_6O$, 510.31; m/z found, 511.3 [M+H]$^+$. $^1$H NMR (400 MHz, CDCl$_3$): 8.51 (br s, 1H), 7.64–7.60 (m, 4H), 7.47–7.27 (m, 10H), 6.49 (br s, 1H), 5.43–5.37 (m, 1H), 3.11 (br s, 2H), 2.94–2.88 (m, 2H), 2.77–2.60 (m, 2H), 2.51–2.40 (m, 2H), 0.93 (t, J=6.5 Hz, 12H).

Example 41

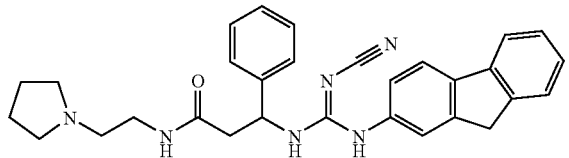

3-[N'-(9H-Fluoren-2-yl)-N''-cyano-guanidino]-3-phenyl-N-(2-pyrrolidin-1-yl-ethyl)-propionamide A. 2-Isothiocyanato-9H-fluorene. Prepared by a route similar to Example 1, step B. MS (electrospray): mass calculated for $C_{14}H_9NS$, 223.05; m/z found, 222.1 [M–H]$^-$. $^1$H NMR (CDCl$_3$, 400 MHz): 7.57 (br s, 1H), 7.15 (br s, 1H), 7.13 (d, J=8.3 Hz, 1H), 7.01–7.04 (m, 2H), 6.84 (dd, J=8.3, 2.8 Hz, 1H), 3.95 (br s, 2H), the other signal was not detected and is believed to be a broad peak in the aromatic region.

B. 1-(9H-Fluoren-2-yl)-3-cyano-thiourea. Prepared by a route similar to Example 1, step C. MS (electrospray): mass calculated for $C_{15}H_{11}N_3S$, 265.07; m/z found, 266.1 [M+H]$^+$, 288.0 [M+Na]$^+$, 264.0 [M–H]$^-$. $^1$H NMR (CD$_3$OD, 400 MHz): 6.42 (br s, 1H), 6.32 (d, J=7.9 Hz, 7H), 6.28 (d, J=7.9 Hz, 1H), 6.11 (d, J=7.4 Hz, 1H), 6.04 (d, J=7.8 Hz, 1H), 5.92 (t, J=7.8 Hz, 1H), 5.83 (t, J=7.4 Hz, 1H), 3.88 (s, 2H).

C. 3-[N'-(9H-Fluoren-2-yl)-N''-cyano-guanidino]-3-phenyl-N-(2-pyrrolidin-1-yl-ethyl)-propionamide. Prepared by a route similar to Example 10, steps A, B and G. MS (electrospray): mass calculated for $C_{30}H_{32}N_6O$, 492.26; m/z found, 493.2 [M+H]$^+$. $^1$H NMR (400 MHz, CDCl$_3$): 8.20 (br s, 1H), 7.81–7.75 (m, 2H), 7.56–7.50 (m, 2H), 7.41–7.25 (m, 8H), 6.53 (br s, 1H), 5.39–5.34 (m, 1H), 3.91 (s, 2H), 3.21 (br s, 2H), 2.77–2.38 (m, 2H), 2.52–2.38 (m, 6H), 1.74–1.68 (m, 4H).

Example 42

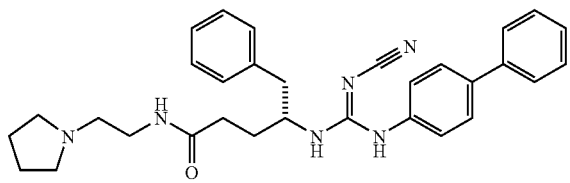

(R)-4-(N'-Biphenyl-4-yl-N''-cyano-guanidino)-5-phenyl-pentanoic Acid (2-pyrrolidin-1-yl-ethyl)-amide Prepared as in Example 1, step D, substituting [(R)-1-benzyl-3-(2-pyrrolidin-1-yl-ethylcarbamoyl)-propyl]-carbamic acid tert-butyl ester (Example 31, step A) for [(S)-2-phenyl-1-(3-pyrrolidin-1-yl-propylcarbamoyl)-ethyl]-carbamic acid tert-butyl ester. MS (electrospray): mass calculated for $C_{13}H_{36}N_6O$, 508.66; m/z found, 509.3 [M+H]$^+$, 531.2 [M+Na]$^+$. $^1$H NMR (CDCl$_3$, 400 MHz): 7.57 (br t, J=9.5 Hz, 5H), 7.46 (br t, J=7.6 Hz, 2H), 7.13–7.30 (m, 8H), 6.34 (br s, 1H), 5.36 (br s, 1H), 4.14 (dt, J=7.3, 7.0 Hz, 1H), 3.24–3.40 (m, 2H), 2.72–2.84 (m, 2H), 2.62 (t, J=6.0 Hz, 1H), 2.25 (br s, 4H), 2.28–2.30 (m, 1H), 2.13–2.18 (m, 1H), 1.68–1.80 (m, 6H).

Example 43

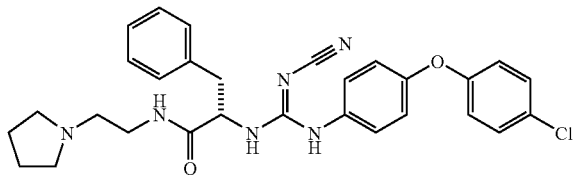

(S)-2-{N'-[4-(4-Chloro-phenoxy)-phenyl]-N''-cyano-guanidino}-3-phenyl-N-(2-pyrrolidin-1-yl-ethyl)-propionamide Prepared by a route similar to Example 1. MS (electrospray): mass calculated for $C_{29}H_{31}ClN_6O_2$, 530.22; m/z found, 531.2 [M+H]$^+$. $^1$H NMR (400 MHz, DMSO-d$_6$): 9.19 (s, 1H), 8.11 (t, J=5.3 Hz, 1H), 7.5–6.98 (m, 13H), 6.92 (d, J=7.9 Hz, 1H), 4.52 (m, 1H), 3.16 (m, 2H), 3.03 (dd, J=13.7, 4.7 Hz, 1H), 2.93 (dd, J=13.7, 9.2 Hz, 1H), 2.49 (br s, 6H), 1.68 (br m, 4H).

Example 44

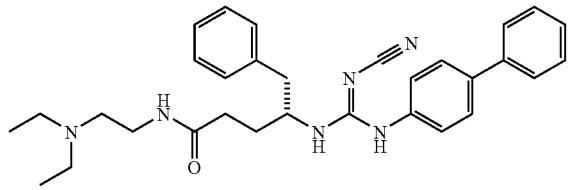

(R)-4-(N'-Biphenyl-4-yl-N''-cyano-guanidino)-5-phenyl-pentanoic Acid (2-diethylamino-ethyl)-amide A. [(E)-(S)-1-Benzyl-3-(2-diethylamino-ethylcarbamoyl)-allyl]-carbamic acid tert-butyl ester. Prepared by a route similar to Example 11, steps A and B. MS (electrospray): mass calculated for $C_{22}H_{35}N_3O_3$, 389.53; m/z found, 390.3 [M+H]$^+$, 412.3 [M+Na]$^+$. $^1$H NMR (CDCl$_3$, 400 MHz): 7.17–7.31 (m, 5H), 6.75–6.79 (m, 1H), 6.19 (br s, 1H), 5.80 (d, J=15.1 Hz, 1H), 4.62 (br s, 2H), 3.32–3.42 (m, 2H), 2.88–2.93 (m, 2H), 2.48–2.56 (m, 6H), 1.40 (s, 9H), 1.00 (t, J=7.1 Hz, 6H).

B. [(R)-1-Benzyl-3-(2-diethylamino-ethylcarbamoyl)-propyl]-carbamic acid tert-butyl ester. Prepared by a route similar to Example 2, Method 1, step C. MS (electrospray): mass calculated for $C_{22}H_{37}N_3O_3$, 391.55; m/z found, 392.3 [M+H]$^+$, 414.3 [M+Na]$^+$. $^1$H NMR (CDCl$_3$, 400 MHz): 7.18–7.32 (m, 5H), 6.28 (br s, 1H), 4.58 (br d, J=8.8 Hz, 1H), 3.80–3.83 (br s, 1H), 3.29–3.32 (m, 2H), 2.85 (dd, J=13.5, 6.0 Hz, 1H), 2.75 (dd, J=13.5, 6.8 Hz, 1H), 2.49–2.57 (m, 6H), 2.17–2.30 (m, 2H), 1.84–1.89 (m, 1H), 1.62–1.71 (m, 1H), 1.41 (s, 9H), 1.00 (t, J=7.1 Hz, 6H).

C. (R)-4-(N'-Biphenyl-4-yl-N''-cyano-guanidino)-5-phenyl-pentanoic acid (2-diethylamino-ethyl)-amide. Prepared by a route similar to Example 1, step D. MS (electrospray): mass calculated for $C_{31}H_{33}N_6O$, 510.68; m/z found, 511.3 [M+H]$^+$. $^1$H NMR (CDCl$_3$, 400 MHz): 9.66 (br s, 1H), 7.24–7.59 (m, 14H), 6.42 (br s, 1H), 5.60 (br s, 1H), 4.20–4.26 (m, 1H), 2.30 (br s, 2H), 2.86–2.89 (br s, 2H), 2.52–2.57 (m, 6H), 2.37 (br s, 1H), 2.19–2.26 (m, 1H), 2.85–2.88 (br s, 2H), 1.02 (t, J=7.1 Hz, 6H).

Example 45

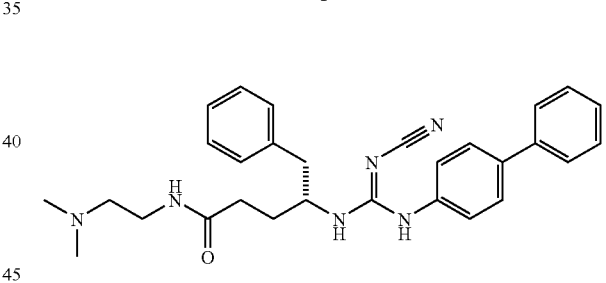

(R)-4-(N'-Biphenyl-4-yl-N''-cyano-guanidino)-5-phenyl-pentanoic Acid (2-dimethylamino-ethyl)-amide A. [(E)-(S)-1-Benzyl-3-(2-dimethylamino-ethylcarbamoyl)-allyl]-carbamic acid tert-butyl ester. Prepared by a route similar to Example 11, steps A and B. MS (electrospray): mass calculated for $C_{20}H_{31}N_3O_3$, 361.48; m/z found, 362.2 [M+H]$^+$, 384.2 [M+Na]$^+$. $^1$H NMR (CDCl$_3$, 400 MHz): 7.17–7.31 (m, 5H), 6.78 (dd, J=14.5, 5.2 Hz, 1H), 6.25 (br s, 1H), 5.82 (dd, J=15.5, 1.6 Hz, 1H), 4.70 (d, J=8.9 Hz, 1H), 4.59 (br s, 1H), 3.34–3.42 (m, 2H), 2.88–2.93 (m, 2H), 2.40–2.44 (m, 2H), 2.22 (s, 6H), 1.40 (s, 9H).

B. [(R)-1-Benzyl-3-(2-dimethylamino-ethylcarbamoyl)-propyl]-carbamic acid tert-butyl ester. Prepared by a route similar to Example 2, Method 1, step C. MS (electrospray): mass calculated for $C_{20}H_{33}N_3O_3$, 363.50; m/z found, 364.2 [M+H]$^+$, 386.2 [M+Na]$^+$. $^1$H NMR (CDCl$_3$, 400 MHz): 7.09–7.22 (m, 5H), 6.15 (br s, 1H), 4.52 (br d, J=8.5 Hz, 1H), 3.72 (br s, 1H), 3.21–3.24 (m, 1H), 2.75 (dd, J=13.3, 6.1 Hz, 1H), 2.66 (dd, J=13.3, 6.7 Hz, 1H), 2.31 (t, J=6.0 Hz, 1H), 2.13 (s, 6H), 1.32 (s, 9H).

C. (R)-4-(N'-Biphenyl-4-yl-N''-cyano-guanidino)-5-phenyl-pentanoic acid (2-dimethylamino-ethyl)-amide. Prepared by a route similar to Example 1, step D. MS (electrospray): mass calculated for $C_{29}H_{34}N_6O$, 482.62; m/z found, 483.3 [M+H]$^+$. $^1$H NMR (CDCl$_3$, 400 MHz): 9.63 (br s, 1H), 7.23–7.58 (m, 15H), 6.54 (br s, 1H), 4.20–4.25 (m, 1H), 3.30 (br s, 2H), 2.86–2.89 (br s, 2H), 2.32–2.42 (m, 3H), 2.23–2.27 (m, 1H), 2.23 (s, 6H), 1.84–1.88 (br s, 2H).

Example 46

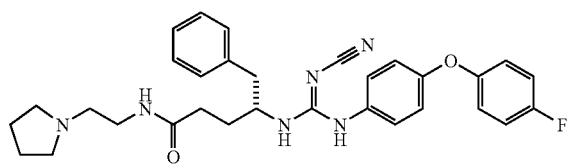

(R)-4-{N'-[4-(4-Fluoro-phenoxy)-phenyl]-N''-cyano-guanidino}-5-phenyl-pentanoic Acid (2-pyrrolidin-1-yl-ethyl)-amide Prepared as in Example 1, step D, from [(R)-1-benzyl-3-(2-pyrrolidin-1-yl-ethylcarbamoyl)-propyl]-carbamic acid tert-butyl ester (Example 31, step A), and substituting 1-(4-(4-fluoro-phenoxy)phen-1-yl)-3-cyano-thiourea for 1-biphenyl-4-yl-3-cyano-thiourea. MS (electrospray): mass calculated for $C_{31}H_{35}FN_6O_2$, 542.28; m/z found, 543.2 [M+H]$^+$. $^1$H NMR (400 MHz, CDCl$_3$): 7.22–7.90 (m, 11H), 6.81 (d, J=8.6 Hz, 2H), 6.43 (br s, 1H), 4.10–4.03 (m, 1H), 3.29–3.19 (m, 2H), 2.76 (d, J=4.8 Hz, 2H), 2.51 (t, J=6.0 Hz, 2H), 2.47–2.41 (m, 4H), 2.30–2.21 (m, 1H), 2.16–2.11 (m, 1H), 1.75–1.68 (m, 6H).

Example 47

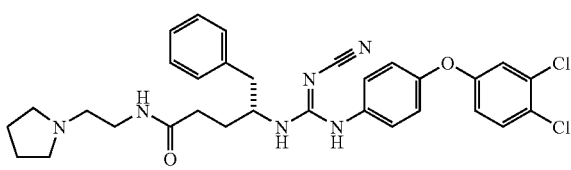

(R)-4-{N'-[4-(3,4-Dichloro-phenoxy)-phenyl]-N''-cyano-guanidino}-5-phenyl-pentanoic Acid (2-pyrrolidin-1-yl-ethyl)-amide Prepared by a route similar to Example 1, step D, from [(R)-1-benzyl-3-(2-pyrrolidin-1-yl-ethylcarbamoyl)-propyl]-carbamic acid tert-butyl ester (Example 31, step A). MS (electrospray): mass calculated for $C_{31}H_{34}Cl_2N_6O_2$, 592.21; m/z found, 593.2 [M+H]$^+$. $^1$H NMR (400 MHz, CDCl$_3$): 7.33–6.95 (m, 9H), 6.86 (d, J=8.7 Hz, 2H), 6.77 (dd, J=2.3, 8.7 Hz, 1H), 6.45 (br s, 1H), 4.12–4.03 (m, 1H), 3.31–3.25 (m, 2H), 2.79 (d, J=5.6 Hz, 2H), 2.54 (t, J=6.0 Hz, 2H), 2.50–2.46 (m, 4H), 2.32–2.27 (m, 1H), 2.18–2.11 (m, 1H), 1.77–1.67 (m, 6H).

Example 48

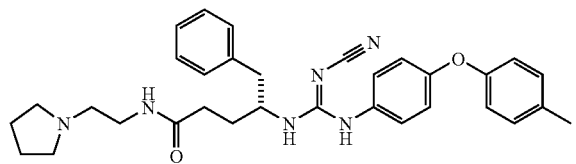

(R)-4-[N'-Cyano-N''-(4-p-tolyloxy-phenyl)-guanidino]-5-phenyl-pentanoic Acid (2-pyrrolidin-1-yl-ethyl)-amide Prepared by a route similar to Example 1, step D, from [(R)-1-benzyl-3-(2-pyrrolidin-1-yl-ethylcarbamoyl)-propyl]-carbamic acid tert-butyl ester (Example 31, step A). MS (electrospray): mass calculated for $C_{32}H_{38}N_6O_2$, 538.31; m/z found, 539.3 [M+H]$^+$. $^1$H NMR (400 MHz, CDCl$_3$): 7.31–7.02 (m, 9H), 6.94–6.89 (m, 4H), 6.52 (br s, 1H), 4.21–4.08 (m, 1H), 3.42–3.26 (m, 2H), 2.81 (d, J=5.6 Hz, 2H), 2.60 (t, J=6.0 Hz, 2H), 2.56–2.50 (m, 4H), 2.35 (s, 3H), 2.34–2.29 (m, 1H), 2.25–2.18 (m, 1H), 1.83–1.78 (m, 6H).

Example 49

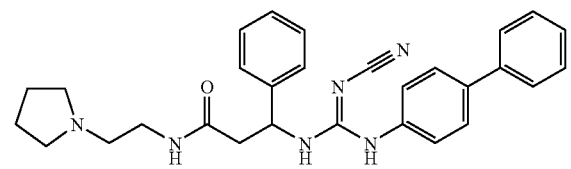

3-(N'-Biphenyl-4-yl-N''-cyano-guanidino)-3-phenyl-N-(2-pyrrolidin-1-yl-ethyl)-propionamide Prepared by a route similar to Example 8. MS (electrospray): mass calculated for $C_{29}H_{32}N_6O$, 480.26; m/z found, 481.3 [M+H]$^+$. $^1$H NMR (400 MHz, CDCl$_3$): 7.51–7.46 (m, 4H), 7.35–7.14 (m, 10H), 6.53 (br s, 1H), 5.29 (d, J=5.2 Hz, 1H), 3.13–3.19 (m, 2H), 2.63–2.59 (m, 2H), 2.39–2.26 (m, 6H), 1.62–1.57 (m, 4H).

Example 50

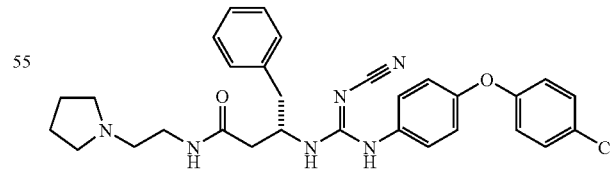

(S)-3-{N'-[4-(4-Chloro-phenoxy)-phenyl]-N''-cyano-guanidino}-4-phenyl-N-(2-pyrrolidin-1-yl-ethyl)-butyramide Prepared as in Example 8 from [(S)-1-benzyl-2-(2-pyrrolidin-1-yl-ethylcarbamoyl)-ethyl]-carbamic acid tert-butyl ester (Example 27, step A) and 1-[4-(4-chloro-phenoxy)-phenyl]-3-cyano-thiourea (Example 32, step A). MS (electrospray): mass calculated for $C_{30}H_{33}ClN_6O_2$, 544.24; m/z found, 545.2 [M+H]$^+$. $^1$H NMR (400 MHz, CDCl$_3$): 7.27–7.08 (m, 9H), 6.91 (t, J=9.4 Hz, 4H), 6.25 (br s, 1H), 4.35–4.26 (m, 1H), 3.35–3.28 (m, 1H), 3.25–3.17 (m, 1H), 2.99 (dd, J=13.5, 6.4 Hz, 1H), 2.7–2.68 (m, 1H), 2.52 (t, J=5.9 Hz, 2H), 2.49–2.41 (m, 4H), 2.41–2.35 (m, 1H), 2.26–2.18 (m, 1H), 1.74–1.69 (m, 6H).

Example 51

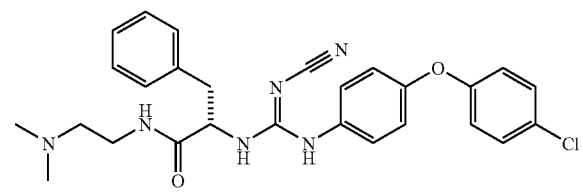

(S)-2-{N'-[4-(4-Chloro-phenoxy)-phenyl]-N''-cyano-guanidino}-N-(2-dimethylamino-ethyl)-3-phenyl-propionamide Prepared by a route similar to Example 1. MS (electrospray): mass calculated for $C_{27}H_{29}ClN_6O_2$, 504.2; m/z found, 505.2 [M+H]$^+$. $^1$H NMR (400 MHz, CD$_3$OD): 7.39–7.35 (m, 2H), 7.32–7.22 (m, 3H), 7.19–7.17 (m, 2H), 7.02–6.93 (m, 6H), 4.62 (dd, J=8.6, 5.9 Hz, 1H), 3.37–3.31 (m, 1H), 3.28–3.24 (m, 1H), 3.16 (dd, J=13.9, 5.8 Hz, 1H), 2.93 (dd, J=13.9, 8.8 Hz, 1H), 2.47–2.43 (m, 2H), 2.29 (s, 6H).

Example 52

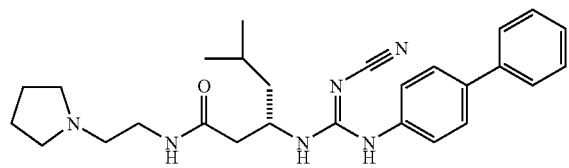

(S)-3-(N'-Biphenyl-4-yl-N''-cyano-guanidino)-5-methyl-hexanoic Acid (2-pyrrolidin-1-yl-ethyl)-amide Prepared as in Example 1, substituting (S)-3-tert-butoxy-carbonylamino-5-methyl-hexanoic acid for (S)-2-tert-butoxycarbonylamino-3-phenyl-propionic acid, and 2-pyrrolidin-1-yl-ethylamine for 3-pyrrolidin-1-yl-propylamine in step A. MS (electrospray): mass calculated for $C_{27}H_{36}N_6O$, 460.3; m/z found, 461.2 [M+H]$^+$. $^1$H NMR (400 MHz, CDCl$_3$): 7.53–7.49 (m, 4H), 7.38–7.35 (m, 4H), 7.29–7.25 (m, 1H), 6.45 (br s, 1H), 4.25–4.19 (m, 1H), 3.32–3.26 (m, 2H), 2.55–2.52 (m, 2H), 2.49–2.44 (m, 5H), 2.35–2.29 (m, 1H), 1.93 (br s, 2H), 1.75–1.68 (m, 4H), 1.56 (br s, 1H), 1.31–1.24 (m, 1H), 0.89–0.86 (m, 6H).

Example 53

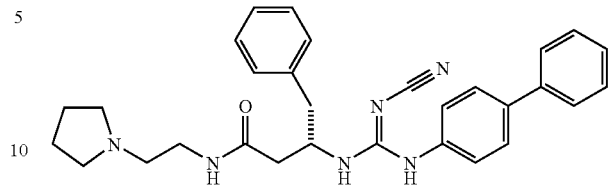

(S)-3-(N'-Biphenyl-4-yl-N''-cyano-guanidino)-4-phenyl-N-(2-pyrrolidin-1-yl-ethyl)-butyramide Prepared by a route similar to Example 1. MS (electrospray): mass calculated for $C_{30}H_{34}ClN_6O$, 494.28; m/z found, 495.3 [M+H]$^+$. $^1$H NMR (400 MHz, CDCl$_3$): 7.60–7.56 (m, 4H), 7.45 (t, J=7.6 Hz, 2H), 7.38–7.25 (m, 8H), 6.75 (d, J=8.2 Hz, 1H), 6.62 (br s, 1H), 4.5–4.42 (m, 1H), 3.44–3.28 (m, 2H), 3.11 (dd, J=13.6, 7.0 Hz, 1H), 2.94–2.8 (m, 1H), 2.60–2.57 (m, 2H), 2.55–2.4 (m, 6H), 1.84–1.75 (m, 4H).

Example 54

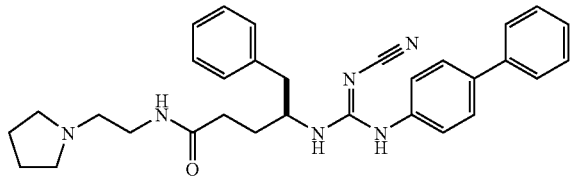

(S)-4-(N'-Biphenyl-4-yl-N''-cyano-guanidino)-5-phenyl-pentanoic Acid (2-pyrrolidin-1-yl-ethyl)-amide A. [(E)-(R)-1-Benzyl-3-(2-pyrrolidin-1-yl-ethylcarbamoyl)-allyl]-carbamic acid tert-butyl ester. Prepared by a route similar to Example 11, steps A and B. MS (electrospray): mass calculated for $C_{22}H_{33}N_3O_3$, 387.25; m/z found, 388.3 [M+H]$^+$. $^1$H NMR (400 MHz, CD$_3$OD): 7.33–7.14 (m, 5H), 6.70 (dd, J=5.5, 15.3 Hz, 1H), 5.88 (d, J=15.3 Hz, 1H), 4.43–4.40 (m, 1H), 3.93 (m, 2H), 2.95–2.83 9 m, 2H), 2.77–2.43 (m, 6H), 1.90–1.85 (m, 4H), 1.36 (s, 9H).

B. [(S)-1-Benzyl-3-(2-pyrrolidin-1-yl-ethylcarbamoyl)-propyl]-carbamic acid tert-butyl ester. Prepared by a route similar to Example 2, Method 1, step C. MS (electrospray): mass calculated for $C_{22}H_{35}N_3O_3$, 389.27; m/z found, 390.3 [M+H]$^+$. $^1$H NMR (400 MHz, CD$_3$OD): 7.26–7.13 (m, 5H), 3.70–3.59 (m, 1H), 3.35–3.27 (m, 2H), 2.71 (d, J=7.2 Hz, 2H), 2.61–2.56 (m, 6H), 2.29–2.14 (m, 2H), 1.85–1.80 (m, 4H), 1.650–1.58 (m, 1H), 1.37 (s, 9H).

C. (S)-4-(N'-Biphenyl-4-yl-N''-cyano-guanidino)-5-phenyl-pentanoic acid (2-pyrrolidin-1-yl-ethyl)-amide. Prepared by a route similar to Example 1, step D. MS (electrospray): mass calculated for $C_{31}H_{36}N_6O$, 508.30; m/z found, 509.3 [M+H]$^+$. $^1$H NMR (400 MHz, CDCl$_3$): 7.57–7.51 (m, 4H), 7.43 (t, J=7.6 Hz, 2H), 7.35–7.21 (m, 8H), 6.81 (br s, 1H), 4.26–4.18 (m, 1H), 3.38–3.29 (m, 2H), 2.88 (d, J=4.4 Hz, 2H), 2.58 (t, J=6.0 Hz, 2H), 2.51 (br s, 4H), 2.37–2.29 (m, 1H), 2.28–2.22 (m, 1H), 1.90–1.82 (m, 2H), 1.76 (br s, 4H).

Example 55

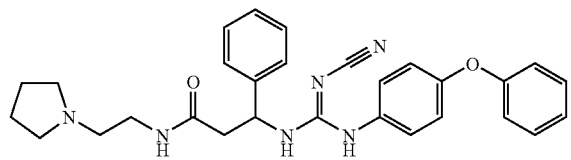

3-[N'-Cyano-1"-(4-phenoxy-phenyl)-guanidino]-3-phenyl-N-(2-pyrrolidin-1-yl-ethyl)-propionamide A. 4-Phenoxy-phenyl isothiocyanate. Prepared by a route similar to Example 1, step B. $^1$H NMR (400 MHz, CDCl$_3$): 7.43 (t, J=8.0 Hz, 2H), 7.19–7.24 (m, 3H), 7.08 (d, J=8.0 Hz, 2H), 6.99 (d, J=9.0 Hz, 2H).

B. 1-Cyano-3-(4-Phenoxy-phenyl)-thiourea. Prepared by a route similar to Example 1, step C. MS (electrospray): mass calculated for C$_{14}$H$_{11}$N$_3$OS, 269.06; m/z found, 268.0 [M–H]$^-$. $^1$H NMR (400 MHz, DMSO-d$_6$): 9.21 (br s, 1H), 7.36 (d, J=9.0 Hz, 2H), 7.33–7.36 (m, 2H), 7.06 (t, J=7.4 Hz, 1H), 6.85–6.93 (m, 4H).

C. 3-[N'-Cyano-N"-(4-phenoxy-phenyl)-guanidino]-3-phenyl-N-(2-pyrrolidin-1-yl-ethyl)-Propionamide. Prepared as in Example 1, step D, from [1-phenyl-2-(2-pyrrolidin-1-yl-ethylcarbamoyl)-ethyl]-carbamic acid tert-butyl ester (Example 10, step B) and 1-cyano-3-(4-phenoxy-phenyl)-thiourea. MS (electrospray): mass calculated for C$_{29}$H$_{32}$N$_6$O$_2$, 496.26; m/z found, 497.3 [M+H]$^+$. $^1$H NMR (400 MHz, CDCl$_3$): 8.04 (br s, 1H), 7.27–7.15 (m, 9H), 7.05–7.01 (m, 1H), 6.97–6.94 (m, 4H), 6.41 (br s, 1H), 5.26–5.21 (m, 1H), 3.12 (d, J=4.8 Hz, 2H), 2.66–2.52 (m, 2H), 2.44–2.28 (m, 6H), 1.67–1.58 (m, 4H).

Example 56

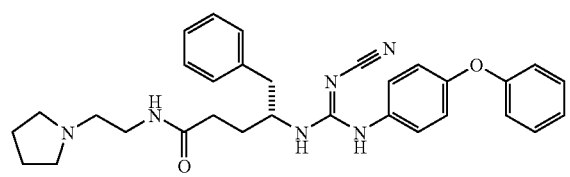

(R)-4-[N'-Cyano-N"-(4-phenoxy-phenyl)-guanidino]-5-phenyl-pentanoic Acid (2-pyrrolidin-1-yl-ethyl)-amide Prepared as in Example 1, step D, from [(R)-1-benzyl-3-(2-pyrrolidin-1-yl-ethylcarbamoyl)-propyl]-carbamic acid tert-butyl ester (Example 31, step A) and 1-cyano-3-(4-phenoxy-phenyl)-thiourea (Example 55, step B). MS (electrospray): mass calculated for C$_{31}$H$_{36}$N$_6$O$_2$, 524.29; m/z found, 525.3 [M+H]$^+$. $^1$H NMR (400 MHz, CDCl$_3$): 7.37–7.10 (m, 10H), 7.02 (d, J=7.9 Hz, 2H), 6.94 (d, J=8.7 Hz, 2H), 6.58 (br s, 1H), 4.21–4.08 (m, 1H), 3.39–3.30 (m, 2H), 2.85 (d, J=6.4 Hz, 2H), 2.58 (t, J=6.0 Hz, 2H), 2.53–2.49 (m, 4H), 2.41–2.30 (m, 1H), 2.25–2.18 (m, 1H), 1.84–1.73 (m, 6H).

Example 57

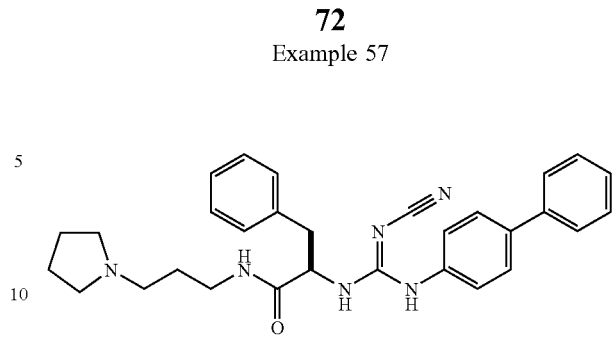

(R)-2-(N'-Biphenyl-4-yl-N"-cyano-guanidino)-3-phenyl-N-(3-pyrrolidin-1-yl-propyl)-propionamide Prepared by a route similar to Example 1. MS (electrospray): mass calculated for C$_{30}$H$_{34}$N$_6$O, 494.28; m/z found, 495.3 [M+H]$^+$. $^1$H NMR (400 MHz, DMSO-d$_6$): 8.14 (t, J=5.2 Hz, 1H), 7.7–7.25 (m, 13H), 7.1 (d, J=8.5 Hz, 2H), 4.57 (m, 1H), 3.15–2.9 (m, 4H), 2.39 (br s, 4H), 2.36 (m, 2H), 1.67 (br m, 4H), 1.53 (m, 2H).

Example 58

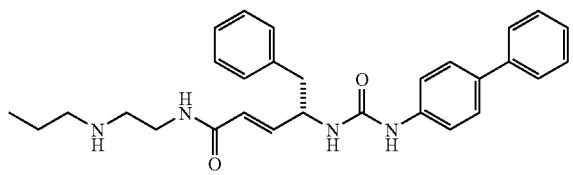

(E)-(S)-4-(3-Biphenyl-4-yl-ureido)-5-phenyl-pent-2-enoic Acid (2-propylamino-ethyl)-amide Prepared as in Example 19, substituting N'-propyl-ethane-1,2-diamine for N',N'-diethyl-ethane-1,2-diamine in step B. MS (electrospray): mass calculated for C$_{29}$H$_{34}$N$_4$O$_2$, 470.27; m/z found, 471.3 [M+H]$^+$, 493.2 [M+Na]$^+$, 941.5 [2M+H]$^+$. $^1$H NMR (400 MHz, CD$_3$OD): 7.54 (d, J=7.6 Hz, 2H), 7.49 (d, J=8.5 Hz, 2H), 7.39–7.35 (m, 4H), 7.28–7.18 (m, 6H), 6.81 (dd, J=15.4, 5.5 Hz, 1H), 6.01 (dd, J=15.4, 1.2 Hz, 1H), 4.75–4.7 (m, 1H), 3.35 (t, J=6.4 Hz, 2H), 2.96 (dd, J=13.7, 6.6 Hz, 1H), 2.89 (dd, J=13.7, 7.7 Hz, 1H), 2.69 (t, J=6.4 Hz, 2H), 2.52 (t, J=7.4 Hz, 2H), 1.54–1.44 (m, 2H), 0.90 (t, J=7.4 Hz, 3H).

Example 59

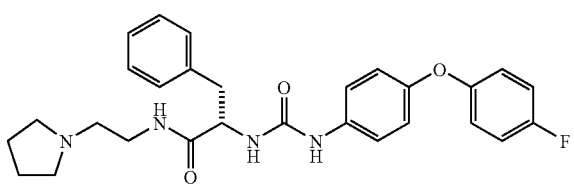

(S)-2-{3-[4-(4-Fluoro-phenoxy)-phenyl]-ureido}-3-phenyl-N-(2-pyrrolidin-1-yl-ethyl)-propionamide To a solution of (S)-2-amino-3-phenyl-N-(2-pyrrolidin-1-yl-ethyl)-propionamide (Example 9, step C) (0.079 g, 0.3 mmol) in THF (3 mL) was added 4-(4-fluoro-phenoxy)-phenylamine (0.124 g, 0.61 mmol). After addition of 1,1'-carbonyldiimidazole (0.063 g, 0.39 mmol), the reaction mixture was heated to 65° C. for 6 h. EtOAc (10 mL) and H$_2$O (10 mL) were then added. The aqueous layer was extracted with EtOAc (3×20 mL) and CH$_2$Cl$_2$ (2×20 mL). The combined organic layers were washed with brine and dried (Na$_2$SO$_4$), and the solvent was removed. Column chromatography using 2–20% MeOH/CH$_2$Cl$_2$ gave 0.04 g (27%) of the desired product. MS (electrospray): mass calculated for C$_{28}$H$_{31}$FN$_4$O$_3$, 490.24; m/z found, 491.2 [M+H]$^+$. $^1$H NMR (400 MHz, CDCl$_3$): 7.8 (s, 1H), 7.23–7.15 (m, 5H), 6.92–6.88 (m, 3H), 6.83–6.79 (m, 2H), 6.77–6.75 (m, 2H), 6.64 (d, J=8.2 Hz, 1H), 4.58 (dd, J=14.6, 8.0 Hz, 1H), 3.29–3.13 (m, 2H), 3.09 (dd, J=13.5, 6.5 Hz, 1H), 2.96 (dd, J=13.4, 8.0 Hz, 1H), 2.54–2.48 (m, 3H), 2.42–2.37 (m, 6H), 1.70–1.67 (m, 4H).

Example 60

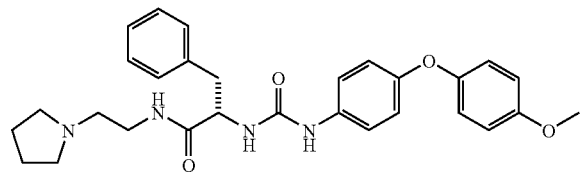

(S)-2-{3-[4-(4-Methoxy-phenoxy)-phenyl]-ureido}-3-phenyl-N-(2-pyrrolidin-1-yl-ethyl)-propionamide A. 4-(4-Methoxy-phenoxy)-nitrobenzene. Prepared from 4-methoxyphenol as in Example 4, step A. $^1$H NMR (400 MHz, CDCl$_3$): 8.20–8.16 (m, 2H), 7.06–7.02 (m, 2H), 7.0–6.7 (m, 4H), 3.85 (s, 3H).

B. 4-(4-Methoxy-phenoxy)-phenylamine. Prepared from 4-(4-methoxy-phenoxy)-nitrobenzene as in Example 4, step B. MS (electrospray): mass calculated for C$_{13}$H$_{13}$NO$_2$, 215.09; m/z found, 216.1 [M+H]$^+$. $^1$H NMR (400 MHz, CDCl$_3$): 6.91–6.88 (m, 2H), 6.85–6.80 (m, 4H), 6.67–6.64 (m, 2H), 3.78 (s, 3H).

C. (S)-2-{3-[4-(4-Methoxy-phenoxy)-phenyl]-ureido}-3-phenyl-N-(2-pyrrolidin-1-yl-ethyl)-propionamide. Prepared as in Example 59, substituting 4-(4-methoxy-phenoxy)-phenylamine for 4-(4-fluoro-phenoxy)-phenylamine. MS (electrospray): mass calculated for C$_{29}$H$_{34}$N$_4$O$_4$, 502.26, m/z found: 503.2, [M+H]$^+$. $^1$H NMR (400 MHz, CD$_3$OD): 7.32–7.28 (m, 2H), 7.25–7.22 (m, 5H), 6.89 (s, 4H), 6.84–6.81 (m, 2H), 4.46–4.42 (m, 1H), 3.77 (s, 3H), 3.37–3.31 (m, 2H), 3.08 (dd, J=13.7, 6.5 Hz, 1H), 2.97 (dd, J=13.6, 7.8 Hz, 1H), 2.69–2.61 (m, 6H), 1.85–1.78 (m, 4H).

Example 61

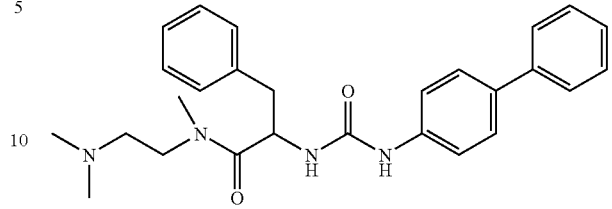

2-(3-Biphenyl-4-yl-ureido)-N-(2-dimethylamino-ethyl)-N-methyl-3-phenyl-propionamide A. (S)-2-(3-Biphenyl-4-yl-ureido)-3-phenyl-propionic acid methyl ester. TEA (1.52 g, 15 mmol) was added to a suspension of (S)-2-amino-3-phenyl-propionic acid methyl ester hydrochloride (2.15 g, 10 mmol) in toluene (30 mL) at 0° C. After a few minutes, a solution of 4-isocyanato-biphenyl (2.05 g, 10.5 mmol) in CH$_2$Cl$_2$ was added dropwise to the mixture. After stirring for 6 h at rt, the mixture was poured into water (50 mL) and extracted with ethyl acetate (3×75 mL). The combined organics were washed with brine (25 mL), and dried (Na$_2$SO$_4$). Removal of the solvents under reduced pressure followed by flash column chromatography on 0.5 g of crude product using 10–50% ethyl acetate/hexanes yielded 0.43 g (86%) of pure product. MS (electrospray): mass calculated for C$_{23}$H$_{22}$N$_2$O$_3$, 374.16; m/z found, 375.2 [M+H]$^+$. $^1$H NMR (400 MHz, CDCl$_3$): 7.51–7.16 (m, 12H), 7.13–7.10 (m, 2H), 6.98 (s, 1H), 5.66 (d, J=8 Hz, 1H), 4.88–4.80 (m, 1H), 3.73 (s, 3H), 3.14 (dd, J=13.9, 5.6 Hz, 1H), 3.01 (dd, J=13.9, 6.5 Hz, 1H).

B. 2-(3-Biphenyl-4-yl-ureido)-3-phenyl-propionic acid. LiOH (0.19 g, 4.5 mmol) was added to 2-(3-biphenyl-4-yl-ureido)-3-phenyl-propionic acid methyl ester (1.12 g, 3 mmol) in THF/MeOH/H$_2$O (28 mL, 1:2:2). After stirring for 4 h, the mixture was poured into H$_2$O (100 mL), and the pH was adjusted to 3–4 with 10% HCl. The aqueous layer was extracted with ethyl acetate (3×75 mL). The combined organics were washed with brine (50 mL) and dried (Na$_2$SO$_4$), and the solvents were removed. The residue was recrystallized from 20% CH$_2$Cl$_2$/hexanes to yield 0.63 g (58%) of a white solid. MS (electrospray): mass calculated for C$_{22}$H$_{20}$N$_2$O$_3$, 360.15; m/z found, 361.1 [M+H]$^+$. $^1$H NMR (400 MHz, DMSO-d$_6$): 13.05 (s, 1H), 8.69 (s, 1H), 7.61–7.21 (m, 14H), 6.37 (d, J=8 Hz, 1H), 4.51–4.35 (m, 1H), 3.10 (dd, J=13.9, 5.2 Hz, 1H), 2.99 (dd, J=13.9, 7.6 Hz, 1H).

C. 2-(3-Biphenyl-4-yl-ureido)-N-(2-dimethylamino-ethyl)-N-methyl-3-phenyl-propionamide. Prepared as in Example 13, step B, substituting N,N,N'-trimethyl-ethane-1,2-diamine for N',N'-diethyl-propane-1,3-diamine. MS (electrospray): mass calculated for C$_{27}$H$_{32}$N$_4$O$_2$, 444.25; m/z found, 445.2 [M+H]$^+$. $^1$H NMR (400 MHz, CD$_3$OD): Mixture of rotamers, 7.7–7.2 (m, 14H), 5.05 (m, 1H), 3.6–3.3 (m, 2H), 3.1–2.9 (m, 2H), 2.89 (s, 1H), 2.87 (s, 2H), 2.38–2.35 (m, 1.34H), 2.24 (s, 2H), 2.21 (s, 1H), 2.18–2.05 (m, 0.66H).

Example 62

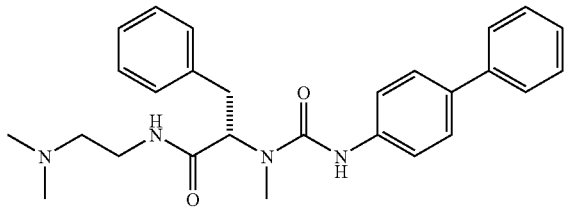

(R)-2-(3-Biphenyl-4-yl-1-methyl-ureido)-N-(2-dimethylamino-ethyl)-3-phenyl-propionamide A. (R)-2-(3-Biphenyl-4-yl-1-methyl-ureido)-3-phenyl-propionic acid. Triethylamine (0.17 g, 1.68 mmol) was added to a suspension of (S)-2-methylamino-3-phenyl-propionic acid (0.2 g, 1.12 mmol) in 1:1 acetone/H$_2$O (80 mL). Once the (S)-2-methylamino-3-phenyl-propionic acid dissolved, 4-biphenylyl isocyanate (0.228 g, 1.17 mmol) was added as a solution in THF (1.5 mL) at 0° C. As the mixture was warmed to rt, solids crashed out of solution. The mixture was stirred for 7 h at rt, and then the solvents were removed. After acidifying with 1 N HCl (10 mL) to bring the pH to 2, the reaction mixture was filtered, and the aqueous filtrate was extracted with EtOAc (3×40 mL). The combined organic layers were washed with brine and dried (MgSO$_4$), and the solvent was removed. Column chromatography using [5–20% (1% NH$_4$OH/MeOH)/CH$_2$Cl$_2$] afforded 0.1 g (24%) of the desired product. MS (electrospray): mass calculated for C$_{23}$H$_{22}$N$_2$O$_3$, 374.16; m/z found, 375.1 [M+H]$^+$, 397.1 [M+Na]$^+$. $^1$H NMR (400 MHz, CD$_3$OD): 7.63–7.59 (m, 4H), 7.45–7.41 (m, 2H), 7.36–7.29 (m, 4H), 7.23–7.21 (m, 2H), 7.04–7.01 (m, 2H), 4.48 (t, J=4.1 Hz, 1H), 3.37–3.33 (m, 1H), 3.25 (dd, J=14.4, 3.8 Hz, 1H), 3.10 (s, 3H).

B. (R)-2-(3-Biphenyl-4-yl-1-methyl-ureido)-N-(2-dimethylamino-ethyl)-3-phenyl-propionamide. Prepared as in Example 13, step B, from (R)-2-(3-biphenyl-4-yl-1-methyl-ureido)-3-phenyl-propionic acid and substituting N',N'-dimethyl-ethane-1,2-diamine for N',N'-diethyl-propane-1,3-diamine. MS (electrospray): mass calculated for C$_{27}$H$_{32}$N$_4$O$_2$, 444.25; m/z found, 445.2 [M+H]$^+$. $^1$H NMR (400 MHz, CD$_3$OD): 7.62–7.50 (m, 4H), 7.45–7.26 (m, 8H), 7.23–7.18 (m, 1H), 5.02 (dd, J=10.3, 5.7 Hz, 1H), 3.42–3.34 (m, 2H), 3.09–3.03 (m, 1H), 2.93 (s, 3H), 2.52 (t, J=6.5 Hz, 1H), 2.32 (s, 6H).

Example 63

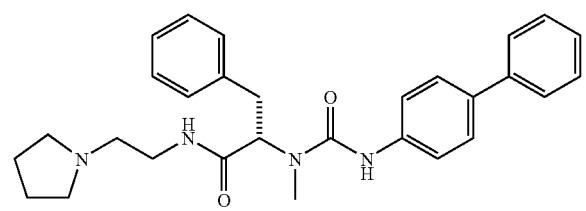

(S)-2-(3-Biphenyl-4-yl-1-methyl-ureido)-3-phenyl-N-(2-pyrrolidin-1-yl-ethyl)-propionamide Prepared as in Example 62, substituting 2-pyrrolidin-1-yl-ethylamine for N',N'-dimethyl-ethane-1,2-diamine. MS (electrospray): mass calculated for C$_{29}$H$_{39}$N$_4$O$_2$, 470.27; m/z found, 471.3 [M+H]$^+$. $^1$H NMR (400 MHz, CD$_3$OD): 7.63–7.51 (m, 4H), 7.42–7.35 (m, 4H), 7.30–7.27 (m, 5H), 7.24–7.18 (m, 1H), 3.48–3.33 (m, 3H), 3.13–3.05 (m, 1H), 2.92 (s, 3H), 2.82–2.60 (m, 6H), 1.88–1.75 (m, 4H).

Example 64

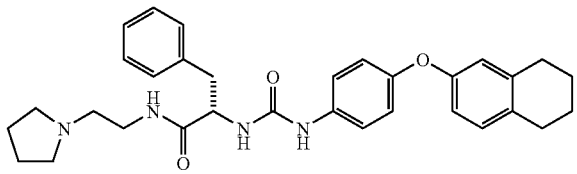

(S)-3-Phenyl-N-(2-pyrrolidin-1-yl-ethyl)-2-{3-[4-(5,6,7,8-tetrahydro-naphthalen-2-yloxy)-phenyl]-ureido}-propionamide A. 6-(4-Nitro-phenoxy)-1,2,3,4-tetrahydro-naphthalene. Prepared by a route similar to Example 4, step A. $^1$H NMR (400 MHz, CDCl$_3$): 8.24–8.18 (m, 2H), 7.12 (d, J=8.0 Hz, 1H), 7.03–6.99 (m, 2H), 6.84–6.78 (m, 2H), 2.83–2.74 (m, 4H), 1.89–1.76 (m, 4H).

B. 4-(5,6,7,8-Tetrahydro-naphthalen-2-yloxy)-phenylamine. Prepared by a route similar to Example 4, step B. MS (electrospray): mass calculated for C$_{16}$H$_{17}$NO, 239.13; m/z found, 240.1 [M+H]$^+$. $^1$H NMR (400 MHz, CDCl$_3$): 6.76 (d, J=8.4 Hz, 1H), 6.67–6.63 (m, 2H), 6.50–6.45 (m, 3H), 6.43 (d, J=2.5 Hz, 1H), 2.53–2.44 (m, 4H), 1.61–1.51 (m, 4H).

C. (S)-3-Phenyl-N-(2-pyrrolidin-1-yl-ethyl)-2-{3-[4-(5,6,7,8-tetrahydro-naphthalen-2-yloxy)-phenyl]-ureido}-propionamide. Prepared as in Example 59, substituting 4-(5,6,7,8-tetrahydro-naphthalen-2-yloxy)-phenylamine for 4-(4-fluoro-phenoxy)-phenylamine. MS (electrospray): mass calculated for C$_{32}$H$_{38}$N$_4$O$_3$, 526.29; m/z found, 527.3 [M+H]$^+$. $^1$H NMR (400 MHz, CD$_3$OD): 7.35–7.22 (m, 7H), 6.99–6.97 (m, 1H), 6.86–6.83 (m, 2H), 6.66–6.64 (m, 1H), 6.62–6.61 (m, 1H), 4.49–4.46 (m, 1H), 3.07 (dd, J=13.8, 6.6 Hz, 1H), 2.97 (dd, J=13.4, 7.6 Hz, 1H), 2.74–2.64 (m, 4H), 2.57–2.45 (m, 6H), 1.82–1.72 (m, 8H).

Example 65

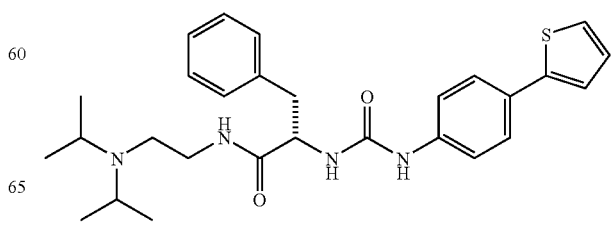

(S)-N-(2-Diisopropylamino-ethyl)-3-phenyl-2-[3-(4-thiophen-2-yl-phenyl)-ureido]-propionamide A. 4-Thiophen-2-yl-phenylamine. To a mixture of 4-bromo aniline (0.34 g, 2 mmol), $Na_2CO_3$ (0.85 g, 8 mmol), 2-thiopheneboronic acid (0.30 g, 2.6 mmol) and tetrakis(triphenylphosphine)-palladium(0) (0.23 g, 0.2 mmol), a solvent mixture of benzene/EtOH/$H_2O$ was added. The mixture was heated at 71° C. for 15 h. The reaction mixture was cooled, diluted with ethyl acetate (75 mL), washed with brine (2×30 mL), and dried ($Na_2SO_4$). The solvents were removed. Flash column chromatography of the residue yielded 83 mg (24%) of the desired product. MS (electrospray): mass calculated for $C_{10}HGNS$, 175.05; m/z found, 176.0 $[M+H]^+$.

B. (4-Thiophen-2-yl-phenyl)-carbamic acid phenyl ester. Prepared by a route similar to Example 3, step A. MS (electrospray): mass calculated for $C_{17}H_{13}NO_2S$, 295.07; m/z found, 296.0 $[M+H]^+$, 318.0 $[M+H]^+$.

C. (S)-N-(2-Diisopropylamino-ethyl)-3-phenyl-2-[3-(4-thiophen-2-yl-phenyl)-ureido]-propionamide. Prepared as in Example 3, step C, substituting 4-thiophen-2-yl-phenyl)-carbamic acid phenyl ester for [4-(4-chloro-phenoxy)-phenyl]-carbamic acid phenyl ester. MS (electrospray): mass calculated for $C_{28}H_{36}N_4O_2S$, 492.26; m/z found, 493.2 $[M+H]^+$. $^1$H NMR (400 MHz, $CD_3OD$): 7.51–7.03 (m, 12H), 4.47 (t, J=7.4 Hz, 1H), 3.31–2.96 (m, 6H), 2.41 (br s, 2H), 0.97 (d, J=10.4 Hz, 12H).

Example 66

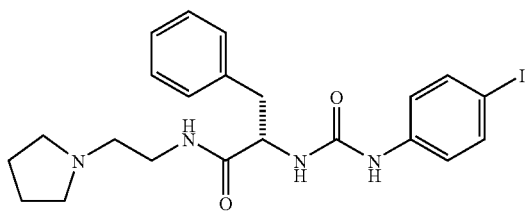

(S)-2-[3-(4-Iodo-phenyl)-ureido]-3-phenyl-N-(2-pyrrolidin-1-yl-ethyl)-propionamide Prepared as in Example 12, from [(S)-2-phenyl-1-(2-pyrrolidin-1-yl-ethylcarbamoyl)-ethyl]-carbamic acid tert-butyl ester (Example 9, step A), and substituting 1-iodo-4-isocyanato-benzene for 4-isocyanato-biphenyl. MS (electrospray): mass calculated for $C_{22}H_{27}IN_4O_2$, 506.12; m/z found, 507.1 $[M+H]^+$. $^1$H NMR (400 MHz, DMSO-$d_6$): 8.78 (s, 1H), 8.07 (t, J=5.4 Hz, 1H), 7.52 (d, J=8.2 Hz, 2H), 7.28–7.18 (m, 7H), 6.36 (d, J=8.2 Hz, 1H), 4.43 (q, J=7.5 Hz, 1H), 3.10 (m, 2H), 2.96 (dd, J=13.6, 5.6 Hz, 1H), 2.83 (dd, J=13.6, 7.5 Hz, 1H), 2.42 (br m, 6H), 1.65 (br s, 4H).

Example 67

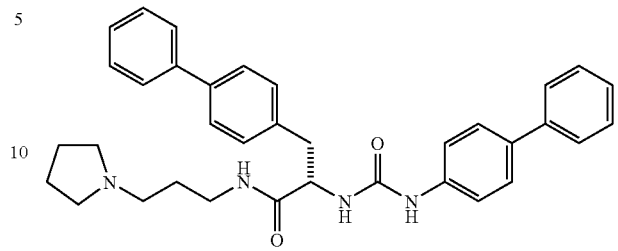

(S)-3-Biphenyl-4-yl-2-(3-biphenyl-4-yl-ureido)-N-(3-pyrrolidin-1-yl-propyl)-propionamide A. A mixture of solid support resin (PS-Indole-CHO, 500 mg, 0.5 mmol), Ti(OiPr)$_4$ (1.0 mmol) and 3-pyrrolidin-1-yl-propylamine (1.0 mmol) in THF (4 mL) was agitated for 4 h. Then 1.5 mL (~0.75 M) of $NaBH_4$ in absolute EtOH was added, and the mixture was agitated for 2.5 h. The resin was filtered off and washed with DMF (2×), MeOH (2×), DCM (2×) and ether (2×).

B. A solution of (S)-3-biphenyl-4-yl-2-(9H-fluoren-9-yl-methoxycarbonylamino)-propionic acid (0.306 g, 0.66 mmol) in DMF/DCM (1:3, 2 mL) was added to a solution of DIC (0.083 g, 0.66 mmol) in DMF/DCM (1 mL) and shaken for 2–3 min. This solution was added to the resin from step A (0.12 g, 0.13 mmol) followed by a small crystal of DMAP. The mixture was agitated for 18 h and filtered, and the resin was washed with DMF (2×), DCM (2×), MeOH (2×), DCM (2×) and ether (2×).

C. A solution of piperidine in DMF (20%, 2 mL) was added to the resin from step B, and the mixture was agitated for 2 h. The resin was filtered off and washed with DMF (2×), DCM (2×), MeOH (2×), DCM (2×) and ether (2×).

D. A solution of 4-isocyanato-biphenyl (0.14 g, 0.73 mmol) in DMF (2 mL) was added to the resin from step C, and the mixture was agitated for 20 h. The resin was filtered off and washed with DMF (2×), DCM (2×), MeOH (2×), DCM (2×) and ether (2×).

E. (S)-3-Biphenyl-4-yl-2-(3-biphenyl-4-yl-ureido)-N-(3-pyrrolidin-1-yl-propyl)-propionamide. A solution of TFA in DCM (50%, 1.5 mL) was added to the resin from step D, and the mixture was agitated for 1.5 h. The resin was filtered off and washed with DCM (2×), and the filtrate and the washings were collected. The crude product was purified by preparative reverse phase HPLC. MS (electrospray): mass calculated for $C_{35}H_{38}N_4O_2$, 546.30; m/z found, 547.26 $[M+H]^+$. $^1$H NMR (500 MHz, DMSO-$d_6$): 8.85 (s, 1H), 8.28 (t, J=5.7 Hz, 1H), 7.65–7.32 (m, 18H), 6.53 (d, J=7.9 Hz, 1H), 4.44 (m, 1H), 3.47 (br s, 2H), 3.18–2.88 (m, 8H), 1.91 (br s, 2H), 1.81 (br s, 2H), 1.75 (m, 2H).

Example 68

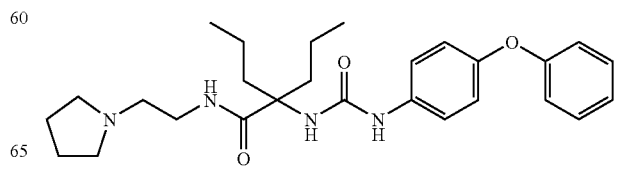

2-[3-(4-Phenoxy-phenyl)-ureido]-2-propyl-pentanoic Acid (2-pyrrolidin-1-yl-ethyl)-amide A. 2-tert-Butoxycarbonylamino-2-propyl-pentanoic acid. To a solution of 2-amino-2-propyl-pentanoic acid (1 g, 6.28 mmol) in acetonitrile (30 mL) was added in tetramethylammonium hydroxide pentahydrate (1.2 g, 6.28 mmol). After 30 min of stirring, the reaction mixture became a solution. Di-tert-butyl dicarbonate (2 g, 9.4 mmol) was then added. The reaction mixture was stirred at rt for 3 days, after which more di-tert-butyl dicarbonate (0.685 g, 3.14 mmol) was added. After stirring overnight, EtOAc (30 mL) and Et$_2$O (30 mL) were added. Citric acid (10%) was used to adjust the pH to 2–3. The aqueous layer was extracted with EtOAc (3×50 mL). The combined organic layers were washed with brine, and dried (MgSO$_4$). Removal of the solvent under reduced pressure afforded 1 g (62%) of the desired product. MS (electrospray): mass calculated for $C_{13}H_{25}NO_4$, 259.18; m/z found, 258.1 [M–H]$^-$. $^1$H NMR (400 MHz, CD$_3$OD): 2.11–2.05 (m, 2H), 1.77–1.70 (m, 2H), 1.43 (s, 9H), 1.31–1.26 (m, 2H), 1.17–1.08 (m, 2H), 0.928 (t, J=7.3 Hz, 6H).

B. [1-Propyl-1-(2-pyrrolidin-1-yl-ethylcarbamoyl)-butyl]-carbamic acid tert-butyl ester. Prepared as in Example 1, step A, from 2-tert-butoxycarbonylamino-2-propyl-pentanoic acid, and substituting 2-pyrrolidin-1-yl-ethylamine for 3-pyrrolidin-1-yl-propylamine. MS (electrospray): mass calculated for $C_{19}H_{37}N_3O_3$, 355.28; m/z found, 356.3 [M+H]$^+$. $^1$H NMR (400 MHz, CD$_3$OD): 3.37–3.33 (m, 2H), 2.64–2.53 (m, 6H), 2.04–1.89 (m, 2H), 1.85–1.77 (m, 4H), 1.75–1.65 (m, 2H), 1.43 (s, 9H), 1.28–1.19 (m, 2H), 1.16–1.10 (m, 2H), 0.91–0.87 (m, 6H).

C. 2-[3-(4-Phenoxy-phenyl)-ureido]-2-propyl-pentanoic acid (2-pyrrolidin-1-yl-ethyl)-amide. Prepared as in Example 12, from [1-propyl-1-(2-pyrrolidin-1-yl-ethylcarbamoyl)-butyl]-carbamic acid tert-butyl ester, and substituting 4-phenoxyphenyl isocyanate for 4-isocyanato-biphenyl. MS (electrospray): mass calculated for $C_{27}H_{38}N_4O_3$, 466.29; m/z found, 467.3 [M+H]$^+$. $^1$H NMR (400 MHz, CD$_3$OD): 7.33–7.28 (m, 4H), 7.07–7.03 (m, 1H), 6.94–6.89 (m, 4H), 3.41 (t, J=6.8 Hz, 2H), 2.78–2.62 (m, 6H), 2.12 (dt, J=13.3, 4.2 Hz, 2H), 1.83–1.73 (m, 6H), 1.35–1.27 (m, 2H), 1.21–1.14 (m, 2H), 0.92 (t, J=7.3 Hz, 6H).

Example 69

B. To the resin from step A (20 g) in DCM (500 mL), ethane 1,2-diamine (7.8 g) was added followed by DIPEA (16.25 g). The mixture was agitated for 24 h. The resin was filtered off, washed with DCM (2×), DMF (2×), MeOH (2×), DCM (3×) and ether (3×), and dried under vacuum.

C. A solution of (S)-3-cyclohexyl-2-(9H-fluoren-9-yl-methoxycarbonylamino)-propionic acid (0.29 g, 0.75 mmol) in DMF/DCM (1:3, 2 mL) was added to a solution of DIC (0.094 g, 0.75 mmol) in DMF/DCM (1 mL) and was shaken for 2–3 min. This solution was added to the resin from step B (0.12 g, 0.156 mmol) followed by a small crystal of DMAP. The mixture was agitated for 20 h and filtered, and the resin was washed with DMF (2×), DCM (2×), MeOH (2×), DCM (2×) and ether (2×).

D. To the resin from step C, a solution of piperidine in DMF (20%, 2 mL) was added and the mixture was agitated for 2 h. The resin was filtered off, and washed with DMF (2×), DCM (2×), MeOH (2×), DCM (2×) and ether (2×).

E. To the resin from step D, a solution of 4-isocyanato-biphenyl (0.195 g, 1 mmol) in DMF (2 mL) was added, and the mixture was agitated for 20 h. The resin was filtered off and washed with DMF (2×), DCM (2×), MeOH (2×), DCM (2×) and ether (2×).

F. (S)-N-(2-Amino-ethyl)-2-(3-biphenyl-4-yl-ureido)-3-cyclohexyl-propionamide. To the resin from step E, a solution of TFA in DCM (50%, 2 mL) was added and the mixture was agitated for 2.5 h. The resin was filtered off and washed with DCM (2×). The filtrate and washings were collected, and the product was isolated by preparative reverse phase HPLC. MS (electrospray): mass calculated for $C_{24}H_{32}N_4O_2$, 408.25; m/z found, 409.2 [M+H]$^+$. $^1$H NMR (500 MHz, DMSO-d$_6$): 8.87 (s, 1H), 8.26 (t, J=5.6 Hz, 1H), 7.84 (br s, 3H), 7.61–7.04 (m, 8H), 7.28 (m, 1H), 6.54 (d, J=7.8 Hz, 1H), 4.20 (m, 1H), 3.29–3.27 (m, 2H), 2.88–2.85 (m, 2H), 1.79 (br d, J=12.2 Hz, 1H), 1.66–1.13 (m, 10H), 0.95–0.86 (m, 2H).

Example 70

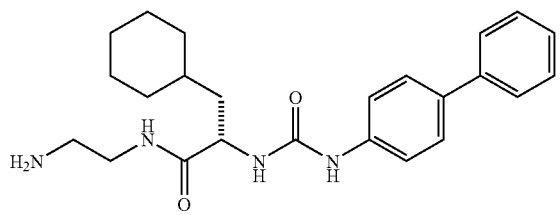

(S)-N-(2-Amino-ethyl)-2-(3-biphenyl-4-yl-ureido)-3-cyclohexyl-propionamide

A. To solid support resin (Wang, 99 g, 1.3 mmol/g) in THF (1000 mL) was added CDI (62.8 g, 387 mmol), and the mixture was agitated for 5 h. Subsequently, the resin was filtered off, washed with THF (3×), MeOH (3×), DCM (3×) and ether (3×), and dried under vacuum.

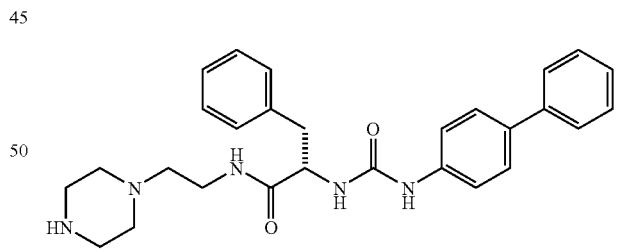

(S)-2-(3-Biphenyl-4-yl-ureido)-3-phenyl-N-(2-piperazin-1-yl-ethyl)-propionamide

Prepared as in Example 13, substituting 2-piperazin-1-yl-ethylamine for N',N'-diethyl-propane-1,3-diamine in step B. MS (electrospray): mass calculated for $C_{28}H_{33}N_5O_2$, 471.26; m/z found, 472.3 [M+H]$^+$. $^1$H NMR (400 MHz, CD$_3$OD): 7.56–7.07 (m, 14H), 4.5 (t, J=7.3 Hz, 1H), 3.28 (m, 2H), 3.12 (dd, J=13.7, 6.6 Hz, 1H), 3.07 (dd, J=13.7, 7.6 Hz, 1H), 2.96 (m, 4H), 2.38 (m, 6H).

Example 71

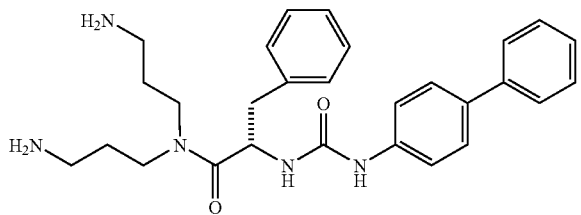

(S)-N,N-Bis-(3-amino-propyl)-2-(3-biphenyl-4-yl-ureido)-3-phenyl-propionamide

A. [3-(3-tert-Butoxycarbonylamino-propylamino)-propyl]-carbamic acid tert-butyl ester. To a solution of N-(3-amino-propyl)-propane-1,3-diamine (0.2 g, 1.5 mmol) in THF (4 mL) at 0° C., a solution of 2-(tert-butoxycarbonyloxyimino)-2-phenylacetonitrile (0.75 g, 3 mmol) in THF was added. After stirring at 0° C. for one h, the mixture was warmed to rt overnight. EtOAc (20 mL) and H$_2$O (20 mL) were then added. The aqueous layer was extracted with EtOAc (3×20 mL). The combined organic layers were washed with 1 N NaOH (20 mL) and brine (20 mL), and dried (MgSO$_4$). The solvent was removed. Column chromatography using [0–20% (1% NH$_4$OH/MeOH)/CH$_2$Cl$_2$] afforded 100 mg (20%) of the desired product. MS (electrospray): mass calculated for C$_{16}$H$_{33}$N$_3$O$_4$, 331.25; m/z found, 332.2 [M+H]$^+$. $^1$H NMR (400 MHz, CDCl$_3$): 5.15 (s, 1H), 3.19–3.09 (m, 4H), 2.60 (t, J=6.5 Hz, 4H), 2.17 (br s, 1H), 1.61 (p, J=6.4 Hz, 4H), 1.37 (s, 18H).

B. {3-[[(S)-2-(3-Biphenyl-4-yl-ureido)-3-phenyl-propionyl]-(3-tert-butoxycarbonylamino-propyl)-amino]-propyl}-carbamic acid tert-butyl ester. Prepared as in Example 13, substituting [3-(3-tert-butoxycarbonylamino-propylamino)-propyl]-carbamic acid tert-butyl ester for N',N'-diethyl-propane-1,3-diamine in step B. MS (electrospray): mass calculated for C$_{38}$H$_{51}$N$_5$O$_6$, 673.38; m/z found, 696.4 [M+Na]$^+$. $^1$H NMR (400 MHz, CDCl$_3$): 7.48–7.42 (m, 4H), 7.37–7.30 (m, 4H), 7.23–7.14 (m, 6H), 5.25 (br s, 1H), 5.06 (br s, 1H), 4.91 (br s, 1H), 3.42 (br s, 1H), 3.17–3.12 (m, 2H), 3.02–2.86 (m, 6H), 1.63–1.50 (m, 6H), 1.40 (s, 9H), 1.34 (s, 9H).

C. (S)—N,N-Bis-(3-amino-propyl)-2-(3-biphenyl-4-yl-ureido)-3-phenyl-propionamide. To a solution of {3-[[(S)-2-(3-biphenyl-4-yl-ureido)-3-phenyl-propionyl]-(3-tert-butoxycarbonylamino-propyl)-amino]-propyl}-carbamic acid tert-butyl ester (0.1 g, 0.148 mmol) in CH$_2$Cl$_2$, was added 4 M HCl/dioxane (2 mL). The reaction mixture was stirred at rt for 2 h, and the solvent was then removed. The residue was dissolved in MeOH and treated with strongly basic ion exchange resin. The mixture was stitrred for 10 min, the resin was filtered off, and the solvent was removed, affording the desired product (0.06 g, 85%). MS (electrospray): mass calculated for C$_{28}$H$_{35}$N$_5$O$_2$, 473.28; m/z found, 474.3 [M+H]$^+$. $^1$H NMR (400 MHz, CD$_3$OD): 7.57–7.51 (m, 4H), 7.42–7.38 (m, 4H), 7.34–7.25 (m, 5H), 3.56–3.46 (m, 1H), 3.45–3.33 (m, 2H), 3.28–3.21 (m, 1H), 3.10–3.04 (m, 1H), 3.02–2.97 (m, 1H), 2.95–2.91 (m, 2H), 2.89–2.74 (m, 2H), 2.06–1.92 (m, 1H), 1.88–1.73 (m, 3H).

Example 72

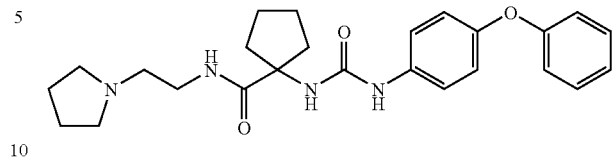

1-[3-(4-Phenoxy-phenyl)-ureido]-cyclopentanecarboxylic Acid (2-pyrrolidin-1-yl-ethyl)-amide A. 1-tert-Butoxycarbonylamino-cyclopentanecarboxylic acid. TEA (1.52 g, 15 mmol) was added dropwise to a solution of 1-amino-cyclopentanecarboxylic acid (1.24 g, 10 mmol) and 2-(tert-butoxycarbonyloxyimino)-2-phenylacetonitrile in acetone/water (40 mL, 1:1). After the reaction mixture was stirred for 4 h, the acetone was evaporated and the remaining aqueous layer was extracted with ether (3×40 mL). The aqueous layer was acidified to pH3 with 10% HCl, and extracted with CH$_2$Cl$_2$ (3×70 mL). The combined organic layers were washed with brine (40 mL), and dried (Na$_2$SO$_4$). Removal of the solvent under reduced pressure yielded the desired crude product. MS (electrospray): mass calculated for C$_{11}$H$_{19}$NO$_4$, 229.13; m/z found, 228.1 [M−H]$^-$. $^1$H NMR (400 MHz, DMSO-d$_6$): 12.45 (br s, 1H), 7.16 (br s, 1H), 1.94–1.85 (br m, 4H), 1.60–1.46 (br s, 4H), 1.36 (s, 9H).

B. 1-[3-(4-Phenoxy-phenyl)-ureido]-cyclopentanecarboxylic acid (2-pyrrolidin-1-yl-ethyl)-amide. Prepared by a route similar to Example 68, steps B and C, substituting 1-tert-butoxycarbonylamino-cyclopentanecarboxylic acid for 2-tert-butoxycarbonylamino-2-propyl-pentanoic acid in step B, and carrying the product of that step forward without purification. MS (electrospray): mass calculated for C$_{25}$H$_{32}$N$_4$O$_3$, 436.25; m/z found, 437.2 [M+H]$^+$. $^1$H NMR (400 MHz, CD$_3$OD): 8.31 (t, J=5.9 Hz, 1H), 7.31 (m, 4H), 7.05 (m, 1H), 6.92 (m, 4H), 3.57 (m, 4H), 3.30 (m, 2H), 3.08 (m, 2H), 2.22 (m, 2H), 2.02 (m, 2H), 1.84 (m, 8H).

Example 73

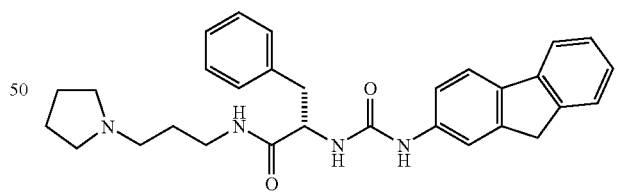

(S)-2-[3-(9H-Fluoren-2-yl)-ureido]-3-phenyl-N-(3-pyrrolidin-1-yl-propyl)-propionamide Prepared by a route similar to Example 12. MS (electrospray): mass calculated for C$_{30}$H$_{34}$N$_4$O$_2$, 482.27; m/z found, 483.2 [M+H]$^+$. $^1$H NMR (400 MHz, DMSO-d$_6$): 8.76 (s, 1H), 8.09 (t, J=5.3 Hz, 1H), 7.76 (m, 3H), 7.51 (d, J=7.5 Hz, 1H), 7.27 (m, 8H), 6.37 (d, J=8.1 Hz, 1H), 4.41 (q, J=7.5 Hz, 1H), 3.84 (s, 2H), 3.03 (m, 2H), 2.97 (dd, J=13.4, 5.8 Hz, 1H), 2.85 (dd, J=13.4, 5.8 Hz, 1H), 2.5 (br s, 4H), 2.32 (m, 2H), 1.65 (br m, 4H), 1.51 (m, 2H).

Example 74

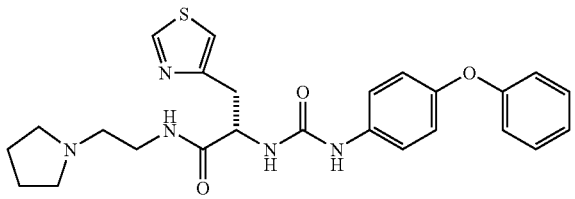

(S)-2-[3-(4-Phenoxy-phenyl)-ureido]-N-(2-pyrrolidin-1-yl-ethyl)-3-thiazol-4-yl-propionamide A. [(S)-1-(2-Pyrrolidin-1-yl-ethylcarbamoyl)-2-thiazol-4-yl-ethyl]-carbamic acid tert-butyl ester. Prepared by a route similar to Example 1, step A, substituting (S)-2-tert-butoxycarbonylamino-3-thiazol-4-yl-propionic acid for (S)-2-tert-butoxycarbonylamino-3-phenyl-propionic acid, and 2-pyrrolidin-1-yl-ethylamine for 3-pyrrolidin-1-yl-propylamine. MS (electrospray): mass calculated for $C_{17}H_{28}N_4O_3S$, 368.19; m/z found, 369.2 [M+H]$^+$. $^1$H NMR (400 MHz, CD$_3$OD): 8.94 (s, 1H), 7.29 (s, 1H), 4.43–4.40 (m, 1H), 3.26–3.25 (m, 2H), 3.12–3.06 (m, 1H), 2.57–2.51 (m, 6H), 1.83–1.76 (m, 4H), 1.39 (s, 9H).

B. (S)-2-[3-(4-Phenoxy-phenyl)-ureido]-N-(2-pyrrolidin-1-yl-ethyl)-3-thiazol-4-yl-propionamide. Prepared by a route similar to Example 12. MS (electrospray): mass calculated for $C_{25}H_{29}N_5O_3S$, 479.6; m/z found, 480.2 [M+H]$^+$. $^1$H NMR (400 MHz, CD$_3$OD): 8.94 (d, J=2.0 Hz, 1H), 7.34–7.28 (m, 5H), 7.06–7.05 (m, 1H), 6.93–6.88 (m, 4H), 4.65 (dd, J=7.6, 5.5 Hz, 1H), 3.29–3.20 (m, 2H), 2.56–2.50 (m, 6H), 1.82–1.73 (m, 4H).

Example 75

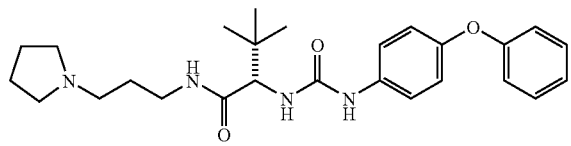

(S)-3,3-Dimethyl-2-[3-(4-phenoxy-phenyl)-ureido]-N-(3-pyrrolidin-1-yl-propyl)-butyramide Prepared as in Example 67, substituting (S)-2-[(9H-fluoren-9-yl)-methoxycarbonyl-amino]-3,3-dimethyl-butyric acid for (S)-3-biphenyl-4-yl-2-(9H-fluoren-9-ylmethoxycarbonylamino)-propionic acid in step B, and 4-phenoxyphenyl isocyanate for 4-isocyanato-biphenyl in step D. MS (electrospray): mass calculated for $C_{26}H_{36}N_4O_3$, 452.28; m/z found, 453.26 [M+H]$^+$. $^1$H NMR (500 MHz, DMSO-d$_6$): 8.63 (s, 1H), 8.15 (t, J=5.6 Hz, 1H), 7.43–7.21 (m, 4H), 6.95 (t, J=7.4 Hz, 1H), 6.83–6.79 (m, 4H), 6.30 (d, J=9.1 Hz, 1H), 3.88 (d, J=9.1 Hz, 1H), 3.39 (br s, 2H), 2.98 (m, 4H), 2.83 (br s, 2H), 1.83–1.60 (m, 6H), 0.91 (s, 9H).

Example 76

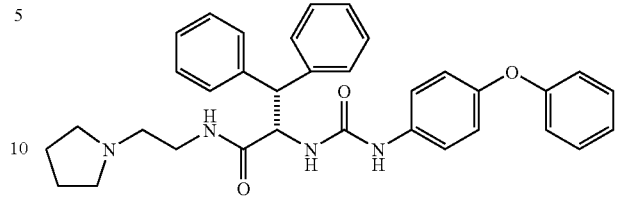

(S)-2-[3-(4-Phenoxy-phenyl)-ureido]-3,3-diphenyl-N-(2-pyrrolidin-1-yl-ethyl)-propionamide

[(S)-2,2-Diphenyl-1-(2-pyrrolidin-1-yl-ethylcarbamoyl)-ethyl]-carbamic acid tert-butyl ester was prepared as in Example 1, step A, from (S)-2-tert-butoxycarbonylamino-3,3-diphenyl-propionic acid, substituting 2-pyrrolidin-1-yl-ethylamine for 3-pyrrolidin-1-yl-propylamine. The title compound was subsequently prepared from the tert-butyl ester as in Example 12, substituting 4-phenoxyphenyl isocyanate for 4-isocyanato-biphenyl. MS (electrospray): mass calculated for $C_{34}H_{36}N_4O_3$, 548.68; m/z found, 549.3 [M+H]$^+$. $^1$H NMR (400 MHz, CDCl$_3$): 7.44 (d, J=7.4 Hz, 2H), 7.32–7.28 (m, 3H), 7.23–7.15 (m, 9H), 7.02–6.96 (m, 3H), 6.87–6.84 (m, 2H), 6.77–6.75 (m, 2H), 6.51–6.46 (m, 2H), 5.16 (dd, J=10.7, 9.5 Hz, 1H), 4.41 (d, J=10.9 Hz, 1H), 3.02–2.97 (m, 1H), 2.96–2.89 (m, 1H), 2.25–2.20 (m, 3H), 2.17–2.15 (m, 1H), 2.02–1.93 (m, 1H), 1.62–1.60 (m, 4H).

Example 77

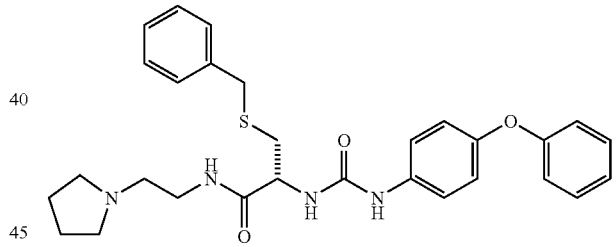

(R)-3-Benzylsulfanyl-2-[3-(4-phenoxy-phenyl)-ureido]-N-(2-pyrrolidin-1-yl-ethyl)-propionamide A. [(R)-2-Benzylsulfanyl-1-(2-pyrrolidin-1-yl-ethylcarbamoyl)-ethyl]-carbamic acid tert-butyl ester. Prepared by a route similar to Example 1, step A. MS (electrospray): mass calculated for $C_{21}H_{33}N_3O_3S$, 407.22; m/z found, 408.2 [M+H]$^+$. $^1$H NMR (400 MHz, CD$_3$OD): 7.34–7.27 (m, 4H), 7.24–7.20 (m, 1H), 4.22 (t, J=6.7 Hz, 1H), 3.75 (s, 2H), 3.37–3.34 (m, 3H), 2.82 (dd, J=13.8, 5.8 Hz, 1H), 2.64–2.57 (m, 6H), 1.82–1.76 (m, 4H), 1.46 (s, 9H).

B. (R)-3-Benzylsulfanyl-2-[3-(4-phenoxy-phenyl)-ureido]-N-(2-pyrrolidin-1-yl-ethyl)-propionamide. Prepared as in Example 12, from [(R)-2-benzylsulfanyl-1-(2-pyrrolidin-1-yl-ethylcarbamoyl)-ethyl]-carbamic acid tert-butyl ester, substituting 4-phenoxyphenyl isocyanate for 4-isocyanato-biphenyl. MS (electrospray): mass calculated for $C_{29}H_{34}N_4O_3S$, 518.6; m/z found, 519 [M+H]$^+$. $^1$H NMR (400 MHz, CD$_3$OD): 7.37–7.33 (m, 4H), 7.32–7.27 (m, 4H), 7.23–7.19 (m, 1H), 7.08–7.03 (m, 1H), 6.96–6.87 (m, 4H), 4.45 (t, J=6.8 Hz, 1H), 3.78 (s, 2H), 3.38 (t, J=6.7 Hz, 2H), 2.86 (dd, J=13.7, 5.9 Hz, 1H), 2.76 (dd, J=13.7, 6.9 Hz, 1H), 2.65 (dt, J=6.9, 1.8 Hz, 2H), 2.61–2.59 (m, 4H), 1.81–1.76 (m, 4H).

Example 78

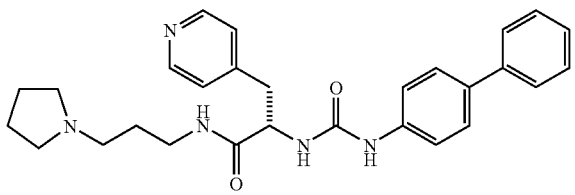

(S)-2-(3-Biphenyl-4-yl-ureido)-3-pyridin-4-yl-N-(3-pyrrolidin-1-yl-propyl)-propionamide Prepared by a route similar to Example 67. MS (electrospray): mass calculated for $C_{28}H_{33}N_5O_2$, 471.26; m/z found, 472.24 [M+H]$^+$. $^1$H NMR (500 MHz, DMSO-d$_6$): 8.94 (s, 1H), 8.66 (d, J=5.9 Hz, 2H), 8.40 (t, J=5.7 Hz, 1H), 7.82–7.32 (m, 11H), 6.71 (d, J=8.1 Hz, 1H), 4.6 (m, 1H), 3.62 (m, 2H), 3.29–3.02 (m, 8H), 2.08–1.72 (m, 6H).

Example 79

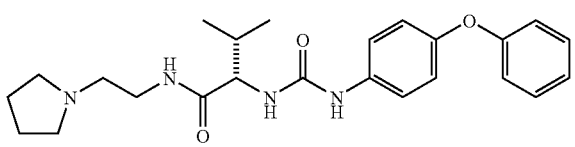

(S)-3-Methyl-2-[3-(4-phenoxy-phenyl)-ureido]-N-(2-pyrrolidin-1-yl-ethyl)-butyramide A. [(S)-2-Methyl-1-(2-pyrrolidin-1-yl-ethylcarbamoyl)-propyl]-carbamic acid benzyl ester. Prepared as in Example 1, step A, from (S)-2-benzyloxycarbonylamino-3-methyl-butyric acid, substituting 2-pyrrolidin-1-yl-ethylamine for 3-pyrrolidin-1-yl-propylamine. MS (electrospray): mass calculated for $C_{19}H_{29}N_3O_3$, 347.22; m/z found, 348.2 [M+H]$^+$. $^1$H NMR (400 MHz, CD$_3$OD): 7.37–7.27 (m, 5H), 5.09 (s, 2H), 3.88 (d, J=6.8 Hz, 1H), 3.39–3.33 (m, 2H), 2.65–2.53 (m, 6H), 2.10–2.01 (m, 1H), 1.82–1.78 (m, 4H), 0.95–0.91 (m, 6H).

B. (S)-2-Amino-3-methyl-N-(2-pyrrolidin-1-yl-ethyl)-butyramide. To a solution of [(S)-2-methyl-1-(2-pyrrolidin-1-yl-ethylcarbamoyl)-propyl]-carbamic acid benzyl ester (0.6 g, 1.73 mmol) in EtOH (17 mL) was added 10% Pd/C (0.21 g). The resulting suspension was stirred under H$_2$ at rt overnight. The suspension was then filtered (diatomaceous earth), and the filtrate was concentrated under reduced pressure. Column chromatography [10–20% (NH$_4$OH/MeOH)/CH$_2$Cl$_2$] afforded the desired product (0.2 g, 54%). MS (electrospray): mass calculated for $C_{11}H_{23}N_3O$, 213.18; m/z found, 214.2 [M+H]$^+$. $^1$H NMR (400 MHz, CD$_3$OD): 3.39–3.35 (m, 2H), 3.34 (s, 1H), 3.05 (d, J=5.8 Hz, 1H), 2.64 (d, J=6.9 Hz, 2H), 2.63–2.59 (m, 4H), 1.95–1.89 (m, 1H), 1.84–1.80 (m, 4H), 0.95 (d, J=6.9 Hz, 3H), 0.91 (d, J=6.8 Hz, 3H).

C. (S)-3-Methyl-2-[3-(4-phenoxy-phenyl)-ureido]-N-(2-pyrrolidin-1-yl-ethyl)-butyramide. 4-Phenoxy-phenyl isocyanate (0.1 g, 0.47 mmol) was added to a solution of (S)-2-amino-3-methyl-N-(2-pyrrolidin-1-yl-ethyl)-butyramide (0.05 g, 0.23 mmol) in CH$_2$Cl$_2$ (2.3 mL). The reaction mixture was stirred at rt overnight, after which EtOAc (10 mL) and H$_2$O (10 mL) were added. The aqueous layer was extracted with EtOAc (3×10 mL). The combined organic layers were washed with brine (20 mL), and dried (MgSO$_4$). The solvent was removed. Purification of the residue by flash column chromatography [0–20% MeOH (1% NH$_4$OH)/CH$_2$Cl$_2$] afforded 0.058 g (50%) of the desired product. MS (electrospray): mass calculated for $C_{24}H_{32}N_4O_3$, 424.5; m/z found, 425.2 [M+H]$^+$. $^1$H NMR (400 MHz, CD$_3$OD): 8.71 (s, 1H), 8.05 (t, J=5.6 Hz, 1H), 7.43–7.37 (m, 2H), 7.36–7.31 (m, 2H), 7.06 (t, J=7.4 Hz, 1H), 6.95–6.91 (m, 4H), 6.3 (d, J=9.0 Hz, 1H), 3.33 (s, 6H), 3.27–3.12 (m, 2H), 2.47–2.38 (m, 5H), 1.99–1.89 (m, 1H), 1.7–1.62 (m, 4H), 0.87 (d, J=6.8 Hz, 3H), 0.84 (d, J=6.8 Hz, 3H).

Example 80

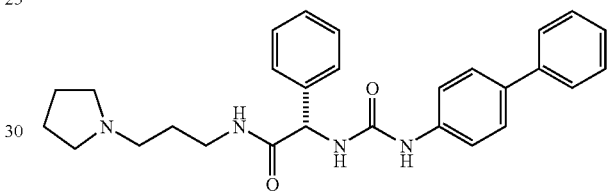

(S)-2-(3-Biphenyl-4-yl-ureido)-2-phenyl-N-(3-pyrrolidin-1-yl-propyl)-acetamide

Prepared by a route similar to Example 67. MS (electrospray): mass calculated for $C_{28}H_{32}N_4O_2$, 456.25; m/z found, 457.26 [M+H]$^+$. $^1$H NMR (400 MHz, DMSO-d$_6$): 8.76 (s, 1H), 8.38 (t, J=5.5 Hz, 1H), 7.46–7.15 (m, 14H), 6.91 (d, J=7.6 Hz, 1H), 5.14 (d, J=7.6 Hz, 1H), 3.31–2.73 (m, 8H), 1.79–1.56 (m, 6H).

Example 81

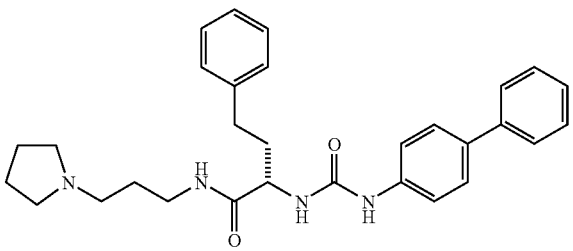

(S)-2-(3-Biphenyl-4-yl-ureido)-4-phenyl-N-(3-pyrrolidin-1-yl-propyl)-butyramide

Prepared by a route similar to Example 67. MS (electrospray): mass calculated for $C_{30}H_{36}N_4O_2$, 484.28; m/z found, 485.24 [M+H]$^+$. $^1$H NMR (500 MHz, DMSO-d$_6$): 8.87 (s, 1H), 8.24 (t, J=5.7 Hz, 1H), 7.61 (d, J=8.4 Hz, 2H), 7.56 (d, J=8.7 Hz, 2H), 7.31–7.19 (m, 6H), 6.66 (d, J=7.6 Hz, 1H), 4.18 (m, 1H), 3.51 (br s, 2H), 3.18–3.09 (m, 4H), 2.94 (br s, 2H), 2.64–2.51 (m, 2H), 1.98–1.77 (m, 8H).

Example 82

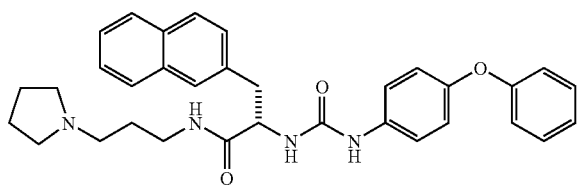

(S)-3-Naphthalen-2-yl-2-[3-(4-phenoxy-phenyl)-ureido]-N-(3-pyrrolidin-1-yl-propyl)-propionamide Prepared by a route similar to Example 67. MS (electrospray): mass calculated for C$_{33}$H$_{36}$N$_4$O$_3$, 536.28; m/z found, 537.27 [M+H]$^+$. $^1$H NMR (500 MHz, DMSO-d$_6$): 8.75 (s, 1H), 8.24 (t, J=5.7 Hz, 1H), 7.85 (m, 3H), 7.73 (s, 1H), 7.48–7.32 (m, 7H), 7.06 (m, 1H), 6.91 (m, 4H), 6.51 (d, J=8.1 Hz, 1H), 4.51 (m, 1H), 3.41 (br s, 2H), 3.16–3.10 (m, 3H), 3.03 (dd, J=13.6, 7.9 Hz, 1H), 2.94 (m, 2H), 2.78 (br s, 2H), 1.90 (br s, 2H), 1.81 (br s, 2H), 1.66 (m, 2H).

Example 83

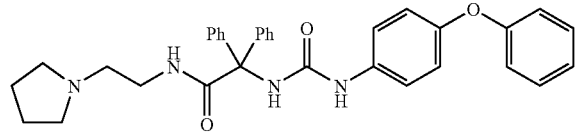

2-[3-(4-Phenoxy-phenyl)-ureido]-2,2-diphenyl-N-(2-pyrrolidin-1-yl-ethyl)-acetamide A. tert-Butoxycarbonylamino-diphenyl-acetic acid. Prepared by a route similar to Example 68, step A. MS (electrospray): mass calculated for C$_{19}$H$_{21}$NO$_4$, 327.15; m/z found, 350.1 [M+Na]$^+$. $^1$H NMR (400 MHz, CDCl$_3$): 7.61–7.29 (m, 10H), 1.56–0.88 (m, 9H).

B. [Diphenyl-(2-pyrrolidin-1-yl-ethylcarbamoyl)-methyl]-carbamic acid tert-butyl ester. Prepared by a route similar to Example 68, step B. MS (electrospray): mass calculated for C$_{25}$H$_{33}$N$_3$O$_3$, 423.25; m/z found, 424.2 [M+H]$^+$. $^1$H NMR (400 MHz, CDCl$_3$): 7.45–7.43 (m, 4H), 7.38–7.30 (m, 6H), 6.61 (br s, 1H), 6.54 (br s, 1H), 3.34 (q, J=5.7 Hz, 2H), 2.51 (t, J=6.2 Hz, 2H), 2.40–2.31 (m, 4H), 1.70–1.61 (m, 4H), 1.39 (br s, 9H).

C. 2-[3-(4-Phenoxy-phenyl)-ureido]-2,2-diphenyl-N-(2-pyrrolidin-1-yl-ethyl)-acetamide. Prepared by a route similar to Example 68, step C. MS (electrospray): mass calculated for C$_{33}$H$_{34}$N$_4$O$_3$, 534.65; m/z found, 535.2 [M+H]$^+$. $^1$H NMR (400 MHz, CD$_3$OD): 7.46–7.43 (m, 4H), 7.36–7.27 (m, 10H), 7.06–7.02 (m, 1H), 6.91–6.86 (m, 4H), 3.39 (t, J=6.7 Hz, 2H), 2.59 (t, J=6.5 Hz, 2H), 2.51 (br s, 4H), 1.74–1.69 (m, 4H).

Example 84

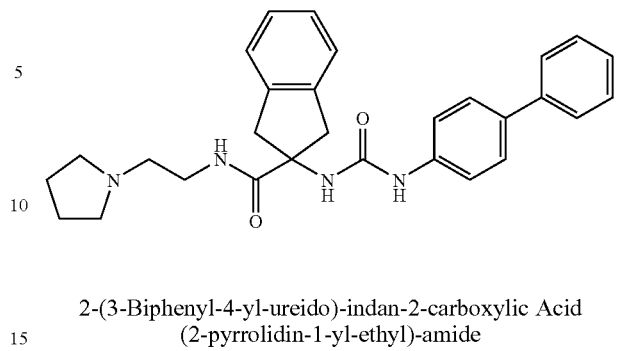

2-(3-Biphenyl-4-yl-ureido)-indan-2-carboxylic Acid (2-pyrrolidin-1-yl-ethyl)-amide A. [2-(2-Pyrrolidin-1-yl-ethylcarbamoyl)-indan-2-yl]-carbamic acid tert-butyl ester. Prepared as in Example 1, step A, substituting 2-tert-butoxycarbonylamino-indan-2-carboxylic acid for 2-tert-butoxycarbonylamino-3-phenyl-propionic acid, and 2-pyrrolidin-1-yl-ethylamine for 3-pyrrolidin-1-yl-propylamine. MS (electrospray): mass calculated for C$_{21}$H$_{31}$N$_3$O$_3$, 373.24; m/z found, 374.2 [M+H]$^+$. $^1$H NMR (400 MHz, CD$_3$OD): 7.18–7.12 (m, 4H), 3.55 (d, J=16.4 Hz, 2H), 3.37 (t, J=7.0 Hz, 2H), 3.14 (d, J=16.5 Hz, 2H), 2.64–2.57 (m, 6H), 1.84–1.76 (m, 4H), 1.42 (s, 9H).

B. 2-(3-Biphenyl-4-yl-ureido)-indan-2-carboxylic acid (2-pyrrolidin-1-yl-ethyl)-amide. Prepared by a route similar to Example 12. MS (electrospray): mass calculated for C$_{29}$H$_{32}$N$_4$O$_2$, 468.2; m/z found, 469.2 [M+H]$^+$. $^1$H NMR (400 MHz, CD$_3$OD): 7.56–7.53 (m, 2H), 7.51–7.48 (m, 2H), 7.41–7.36 (m, 4H), 7.28–7.26 (m, 1H), 7.25–7.22 (m, 2H), 7.19–7.12 (m, 2H), 3.65 (d, J=16.5 Hz, 2H), 3.41 (t, J=6.8 Hz, 2H), 3.21 (d, J=16.5 Hz, 2H), 2.66 (t, J=6.7 Hz, 2H), 2.59–2.57 (m, 4H), 1.82–1.71 (m, 4H).

Example 85

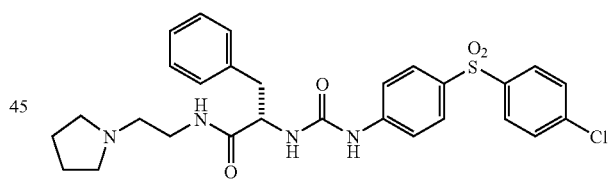

(S)-2-{3-[4-(4-Chloro-benzenesulfonyl)-phenyl]-ureido}-3-phenyl-N-(2-pyrrolidin-1-yl-ethyl)-propionamide A. 4-(4-Chloro-phenylsulfanyl)-nitrobenzene. Prepared by a route similar to Example 4, step A. $^1$H NMR (400 MHz, CDCl$_3$): 8.11–8.07 (m, 2H), 7.50–7.41 (m, 4H), 7.22–7.18 (m, 2H).

B. 4-(4-Chloro-phenylsulfanyl)-phenylamine. Prepared by a route similar to Example 4, step B. MS (electrospray): mass calculated for C$_{12}$H$_{10}$ClNS, 235.02; m/z found, 236.0 [M+H]$^+$. $^1$H NMR (400 MHz, CDCl$_3$): 7.23–7.20 (m, 2H), 7.10–7.07 (m, 2H), 6.97–6.93 (m, 2H), 6.62–6.56 (m, 2H).

C. [4-(4-Chloro-phenylsulfanyl)-phenyl]-carbamic acid phenyl ester. Prepared by a route similar to Example 3, step A. MS (electrospray): mass calculated for C$_{19}$H$_{14}$ClNO$_2$S, 355.04; m/z found, 356.0 [M+H]$^+$, 378.0 [M+Na]$^+$. $^1$H NMR (400 MHz, CDCl₃): 7.39–7.30 (m, 4H), 7.20–7.15 (m, 4H), 7.13–7.08 (m, 4H), 6.77–6.75 (m, 1H).

D. [4-(4-Chloro-benzenesulfonyl)-phenyl]-carbamic acid phenyl ester. To a solution of [4-(4-chloro-phenylsulfanyl)-phenyl]-carbamic acid phenyl ester (0.13 g, 0.37 mmol) in CH₂Cl₂ (4 mL), was added 3-chloro-peroxybenzoic acid (0.063 g, 0.37 mmol) in batches at 0° C. After stirring at 0° C. for 20 min, the reaction mixture was warmed to rt for 1 h and then cooled back down to 0° C., and more 3-chloro-peroxybenzoic acid (0.076 g, 0.44 mmol) was added. The reaction mixture was then allowed to warm to rt overnight. The next day, more 3-chloro-peroxybenzoic acid (0.076 g, 0.44 mmol) was added to the mixture at 0° C. The mixture was stirred another 3 h at rt, and 1 N NaOH (5 mL) and CH₂Cl₂ (20 mL) were added. The aqueous layer was extracted with CH₂Cl₂ (3×30 mL), and the combined organic layers were washed with brine, dried (MgSO₄), and concentrated under reduced pressure. Column chromatography using 0–50% EtOAc/hexane, and then 10% MeOH/EtOAc afforded 0.11 g (77%) of the desired product. MS (electrospray): mass calculated for $C_{19}H_{14}ClNO_4S$, 387.03; m/z found, 388.0 [M+H]⁺, 410.0 [M+Na]⁺. ¹H NMR (400 MHz, CD₃OD): 7.94–7.89 (m, 4H), 7.73–7.71 (m, 2H), 7.60–7.57 (m, 2H), 7.42–7.38 (m, 2H), 7.27–7.23 (m, 1H), 7.19–7.15 (m, 2H).

E. (S)-2-{3-[4-(4-Chloro-benzenesulfonyl)-phenyl]-ureido}-3-phenyl-N-(2-pyrrolidin-1-yl-ethyl)-propionamide. Prepared as in Example 3, step C, substituting [(S)-2-phenyl-1-(2-pyrrolidin-1-yl-ethylcarbamoyl)-ethyl]-carbamic acid tert-butyl ester (Example 9, step A) for [(S)-1-(2-diisopropylamino-ethylcarbamoyl)-2-phenyl-ethyl]-carbamic acid tert-butyl ester, and [4-(4-chloro-benzenesulfonyl)-phenyl]-carbamic acid phenyl ester for [4-(4-chloro-phenoxy)-phenyl]-carbamic acid phenyl ester. MS (electrospray): mass calculated for $C_{28}H_{31}ClN_4O_4S$, 554.18; m/z found, 555.2 [M+H]⁺. ¹H NMR (400 MHz, CD₃OD): 7.91–7.88 (m, 2H), 7.82–7.79 (m, 2H), 7.58–7.52 (m, 4H), 7.3–7.17 (m, 5H), 4.47 (dd, J=7.5, 6.6 Hz, 1H), 3.28 (s, 1H), 3.07 (dd, J=13.7, 6.6 Hz, 1H), 2.96 (dd, J=13.7, 7.6 Hz, 1H), 2.56–2.44 (m, 6H), 1.8–1.7 (m, 4H).

Example 86

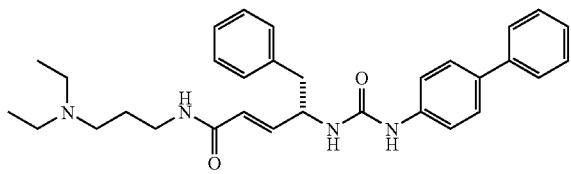

(E)-(S)-4-(3-Biphenyl-4-yl-ureido)-5-phenyl-pent-2-enoic Acid (3-diethylamino-propyl)-amide Prepared by a route similar to Example 19. MS (electrospray): mass calculated for $C_{31}H_{38}N_4O_2$, 498.30; m/z found, 499.3 [M+H]⁺. ¹H NMR (400 MHz, CDCl₃): 8.29 (s, 1H), 8.29 (t, J=4.8 Hz, 1H), 7.52–7.36 (m, 8H), 7.31–7.20 (m, 6H), 6.70 (dd, J=15.4, 6.8 Hz, 1H), 6.66 (d, J=9.7 Hz, 1H), 5.97 (dd, J=15.4, 0.9 Hz, 1H), 4.90–4.83 (m, 1H), 3.45–3.31 (m, 2H), 2.99 (dd, J=13.7, 6.9 Hz, 1H), 2.89 (dd, J=13.7, 7.2 Hz, 1H), 2.52–2.44 (m, 6H), 1.71–1.60 (m, 2H), 0.98 (t, J=7.1 Hz, 6H).

Example 87

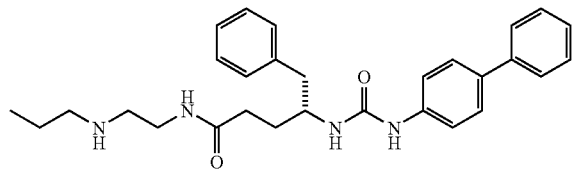

(R)-4-(3-Biphenyl-4-yl-ureido)-5-phenyl-pentanoic Acid (2-propylamino-ethyl)-amide A. (R)-4-(3-Biphenyl-4-yl-ureido)-5-phenyl-pentanoic acid. (R)-4-(3-Biphenyl-4-yl-ureido)-5-phenyl-pentanoic acid methyl ester (Example 2, method 1, step C) was hydrolyzed to provide the desired acid. MS (electrospray): mass calculated for $C_{24}H_{24}N_2O_3$, 388.46; m/z found, 389.2 [M+H]⁺, 441.1 [M+Na]⁺; 387.1 [M–H]⁻, 501.1 [M+TFA]⁻. ¹H NMR (DMSO-d₆, 400 MHz): 12.12 (br s, 1H), 8:44 (br s, 1H), 7.60 (d, J=7.3 Hz, 2H), 7.53 (d, J=8.7 Hz, 2H), 7.40–7.47 (m, 4H), 7.28–7.32 (m, 3H), 7.18–7.24 (m, 3H), 6.06 (d, J=8.6 Hz, 1H), 3.85–3.90 (m, 1H), 2.72–2.80 (m, 2H), 2.26–2.33 (m, 2H), 1.70–1.79 (m, 1H), 1.46–1.56 (m, 1H).

B. (R)-4-(3-Biphenyl-4-yl-ureido)-5-phenyl-Pentanoic acid (2-propylamino-ethyl)-amide. Prepared as in Example 18, step B, substituting (R)-4-(3-biphenyl-4-yl-ureido)-5-phenyl-pentanoic acid for (E)-(S)-4-[3-(4-phenoxy-phenyl)-ureido]-5-phenyl-pent-2-enoic acid, and N'-propyl-ethane-1,2-diamine for N'-methyl-ethane-1,2-diamine. MS (electrospray): mass calculated for $C_{29}H_{36}N_4O_2$, 472.28; m/z found, 473.3 [M+H]⁺, 495.3 [M+Na]⁺. ¹H NMR (400 MHz, CDCl₃): 7.87–7.83 (m, 1H), 7.50–7.09 (m, 14H), 6.91–6.82 (m, 1H), 5.70–5.64 (m, 1H), 4.07–3.98 (m, 1H), 3.27–3.16 (m, 2H), 2.83–2.77 (m, 1H), 2.69–2.57 (m, 4H), 2.41 (t, J=7.4 Hz, 2H), 2.24–2.18 (m, 2H), 1.78–1.74 (m, 1H), 1.66–1.61 (m, 1H), 1.40–1.30 (m, 1H), 1.21–1.15 (m, 1H), 0.77 (t, J=7.4 Hz, 3H).

Example 88

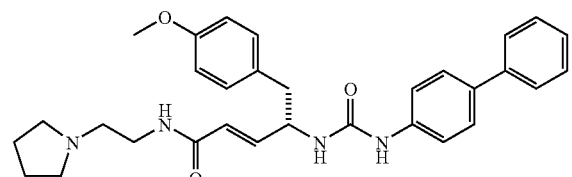

(E)-(S)-4-(3-Biphenyl-4-yl-ureido)-5-(4-methoxy-phenyl)-pent-2-enoic Acid (2-pyrrolidin-1-yl-ethyl)-amide A. (S)-2-tert-Butoxycarbonylamino-3-(4-methoxy-phenyl)-propionic acid methyl ester. Prepared by a route similar to Example 25, step A. MS (electrospray): mass calculated for $C_{16}H_{23}NO_5$, 309.36; m/z found, 332.2 [M+Na]⁺. ¹H NMR (CDCl₃, 400 MHz): 7.04 (d, J=8.6 Hz, 2H), 6.80–6.85 (m, 2H), 4.97 (d, J=7.6 Hz, 1H), 4.57 (m, 1H), 3.78 (s, 3H), 3.71 (s, 3H), 2.97–3.08 (m, 2H), 1.42 (s, 9H).

B. (E)-(S)-4-tert-Butoxycarbonylamino-5-(4-methoxyphenyl)-pent-2-enoic acid methyl ester. Prepared by a route similar to Example 25, step B. MS (electrospray): mass calculated for $C_{18}H_{25}NO_5$, 335.40; m/z found, 358.2 [M+Na]$^+$. $^1$H NMR (CDCl$_3$, 400 MHz): 7.09 (d, J=8.4 Hz, 2H), 6.92 (dd, J=15.5, 4.9 Hz, 1H), 6.86 (d, J=8.4 Hz, 1H), 5.87 (dd, J=15.5, 1.5 Hz, 1H), 4.56 (br s, 1H), 3.81 (s, 3H), 3.74 (s, 3H), 2.81–2.89 (m, 2H), 1.42 (s, 9H).

C. (E)-(S)-4-tert-Butoxycarbonylamino-5-(4-methoxyphenyl)-pent-2-enoic acid. Prepared by a route similar to Example 11, step A. MS (electrospray): mass calculated for $C_{17}H_{23}NO_5$, 321.37; m/z found, 320.1 [M–H]$^-$. $^1$H NMR (DMSO-d$_6$, 400 MHz): 12.29 (br s, 1H), 7.13 (d, J=8.3 Hz, 2H), 6.84 (d, J=8.3 Hz, 1H), 6.75 (dd, J=15.8, 5.7 Hz, 1H), 5.72 (d, J=15.8 Hz, 1H), 4.26 (br s, 1H), 3.71 (s, 3H), 2.75 (dd, J=13.8, 5.9 Hz, 1H), 2.65 (dd, J=13.8, 9.1 Hz, 1H), 1.33 (s, 9H).

D. [(E)-(S)-1-(4-Methoxy-benzyl)-3-(2-pyrrolidin-1-yl-ethylcarbamoyl)-allyl]-carbamic acid tert-butyl ester. Prepared by a route similar to Example 11, step B. MS (electrospray): mass calculated for $C_{25}H_{24}N_2O_4$, 416.47; m/z found, 417.1 [M+H]$^+$, 439.1 [M+Na]$^+$. $^1$H NMR (DMSO-d$_6$, 400 MHz): 12.24 (br s, 1H), 8.62 (br s, 1H), 7.52–7.65 (m, 4H), 7.38–7.48 (m, 2H), 7.27–7.36 (m, 3H), 7.12–7.17 (m, 2H), 6.83–6.89 (m, 2H), 6.75 (dd, J=15.8, 5.8 Hz, 1H), 6.38 (d, J=8.6 Hz, 1H), 5.73 (d, J=15.8 Hz, 1H), 4.26 (br s, 1H), 3.70 (s, 3H), 2.76–2.89 (m, 2H).

E. (E)-(S)-4-(3-Biphenyl-4-yl-ureido)-5-(4-methoxy-phenyl)-pent-2-enoic acid (2-pyrrolidin-1-yl-ethyl)-amide. Prepared by a route similar to Example 11, step C, from [(E)-(S)-1-(4-methoxy-benzyl)-3-(2-pyrrolidin-1-yl-ethylcarbamoyl)-allyl]-carbamic acid tert-butyl ester, substituting biphenyl-4-ylamine for 4-(4-fluoro-phenoxy)-phenylamine. MS (electrospray): mass calculated for $C_{31}H_{36}N_4O_3$, 512.65; m/z found, 513.3 [M+H]$^+$. $^1$H NMR (CDCl$_3$, 400 MHz): 7.94 (br s, 1H), 7.47 (d, J=7.1 Hz, 7H), 7.37–7.43 (m, 2H), 7.02 (d, J=8.6 Hz, 1H), 6.72 (d, J=8.6 Hz, 2H), 6.66 (dd, J=15.4, 5.2 Hz, 1H), 5.84 (dd, J=15.4, 1.5 Hz, 1H), 5.78 (br s, 1H), 4.67 (br s, 1H), 3.66 (s, 3H), 3.46–3.54 (m, 1H), 3.14–3.23 (m, 1H), 2.81 (dd, J=13.8, 7.2 Hz, 1H), 2.64–2.71 (m, 2H), 2.48–2.56 (m, 5H), 1.70 (br s, 4H).

Example 89

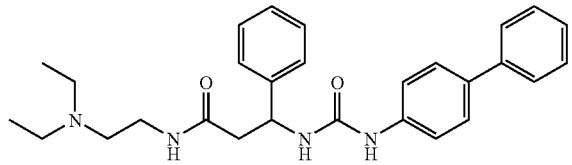

3-(3-Biphenyl-4-yl-ureido)-N-(2-diethylamino-ethyl)-3-phenyl-propionamide

Prepared as in Example 6, steps A and B, from 3-amino-3-phenylpropionic acid in step A, and substituting N',N'-diethyl-ethane-1,2-diamine for 2-pyrrolidin-1-yl-ethylamine in step B. MS (electrospray): mass calculated for $C_{28}H_{34}N_4O_2$, 458.27; m/z found, 459.3 [M+H]$^+$. $^1$H NMR (400 MHz, CDCl$_3$): 8.41 (s, 1H), 7.60 (br s, 1H), 7.47–7.45 (m, 2H), 7.39–7.34 (m, 8H), 7.30–7.18 (m, 4H), 5.56–5.50 (m, 1H), 3.30–3.24 (m, 2H), 2.94–2.78 (m, 2H), 2.50–2.40 (m, 6H), 0.89 (t, J=7.1 Hz, 6H).

Example 90

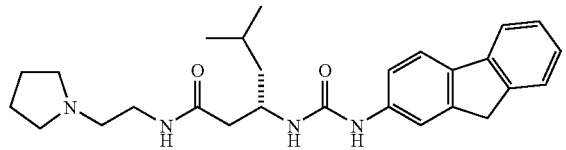

(S)-3-[3-(9H-Fluoren-2-yl)-ureido]-5-methyl-hexanoic Acid (2-pyrrolidin-1-yl-ethyl)-amide A. {(S)-3-Methyl-1-[(2-pyrrolidin-1-yl-ethylcarbamoyl)-methyl]-butyl}-carbamic acid tert-butyl ester. Prepared by a route similar to Example 15, step A. MS (electrospray): mass calculated for $C_{18}H_{35}N_3O_3$, 341.27, m/z found, 342.3 [M+H]$^+$. $^1$H NMR (400 MHz, CDCl$_3$): 6.17 (br s, 1H), 5.48 (br d, J=7.7 Hz, 1H), 3.97–3.91 (m, 1H), 3.49–3.40 (m, 1H), 3.35–3.28 (m, 1H), 2.64–2.57 (m, 2H), 2.53 (br s, 4H), 2.48–2.44 (m, 1H), 2.34 (dd, J=14.2, 4.9 Hz, 1H), 1.82–1.75 (m, 4H), 1.68–1.60 (m, 1H), 1.52–1.44 (m, 10H), 1.35–1.26 (m, 1H), 0.93 (d, J=2.6 Hz, 3H), 0.91 (d, J=2.8 Hz, 3H).

B. (S)-3-[3-(9H-Fluoren-2-yl)-ureido]-5-methyl-hexanoic acid (2-pyrrolidin-1-yl-ethyl)-amide. Prepared by a route similar to Example 15, step B. MS (electrospray): mass calculated for $C_{27}H_{36}N_4O_2$, 448.3; m/z found, 449.3 [M+H]$^+$. $^1$H NMR (400 MHz, CD$_3$OD): 7.72 (d, J=4.8 Hz, 2H), 7.69 (d, J=5.5 Hz, 2H), 7.64 (s, 1H), 7.57 (d, J=11.5 Hz, 1H), 7.32 (t, J=7.5 Hz, 1H), 7.27 (dd, J=8.2, 1.9 Hz, 1H), 7.23 (dt, J=7.5, 1.0 Hz, 1H), 4.30–4.19 (m, 1H), 3.85 (s, 1H), 3.43–3.36 (m, 2H), 2.97–2.72 (m, 6H), 2.42 (dd, J=13.7, 4.6 Hz, 1H), 2.29 (dd, J=13.5, 8.3 Hz, 1H), 1.8–1.7 (m, 4H), 1.55–1.47 (m, 1H), 1.39–1.32 (m, 1H), 0.97 (d, J=6.6 Hz, 6H).

Example 91

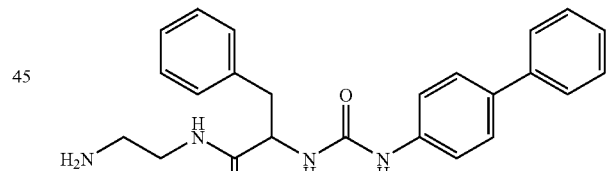

N-(2-Amino-ethyl)-2-(3-biphenyl-4-yl-ureido)-3-phenyl-propionamide

A. {2-[2-(3-Biphenyl-4-yl-ureido)-3-phenyl-propionylamino]-ethyl}-carbamic acid tert-butyl ester. Prepared as in Example 1, step A, from 2-(3-biphenyl-4-yl-ureido)-3-phenyl-propionic acid (racemate of Example 61, step B), substituting (2-amino-ethyl)-carbamic acid tert-butyl ester for 3-pyrrolidin-1-yl-propylamine. MS (electrospray): mass calculated for $C_{29}H_{34}N_4O_4$, 502.26; m/z found, 503.3 [M+H]$^+$, 403.3 [M-Boc]$^+$. $^1$H NMR (400 MHz, DMSO-d$_6$): 8.77 (s, 1H), 8.16 (t, J=5.3 Hz, 1H), 7.61–7.19 (m, 14H), 6.75 (t, J=5.4 Hz, 1H), 6.36 (d, J=8.2 Hz, 1H), 4.46 (q, J=7.5 Hz, 1H), 3.15–2.95 (m, 5H), 2.83 (dd, J=13.7, 7.5 Hz, 1H), 1.37 (s, 9H).

B. N-(2-Amino-ethyl)-2-(3-biphenyl-4-yl-ureido)-3-phenyl-propionamide. To a solution of {2-[2-(3-biphenyl-4-yl-ureido)-3-phenyl-propionylamino]-ethyl}-carbamic acid tert-butyl ester (0.25 g, 0.4974 mmol) in CH$_2$Cl$_2$ (20 mL), neat TFA (0.66 mL, 8.56 mmol) was added, and the mixture was stirred for 17 h at rt. The solvents were removed, and the residue was dissolved in ethyl acetate (100 mL). The solution was washed with saturated NaHCO$_3$ (2×25 mL) and brine (25 mL), and dried (Na$_2$SO$_4$), and the solvents were removed. Purification of the residue by flash column chromatography using 0–20% MeOH (1% NH$_4$OH)/CH$_2$Cl$_2$ afforded the desired product (0.15 g, 75%). MS (electrospray): mass calculated for C$_{24}$H$_{26}$N$_4$O$_2$, 402.21; m/z found, 403.2 [M+H]$^+$. $^1$H NMR (400 MHz, CDCl$_3$): 8.24 (br s, 1H), 7.58 (br s, 1H), 7.42–7.19 (m, 14H), 6.81 (d, J=7.6 Hz, 1H), 4.7 (q, J=7.2 Hz, 1H), 3.18 (br s, 2H), 3.06 (m, 2H), 2.67 (m, 2H), 2.50 (br s, 2H).

Example 92

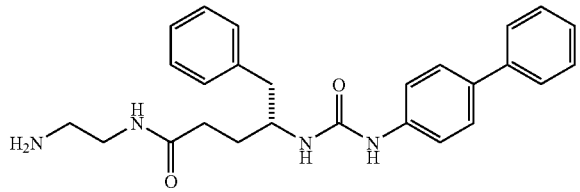

(R)-4-(3-Biphenyl-4-yl-ureido)-5-phenyl-pentanoic Acid (2-amino-ethyl)-amide

A. (R)-4-(3-Biphenyl-4-yl-ureido)-5-phenyl-pentanoic acid. Prepared as in Example 11, step A, substituting (R)-4-(3-biphenyl-4-yl-ureido)-5-phenyl-pentanoic acid methyl ester for (E)-(S)-4-tert-butoxycarbonylamino-5-phenyl-pent-2-enoic acid methyl ester. MS (electrospray): mass calculated for C$_{24}$H$_{24}$N$_2$O$_3$, 388.46; m/z found, 389.2 [M+H]$^+$, 411.1 [M+Na]$^+$, 387.1 [M–H]$^-$. $^1$H NMR (DMSO-d$_6$, 400 MHz): 12.00 (br s, 1H), 8.44 (br s, 1H), 7.52–7.62 (m, 4H), 7.40–7.47 (m, 4H), 7.28–7.32 (m, 4H), 7.18–7.24 (m 2H), 6.06 (d, J=8.6 Hz, 1H), 3.85–3.94 (m, 1H), 2.72–2.80 (m, 2H), 2.20–2.38 (m, 2H), 1.71–1.79 (m, 1H), 1.49–1.57 (m, 1H).

B. {2-[(R)-4-(3-Biphenyl-4-yl-ureido)-5-phenyl-pentanoylamino]-ethyl}-carbamic acid tert-butyl ester. Prepared as in Example 1, step A, from (R)-4-(3-biphenyl-4-yl-ureido)-5-phenyl-pentanoic acid, substituting (2-amino-ethyl)-carbamic acid tert-butyl ester for 3-pyrrolidin-1-yl-propylamine. MS (electrospray): mass calculated for C$_3$,H$_{38}$N$_4$O$_4$, 530.66; m/z found, 531.3 [M+H]$^+$, 553.3 [M+Na]$^+$. $^1$H NMR (DMSO-d$_6$, 400 MHz): 8.64 (br s, 1H), 7.84 (br s, 1H), 7.60 (d, J=8.1 Hz, 2H), 7.53 (d, J=8.5 Hz, 2H), 7.40–7.47 (m, 4H), 7.28–7.32 (m, 3H), 7.18–7.23 (m, 3H), 6.77 (br t, J=5.4 Hz, 1H), 6.03 (d, J=8.6 Hz, 1H), 3.86 (br s, 1H), 3.02–3.07 (m, 2H), 2.94–2.99 (m, 2H), 2.74 (d, J=6.4 Hz, 2H), 2.08–2.19 (m, 2H), 1.70–1.75 (m, 1H), 1.51–1.56 (m, 1H), 1.36 (s, 9H).

C. (R)-4-(3-Biphenyl-4-yl-ureido)-5-phenyl-pentanoic acid (2-amino-ethyl)-amide. Prepared by a route similar to Example 91, step B using 4 M HCl in dioxane instead of TFA. MS (electrospray): mass calculated for C$_{26}$H$_{30}$N$_4$O$_2$, 430.54; m/z found, 431.2 [M+H]$^+$. $^1$H NMR (DMSO-d$_6$, 400 MHz): 8.52 (br s, 1H), 7.79 (br t, J=5.1 Hz, 1H), 7.60 (d, J=7.3 Hz, 2H), 7.53 (d, J=8.7 Hz, 2H), 7.39–7.45 (m, 4H), 7.27–7.32 (m, 3H), 7.18–7.24 (m, 3H), 6.07 (d, J=8.6 Hz, 1H), 3.84–3.90 (m, 1H), 2.91–3.02 (m, 2H), 2.75 (d, J=6.5 Hz, 2H), 2.49 (br s, 2H), 2.13–2.18 (m, 2H), 1.68–1.76 (m, 1H), 1.49–1.59 (m, 1H).

Example 93

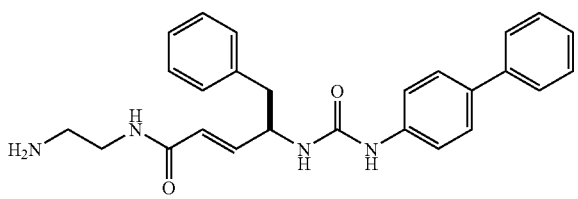

(E)-(R)-4-(3-Biphenyl-4-yl-ureido)-5-phenyl-pent-2-enoic Acid (2-amino-ethyl)-amide A. (E)-(R)-4-tert-Butoxycarbonylamino-5-phenyl-pent-2-enoic acid methyl ester. Prepared by a route similar to Example 2, Method 1, step A. MS (electrospray): mass calculated for C$_{17}$H$_{23}$NO$_4$, 305.16; m/z found, 328.1 [M+Na]$^+$. $^1$H NMR (400 MHz, CDCl$_3$): 7.16–7.31 (m, 5H), 6.92 (dd, J=15.7, 5.1 Hz, 1H), 5.90 (d, J=15.7 Hz, 1H), 4.79 (br s, 1H), 4.61 (br s, 1H), 3.70 (s, 3H), 2.88 (d, J=6.4 Hz, 2H), 1.39 (s, 9H).

B. (E)-(R)-4-tert-Butoxycarbonylamino-5-phenyl-pent-2-enoic acid. Prepared by a route similar to Example 11, step A. MS (electrospray): mass calculated for C$_{16}$H$_{21}$NO$_4$, 291.15; m/z found, 314.1 [M+Na]$^+$. $^1$H NMR (400 MHz, CDCl$_3$): 7.22–7.26 (m, 2H), 7.08–7.11 (m, 2H), 6.93 (dd, J=15.5, 4.7 Hz, 1H), 5.79 (d, J=15.5 Hz, 1H), 4.58 (br s, 1H), 4.48 (br s, 1H), 2.84 (d, J=6.8 Hz, 2H), 1.33 (s, 9H), remaining peak in the aromatic region was not detected and is believed to overlap with the solvent peak at 7.56 ppm.

C. (E)-(R)-4-(3-Biphenyl-4-yl-ureido)-5-phenyl-pent-2-enoic acid. Prepared by a route similar to Example 19, step A. MS (electrospray): mass calculated for C$_{24}$H$_{22}$N$_2$O$_3$, 386.16; n/z found, 387.1 [M+H]$^+$, 409.1 [M+Na]$^+$. $^1$H NMR (400 MHz, DMSO-d$_6$): 12.33 (br s, 1H), 8.59 (br s, 1H), 7.59–7.62 (m, 2H), 7.52–7.55 (m, 2H), 7.39–7.47 (m, 4H), 7.20–7.34 (m, 6H), 6.89 (dd, J=15.7, 5.1 Hz, 1H), 6.40 (d, J=8.4 Hz, 1H), 5.78 (dd, J=15.7, 1.6 Hz, 1H), 4.66 (br s, 1H), 2.94 (dd, J=13.7, 6.2 Hz, 1H), 2.86 (dd, J=13.7, 8.0 Hz, 1H).

D. {2-[(E)-(R)-4-(3-Biphenyl-4-yl-ureido)-5-phenyl-pent-2-enoylamino]-ethyl}-carbamic acid tert-butyl ester. Prepared as in Example 18, step B, from 4-(3-biphenyl-4-yl-ureido)-5-phenyl-pent-2-enoic acid, substituting (2-amino-ethyl)-carbamic acid tert-butyl ester for N'-methyl-ethane-1,2-diamine. MS (electrospray): mass calculated for C$_3$,H$_{36}$N$_4$O$_4$, 528.65; m/z found, 529.3 [M+H]$^+$, 551.1 [M+Na]$^+$. $^1$H NMR (400 MHz, CD$_3$OD): 7.49–7.60 (m, 4H), 7.36–7.40 (m, 4H), 7.21–7.30 (m, 6H), 6.79 (dd, J=15.4, 5.6 Hz, 1H), 5.99 (d, J=15.4 Hz, 1H), 4.72 (dd, J=12.3, 6.2 Hz, 1H), 3.29 (br t, J=6.1 Hz, 1H), 3.15 (br t, J=6.1 Hz, 1H), 2.97 (dd, J=13.7, 6.5 Hz, 1H), 2.89 (dd, J=13.7, 7.8 Hz, 1H), 1.36 (s, 9H).

E. (E)-(R)-4-(3-Biphenyl-4-yl-ureido)-5-phenyl-pent-2-enoic acid (2-amino-ethyl)-amide. Prepared by a route similar to Example 92, step C. MS (electrospray): mass calculated for C$_{26}$H$_{28}$N$_4$O$_2$, 428.22; m/z found, 429.2 [M+H]$^+$. $^1$H NMR (CD$_3$OD, 400 MHz): 7.40–7.47 (m, 4H), 7.27–7.31 (m, 4H), 7.12–7.22 (m, 6H), 6.72 (dd, J=15.4, 5.6 Hz, 1H), 5.92 (dd, J=15.4, 1.5 Hz, 1H), 4.62 (dd, J=12.4, 6.2 Hz, 1H), 3.27 (br t, J=6.2 Hz, 1H), 2.89 (dd, J=13.7, 6.7 Hz, 1H), 2.82 (dd, J=13.7, 7.8 Hz, 1H), 2.59 (br t, J=6.2 Hz, 1H).

Example 94

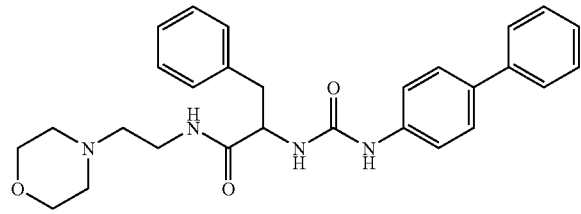

2-(3-Biphenyl-4-yl-ureido)-N-(2-morpholin-4-yl-ethyl)-3-phenyl-propionamide

Prepared as in Example 61, steps A and B, and Example 13, step B, substituting 2-morpholin-4-yl-ethylamine for N',N'-diethyl-propane-1,3-diamine. MS (electrospray): mass calculated for $C_{28}H_{32}N_4O_3$, 472.25; m/z found, 473.2 [M+H]$^+$. $^1$H NMR (400 MHz, CDCl$_3$): 8.17 (s, 1H), 7.47–7.02 (m, 14H), 4.83 (m, 1H), 3.58 (m, 4H), 3.24 (m, 2H), 3.15 (dd, J=13.2, 6.3 Hz, 1H), 3.02 (dd, J=13.2, 8.9 Hz, 1H), 2.37–2.17 (m, 6H).

Example 95

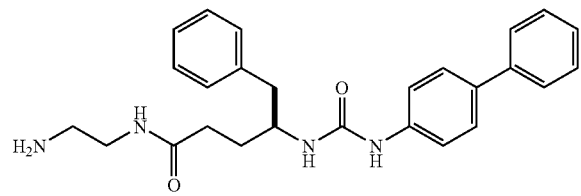

(S)-4-(3-Biphenyl-4-yl-ureido)-5-phenyl-pentanoic Acid (2-amino-ethyl)-amide

A. {2-[(S)-4-(3-Biphenyl-4-yl-ureido)-5-phenyl-pentanoylamino]-ethyl}-carbamic acid tert-butyl ester. Prepared as in Example 2, Method 1, step C, from {2-[(E)-(R)-4-(3-biphenyl-4-yl-ureido)-5-phenyl-pent-2-enoylamino]-ethyl}-carbamic acid tert-butyl ester (Example 93, step D). MS (electrospray): mass calculated for $C_{32}H_{38}N_4O_4$, 530.66; m/z found, 531.3 [M+H]$^+$, 553.2 [M+Na]$^+$. $^1$H NMR (400 MHz, CD$_3$OD): 7.44–7.47 (m, 2H), 7.39–7.42 (m, 2H), 7.27–7.31 (m, 4H), 7.06–7.21 (m, 6H), 3.87–3.94 (m, 2H), 3.14–3.18 (m, 1H), 3.00–3.10 (m, 3H), 2.68–2.77 (m, 2H), 2.18 (t, J=7.4 Hz, 2H), 1.75–1.84 (m, 1H), 1.53–1.62 (m, 1H), 1.30 (s, 9H).

B. (S)-4-(3-Biphenyl-4-yl-ureido)-5-phenyl-pentanoic acid (2-amino-ethyl)-amide. Prepared by a route similar to Example 92, step C. MS (electrospray): mass calculated for $C_{26}H_{30}N_4O_2$, 430.24; m/z found, 431.2 [M+H]$^+$, 453.2 [M+Na]$^+$, 883.4 [2M+Na]$^+$. $^1$H NMR (400 MHz, CDCl$_3$): 7.56 (br s, 1H), 7.47–7.13 (m, 14H), 6.70–6.66 (m, 1H), 5.22 (d, J=5.9 Hz, 1H), 4.08–4.01 (m, 1H), 3.27–3.18 (m, 2H), 2.81 (dd, J=13.6, 6.1 Hz, 1H), 2.73–2.67 (m, 3H), 2.29–2.12 (m, 2H), 1.79 (br s, 2H), 1.74–1.63 (m, 2H).

Example 96

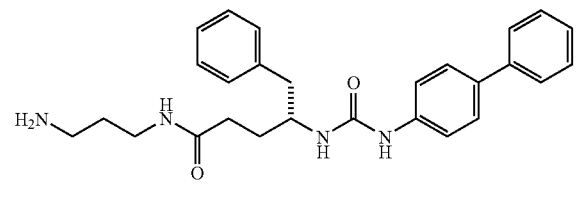

(R)-4-(3-Biphenyl-4-yl-ureido)-5-phenyl-pentanoic Acid (3-amino-propyl)-amide

A. {3-[(E)-(S)-4-(3-Biphenyl-4-yl-ureido)-5-phenyl-pent-2-enoylamino]-propyl}-carbamic acid tert-butyl ester. Prepared as in Example 18, step B, from (E)—(S)-4-(3-biphenyl-4-yl-ureido)-5-phenyl-pent-2-enoic acid (Example 19, step A), substituting (3-amino-propyl)-carbamic acid tert-butyl ester for N'-methyl-ethane-1,2-diamine. MS (electrospray): mass calculated for $C_{32}H_{38}N_4O_4$, 542.67; m/z found, 543.2 [M+H]$^+$. $^1$H NMR (400 MHz, DMSO-d$_6$): 8.62 (br s, 1H), 8.03 (br t, J=5.7 Hz, 1H), 7.60–7.66 (m, 5H), 7.42–7.48 (m, 4H), 7.25–7.33 (m, 5H), 6.79 (br t, J=5.7 Hz, 1H), 6.68 (dd, J=15.2, 5.2 Hz, 1H), 6.36 (d, J=8.6 Hz, 1H), 5.95 (dd, J=15.2, 1.4 Hz, 1H), 4.62 (br s, 1H), 3.05–3.13 (m, 2H), 2.80–2.95 (m, 4H), 1.47–1.55 (m, 2H), 1.36 (s, 9H).

B. {3-[(R)-4-(3-Biphenyl-4-yl-ureido)-5-phenyl-pentanoylamino]-propyl}-carbamic acid tert-butyl ester. Prepared by a route similar to Example 2, Method 1, step C. MS (electrospray): mass calculated for $C_{32}H_{40}N_4O_4$, 544.69; m/z found, 545.3 [M+H]$^+$, 567.3 [M+Na]$^+$. $^1$H NMR (400 MHz, CD$_3$OD): 7.39–7.47 (m, 4H), 7.27–7.31 (m, 4H), 3.86–3.93 (m, 1H), 3.00–3.10 (m, 2H), 2.90–2.95 (m, 2H), 2.72 (d, J=6.9 Hz, 2H), 2.14–2.22 (m, 4H), 1.74–1.83 (m, 1H), 1.47–1.63 (m, 3H), 1.31 (s, 9H).

C. (R)-4-(3-Biphenyl-4-yl-ureido)-5-phenyl-pentanoic acid (3-amino-propyl)-amide. Prepared by a route similar to Example 92, step C. MS (electrospray): mass calculated for $C_{27}H_{32}N_4O_2$, 444.25; m/z found, 445.2 [M+H]$^+$, 467.2 [M+Na]$^+$, 911.5 [2M+Na]. $^1$H NMR (400 MHz, CDCl$_3$): 8.04 (br s, 1H), 7.50–7.32 (m, 8H), 7.23–7.10 (m, 6H), 7.05 (t, J=5.1 Hz, 1H), 5.64 (br d, J=7.6 Hz, 1H), 4.06–3.95 (m, 1H), 3.30–3.13 (m, 2H), 2.84 (dd, J=13.5, 5.9 Hz, 1H), 2.67 (dd, J=13.5, 5.7 Hz, 1H), 2.60 (t, J=5.7 Hz, 2H), 2.26–2.11 (m, 2H), 2.00 (br s, 2H), 1.75–1.63 (m, 2H), 1.46 (t, J=5.9 Hz, 2H).

Example 97

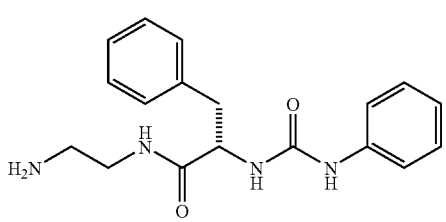

(S)-N-(2-Amino-ethyl)-3-phenyl-2-(3-phenyl-ureido)-propionamide

Prepared as in Example 69, substituting (S)-2-[(9H-fluoren-9-yl)-methoxycarbonyl-amino]-3-phenyl-propionic acid for (S)-3-cyclohexyl-2-(9H-fluoren-9-ylmethoxycarbonylamino)-propionic acid in step C, and isocyanato-benzene for 4-isocyanato-biphenyl in step E. MS (electrospray): mass calculated for $C_{18}H_{22}N_4O_2$, 326.17; m/z found, 327.1 [M+H]$^+$. $^1$H NMR (400 MHz, DMSO-d$_6$): 8.76 (s, 1H), 8.31 (t, J=5.6 Hz, 1H), 7.82 (br s, 3H), 7.35–7.18 (m, 9H), 6.88 (t, J=7.3 Hz, 1H), 6.47 (d, J=7.8 Hz, 1H), 4.42 (m, 1H), 3.29–3.26 (m, 2H), 3.02 (dd, J=13.8, 5.3 Hz, 1H), 2.87–2.77 (m, 3H).

Example 98

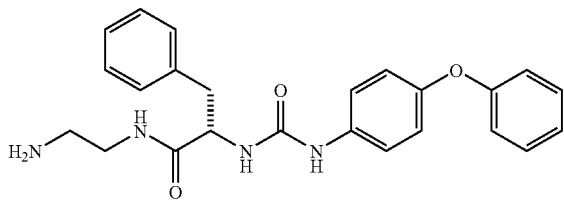

(S)-N-(2-Amino-ethyl)-2-[3-(4-phenoxy-phenyl)-ureido]-3-phenyl-propionamide

Prepared as in Example 69, substituting (S)-2-[(9H-fluoren-9-yl)-methoxycarbonyl-amino]-3-phenyl-propionic acid for (S)-3-cyclohexyl-2-(9H-fluoren-9-ylmethoxycarbonylamino)-propionic acid in step C, and 4-phenoxyphenyl isocyanate for 4-isocyanato-biphenyl in step E. MS (electrospray): mass calculated for $C_{24}H_{26}N_4O_3$, 418.20; m/z found, 419.2 [M+H]$^+$. $^1$H NMR (500 MHz, DMSO-d$_6$): 8.81 (s, 1H), 8.3 (t, J=5.6 Hz, 1H), 7.83 (br s, 3H), 7.37–7.21 (m, 9H), 7.06 (m, 1H), 6.92 (m, 4H), 6.47 (d, J=7.8 Hz, 1H), 4.42 (m, 1H), 3.29–3.25 (m, 2H), 3.03 (dd, J=, 13.8, 5.3 Hz, 1H), 2.87–2.78 (m, 3H).

Example 99

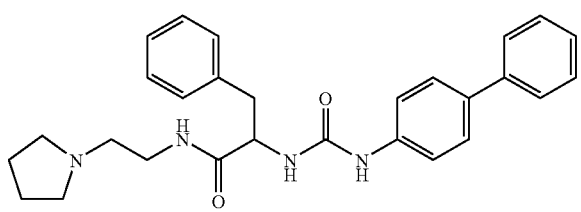

2-(3-Biphenyl-4-yl-ureido)-3-phenyl-N-(2-pyrrolidin-1-yl-ethyl)-propionamide Prepared as in Example 61, steps A and B, and Example 13, step B, substituting 2-pyrrolidin-1-yl-ethylamine for N',N'-diethyl-propane-1,3-diamine. MS (electrospray): mass calculated for $C_{28}H_{32}N_4O_2$, 456.25; m/z found, 457.2 [M+H]$^+$. $^1$H NMR (400 MHz, DMSO-d$_6$): 8.77 (s, 1H), 8.07 (t, J=4.2 Hz, 1H), 7.8–7.03 (m, 14H), 6.37 (d, J=8.2 Hz, 1H), 4.48 (q, J=7.4 Hz, 1H), 3.15 (m, 2H), 2.97 (dd, J=13.7, 7.5 Hz, 1H), 2.85 (dd, J=13.7, 7.4 Hz, 1H), 2.43 (br s, 6H), 1.58 (br s, 4H).

Example 100

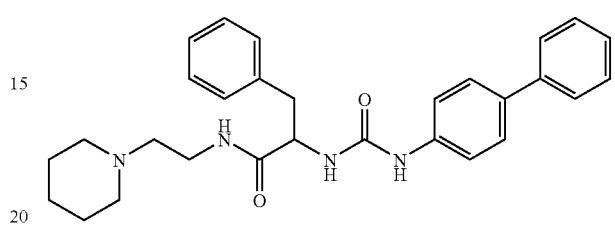

2-(3-Biphenyl-4-yl-ureido)-3-phenyl-N-(2-piperidin-1-yl-ethyl)-propionamide

Prepared as in Example 61, steps A and B, and Example 13, step B, substituting 2-piperidin-1-yl-ethylamine for N',N'-diethyl-propane-1,3-diamine. MS (electrospray): mass calculated for $C_{29}H_{34}N_4O_2$, 470.27; m/z found, 471.3 [M+H]$^+$. $^1$H NMR (500 MHz, DMSO-d$_6$): 8.78 (s, 1H), 7.99 (t, J=5.4 Hz, 1H), 7.61–7.05 (m, 14H), 6.37 (dd, J=8.2, 2.3 Hz, 1H), 4.49–4.45 (m, 1H), 3.21–3.08 (m, 2H), 2.99 (dd, J=13.7, 5.6 Hz, 1H), 2.85 (dd, J=13.7, 7.7 Hz, 1H), 2.31–2.15 (m, 6H), 1.49–1.34 (m, 6H).

Example 101

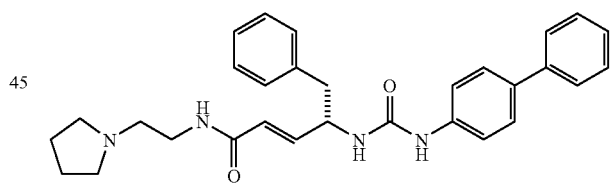

(E)-(S)-4-(3-Biphenyl-4-yl-ureido)-5-phenyl-pent-2-enoic Acid (2-pyrrolidin-1-yl-ethyl)-amide Prepared as in Example 18, step B, from (E)-(S)-4-(3-biphenyl-4-yl-ureido)-5-phenyl-pent-2-enoic acid (Example 19, step A), substituting 2-pyrrolidin-1-yl-ethylamine for N'-methyl-ethane-1,2-diamine. MS (electrospray): mass calculated for $C_{30}H_3N_4O_2$, 482.27; m/z found, 483.3 [M+H]$^+$, 505.2 [M+Na]$^+$, 987.5 [2M+H]$^+$. $^1$H NMR (400 MHz, CDCl$_3$): 7.99 (s, 1H), 7.53 (d, J=7.4 Hz, 2H), 7.49–7.37 (m, 7H), 7.32–7.20 (m, 5H), 6.80 (dd, J=15.3, 5.1 Hz, 1H), 5.97–5.93 (m, 2H), 4.89–4.83 (m, 1H), 4.51–4.45 (m, 1H), 3.63–3.55 (m, 1H), 3.28–3.21 (m, 1H), 2.95 (dd, J=13.7, 7.3 Hz, 1H), 2.87 (dd, J=13.7, 7.3 Hz, 1H), 2.72–2.65 (m, 2H), 2.53–2.45 (m, 4H), 1.78–1.69 (m, 4H).

Example 102

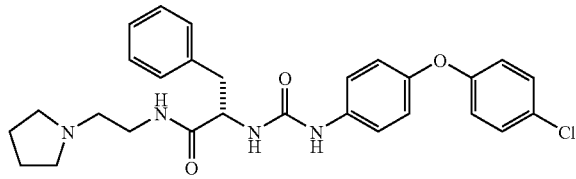

(S)-2-{3-[4-(4-Chloro-phenoxy)-phenyl]-ureido}-3-phenyl-N-(2-pyrrolidin-1-yl-ethyl)-propionamide Prepared by a route similar to Example 3. MS (electrospray): mass calculated for $C_{28}H_{31}ClN_4O_3$, 506.21; m/z found, 507.2 $[M+H]^+$. $^1H$ NMR (400 MHz, $CD_3OD$): 7.31–7.25 (m, 9H), 6.97–6.81 (m, 4H), 4.41–4.37 (m, 1H), 3.51–3.46 (m, 1H), 3.39–3.32 (m, 1H), 3.10 (dd, J=13.7, 6.3 Hz, 1H), 2.97–2.89 (m, 7H), 1.91–1.89 (m, 5H).

Example 103

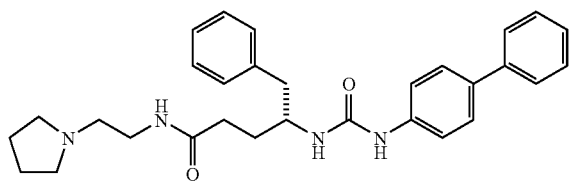

(R)-4-(3-Biphenyl-4-yl-ureido)-5-phenyl-pentanoic Acid (2-pyrrolidin-1-yl-ethyl)-amide Prepared as in Example 2, Method 1, step C, from (E)-(S)-4-(3-biphenyl-4-yl-ureido)-5-phenyl-pent-2-enoic acid (2-pyrrolidin-1-yl-ethyl)-amide (Example 101). MS (electrospray): mass calculated for $C_{30}H_{36}N_4O_2$, 484.28; m/z found, 485.2 $[M+H]^+$, 507.2 $[M+Na]^+$, 991.5 $[2M+Na]^+$. $^1H$ NMR (400 MHz, $CDCl_3$): 8.23 (s, 1H), 7.52–7.37 (m, 9H), 7.32–7.14 (m, 5H), 6.06 (br d, J=6.6 Hz, 1H), 4.13–4.05 (m, 1H), 3.99 (br s, 1H), 3.42–3.36 (m, 1H), 3.33–3.25 (m, 1H), 2.89 (dd, J=13.4, 6.2 Hz, 1H), 2.75 (dd, J=13.4, 7.0 Hz, 1H), 2.61 (t, J=6.0 Hz, 2H), 2.57–2.51 (m, 4H), 2.31 (t, J=7.0 Hz, 2H), 1.90–1.83 (m, 1H), 1.77–1.64 (m, 5H).

Example 104

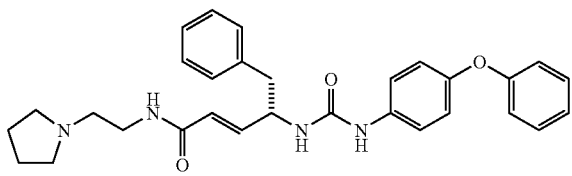

(E)-(S)-4-[3-(4-Phenoxy-phenyl)-ureido]-5-phenyl-pent-2-enoic Acid (2-pyrrolidin-1-yl-ethyl)-amide Prepared by a route similar to Example 18. MS (electrospray): mass calculated for $C_{30}H_{34}N_4O_3$, 498.26; m/z found, 499.2 $[M+H]^+$, 997.4 $[2M+H]^+$. $^1H$ NMR (400 MHz, $CDCl_3$): 8.31 (s, 1H), 7.59 (br t, J=5.2 Hz, 1H), 7.34–7.31 (m, 2H), 7.30–7.24 (m, 4H), 7.20–7.18 (m, 3H), 7.07–7.03 (m, 1H), 6.93–6.88 (m, 4H), 6.75 (dd, J=15.3, 5.2 Hz, 1H), 6.21 (d, J=8.2 Hz, 1H), 5.95 (dd, J=15.3, 1.3 Hz, 1H), 4.78–4.72 (m, 1H), 3.53–3.45 (m, 1H), 3.33–3.25 (m, 1H), 2.88 (dd, J=13.7, 7.5 Hz, 1H), 2.81 (dd J=13.7, 7.2 Hz, 1H), 2.76–2.70 (m, 1H), 2.66–2.58 (m, 5H), 1.82–1.74 (m, 4H).

Example 105

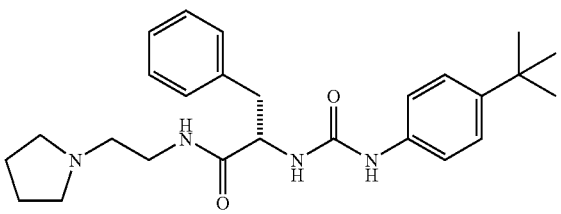

(S)-2-[3-(4-tert-Butyl-phenyl)-ureido]-3-phenyl-N-(2-pyrrolidin-1-yl-ethyl)-propionamide Prepared as in Example 12 from [(S)-2-phenyl-1-(2-pyrrolidin-1-yl-ethylcarbamoyl)-ethyl]-carbamic acid tert-butyl ester (Example 9, step A), and substituting 1-tert-butyl-4-isocyanato-benzene for 4-isocyanato-biphenyl. MS (electrospray): mass calculated for $C_{26}H_{36}N_4O_2$, 436.28; m/z found, 437.3 $[M+H]^+$. $^1H$ NMR (400 MHz, $CD_3OD$): 7.27–7.00 (m, 9H), 4.51 (t, J=7.6 Hz, 1H), 3.25 (m, 2H), 3.06 (dd, J=14.0, 6.6 Hz, 1H), 2.99 (dd, J=14.0, 7.6 Hz, 1H), 2.45 (br m, 6H), 1.73 (br s, 4H), 1.26 (s, 9H).

Example 106

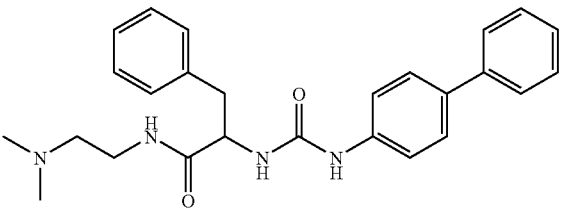

2-(3-Biphenyl-4-yl-ureido)-N-(2-dimethylamino-ethyl)-3-phenyl-propionamide

Prepared as in Example 61, steps A and B, and Example 13, step B, substituting N',N'-dimethyl-ethane-1,2-diamine for N',N'-diethyl-propane-1,3-diamine. MS (electrospray): mass calculated for $C_{26}H_{30}N_4O_2$, 430.24; m/z found, 431.2 $[M+H]^+$. $^1H$ NMR (400 MHz, $CD_3OD$): 7.46–7.15 (m, 14H), 4.4 (t, J=7.5 Hz, 1H), 3.18 (m, 2H), 3.0 (dd, J=13.6, 6.5 Hz, 1H), 2.89 (dd, J=13.6, 7.6 Hz, 1H), 2.25 (m, 2H), 2.13 (s, 6H).

Example 107

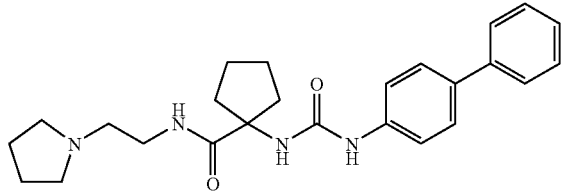

1-(3-Biphenyl-4-yl-ureido)-cyclopentanecarboxylic Acid (2-pyrrolidin-1-yl-ethyl)-amide Prepared by a route similar to Example 72. MS (electrospray): mass calculated for $C_{25}H_{32}N_4O_2$, 420.25; m/z found, 421.2 [M+H]$^+$. $^1$H NMR (400 MHz, CD$_3$OD): 8.33 (t, J=5.81 Hz, 1H), 7.76–7.27 (m, 9H), 3.78 (m, 4H), 3.30 (m, 2H), 3.02 (m, 2H), 2.07 (m, 2H), 2.01 (m, 2H), 1.88 (m, 8H).

Example 108

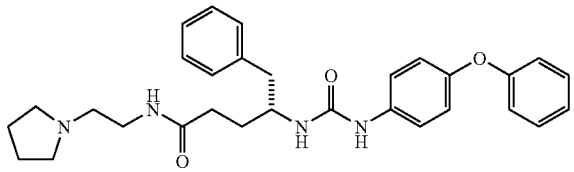

(R)-4-[3-(4-Phenoxy-phenyl)-ureido]-5-phenyl-pentanoic Acid (2-pyrrolidin-1-yl-ethyl)-amide Prepared as in Example 2, Method 1, step C, from (E)-(S)-4-[3-(4-phenoxy-phenyl)-ureido]-5-phenyl-pent-2-enoic acid (2-pyrrolidin-1-yl-ethyl)-amide (Example 104). MS (electrospray): mass calculated for $C_{30}H_{36}N_4O_3$, 500.28; m/z found, 501.3 [M+H]$^+$, 523.2 [M+Na]$^+$. $^1$H NMR (400 MHz, CDCl$_3$): 7.74 (br s, 1H), 7.23–7.17 (m, 6H), 7.13–7.09 (m, 3H), 6.97 (t, J=7.4 Hz, 1H), 6.87–6.82 (m, 4H), 5.68 (br d, J=4.8 Hz, 1H), 3.99–3.95 (m, 1H), 3.85 (br s, 1H), 3.34–3.30 (m, 1H), 3.23–3.18 (m, 1H), 2.80 (dd, J=13.6, 6.2 Hz, 1H), 2.66 (dd, J=1013.6, 7.0 Hz, 1H), 2.56 (t, J=6.0 Hz, 2H), 2.52–2.48 (m, 4H), 2.24–2.19 (m, 2H), 1.78–1.73 (m, 1H), 1.71–1.67 (m, 4H), 1.62–1.55 (m, 1H).

Example 109

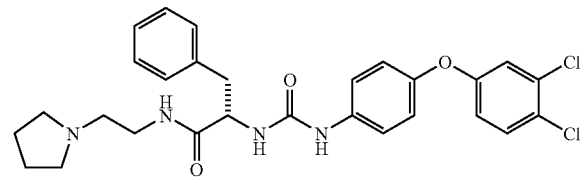

(S)-2-{3-[4-(3,4-Dichloro-phenoxy)-phenyl]-ureido}-3-phenyl-N-(2-pyrrolidin-1-yl-ethyl)-propionamide Prepared by a route similar to Example 59. MS (electrospray): mass calculated for $C_{28}H_{30}Cl_2N_4O_3$, 540.17; m/z found, 541.2 [M+H]$^+$. $^1$H NMR (400 MHz, CD$_3$OD): 7.43 (d, J=8.9 Hz, 1H), 7.36–7.34 (m, 2H), 7.32–7.20 (m, 6H), 7.04 (d, J=2.8 Hz, 1H), 6.97–6.93 (m, 2H), 6.86 (dd, J=8.9, 2.8 Hz, 1H), 4.51–4.47 (m, 1H), 3.29–3.27 (m, 2H), 3.08 (dd, J=13.6, 6.6 Hz, 1H), 2.98 (dd, J=13.6, 7.6 Hz, 1H), 2.55–2.48 (m, 6H), 1.79–1.76 (m, 4H).

Example 110

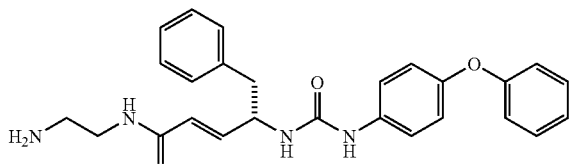

(E)-(S)-4-[3-(4-Phenoxy-phenyl)-ureido]-5-phenyl-pent-2-enoic Acid (2-amino-ethyl)-amide A. (2-{(E)-(S)-4-[3-(4-Phenoxy-phenyl)-ureido]-5-phenyl-pent-2-enoylamino}-ethyl)-carbamic acid tert-butyl ester. Prepared as in Example 18, step B substituting (2-amino-ethyl)-carbamic acid tert-butyl ester for N-methyl-ethane-1,2-diamine. MS (electrospray): mass calculated for $C_{31}H_{36}N_4O_5$, 544.27; m/z found, 567.2 [M+Na]$^+$. $^1$H NMR (400 MHz, DMSO-d$_6$): 8.49 (br s, 1H), 8.05 (br t, J=5.9 Hz, 1H), 7.29–7.38 (m, 6H), 7.19–7.25 (m, 3H), 7.04–7.08 (m, 1H), 6.89–6.93 (m, 4H), 6.81 (br t, J=5.8 Hz, 1H), 6.66 (dd J=15.5, 5.4 Hz, 1H), 6.27 (d, J=8.4 Hz, 1H), 5.92 (dd, J=15.5, 1.3 Hz, 1H), 4.58 (br s, 1H), 3.09–3.14 (m, 2H), 2.93–2.99 (m, 2H), 2.91 (dd, J=13.7, 6.2 Hz, 1H), 2.80 (dd, J=13.7, 8.1 Hz, 1H), 1.36 (s, 9H).

B. (E)-(S)-4-[3-(4-Phenoxy-phenyl)-ureido]-5-phenyl-pent-2-enoic acid (2-amino-ethyl)-amide. Prepared by a route similar to Example 92, step C. MS (electrospray): mass calculated for $C_{26}H_{28}N_4O_3$, 444.22; m/z found, 445.2 [M+H]$^+$, 467.2 [M+Na]$^+$, 889.4 [2M+H]$^+$, 911.4 [2M+Na]$^+$. $^1$H NMR (400 MHz, CDCl$_3$): 8.07 (br s, 1H), 7.45 (br t, J=5.6 Hz, 1H), 7.20–7.04 (m, 8H), 6.96–6.92 (m, 2H), 6.86–6.76 (m, 4H), 6.66 (dd J=15.3, 5.5 Hz, 1H), 6.14 (d, J=7.7 Hz, 1H), 5.88 (d, J=15.0 Hz, 1H), 4.65–4.57 (m, 1H), 3.21–3.14 (m, 1H), 3.11–3.03 (m, 1H), 2.75 (d, J=7.0 Hz, 2H), 2.63–2.59 (m, 2H), (2.08 br s, 2H).

Example 111

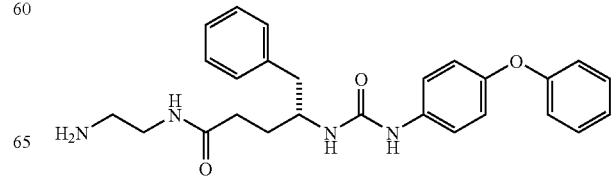

(R)-4-[3-(4-Phenoxy-phenyl)-ureido]-5-phenyl-pentanoic Acid (2-amino-ethyl)-amide A. (2-{(R)-4-[3-(4-Phenoxy-phenyl)-ureido]-5-phenyl-pentanoylamino}-ethyl)-carbamic acid tert-butyl ester. Prepared as in Example 2, Method 1, step C, from (2-{(E)-(S)-4-[3-(4-phenoxy-phenyl)-ureido]-5-phenyl-pent-2-enoylamino}-ethyl)-carbamic acid tert-butyl ester (Example 110, step A). MS (electrospray): mass calculated for $C_{31}H_{38}N_4O_5$, 546.28; m/z found, 547.2 [M+H]$^+$, 569.3 [M+Na]$^+$. $^1$H NMR (400 MHz, CDCl$_3$): 7.54 (br s, 1H), 7.14–7.21 (m, 5H), 7.05–7.11 (m, 6H), 6.96 (t, J=7.3 Hz, 1H), 6.77–6.85 (m, 4H), 5.55 (br d, J=7.8 Hz, 1H), 5.30 (br s, 1H), 3.95 (br s, 1H), 3.03–3.29 (m, 4H), 2.64–2.74 (m, 2H), 2.17 (br t, J=6.8 Hz, 1H), 1.70–1.79 (m, 1H), 1.54–1.64 (m, 1H), 1.32 (s, 9H).

B. (R)-4-[3-(4-Phenoxy-phenyl)-ureido]-5-phenyl-pentanoic acid (2-amino-ethyl)-amide. Prepared by a route similar to Example 92, step C. MS (electrospray): mass calculated for $C_{26}H_{30}N_4O_3$, 446.23; m/z found, 447.2 [M+H]$^+$, 469.2 [M+Na]$^+$, 915.4 [2M+Na]$^+$. $^1$H NMR (400 MHz, CDCl$_3$): 7.77 (br s, 1H), 7.24–7.08 (m, 8H), 7.00–6.93 (m, 2H), 6.88–6.79 (m, 4H), 5.49 (d, J=8.6 Hz, 1H), 4.03–3.94 (m, 1H), 3.20–3.11 (m, 2H), 2.75 (dd, J=6.4, 3.6 Hz, 1H), 2.70–2.65 (m, 3H), 2.25–2.13 (m, 2H), 1.80–1.71 (m, 2H).

Example 112

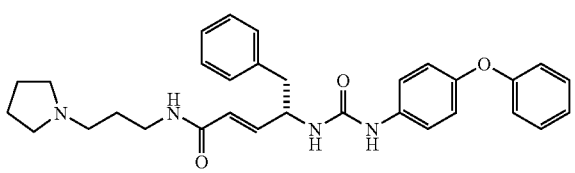

(E)-(S)-4-[3-(4-Phenoxy-phenyl)-ureido]-5-phenyl-pent-2-enoic Acid (3-pyrrolidin-1-yl-propyl)-amide Prepared by a route similar to Example 18. MS (electrospray): mass calculated for $C_{31}H_{36}N_4O_3$, 512.28; m/z found, 513.3 [M+H]$^+$. $^1$H NMR (400 MHz, CDCl$_3$): 8.51 (s, 1H), 7.93 (br t, J=5.0 Hz, 1H), 7.31–7.15 (m, 9H), 7.05–7.01 (m, 1H), 6.91–6.85 (m, 4H), 6.69 (dd, J=15.4, 5.8 Hz, 1H), 6.50 (d, J=8.0 Hz, 1H), 5.96 (dd, J=14.6, 0.72 Hz, 1H), 4.77–4.70 (m, 1H), 3.35–3.21 (m, 2H), 2.91–2.79 (m, 2H), 2.60 (s, 6H), 1.76–1.68 (m, 6H).

Example 113

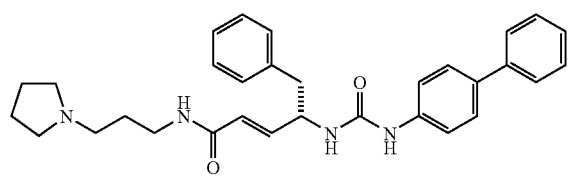

(E)-(S)-4-(3-Biphenyl-4-yl-ureido)-5-phenyl-pent-2-enoic Acid (3-pyrrolidin-1-yl-propyl)-amide Prepared by a route similar to Example 19. MS (electrospray): mass calculated for $C_{31}H_{36}N_4O_2$, 496.28; m/z found, 497.3 [M+H]$^+$. $^1$H NMR (400 MHz, CDCl$_3$): 7.95 (s, 1H), 7.77 (br s, 1H), 7.25–6.99 (m, 14H), 6.43 (dd, J=15.2, 6.1 Hz, 1H), 6.31 (d, J=7.5 Hz, 1H), 5.69 (d, J=15.2 Hz, 1H), 4.61–4.57 (m, 1H), 3.20–3.07 (m, 2H), 2.72–2.62 (m, 3H), 2.32–2.18 (m, 6H), 1.47 (s, 6H).

Example 114

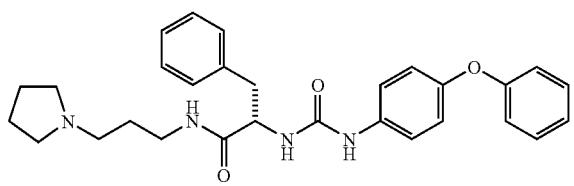

(S)-2-[3-(4-Phenoxy-phenyl)-ureido]-3-phenyl-N-(3-pyrrolidin-1-yl-propyl)-propionamide Prepared as in Example 7 from [(S)-2-phenyl-1-(3-pyrrolidin-1-yl-propylcarbamoyl)-ethyl]-carbamic acid tert-butyl ester (Example 1, step A). MS (electrospray): mass calculated for $C_{29}H_{34}N_4O_3$, 486.26; m/z found, 487.2 [M+H]$^+$. $^1$H NMR (400 MHz, CD$_3$OD): 7.32–6.86 (m, 14H), 4.47 (t, J=7.3 Hz, 1H), 3.15 (m, 2H), 3.05 (dd, J=13.6, 6.8 Hz, 1H), 2.97 (dd, J=13.6, 7.3 Hz, 1H), 2.47 (br m, 4H), 2.39 (m, 2H), 1.75 (m, 4H), 1.62 (m, 2H).

Example 115

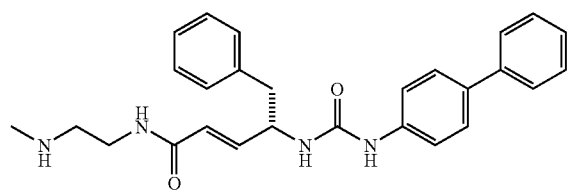

(E)-(S)-4-(3-Biphenyl-4-yl-ureido)-5-phenyl-pent-2-enoic Acid (2-methylamino-ethyl)-amide Prepared by a route similar to Example 19. MS (electrospray): mass calculated for $C_{27}H_{30}N_4O_2$, 442.24; m/z found, 443.2 [M+H]$^+$, 465.2 [M+Na]$^+$, 885.4 [2M+H]$^+$, 907.4 [2M+Na]$^+$. $^1$H NMR (400 MHz, CDCl$_3$): 8.23 (br s, 1H), 7.46 (br t, J=5.0 Hz, 1H), 7.40–7.26 (m, 9H), 7.21–7.06 (m, 5H), 6.65 (dd, J=15.3, 5.3 Hz, 1H), 6.19 (d, J=7.8 Hz, 1H), 5.85 (d, J=14.9 Hz, 1H), 4.68–4.62 (m, 1H), 3.35–3.30 (m, 1H), 3.19–3.14 (m, 1H), 2.76–2.54 (m, 5H), 2.24 (s, 3H).

Example 116

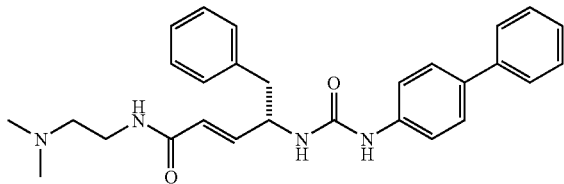

(E)-(S)-4-(3-Biphenyl-4-yl-ureido)-5-phenyl-pent-2-enoic Acid (2-dimethylamino-ethyl)-amide Prepared by a route similar to Example 19. MS (electrospray): mass calculated for C$_{28}$H$_{32}$N$_4$O$_2$, 456.25; m/z found, 457.2 [M+H]$^+$, 479.2 [M+Na]$^+$. $^1$H NMR (400 MHz, CDCl$_3$): 8.29 (s, 1H), 7.37–7.04 (m, 14H), 6.65 (dd, J=15.3, 5.7 Hz, 1H), 6.28 (d, J=8.1 Hz, 1H), 5.88 (dd, J=15.3, 0.8 Hz, 1H), 4.70–4.63 (m, 1H), 3.31–3.25 (m, 1H), 3.21–3.15 (m, 1H), 2.80–2.69 (m, 2H), 2.37–2.26 (m, 2H), 2.09 (s, 6H).

Example 117

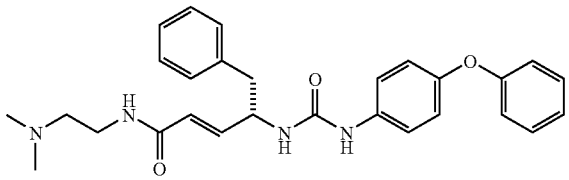

(E)-(S)-4-[3-(4-Phenoxy-phenyl)-ureido]-5-phenyl-pent-2-enoic Acid (2-dimethylamino-ethyl)-amide Prepared by a route similar to Example 18. MS (electrospray): mass calculated for C$_{28}$H$_{32}$N$_4$O$_3$, 472.59; m/z found, 473.2 [M+H]$^+$, 495.2 [M+Na]$^+$. $^1$H NMR (400 MHz, CDCl$_3$): 7.90 (s, 1H), 7.20–7.07 (m, 9H), 6.97–6.92 (m, 1H), 6.84–6.78 (m, 1H), 6.64 (dd, J=15.3, 5.7 Hz, 1H), 5.95 (d, J=8.4 Hz, 1H), 5.85 (dd, J=15.3, 1.2 Hz, 1H), 4.71–4.62 (m, 1H), 3.38–3.31 (m, 1H), 3.20–3.15 (m, 1H), 2.80–2.39 (m, 2H), 2.39–2.27 (m, 2H), 2.13 (s, 6H).

Example 118

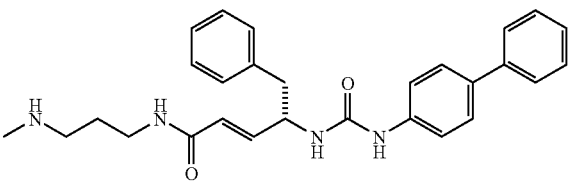

(E)-(S)-4-(3-Biphenyl-4-yl-ureido)-5-phenyl-pent-2-enoic Acid (3-methylamino-propyl)-amide Prepared by a route similar to Example 19. MS (electrospray): mass calculated for C$_{28}$H$_{32}$N$_4$O$_2$, 456.25; m/z found, 457.2 [M+H]$^+$, 479.2 [M+Na]$^+$, 935.4 [2M+Na]$^+$.

Example 119

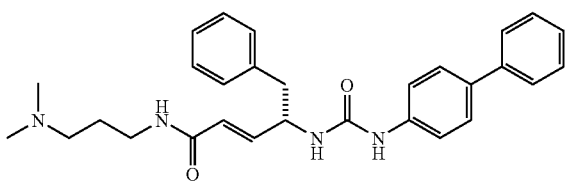

(E)-(S)-4-(3-Biphenyl-4-yl-ureido)-5-phenyl-pent-2-enoic Acid (3-dimethylamino-propyl)-amide Prepared by a route similar to Example 19. MS (electrospray): mass calculated for C$_{29}$H$_{34}$N$_4$O$_2$, 470.27; m/z found, 471.3 [M+H]$^+$. $^1$H NMR (400 MHz, CDCl$_3$): 8.13 (s, 1H), 7.81 (t, J=5.0 Hz, 1H), 7.50–7.33 (m, 8H), 7.30–7.19 (m, 6H), 6.67 (dd, J=15.4, 6.8 Hz, 1H), 6.54 (d, J=8.6 Hz, 1H), 5.98 (d, J=17.6 Hz, 1H), 4.88–4.81 (m, 1H), 3.47–3.29 (m, 2H), 2.96 (dd, J=13.6, 7.0 Hz, 1H), 2.88 (dd, J=13.6, 7.0 Hz, 1H), 2.34 (t, J=6.4 Hz, 2H), 2.17 (s, 6H), 1.69–1.63 (m, 2H).

Example 120

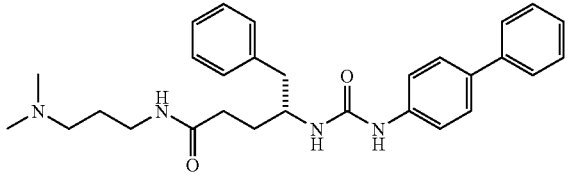

(R)-4-(3-Biphenyl-4-yl-ureido)-5-phenyl-pentanoic Acid (3-dimethylamino-propyl)-amide Prepared from (E)-(S)-4-(3-biphenyl-4-yl-ureido)-5-phenyl-pent-2-enoic acid (3-dimethylamino-propyl)-amide (Example 119) as in Example 2, Method 1, step C. MS (electrospray): mass calculated for C$_{28}$H$_{34}$N$_4$O$_2$, 458.27; m/z found, 459.3 [M+H]$^+$. $^1$H NMR (400 MHz, CDCl$_3$): 7.86 (br s, 1H), 7.44–7.29 (m, 8H), 7.23–7.09 (m, 6H), 6.72 (t, J=4.0 Hz, 1H), 5.73 (d, J=7.4 Hz, 1H), 4.06–3.99 (m, 1H), 3.27–3.14 (m, 2H), 2.82 (dd, J=6.0, 13.6 Hz, 1H), 2.66 (dd, J=13.6, 7.2 Hz, 1H), 2.29 (t, J=6.0 Hz, 2H), 2.56–2.19 (m, 2H), 2.08 (s, 6H), 1.78–1.73 (m, 1H), 1.66–1.60 (m, 1H).

Example 121

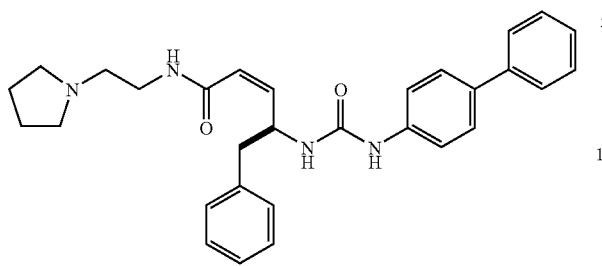

(Z)-(S)-4-(3-Biphenyl-4-yl-ureido)-5-phenyl-pent-2-enoic Acid (2-pyrrolidin-1-yl-ethyl)-amide A. (Z)-(S)-4-tert-Butoxycarbonylamino-5-phenyl-pent-2-enoic acid methyl ester. To a solution of bis(2,2,2-trifluoroethyl)(methoxycarbonylmethyl)-phosphonate (0.32 g, 1.0 mmol) in THF (10 mL) was added 18-crown-6 (0.265 g, 1.0 mmol), and the resulting solution was cooled (−78° C.). The solution was treated with potassium bis(trimethylsilyl)amide (0.2 g, 1.0 mmol) and ((S)-1-benzyl-2-oxo-ethyl)-carbamic acid tert-butyl ester (0.25 g, 1.0 mmol), and stirred (−78° C., 0.5 h). The reaction mixture was quenched with saturated aqueous NH$_4$Cl (50 mL) and extracted with EtOAc (2×50 mL). The organic layers were washed with brine (50 mL), dried (Na$_2$SO$_4$), filtered, and concentrated in vacuo. The resulting residue was purified by column chromatography using 0–40% (EtOAc/hexanes) to provide the desired product as a white solid (0.185 g, 59%): MS (electrospray): mass calculated for C$_{17}$H$_{23}$NO$_4$, 305.37; m/z found, 328.1 [M+Na]$^+$. $^1$H NMR (CDCl$_3$, 400 MHz): 7.31–7.38 (m, 2H), 7.20–7.26 (m, 3H), 6.23 (br s, 1H), 5.86 (dd, J=11.6, 1.0 Hz, 1H), 5.36 (br s, 1H), 4.79 (br s, 1H), 3.75 (s, 3H), 2.99–3.04 (m, 1H), 2.91 (br s, 1H), 1.39 (s, 9H).

B. [(Z)-(S)-1-Benzyl-3-(2-pyrrolidin-1-yl-ethylcarbamoyl)-allyl]-carbamic acid tert-butyl ester. To a solution of (Z)-(S)-4-tert-butoxycarbonylamino-5-phenyl-pent-2-enoic acid methyl ester (0.10 g, 0.33 mmol) in toluene (3.6 mL) was added aminoethylpyrrolidine (0.041 g, 0.36 mmol) and trimethylaluminum (2 M in hexanes, 0.026 g, 0.36 mmol), and the solution was stirred (25° C., 4 h). The solvent was removed in vacuo, and the residue was partitioned with 1 N NaOH and CH$_2$Cl$_2$ (50 mL each). The organic layer was dried (Na$_2$SO$_4$), filtered, and concentrated in vacuo. The resulting residue was purified by column chromatography using 0–20% (1% NH$_4$OH/MeOH in CH$_2$Cl$_2$) to provide the desired product as a clear oil (0.02 g, 16%): MS (electrospray): mass calculated for C$_{22}$H$_{33}$N$_3$O$_3$, 387.25; m/z found, 388.2 [M+H]$^+$; 410.2 [M+Na]$^+$. $^1$H NMR (CDCl$_3$, 400 MHz): 7.20–7.25 (m, 2H), 7.13–7.18 (m, 3H), 5.72–5.81 (m, 2H), 5.08 (br s, 1H), 4.94 (br s, 1H), 3.28–3.45 (m, 2H), 2.91 (dd, J=13.4, 5.6 Hz, 1H), 2.77–2.86 (m, 1H), 2.51–2.61 (m, 2H), 2.42–2.47 (m, 4H), 1.65–1.71 (m, 4H), 1.32 (s, 9H).

C. (Z)-(S)-4-(3-Biphenyl-4-yl-ureido)-5-phenyl-Pent-2-enoic acid (2-pyrrolidin-1-yl-ethyl)-amide. Prepared by a route similar to Example 11, step C. MS (electrospray): mass calculated for C$_{30}$H$_{34}$N$_4$O$_2$, 482.62; m/z found, 483.3 [M+H]$^+$. $^1$H NMR (CDCl$_3$, 400 MHz): 7.45–7.49 (m, 4H), 7.39–7.42 (m, 2H), 7.33 (t, J=7.3 Hz, 2H), 7.18–7.26 (m, 3H), 7.11–7.17 (m, 3H), 5.71–5.77 (m, 2H), 5.45 (br s, 1H), 3.38–3.46 (m, 2H), 3.24–3.35 (m, 1H), 2.87 (dd, J=13.6, 6.8 Hz, 1H), 2.76 (dd, J=13.6, 6.8 Hz, 1H), 2.54–2.64 (m, 2H), 2.48 (br s, 4H), 1.71 (br s, 4H).

Example 122

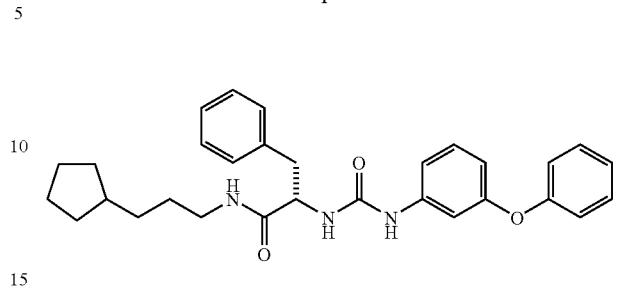

(S)-2-[3-(3-Phenoxy-phenyl)-ureido]-3-phenyl-N-(3-pyrrolidin-1-yl-propyl)-propionamide Prepared by a route similar to Example 7. MS (electrospray): mass calculated for C$_{29}$H$_{34}$N$_4$O$_3$, 486.26; m/z found, 487.2 [M+H]$^+$. $^1$H NMR (400 MHz, DMSO-d$_6$): 8.77 (s, 1H), 8.05 (t, J=5.6 Hz, 1H), 7.39–6.98 (m, 13H), 6.54 (m, 1H), 6.31 (d, J=8.3 Hz, 1H), 4.38 (q, J=7.6 Hz, 1H), 3.01 (m, 2H), 2.92 (dd, J=13.7, 5.8 Hz, 1H), 2.8 (dd, J=13.6, 7.6 Hz, 1H), 2.35 (m, 4H), 2.28 (m, 2H), 1.65 (m, 4H), 1.46 (m, 2H).

Example 123

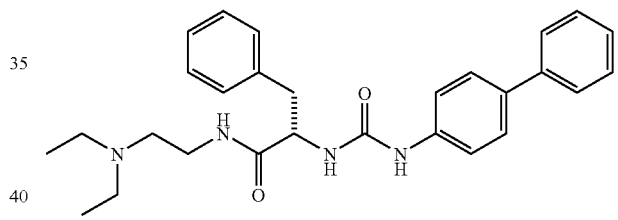

(S)-2-(3-Biphenyl-4-yl-ureido)-N-(2-diethylamino-ethyl)-3-phenyl-propionamide

Prepared by a route similar to Example 13. MS (electrospray): mass calculated for C$_{28}$H$_{34}$N$_4$O$_2$, 458.27; m/z found, 459.2 [M+H]$^+$. $^1$H NMR (400 MHz, DMSO-d$_6$): 8.82 (s, 1H), 7.98 (t, J=5.4 Hz, 1H), 7.74–7.04 (m, 14H), 6.43 (d, J=8.2 Hz, 1H), 4.58 (q, J=7.8 Hz, 1H), 3.1 (m, 2H), 2.99 (dd, J=13.7, 5.7 Hz, 1H), 2.84 (dd, J=13.7, 7.8 Hz, 1H), 2.45 (m, 6H), 0.92 (t, J=7.1 Hz, 6H).

Example 124

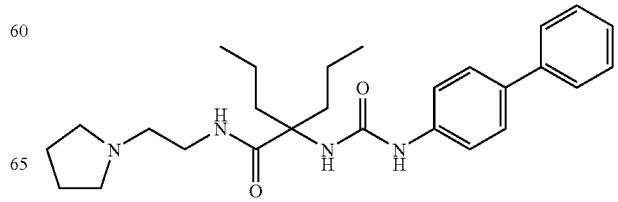

2-(3-Biphenyl-4-yl-ureido)-2-propyl-pentanoic Acid (2-pyrrolidin-1-yl-ethyl)-amide Prepared by a route similar to Example 68. MS (electrospray): mass calculated for C$_{27}$H$_{38}$N$_4$O$_2$, 450; m/z found, 451.3 [M+H]$^+$. $^1$H NMR (400 MHz, CD$_3$OD): 7.60–7.52 (m, 4H), 7.43–7.37 (m, 4H), 7.29–7.25 (m, 1H), 3.42 (t, J=6.7 Hz, 2H), 2.71 (m, 5H), 2.13 (td, J=4.1, 13 Hz, 2H), 1.85–1.81 (m, 4H), 1.79–1.74 (m, 2H), 1.40–1.29 (m, 2H), 1.23–1.15 (m, 2H), 0.93 (t, J=7.31 Hz, 6H).

Example 125

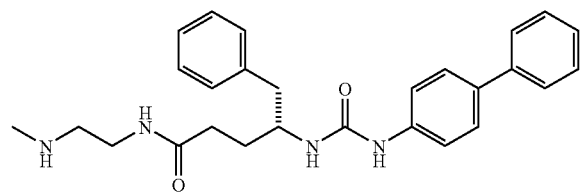

(R)-4-(3-Biphenyl-4-yl-ureido)-5-phenyl-pentanoic Acid (2-methylamino-ethyl)-amide Prepared as in Example 2, Method 1, step C, from (E)-(S)-4-(3-biphenyl-4-yl-ureido)-5-phenyl-pent-2-enoic acid (2-methylamino-ethyl)-amide (Example 115). MS (electrospray): mass calculated for C$_{27}$H$_{32}$N$_4$O$_2$, 444.25; m/z found, 445.2 [M+H]$^+$, 467.2 [M+Na]$^+$. $^1$H NMR (400 MHz, CDCl$_3$): 8.50 (br s, 1H), 7.71 (s, 1H), 7.40–7.34 (m, 4H), 7.30–7.19 (m, 6H), 7.15–7.04 (m, 4H), 6.14 (d, J=8.7 Hz, 1H), 3.94–3.86 (m, 1H), 3.55–3.46 (m, 1H), 3.26–3.18 (m, 1H), 2.98–2.90 (m, 1H), 2.73–2.62 (m, 3H), 2.40 (s, 3H), 2.29–2.11 (m, 2H), 1.91–1.80 (m, 1H), 1.50–1.36 (m, 1H).

Example 126

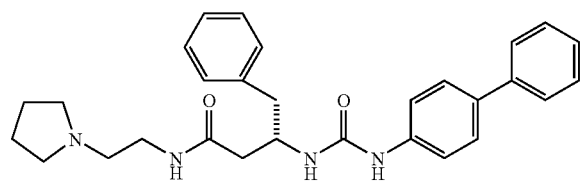

(S)-3-(3-Biphenyl-4-yl-ureido)-4-phenyl-N-(2-pyrrolidin-1-yl-ethyl)-butyramide

Prepared as in Example 15 from (S)-3-tert-butoxycarbonylamino-4-phenyl-butyric acid. MS (electrospray): mass calculated for C$_{29}$H$_{34}$N$_4$O$_2$, 470.27; m/z found, 471.3 [M+H]$^+$. $^1$H NMR (400 MHz, CD$_3$OD): 7.57–7.51 (m, 4H), 7.41–7.27 (m, 9H), 7.24–7.20 (m, 1H), 4.43–4.37 (m, 1H), 3.49–3.37 (m, 2H), 2.95–2.86 (m, 8H), 2.50 (dd, J=13.9, 4.2 Hz, 1H), 2.31 (dd, J=13.9, 9.0 Hz, 1H), 1.89–1.79 (m, 4H).

Example 127

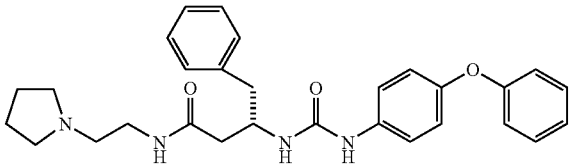

(S)-3-[3-(4-Phenoxy-phenyl)-ureido]-4-phenyl-N-(2-pyrrolidin-1-yl-ethyl)-butyramide Prepared as in Example 15 from (S)-3-tert-butoxycarbonylamino-4-phenyl-butyric acid, and substituting 4-phenoxyphenyl isocyanate for 4-isocyanato-biphenyl in step B. MS (electrospray): mass calculated for C$_{14}$H$_{12}$ClNO$_3$, 486.3; m/z found, 487.3 [M+H]$^+$. $^1$H NMR (400 MHz, CD$_3$OD): 7.33–7.19 (m, 9H), 7.07–7.04 (m, 1H), 6.93–6.88 (m, 4H), 4.39–4.33 (m, 1H), 3.37 (t, J=6.62 Hz, 2H), 2.88 (d, J=7 Hz, 2H), 2.79 (t, J=6.09, Hz, 6H), 2.46 (dd, J=4.7, 14.1 Hz, 1H), 2.33 (dd, J=8.5, 14.1 Hz, 1H), 1.83–1.76 (m, 4H).

Example 128

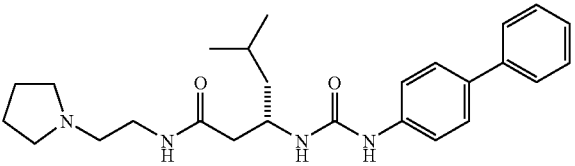

(S)-3-(3-Biphenyl-4-yl-ureido)-5-methyl-hexanoic Acid (2-pyrrolidin-1-yl-ethyl)-amide Prepared by a route similar to Example 15. MS (electrospray): mass calculated for C$_{26}$H$_{36}$N$_4$O$_2$, 436; m/z found, 437.3 [M+H]$^+$. $^1$H NMR (400 MHz, CD$_3$OD): 7.58–7.51 (m, 4H), 7.44–7.34 (m, 4H), 7.30–7.26 (m, 1H) 4.23–4.16 (m, 1H), 3.36 (t, J=6.8 Hz, 2H), 2.70–2.65 (m, 6H), 2.67 (dd, J=5.45, 13.9 Hz, 1H), 2.34 (dd, J=7.4, 13.9 Hz, 1H), 1.79–1.76 (m, 4H), 1.74–1.69 (m, 1H), 1.54–1.46 (m, 1H), 1.38–1.31 (m, 1H), 0.96 (d, J=6.8 Hz, 6H).

Example 129

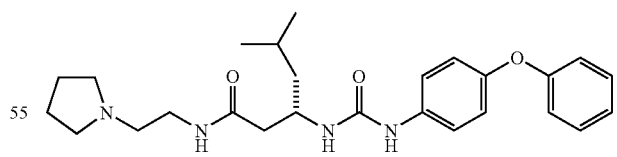

(S)-5-Methyl-3-[3-(4-phenoxy-phenyl)-ureido]-hexanoic Acid (2-pyrrolidin-1-yl-ethyl)-amide Prepared by a route similar to Example 15. MS (electrospray): mass calculated for C$_{26}$H$_{36}$N$_4$O$_3$, 452.28; m/z found, 453.3 [M+H]$^+$. $^1$H NMR (400 MHz, CD$_3$OD): 7.35–7.23 (m, 4H), 7.08–7.03 (m, 1H), 6.96–6.88 (m, 4H), 4.20–4.13 (m, 1H), 3.44–3.34 (m, 2H), 2.63–2.49 (m, 6H), 2.38–2.37 (m, 2H), 1.80–1.76 (m, 4H), 1.74–1.65 (m, 1H), 1.52–1.45

(m, 1H), 1.37–1.27 (m, 1H), 0.96 (d, J=1.06 Hz, 3H), 0.94 (d, J=0.75 Hz, 3H).

Example 130

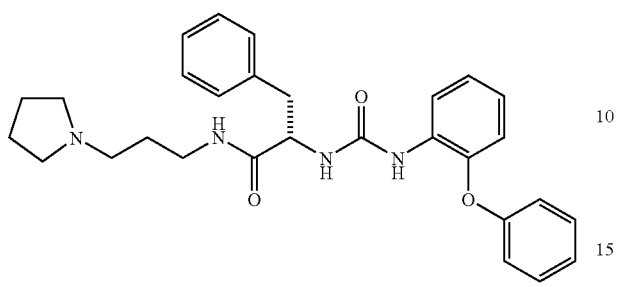

(S)-2-[3-(2-Phenoxy-phenyl)-ureido]-3-phenyl-N-(3-pyrrolidin-1-yl-propyl)-propionamide Prepared as in Example 7 from [(S)-2-phenyl-1-(3-pyrrolidin-1-yl-propylcarbamoyl)-ethyl]-carbamic acid tert-butyl ester (Example 1, step A), and substituting 2-phenoxyphenylisocyanate for 4-phenoxyphenylisocyanate. MS (electrospray): mass calculated for $C_{29}H_{34}N_4O_3$, 486.26; m/z found, 487.2 [M+H]$^+$. $^1$H NMR (400 MHz, CD$_3$OD): 8.06 (d, J=8.2 Hz, 1H), 7.44–6.6 (m, 14H), 4.46 (t, J=7.0 Hz, 1H), 3.13 (m, 2H), 3.01 (dd, J=13.6, 6.9 Hz, 1H), 2.88 (dd, J=13.6, 7.0 Hz, 1H), 2.45 (m, 4H), 2.36 (m, 2H), 1.74 (m, 4H), 1.57 (m, 2H).

Example 131

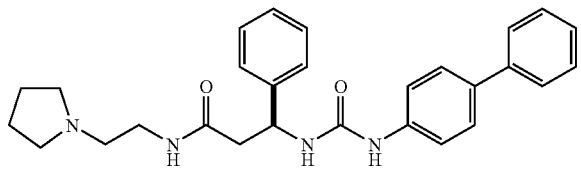

(S)-3-(3-Biphenyl-4-yl-ureido)-3-phenyl-N-(2-pyrrolidin-1-yl-ethyl)-propionamide Prepared as in Example 6 from 3-amino-3-phenylpropionic acid. MS (electrospray): mass calculated for $C_{28}H_{32}N_4O_2$, 456.25; m/z found, 457.3 [M+H]$^+$, 479.2 [M+Na]$^+$, 935.4 [2M+Na]$^+$. $^1$H NMR (400 MHz, CD$_3$OD): 7.56–7.49 (m, 4H), 7.43–7.32 (m, 8H), 7.29–7.23 (m, 2H), 5.27 (t, J=6.9 Hz, 1H), 3.32–3.29 (m, 2H), 2.70 (d, J=6.6 Hz, 2H), 2.62–2.57 (m, 6H), 1.79–1.76 (m, 4H).

Example 132

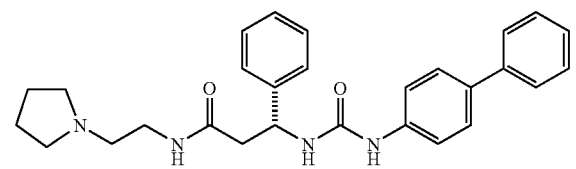

(R)-3-(3-Biphenyl-4-yl-ureido)-3-phenyl-N-(2-pyrrolidin-1-yl-ethyl)-propionamide Prepared as in Example 6 from 3-amino-3-phenylpropionic acid. MS (electrospray): mass calculated for $C_{28}H_{32}N_4O_2$, 456.25; m/z found, 457.3 [M+H]$^+$, 479.2 [M+Na]$^+$, 935.4 [2M+Na]$^+$. $^1$H NMR (400 MHz, CD$_3$OD): 7.56–7.49 (m, 4H), 7.43–7.32 (m, 8H), 7.29–7.23 (m, 2H), 5.27 (t, J=6.9 Hz, 1H), 3.32–3.29 (m, 2H), 2.70 (d, J=6.6 Hz, 2H), 2.62–2.57 (m, 6H), 1.79–1.76 (m, 4H).

Example 133

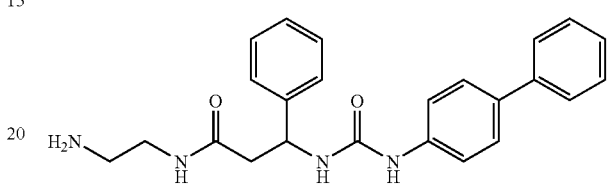

N-(2-Amino-ethyl)-3-(3-biphenyl-4-yl-ureido)-3-phenyl-propionamide

A. {2-[3-(3-Biphenyl-4-yl-ureido)-3-phenyl-propionylamino]-ethyl}-carbamic acid tert-butyl ester. Prepared as in Example 6, steps A and B, from 3-amino-3-phenylpropionic acid in step A, and substituting (2-amino-ethyl)-carbamic acid tert-butyl ester for 2-pyrrolidin-1-yl-ethylamine in step B. MS (electrospray): mass calculated for $C_{29}H_{34}N_4O_4$, 502.26; m/z found, 503.3 [M+H]$^+$, 525.3 [M+Na]$^+$. $^1$H NMR (400 MHz, DMSO-d$_6$): 8.81 (br t, J=8.9 Hz, 1H), 7.94 (br t, J=5.6 Hz, 1H), 7.51–7.66 (m, 5H), 7.39–7.47 (m, 4H), 7.30–7.32 (m, 5H), 6.94 (d, J=9.2 Hz, 1H), 6.68 (br t, J=5.6 Hz, 1H), 5.31 (dd, J=14.8, 6.8 Hz, 1H), 2.93–3.05 (m, 2H), 2.81–2.90 (m, 2H), 2.58 (d, J=6.7 Hz, 2H), 1.37 (s, 9H).

B. N-(2-Amino-ethyl)-3-(3-biphenyl-4-yl-ureido)-3-phenyl-propionamide. Prepared by a route similar to Example 92, step C. MS (electrospray): mass calculated for $C_{24}H_{26}N_4O_2$, 402.21; m/z found, 403.2 [M+H]$^+$, 425.2 [M+Na]$^+$, 827.4 [2M+Na]$^+$. $^1$H NMR (400 MHz, CD$_3$OD): 7.55–7.48 (m, 4H), 7.44–7.32 (m, 8H), 7.28–7.21 (m, 2H), 3.31–3.30 (m, 1H), 3.17 (t, J=6.0 Hz, 2H), 2.72 (dd, J=3.0, 7.0 Hz, 2H), 2.59 (t, J=6.0 Hz, 2H).

Example 134

(R)-4-(3-Biphenyl-4-yl-ureido)-5-phenyl-pentanoic Acid (2-diethylamino-ethyl)-amide Prepared as in Example 2, Method 1 step C, from (E)-(S)-4-(3-biphenyl-4-yl-ureido)-5-phenyl-pent-2-enoic acid (2-diethylamino-ethyl)-amide (Example 19). MS (electrospray): mass calculated for $C_{30}H_{38}N_4O_2$, 486.30; m/z found, 487.3 [M+H]+. 1H NMR (400 MHz, CDCl3): 7.89 (s, 1H), 7.44–7.29 (m, 8H), 7.23–7.09 (m, 6H), 6.74 (br s, 1H), 5.84 (br s, 1H), 4.05–3.96 (m, 1H), 3.30–3.22 (m, 1H), 3.17–3.10 (m, 1H), 2.83 (dd, J=13.6, 6.0 Hz, 1H), 2.66 (dd, J=13.6, 7.2 Hz, 1H), 2.47–2.41 (m, 6H), 2.22 (t, J=7.0 Hz, 2H), 1.79–1.72 (m, 1H), 1.67–1.59 (m, 1H), 0.88 (t, J=7.2 Hz, 6H).

Example 135

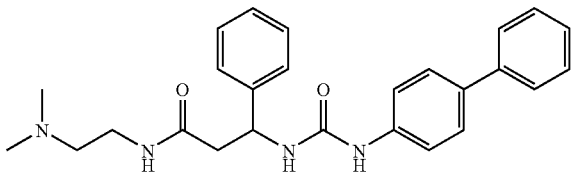

3-(3-Biphenyl-4-yl-ureido)-N-(2-dimethylamino-ethyl)-3-phenyl-propionamide

Prepared by a route similar to Example 6, steps A and B, from 3-amino-3-phenylpropionic acid in step A, and substituting N',N'-dimethyl-ethane-1,2-diamine for 2-pyrrolidin-1-yl-ethylamine in step B. MS (electrospray): mass calculated for $C_{26}H_{30}N_4O_2$, 430.24; m/z found, 431.2 [M+H]+, 453.2 [M+Na]+, 883.5 [2M+Na]+. 1H NMR (400 MHz, CDCl3): 7.71 (s, 1H), 7.46–7.34 (m, 14H), 6.90 (br s, 1H), 6.72 (br s, 1H), 5.29–5.23 (m, 1H), 3.34–3.28 (m, 1H), 3.16–3.10 (m, 1H), 2.71 (dd, J=14.1, 4.2 Hz, 1H), 2.62 (dd, J=14.1, 8.0 Hz, 1H), 2.42–2.29 (m, 2H), 2.15 (t, J=7.0 Hz, 6H).

Example 136

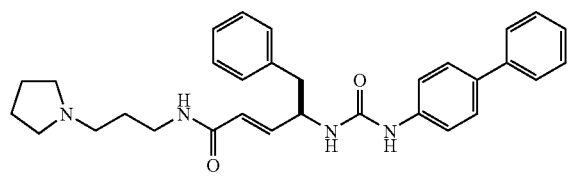

(E)-(R)-4-(3-Biphenyl-4-yl-ureido)-5-phenyl-pent-2-enoic Acid (3-pyrrolidin-1-yl-propyl)-amide Prepared by a route similar to Example 19 from (E)-(R)-4-tert-butoxycarbonyl-amino-5-phenyl-pent-2-enoic acid (Example 93, step B). MS (electrospray): mass calculated for $C_{31}H_{36}N_4O_2$, 496.28; m/z found, 497.3 [M+H]+. 1H NMR (400 MHz, CDCl3): 8.22 (s, 1H), 7.99 (t, J=5.4 Hz, 1H), 7.50–7.35 (m, 8H), 7.30–7.18 (m, 6H), 6.69 (dd, J=15.3, 6.5 Hz, 1H), 6.55 (d, J=8.5 Hz, 1H), 5.94 (dd, J=15.3, 1.0 Hz, 1H), 4.87–4.80 (m, 1H), 3.45–3.29 (m, 2H), 2.98–2.89 (m, 2H), 2.54 (t, J=6.6 Hz, 2H), 2.45 (br s, 4H), 1.77–1.67 (m, 6H).

Example 137

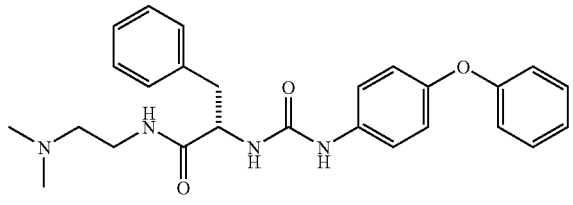

(S)-N-(2-Dimethylamino-ethyl)-2-[3-(4-phenoxy-phenyl)-ureido]-3-phenyl-propionamide Prepared by a route similar to Example 7. MS (electrospray): mass calculated for $C_{26}H_{30}N_4O_3$, 446.26; m/z found: 447.2, [M+H]+. 1H NMR (400 MHz, DMSO-d6): 8.68 (s, 1H), 8.01 (t, J=5.6 Hz, 1H), 7.41–6.9 (m, 14H), 6.3 (d, J=8.3 Hz, 1H), 4.46 (m, 1H), 3.1 (m, 2H), 2.97 (dd, J=13.6, 5.6 Hz, 1H), 2.81 (dd, J=13.6, 7.7 Hz, 1H), 2.23 (m, 2H), 2.20 (s, 3H), 2.13 (s, 3H).

Example 138

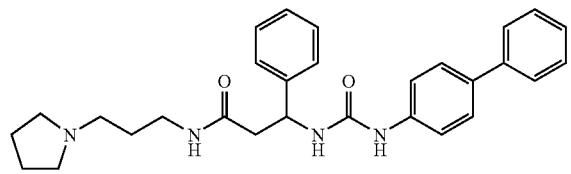

3-(3-Biphenyl-4-yl-ureido)-3-phenyl-N-(3-pyrrolidin-1-yl-propyl)-propionamide

Prepared by a route similar to Example 6, steps A and B. MS (electrospray): mass calculated for $C_{29}H_{34}N_4O_2$, 470.61; m/z found, 471.3 [M+H]+, 493.2 [M+Na]+. 1H NMR (400 MHz, CD3OD): 7.50–7.59 (m, 4H), 7.32–7.44 (m, 8H), 7.23–7.27 (m, 2H), 5.26 (t, J=6.8 Hz, 1H), 3.16 (t, J=6.8 Hz, 2H), 2.70 (d, J=7.2 Hz, 2H), 2.45–2.50 (m, 4H), 2.32–2.36 (m, 2H), 1.73–1.76 (m, 4H), 1.57–1.64 (m, 2H).

Example 139

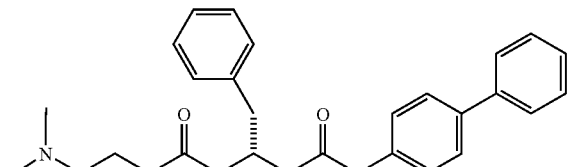

(S)-3-(3-Biphenyl-4-yl-ureido)-N-(2-dimethylamino-ethyl)-4-phenyl-butyramide

A. [(S)-1-Benzyl-2-(2-dimethylamino-ethylcarbamoyl)-ethyl]-carbamic acid tert-butyl ester. Prepared as in Example 15, step A, substituting (S)-3-tert-butoxycarbonylamino-4-phenyl-butyric acid for (R)-3-tert-butoxycarbonylamino-4- methyl-pentanoic acid, and N',N'-dimethyl-ethane-1,2-diamine for 2-pyrrolidin-1-yl-ethylamine. MS (electrospray): mass calculated for $C_{19}H_{31}N_3O_3$, 349.24; m/z found, 350.2 [M+H]$^+$. $^1$H NMR (400 MHz, CDCl$_3$): 7.23–7.12 (m, 5H), 6.02 (br s, 1H), 5.66 (br s, 1H), 4.05–3.97 (m, 1H), 3.29–3.25 (m, 2H), 2.99–2.86 (m, 1H), 2.75–2.70 (m, 1H), 2.37–2.28 (m, 3H), 2.21–2.18 (m, 7H), 1.34 (s, 9H).

B. (S)-3-(3-Biphenyl-4-yl-ureido)-N-(2-dimethylamino-ethyl)-4-phenyl-butyramide. Prepared by a route similar to Example 15, step B. MS (electrospray): mass calculated for $C_{27}H_{32}N_4O_2$, 444.57; m/z found, 445.3 [M+H]$^+$. $^1$H NMR (400 MHz, CDCl$_3$): 7.49–7.42 (m, 4H), 7.36–7.32 (m, 4H), 7.26–7.14 (m, 6H), 6.32–6.25 (m, 1H), 6.00 (br s, 1H), 4.33–4.24 (m, 1H), 3.33–3.24 (m, 1H), 3.22–3.17 (m, 1H), 3.04 (dd, J=13.5, 6.1 Hz, 1H), 2.74 (dd, J=13.5, 8.6 Hz, 1H), 2.42 (dd, J=14.8, 4.3 Hz, 1H), 2.35 (t, J=5.9 Hz, 2H), 2.23 (dd, J=14.8, 6.7 Hz, 1H), 2.16 (s, 6H).

Example 140

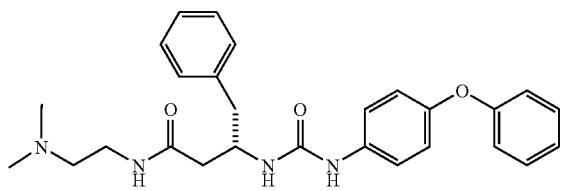

(S)-N-(2-Dimethylamino-ethyl)-3-[3-(4-phenoxy-phenyl)-ureido]-4-phenyl-butyramide Prepared as in Example 15, step B, from [(S)-1-benzyl-2-(2-dimethylamino-ethylcarbamoyl)-ethyl]-carbamic acid tert-butyl ester (Example 139, step A), and substituting 4-phenoxyphenyl isocyanate for 4-isocyanato-biphenyl. MS (electrospray): mass calculated for $C_{27}H_{32}N_4O_3$, 460.57; m/z found, 461.3 [M+H]$^+$. $^1$H NMR (400 MHz, CDCl$_3$): 7.37–7.28 (m, 6H), 7.25–7.23 (m, 3H), 7.10–7.07 (m, 1H), 6.99–6.94 (m, 4H), 6.55–6.49 (m, 1H), 6.1.2–6.05 (m, 1H), 4.4–4.32 (m, 1H), 3.51–3.36 (m, 1H), 3.32–3.25 (m, 1H), 3.09 (dd, J=13.5, 6.9 Hz, 1H), 2.82 (dd, J=13.5, 8.4 Hz, 1H), 2.51–2.43 (m, 3H), 2.32 (dd, J=14.8, 7.1 Hz, 1H), 2.27 (s, 6H).

Example 141

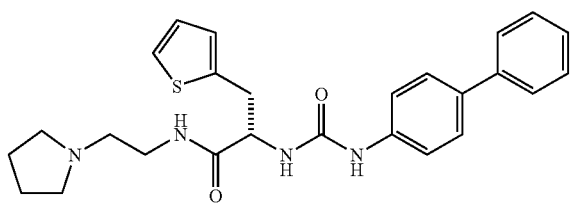

(S)-2-(3-Biphenyl-4-yl-ureido)-N-(2-pyrrolidin-1-yl-ethyl)-3-thiophen-2-yl-propionamide Prepared by a route similar to Example 67. MS (electrospray): mass calculated for $C_{26}H_{30}N_4O_2S$, 462.21; m/z found, 463.16 [M+H]$^+$. $^1$H NMR (400 MHz, DMSO-d$_6$): 8.95 (s, 1H), 8.43 (t, J=5.6 Hz, 1H), 7.62–7.36 (m, 10H), 6.98–6.90 (m, 2H), 6.57 (d, J=7.8 Hz, 1H), 4.45 (m, 1H), 3.58–3.95 (m, 10H), 1.98 (br s, 2H), 1.84 (br s, 2H).

Example 142

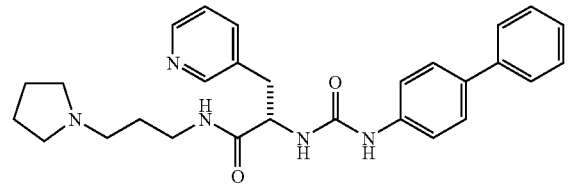

(S)-2-(3-Biphenyl-4-yl-ureido)-3-pyridin-3-yl-N-(3-pyrrolidin-1-yl-propyl)-propionamide Prepared by a route similar to Example 67. MS (electrospray): mass calculated for $C_{28}H_{33}N_5O_2$, 471.26; m/z found, 472.21 [M+H]$^+$. $^1$H NMR (500 MHz, DMSO-d$_6$): 8.86 (s, 1H), 8.47 (m, 2H), 8.29 (t, J=5.7 Hz, 1H), 7.70 (d, J=7.8 Hz, 1H), 7.59–7.28 (m, 11H), 6.59 (d, J=8.0 Hz, 1H), 4.50 (m, 1H), 3.51 (br s, 2H), 3.19–2.88 (m, 8H), 1.98 (br s, 2H), 1.91 (br s, 2H), 1.77 (m, 2H).

Example 143

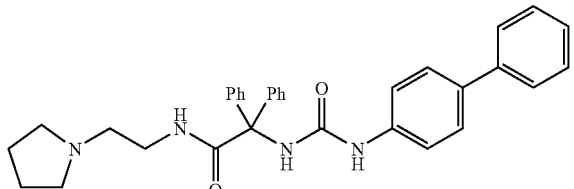

2-(3-Biphenyl-4-yl-ureido)-2,2-diphenyl-N-(2-pyrrolidin-1-yl-ethyl)-acetamide

Prepared by a route similar to Example 68. MS (electrospray): mass calculated for $C_{33}H_{34}N_4O_2$, 518.6; m/z found, 519.3 [M+H]$^+$. $^1$H NMR (400 MHz, CD$_3$OD): 7.61–7.50 (m, 4H), 7.46–7.44 (m, 4H), 7.40–7.25 (m, 11H), 3.45 (t, J=6.3 Hz, 2H), 2.55–2.51 (m, 6H), 1.56–1.54 (m, 4H).

Example 144

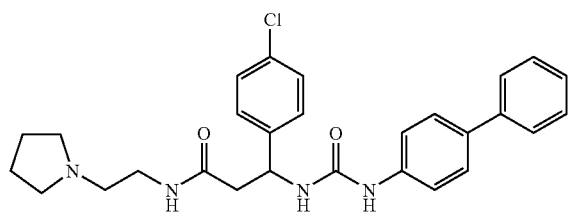

3-(3-Biphenyl-4-yl-ureido)-3-(4-chloro-phenyl)-N-(2-pyrrolidin-1-yl-ethyl)-propionamide Prepared by a route similar to Example 6, steps A and B. MS (electrospray): mass calculated for $C_{28}H_{31}ClN_4O_2$, 491.03; m/z found, 492.3 [M+H]$^+$, 514.2 [M+Na]$^+$. $^1$H NMR (400 MHz, CD$_3$OD): 7.50–7.53 (m, 4H), 7.35–7.39 (m, 7H), 7.25–7.27 (m, 2H), 5.23 (t, J=6.8 Hz, 1H), 3.20–3.28 (m, 2H), 2.65–2.70 (m, 2H), 2.46–2.50 (m, 6H), 1.72–1.77 (m, 4H).

Example 145

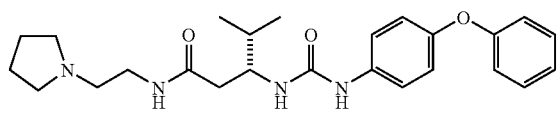

(R)-4-Methyl-3-[3-(4-phenoxy-phenyl)-ureido]-pentanoic Acid (2-pyrrolidin-1-yl-ethyl)-amide Prepared by a route similar to Example 15. MS (electrospray): mass calculated for $C_{25}H_{34}N_4O_3$, 438.26; m/z found, 439.21 [M+H]$^+$. $^1$H NMR (400 MHz, CDCl$_3$): 7.29–7.21 (m, 4H), 7.0–6.96 (m, 1H), 6.90–6.86 (m, 4H), 6.49 (br s, 1H), 3.85–3.78 (m, 1H), 3.34–3.24 (m, 2H), 2.53–2.48 (m, 2H), 2.46–2.43 (m, 4H), 2.31 (dd, J=14.9, 8.4 Hz, 1H), 1.83–1.76 (m, 4H), 1.74–1.66 (m, 4H), 0.89 (q, J=3.3 Hz, 6H).

Example 146

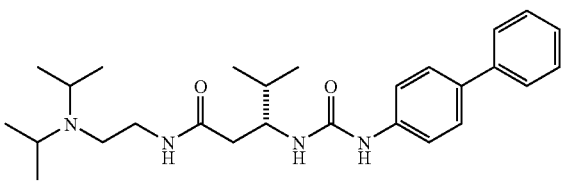

(R)-3-(3-Biphenyl-4-yl-ureido)-4-methyl-pentanoic Acid (2-diisopropylamino-ethyl)-amide A. {(R)-1-[(2-Diisopropylamino-ethylcarbamoyl)-methyl]-2-methyl-propyl}-carbamic acid tert-butyl ester. Prepared by a route similar to Example 15, step A. $^1$H NMR (400 MHz, CDCl$_3$): 6.29 (br s, 1H), 5.33 (d, J=9.2 Hz, 1H), 3.66–3.56 (m, 1H), 3.27–3.13 (m, 2H), 3.0 (q, J=6.6 Hz, 2H), 2.56 (t, J=6.2 Hz, 2H), 2.44 (dd, J=14.9, 4.4 Hz, 1H), 2.36 (dd, J=14.9, 6.5 Hz, 1H), 1.90 (m, 1H), 1.43 (s, 9H), 1.0 (d, J=6.5 Hz, 12H), 0.92 (d, J=6.7 Hz, 3H), 0.916 (d, J=6.8 Hz, 3H).

B. (R)-3-(3-Biphenyl-4-yl-ureido)-4-methyl-pentanoic acid (2-diisopropylamino-ethyl)-amide. Prepared by a route similar to Example 15, step B. MS (electrospray): mass calculated for $C_{27}H_{40}N_4O_2$, 452.32; m/z found, 453.3 [M+H]$^+$. $^1$H NMR (400 MHz, CDCl$_3$): 7.54–7.50 (m, 2H), 7.47–7.42 (m, 4H), 7.40–7.35 (m, 2H), 7.31–7.26 (m, 1H), 6.58 (br s, 1H), 3.94–3.87 (m, 1H), 3.28–3.11 (m, 2H), 3.04–2.92 (m, 2H), 2.64–2.5 (m, 3H), 2.38 (dd, J=14.8, 8.2 Hz, 1H), 1.96–1.87 (m, 1H), 1.02–0.95 (m, 18H).

Example 147

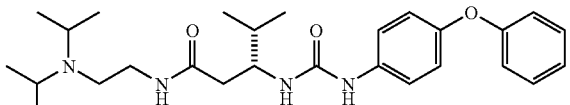

(R)-4-Methyl-3-[3-(4-phenoxy-phenyl)-ureido]-pentanoic Acid (2-diisopropylamino-ethyl)-amide Prepared by a route similar to Example 15. MS (electrospray): mass calculated for $C_{27}H_{40}N_4O_2$, 452.32; m/z found, 453.3 [M+H]$^+$. $^1$H NMR (400 MHz, CDCl$_3$): 7.35–7.33 (m, 2H), 7.31–7.26 (m, 2H), 7.05–7.02 (m, 1H), 6.95–6.85 (m, 4H), 6.61 (br s, 1H), 3.90–3.83 (m, 1H), 3.23–3.18 (m, 2H), 3.0–2.94 (m, 2H), 2.56–2.51 (m, 3H), 2.37 (dd, J=14.8, 8.2 Hz, 1H), 1.92–1.85 (m, 1H), 0.99–0.96 (m, 18H).

Example 148

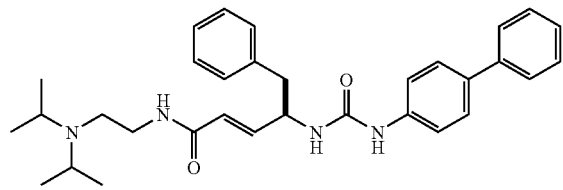

(E)-(R)-4-(3-Biphenyl-4-yl-ureido)-5-phenyl-pent-2-enoic Acid (2-diisopropylamino-ethyl)-amide Prepared by a route similar to Example 19. MS (electrospray): mass calculated for $C_{32}H_{40}N_4O_2$, 512.32; m/z found, 513.3 [M+H]$^+$. $^1$H NMR (400 MHz, CD$_3$OD): 7.55–7.46 (m, 4H), 7.40–7.35 (m, 4H), 7.30–7.18 (m, 6H), 6.79 (dd, J=5.6, 15.4 Hz, 1H), 5.99 (dd, J=1.6, 15.4 Hz, 1H), 4.75–4.70 (m, 1H), 3.21 (t, J=7.6 Hz, 2H), 3.04–2.86 (m, 4H), 2.54 (t, J=7.4 Hz, 2H), 1.02 (d, J=6.4 Hz, 12H).

Example 149

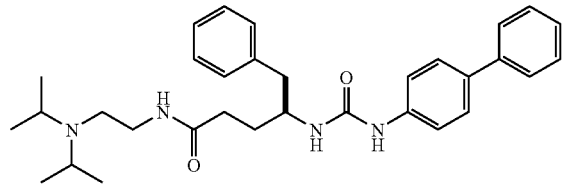

(S)-4-(3-Biphenyl-4-yl-ureido)-5-phenyl-pentanoic Acid (2-diisopropylamino-ethyl)-amide Prepared as in Example 2, Method 1, step C, from (E)-(R)-4-(3-biphenyl-4-yl-ureido)-5-phenyl-pent-2-enoic acid (2-diisopropylamino-ethyl)-amide (Example 148). MS (electrospray): mass calculated for $C_{32}H_{42}N_4O_2$, 514.33;

m/z found, 515.3 [M+H]+. 1H NMR (400 MHz, CDCl3): 8.07 (br s, 1H), 7.53 (d, J=7.5 Hz, 2H), 7.49–7.39 (m, 6H), 7.33–7.20 (m, 6H), 6.70 (br s, 1H), 6.08 (br s, 1H), 4.17–4.09 (m, 1H), 3.31–3.24 (m, 1H), 3.19–3.13 (m, 1H), 3.00–2.92 (m, 3H), 2.77 (dd, J=13.5, 7.3 Hz, 1H), 2.54 (t, J=6.0 Hz, 2H), 2.38–2.23 (m, 2H), 1.85–1.71 (m, 2H), 0.98 (d, J=3.9 Hz, 6H), 0.97 (d, J=3.9 Hz, 6H).

Example 150

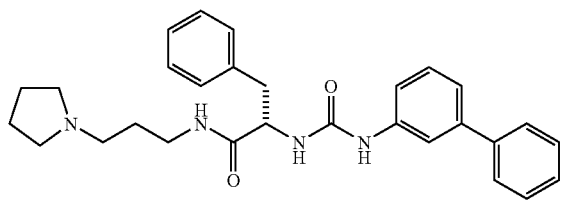

(S)-2-(3-Biphenyl-3-yl-ureido)-3-phenyl-N-(3-pyrrolidin-1-yl-propyl)-propionamide A. Biphenyl-3-yl-carbamic acid phenyl ester. Prepared by a route similar to Example 3, step A. MS (electrospray): mass calculated for $C_{19}H_{15}NO_2$, 289.11; m/z found, 312.0 [M+Na]+.

B. (S)-2-(3-Biphenyl-3-yl-ureido)-3-phenyl-N-(3-pyrrolidin-1-yl-propyl)-propionamide. Prepared by a route similar to Example 3, step C, substituting [(S)-2-phenyl-1-(3-pyrrolidin-1-yl-propylcarbamoyl)-ethyl]-carbamic acid tert-butyl ester (Example 1, step A) for [(S)-1-(2-diisopropylamino-ethylcarbamoyl)-2-phenyl-ethyl]-carbamic acid tert-butyl ester. MS (electrospray): mass calculated for $C_{29}H_{34}N_4O_2$, 470.27; m/z found, 471.3 [M+H]+. 1H NMR (400 MHz, CD3OD): 7.64 (t, J=2 Hz, 1H), 7.55–7.15 (m, 13H), 4.50 (t, J=7.2 Hz, 1H), 3.18 (m, 2H), 3.06 (dd, J=13.6, 6.8 Hz, 1H), 2.98 (dd, J=13.6, 7.2 Hz, 1H), 2.46 (br m, 4H), 2.35 (m, 2H), 1.68 (br m, 4H), 1.59 (m, 2H).

Example 151

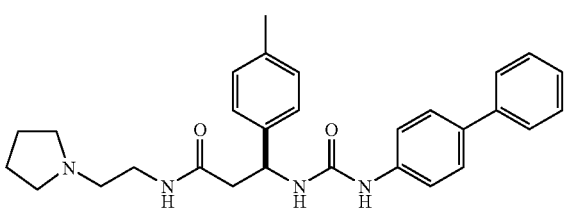

(S)-3-(3-Biphenyl-4-yl-ureido)-N-(2-pyrrolidin-1-yl-ethyl)-3-p-tolyl-propionamide Prepared by a route similar to Example 6. MS (electrospray): mass calculated for $C_{29}H_{34}N_4O_2$, 470.27; m/z found, 471.3 [M+H]+. 1H NMR (400 MHz, CD3OD): 7.57–7.50 (m, 4H), 7.43–7.37 (m, 4H), 7.29–7.25 (m, 3H), 7.16 (d, J=7.9 Hz, 2H), 5.22 (t, J=6.9 Hz, 1H), 3.28–3.23 (m, 2H), 2.68 (d, J=6.4 Hz, 2H), 2.52–2.48 (m, 6H), 2.31 (s, 3H), 1.77–1.75 (m, 4H).

Example 152

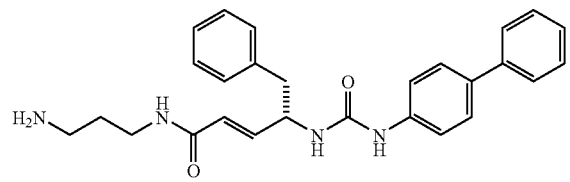

(E)-(S)-4-(3-Biphenyl-4-yl-ureido)-5-phenyl-pent-2-enoic Acid (3-amino-propyl)-amide Prepared by a route similar to Example 93. MS (electrospray): mass calculated for $C_{27}H_{30}N_4O_2$, 442.24; m/z found, 443.2 [M+H]+, 885.5 [2M+H]+. 1H NMR (400 MHz, CDCl3): 7.73 (s, 1H), 7.45–7.11 (m, 14H), 6.62 (dd, J=6.2, 15.3 Hz, 1H), 5.94 (d, J=7.2 Hz, 1H), 5.85 (d, J=15.3 Hz, 1H), 4.74–4.67 (m, 1H), 3.33–3.22 (m, 2H), 2.89–2.78 (m, 2H), 2.70–2.63 (m, 2H), 1.58 (br s, 2H), 1.52 (t, J=6.4 Hz, 2H).

Example 153

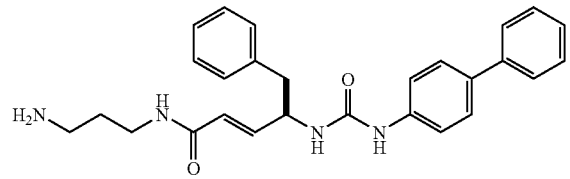

(E)-(R)-4-(3-Biphenyl-4-yl-ureido)-5-phenyl-pent-2-enoic Acid (3-amino-propyl)-amide A. {3-[(E)-(R)-4-(3-Biphenyl-4-yl-ureido)-5-phenyl-pent-2-enoylamino]-propyl}-carbamic acid tert-butyl ester. Prepared by a route similar to Example 19. MS (electrospray): mass calculated for $C_{32}H_{38}N_4O_4$, 542.29; m/z found, 443.2 [M−BOC]+. 1H NMR (400 MHz, CDCl3): 7.80 (br s, 1H), 7.33–7.39 (m, 4H), 7.26–7.30 (m, 4H), 7.15–7.21 (m, 4H), 7.11–7.13 (m, 2H), 6.86 (t, J=5.7 Hz, 1H), 6.67 (dd, J=15.3, 5.1 Hz, 1H), 5.93 (d, J=8.2 Hz, 1H), 5.83 (d, J=15.3 Hz, 1H), 4.96 (br s, 1H), 4.71 (br s, 1H), 3.23–3.33 (m, 1H), 2.97–3.12 (m, 3H), 2.74–2.85 (m, 2H), 1.48–1.55 (b, 2H), 1.34 (s, 9H).

B. (E)-(R)-4-(3-Biphenyl-4-yl-ureido)-5-phenyl-pent-2-enoic Acid (3-amino-propyl)-amide. Prepared by a route similar to Example 92, step C. MS (electrospray): mass calculated for $C_{27}H_{30}N_4O_2$, 442.24; m/z found, 443.2 [M+H]+, 465.2 [M+Na]+, 885.5 [2M+H]+, 907.4 [2M+Na]+. 1H NMR (400 MHz, CDCl3): 8.04 (s, 1H), 7.38–7.09 (m, 14H), 6.63 (dd, J=15.3, 6.0 Hz, 1H), 6.20 (d, J=7.7 Hz, 1H), 5.87 (d, J=15.3 Hz, 1H), 4.71–4.67 (m, 1H), 3.26–3.22 (m, 2H), 2.85–2.76 (m, 2H), 2.62–2.53 (m, 2H), 1.79 (br s, 2H), 1.47 (t, J=5.6 Hz, 2H).

Example 154

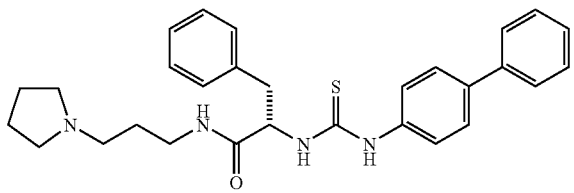

(S)-2-(3-Biphenyl-4-yl-thioureido)-3-phenyl-N-(3-pyrrolidin-1-yl-propyl)-propionamide Prepared as in Example 9, substituting 3-pyrrolidin-1-yl-propylamine for 2-pyrrolidin-1-yl-ethylamine in step A, and 4-isothiocyanato-biphenyl for 4-(4-chloro-phenoxy)-phenylisothiocyanate in step C. MS (electrospray): mass calculated for $C_{29}H_{34}N_4OS$, 486.25; m/z found, 487.2 [M+H]$^+$. $^1$H NMR (400 MHz, CD$_3$OD): 7.61–7.18 (m, 14H), 5.36 (t, J=7.1 Hz, 1H), 3.20–3.15 (m, 3H), 3.09 (dd, J=13.7, 7.4 Hz, 1H), 2.50 (br m, 4H), 2.45 (m, 2H), 1.78 (m, 4H), 1.66 (m, 2H).

Example 155

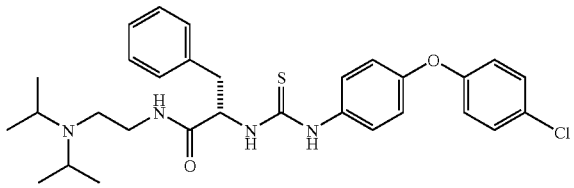

(S)-2-{3-[4-(4-Chloro-phenoxy)-phenyl]-thioureido}-N-(2-diisopropylamino-ethyl)-3-phenyl-propionamide Prepared as in Example 9, substituting N',N'-diisopropyl-ethane-1,2-diamine for 2-pyrrolidin-1-yl-ethylamine in step A. MS (electrospray): mass calculated for $C_{30}H_{37}ClN_4O_2S$, 552.23; m/z found, 553.2 [M+H]$^+$. $^1$H NMR (400 MHz, CD$_3$OD): 7.35–6.93 (m, 13H), 5.18 (t, J=7.02 Hz, 1H), 3.18–2.99 (m, 6H), 2.45 (br s, 2H), 1.02 (d, J=6.6 Hz, 12H).

Example 156

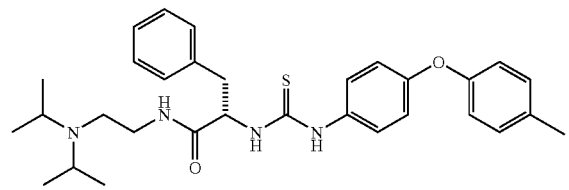

(S)-N-(2-Diisopropylamino-ethyl)-3-phenyl-2-[3-(4-p-tolyloxy-phenyl)-thioureido]-propionamide Prepared as in Example 20, substituting 4-(4-methyl-phenoxy)-phenylisothiocyanate for 4-(4-fluoro-phenoxy)-phenylisothiocyanate. MS (electrospray): mass calculated for $C_{31}H_{40}N_4O_2S$, 532.29; m/z found, 533.3 [M+H]$^+$. $^1$H NMR (400 MHz, CD$_3$OD): 7.32–7.11 (m, 9H), 6.88–6.84 (m, 4H), 5.17 (t, J=7.0 Hz, 1H), 3.17–2.98 (m, 6H), 2.47 (m, 2H), 1.01 (d, J=6.6 Hz, 12H).

Example 157

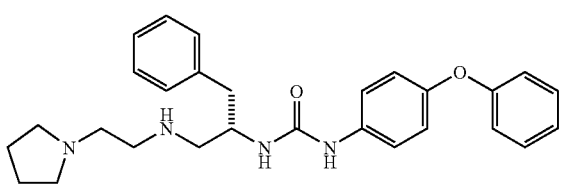

1-[(S)-1-Benzyl-2-(2-pyrrolidin-1-yl-ethylamino)-ethyl]-3-(4-phenoxy-phenyl)-urea A. (S)-2-[3-(4-Phenoxy-phenyl)-ureido]-3-phenyl-N-(2-pyrrolidin-1-yl-ethyl)-propionamide. To a solution of [(S)-2-phenyl-1-(2-pyrrolidin-1-yl-ethylcarbamoyl)-ethyl]-carbamic acid tert-butyl ester (Example 9, step A) (0.1 g, 0.28 mmol) in CH$_2$Cl$_2$ (3 mL), a 4 M solution of HCl in dioxane (2.5 mL, 10 mmol) was added, and the mixture was stirred for 4 h at rt. The solvents were removed, and the residue was treated with CH$_2$Cl$_2$. The solvents were removed again under reduced pressure. The residue was dissolved in CH$_2$Cl$_2$ (3 mL), and TEA (0.07 g, 0.69 mmol) was added at 0° C. followed by 4-phenoxyphenylisocyanate (0.07 g, 0.33 mmol). The mixture was warmed to rt over a period of 4 h and then diluted with EtOAc (75 mL). The organic layer was washed with saturated NaHCO$_3$ (25 mL) and brine (25 mL), and dried (Na$_2$SO$_4$). The solvent was removed, and the residue was purified by flash column chromatography using 0–20% MeOH (1% NH$_4$OH)/CH$_2$Cl$_2$ to afford 0.03 g (25%) of the desired product. MS (electrospray): mass calculated for $C_{28}H_{32}N_4O_3$, 472.25; m/z found, 473.2 [M+H]$^+$, 495.2 [M+Na]$^+$. $^1$H NMR (400 MHz, DMSO-d$_6$): 8.68 (s, 1H), 8.04 (t, J=5.5 Hz, 1H), 7.36–6.89 (m, 14H), 6.30 (d, J=8.3 Hz, 1H), 4.46 (m, 1H), 3.15 (m, 2H), 2.96 (dd, J=13.6, 5.6 Hz, 1H), 2.82 (dd, J=13.6, 7.7 Hz, 1H), 2.42–2.37 (m, 6H), 1.67–1.63 (m, 4H).

B. 1-[(S)-1-Benzyl-2-(2-pyrrolidin-1-yl-ethylamino)-ethyl]-3-(4-phenoxy-phenyl)-urea. To a solution of (S)-2-[3-(4-phenoxy-phenyl)-ureido]-3-phenyl-N-(2-pyrrolidin-1-yl-ethyl)-propionamide (0.1 g, 0.21 mmol) in THF (3 mL), borane dimethylsulfide complex (1 M, 0.63 mL, 0.63 mmol) was added, and the mixture was heated to 60° C. After 14 h of stirring, the mixture was cooled to rt and quenched with MeOH. The mixture was heated to 60° C. for 1 h and then cooled. The solvents were removed, and the residue was redissolved in 4 M HCl in dioxane and stirred for 1 h. The mixture was diluted with EtOAc (75 mL), washed sequentially with 1 N NaOH (2×25 mL) and brine (25 mL), and dried (Na$_2$SO$_4$). The solvents were removed and the residue was purified by flash column chromatography using 0–20% MeOH (1% NH$_4$OH)/CH$_2$Cl$_2$ to afford 0.07 g (72%) of the desired product. MS (electrospray): mass calculated for $C_{28}H_{34}N_4O_2$, 458.27; m/z found, 459.3 [M+H]$^+$, 481.2 [M+Na]$^+$. $^1$H NMR (400 MHz, CD$_3$OD): 7.31–7.17 (m, 9H), 7.05–7.02 (m, 1H), 6.92–6.87 (m, 4H), 4.13 (m, 1H), 2.83–2.52 (m, 12H), 1.77–1.73 (m, 4H).

Example 158

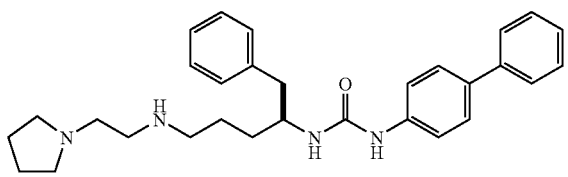

1-[(S)-1-Benzyl-4-(2-pyrrolidin-1-yl-ethylamino)-butyl]-3-biphenyl-4-yl-urea

Prepared by a route similar to Example 2, Method 1. MS (electrospray): mass calculated for $C_{30}H_{38}N_4O$, 470.65; m/z found, 471.3 [M+H]$^+$, 493.3 [M+Na]$^+$. $^1$H NMR (CDCl$_3$, 400 MHz): 10.0 (br s, 1H), 7.41–7.49 (m, 5H), 7.36 (t, J=8.1 Hz, 2H), 7.18–7.25 (m, 5H), 6.30 (d, J=9.8 Hz, 1H), 4.23 (br s, 1H), 3.02–3.10 (m, 1H), 2.89–2.92 (m, 3H), 2.70–2.83 (m, 5H), 2.61 (dd, J=6.2, 7.2, 1H), 2.45–2.51 (m, 1H), 1.77–1.84 (m, 4H), 1.60–1.67 (m, 1H), 1.31–1.37 (m, 1H), 1.00–1.06 (m, 1H), 0.76–0.82 (m, 1H).

Assay Method

Cos-7 cells (African green monkey, kidney) from American Type Culture Collection were grown in DMEM supplemented with 10% fetal bovine serum. The entire coding region of the human GlyT2 cDNA was cloned into the mammalian expression vector pClNeo, and then stably transfected into Cos-7 cells. Transfection was performed essentially as described by T. W. Lovenberg et al. (Mol. Pharmacol. 1999, 55:1101–1107): Briefly, cells were grown to 70–80% confluence, removed from the plate with trypsin, and pelleted in a clinical centrifuge. The pellet was resuspended in 400 μL complete medium and transferred to an electroporation cuvette with a 0.4 cm gap between the electrodes (Bio-Rad, 165–2088). One microgram of supercoiled GlyT2 cDNA was added to the cells, and the suspension was mixed. The voltage for the electroporation was set at 0.25 kV, and the capacitance was set at 960 μF. After electroporation, the cuvette contents were diluted to 10 mL with complete medium, and 0.5 mL, 1.0 mL, 2.0 mL and remainder (~6.5 mL) portions were plated onto four 10-cm dishes. The cells were incubated 24 h before adding 600 μg/mL G418. Colonies that survived selection were isolated and tested for GlyT2 expression.

The day before the assay, the GlyT2 expressing cells were plated into 96-well scintillating microplates (Amersham, RPNQ 0160) at a density of approximately 20,000 cells per well. Cells were grown overnight at 37° C. in 5% CO$_2$ and then washed once with 37° C. HEPES buffered saline (HBS: 150 mM NaCl, 20 mM HEPES, 1 mM CaCl$_2$, 10 mM glucose, 5 mM KCl, 1 mM MgCl$_2$; pH 7.4). Eighty microliters of 37° C. HBS was subsequently added to each well. Test solutions of GlyT2 inhibitors were prepared in HBS from DMSO stock solutions, and 5 μL of test solution was added to each test well. Total transport and non-specific background were determined by adding 5 μL HBS or 5 μL 2 M glycine, respectively, to the appropriate control wells. Plates were then left at rt for 5 min before the addition of 20 μL of 100 μM $^{14}$C-glycine (NEN, NEC 048H) to each well for a final concentration of 20 μM. Plates were incubated for 2 h at 37° C. with 5% CO$_2$. After 2 h the reaction mixtures were removed by aspiration, and the plates were washed once with ice-cold HBS. Plates were sealed with TopSeal (Packard, 6005185) and counted on a Packard TopCount® scintillation counter.

TABLE 1

| Example | IC$_{50}$ (nM) |
|---------|----------------|
| 1 | 11 |
| 8 | 31 |
| 42 | 93 |
| 53 | 103 |

TABLE 2

| Example | IC$_{50}$ (nM) |
|---------|----------------|
| 2 | 18 |
| 3 | 18 |
| 6 | 27 |
| 11 | 39 |
| 19 | 48 |
| 21 | 52 |
| 26 | 57 |
| 27 | 58 |
| 28 | 95 |
| 61 | 3,500 |
| 65 | 405 |
| 74 | 1062 |
| 84 | 10,000 |
| 85 | 269 |
| 87 | 76 |
| 98 | 398 |
| 101 | 112 |
| 111 | 500 |
| 122 | 440 |
| 142 | 685 |
| 143 | 8,000 |
| 146 | 595 |
| 150 | 998 |
| 152 | 3,162 |
| 157 | 181 |
| 158 | 340 |

TABLE 3

| Example | IC$_{50}$ (nM) |
|---------|----------------|
| 9 | 32 |
| 31 | 89 |

What is claimed is:
1. A compound of formula (I):

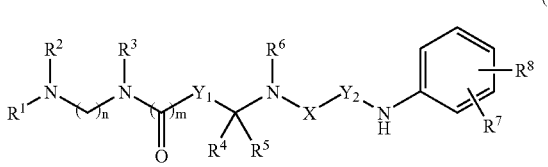

wherein,
R$^1$ and R$^2$ are independently selected from the group consisting of H, C$_{1-6}$ alkyl, C$_{2-6}$ alkenyl, C$_{3-7}$ cycloalkyl and benzyl, or alternatively R$^1$ and R$^2$ taken together with the nitrogen atom to which they are attached form a pyrrolidinyl or piperidinyl ring optionally substituted with 1–3 independently selected C$_{1-6}$ alkyl substituents;
R$^3$ is H or C$_{1-6}$ alkyl, optionally substituted with NH$_2$;
n is 2, 3, 4 or 5;
m is 0 or 1;

Y$_1$ is a covalent bond, C$_{1-4}$ alkane-diyl, or cis or trans C$_{2-4}$ alkene-diyl, optionally substituted with 1 or 2 independently selected C$_{1-4}$ alkyl substituents;

R$^4$ is H, C$_{1-4}$ alkyl or phenyl;

R$^5$ is selected from the group consisting of C$_{1-6}$ alkyl, C$_{2-6}$ alkenyl, C$_{3-7}$ cycloalkyl, phenyl, thienyl, benzhydryl and —Y$_3$-R$^a$, where Y$_3$ is C$_{1-3}$ alkane-diyl or C$_{2-3}$ alkene-diyl, and R$^a$ is selected from the group consisting of C$_{3-7}$ cycloalkyl, phenyl, naphthyl, biphenyl, benzylsulfanyl, benzyloxy, thienyl, furyl, thiazolyl, oxazolyl, imidazolyl, 1H-indol-2-yl, 1H-indol-3-yl and pyridyl;

or alternatively R$^4$ and R$^5$ taken together with the carbon atom to which they are attached form a 3- to 7-membered monocyclic carbocyclyl ring, optionally benzofused;

where R$^5$ is substituted at any stable position except Y$_3$ with 0, 1 or 2 substituents independently selected from the group consisting of hydroxy, sulfanyl, halo, C$_{1-4}$ alkyl, C$_{1-4}$ haloalkyl, C$_{1-4}$ alkoxy, C$_{1-4}$ alkylsulfanyl, carboxy, amino and carbamoyl, and Y$_3$ is substituted with 0, 1 or 2 substituents independently selected from the group consisting of fluoro, C$_{1-4}$ alkyl, C$_{1-4}$ haloalkyl, C$_{1-4}$ alkoxy and amino; or alternatively R$^4$ and R$^5$ taken together is substituted with 0, 1 or 2 substituents independently selected from the group consisting of hydroxy, halo, C$_{1-4}$ alkyl, C$_{1-4}$ haloalkyl, C$_{1-4}$ alkoxy and amino;

R$^6$ is H or C$_{1-4}$ alkyl;

X is selected from the group consisting of >C=O, >C=S, >C=N—CN and >C=CHNO$_2$;

Y$_2$ is a covalent bond or methylene;

R$^7$ is H, halo or C$_{1-4}$ alkyl;

R$^8$ is selected from the group consisting of H, phenyl, —O-phenyl, —O-tetrahydronaphthyl, —SO$_2$-phenyl, thienyl and pyridyl;

or alternatively R$^7$ and R$^8$ taken together with the phenyl to which they are attached form fluorenyl or tetrahydronaphthyl;

where R$^8$, or R$^7$ and R$^8$ taken together, is substituted with 0, 1 or 2 substituents independently selected from the group consisting of hydroxy, cyano, nitro, amino, dimethylamino, halo, C$_{1-4}$ alkyl, C$_{1-4}$ haloalkyl, C$_{1-4}$ alkoxy, —(CO)—C$_{1-4}$ alkyl and —(SO$_2$)—C$_{1-4}$ alkyl;

and stereoisomers, solvates, pharmaceutically acceptable salts, thereof.

2. The compound of claim 1 wherein R$^1$ and R$^2$ are independently selected from the group consisting of H, methyl, ethyl, propyl, i-propyl, ethenyl, allyl, cyclopropyl, cyclobutyl, cyclopentyl, cyclohexyl, and benzyl.

3. The compound of claim 1 wherein, optionally substituted, R$^1$ and R$^2$ taken together with the nitrogen atom to which they are attached is selected from the group consisting of, pyrrolin-1-yl, and piperidin-1-yl.

4. The compound of claim 1 wherein, optionally substituted, R$^3$ is independently selected from the group consisting of H, methyl, ethyl and propyl.

5. The compound of claim 1 wherein n is 2 or 3.

6. The compound of claim 1 wherein m is 1.

7. The compound of claim 1 wherein, optionally substituted, Y$_1$ is independently selected from the group consisting of a covalent bond, methdiyl, eth-1,2-diyl, prop-1,3-diyl, but-1,4-diyl, cis-ethen-1,2-diyl and trans-ethen-1,2-diyl.

8. The compound of claim 1 wherein R$^4$ is independently selected from the group consisting of H, methyl, ethyl, propyl and phenyl.

9. The compound of claim 1 wherein, optionally substituted, R$^5$ is independently selected from the group consisting of methyl, ethyl, propyl, i-propyl, butyl, t-butyl, i-butyl, ethenyl, allyl, cyclopropyl, cyclobutyl, cyclopentyl, cyclohexyl, phenyl, thienyl, benzhydryl, cyclopropylmethyl, cyclobutylmethyl, cyclopentylmethyl, cyclohexylmethyl, benzyl, naphthylmethyl, biphenylmethyl, benzylsulfanylmethyl, benzyloxymethyl, thienylmethyl, furylmethyl, thiazolylmethyl, oxazolylmethyl, imidazolylmethyl, 1H-indol-2-ylmethyl, 1H-indol-3-ylmethyl, pyridylmethyl and phenylethyl.

10. The compound of claim 1 wherein R$^4$ and R$^5$ taken together with the carbon atom to which they are attached is selected from the group consisting of cyclobutan-1,1-diyl, cyclopentan-1,1-diyl, cyclohexan-1,1-diyl and indan-2,2-diyl.

11. The compound of claim 1 wherein R$^6$ is selected from the group consisting of H, methyl, ethyl and propyl.

12. The compound of claim 1 wherein Y$_2$ is a covalent bond.

13. The compound of claim 1 wherein X is >C=O.

14. The compound of claim 1 wherein X is >C=S.

15. The compound of claim 1 wherein X is >C=N—CN.

16. The compound of claim 1 wherein X is >C=CHNO$_2$.

17. The compound of claim 1 wherein R$^7$ is selected from the group consisting of H, bromo, chloro, fluoro, iodo, methyl, ethyl, propyl, and t-butyl.

18. The compound of claim 1 wherein, optionally substituted, R$^8$ is selected from the group consisting of phenyl and —O-phenyl.

19. The compound of claim 1 wherein, optionally substituted, R$^7$ and R$^8$ taken together with the phenyl to which they are attached is fluorenyl.

20. The compound of claim 1 selected from the group consisting of:
(S)-2-(N'-Biphenyl-4-yl-N"-cyano-guanidino)-3-phenyl-N-(3-pyrrolidin-1-yl-propyl)-propionamide;
(S)-2-{N'-[4-(4-Fluoro-phenoxy)-phenyl]-N"-cyano-guanidino}-3-phenyl-N-(3-pyrrolidin-1-yl-propyl)-propionamide;
(R)-3-(N'-Biphenyl-4-yl-N"-cyano-guanidino)-3-phenyl-N-(2-pyrrolidin-1-yl-ethyl)-propionamide;
3-{N'-[4-(3,4-Dichloro-phenoxy)-phenyl]-N"-cyano-guanidino}-3-phenyl-N-(2-pyrrolidin-1-yl-ethyl)-propionamide;
3-{N'-[4-(4-Chloro-phenoxy)-phenyl]-N"-cyano-guanidino}-3-phenyl-N-(2-pyrrolidin-1-yl-ethyl)-propionamide;
3-[N'-Methyl-N"-(4-p-tolyloxy-phenyl)-guanidino]-3-phenyl-N-(2-pyrrolidin-1-yl-ethyl)-propionamide;
(S)-2-{N'-[4-(4-Chloro-phenoxy)-phenyl]-N"-cyano-guanidino}-3-phenyl-N-(3-pyrrolidin-1-yl-propyl)-propionamide;
3-{N'-[4-(4-Fluoro-phenoxy)-phenyl]-N"-cyano-guanidino}-3-phenyl-N-(2-pyrrolidin-1-yl-ethyl)-propionamide;
(S)-2-{N'-[4-(4-Chloro-phenoxy)-phenyl]-N"-cyano-guanidino}-N-(2-diisopropylamino-ethyl)-3-phenyl-propionamide;
(R)-2-{N'-[4-(4-Chloro-phenoxy)-phenyl]-N"-cyano-guanidino}-3-phenyl-N-(2-pyrrolidin-1-yl-ethyl)-propionamide;
(R)-4-{N'-[4-(4-Chloro-phenoxy)-phenyl]-N"-cyano-guanidino}-5-phenyl-pentanoic acid (2-pyrrolidin-1-yl-ethyl)-amide;
(R)-4-(N'-Biphenyl-4-yl-N"-cyano-guanidino)-5-phenyl-pentanoic acid (2-isopropylamino-ethyl)-amide;

3-(N'-Biphenyl-4-yl-N"-cyano-guanidino)-N-(2-diisopropylamino-ethyl)-3-phenyl-propionamide;
3-[N'-(9H-Fluoren-2-yl)-N"-cyano-guanidino]-3-phenyl-N-(2-pyrrolidin-1-yl-ethyl)-propionamide;
(R)-4-(N'-Biphenyl-4-yl-N"-cyano-guanidino)-5-phenyl-pentanoic acid (2-pyrrolidin-1-yl-ethyl)-amide;
(S)-2-{N'-[4-(4-Chloro-phenoxy)-phenyl]-N"-cyano-guanidino}-3-phenyl-N-(2-pyrrolidin-1-yl-ethyl)-propionamide;
(R)-4-(N'-Biphenyl-4-yl-N"-cyano-guanidino)-5-phenyl-pentanoic acid (2-diethylamino-ethyl)-amide;
(R)-4-(N'-Biphenyl-4-yl-N"-cyano-guanidino)-5-phenyl-pentanoic acid (2-dimethylamino-ethyl)-amide;
(R)-4-{N'-[4-(4-Fluoro-phenoxy)-phenyl]-N"-cyano-guanidino}-5-phenyl-pentanoic acid (2-pyrrolidin-1-yl-ethyl)-amide;
(R)-4-{N'-[4-(3,4-Dichloro-phenoxy)-phenyl]-N"-cyano-guanidino}-5-phenyl-pentanoic acid (2-pyrrolidin-1-yl-ethyl)-amide;
(R)-4-[N'-Cyano-N"-(4-p-tolyloxy-phenyl)-guanidino]-5-phenyl-pentanoic acid (2-pyrrolidin-1-yl-ethyl)-amide;
3-(N'-Biphenyl-4-yl-N"-cyano-guanidino)-3-phenyl-N-(2-pyrrolidin-1-yl-ethyl)-propionamide;
(S)-3-{N'-[4-(4-Chloro-phenoxy)-phenyl]-N"-cyano-guanidino}-4-phenyl-N-(2-pyrrolidin-1-yl-ethyl)-butyramide;
(S)-2-{N'-[4-(4-Chloro-phenoxy)-phenyl]-N"-cyano-guanidino}-N-(2-dimethylamino-ethyl)-3-phenyl-propionamide;
(S)-3-(N'-Biphenyl-4-yl-N"-cyano-guanidino)-5-methyl-hexanoic acid (2-pyrrolidin-1-yl-ethyl)-amide;
(S)-3-(N'-Biphenyl-4-yl-N"-cyano-guanidino)-4-phenyl-N-(2-pyrrolidin-1-yl-ethyl)-butyramide;
(S)-4-(N'-Biphenyl-4-yl-N"-cyano-guanidino)-5-phenyl-pentanoic acid (2-pyrrolidin-1-yl-ethyl)-amide;
3-[N'-Cyano-N"-(4-phenoxy-phenyl)-guanidino]-3-phenyl-N-(2-pyrrolidin-1-yl-ethyl)-propionamide;
(R)-4-[N'-Cyano-N"-(4-phenoxy-phenyl)-guanidino]-5-phenyl-pentanoic acid (2-pyrrolidin-1-yl-ethyl)-amide; and
(R)-2-(N'-Biphenyl-4-yl-N"-cyano-guanidino)-3-phenyl-N-(3-pyrrolidin-1-yl-propyl)-propionamide;
and stereoisomers, solvates, and pharmaceutically acceptable salts thereof.

21. The compound of claim 1 selected from the group consisting of:
1-[(R)-1-Benzyl-4-(2-pyrrolidin-1-yl-ethylamino)-butyl]-3-biphenyl-4-yl-urea;
(S)-2-{3-[4-(4-Chloro-phenoxy)-phenyl]-ureido}-N-(2-diisopropylamino-ethyl)-3-phenyl-propionamide;
(S)-2-{3-[4-(4-Chloro-phenoxy)-phenyl]-ureido}-N-(2-dimethylamino-ethyl)-3-phenyl-propionamide;
(R)-3-(3-Biphenyl-4-yl-ureido)-N-(2-pyrrolidin-1-yl-ethyl)-3-p-tolyl-propionamide;
(S)-N-(2-Diisopropylamino-ethyl)-2-[3-(4-phenoxy-phenyl)-ureido]-3-phenyl-propionamide;
(E)-(S)-4-{3-[4-(4-Fluoro-phenoxy)-phenyl]-ureido}-5-phenyl-pent-2-enoic acid (2-pyrrolidin-1-yl-ethyl)-amide;
(S)-2-(3-Biphenyl-4-yl-ureido)-3-phenyl-N-(3-pyrrolidin-1-yl-propyl)-propionamide;
(S)-2-(3-Biphenyl-4-yl-ureido)-N-(3-diethylamino-propyl)-3-phenyl-propionamide;
(S)-2-(3-Biphenyl-4-yl-ureido)-N-(2-isopropylamino-ethyl)-3-phenyl-propionamide;
(R)-3-(3-Biphenyl-4-yl-ureido)-4-methyl-pentanoic acid (2-pyrrolidin-1-yl-ethyl)-amide;
(S)-2-{3-[4-(4-Chloro-phenoxy)-phenyl]-ureido}-N-(2-methylamino-ethyl)-3-phenyl-propionamide;
(S)-2-(3-Biphenyl-4-yl-ureido)-N-(3-pyrrolidin-1-yl-propyl)-3-thiophen-2-yl-propionamide;
(E)-(S)-4-[3-(4-Phenoxy-phenyl)-ureido]-5-phenyl-pent-2-enoic acid (2-methylamino-ethyl)-amide;
(E)-(S)-4-(3-Biphenyl-4-yl-ureido)-5-phenyl-pent-2-enoic acid (2-diethylamino-ethyl)-amide;
(E)-(S)-4-(3-Biphenyl-4-yl-ureido)-5-phenyl-pent-2-enoic acid (2-isopropylamino-ethyl)-amide;
(E)-(S)-4-[3-(4-Phenoxy-phenyl)-ureido]-5-phenyl-pent-2-enoic acid (2-ethylamino-ethyl)-amide;
3-(3-Biphenyl-4-yl-ureido)-3-phenyl-N-(2-pyrrolidin-1-yl-ethyl)-propionamide;
3-(3-Biphenyl-4-yl-ureido)-3-(4-methoxy-phenyl)-N-(2-pyrrolidin-1-yl-ethyl)-propionamide;
(E)-(S)-4-(3-Biphenyl-4-yl-ureido)-5-(3-chloro-phenyl)-pent-2-enoic acid (2-pyrrolidin-1-yl-ethyl)-amide;
(R)-4-(3-Biphenyl-4-yl-ureido)-5-phenyl-pentanoic acid (2-isopropylamino-ethyl)-amide;
(S)-2-{2-[4-(4-Chloro-phenoxy)-phenylamino]-acetylamino}-3-phenyl-N-(2-pyrrolidin-1-yl-ethyl)-propionamide;
(S)-3-{2-[4-(4-Chloro-phenoxy)-phenylamino]-acetylamino}-4-phenyl-N-(2-pyrrolidin-1-yl-ethyl)-butyramide;
3-(3-Biphenyl-4-yl-ureido)-N-(2-isopropylamino-ethyl)-3-phenyl-propionamide;
(S)-2-(3-Biphenyl-4-yl-ureido)-N-(2-diisopropylamino-ethyl)-3-phenyl-propionamide;
(E)-(S)-4-(3-Biphenyl-4-yl-ureido)-5-phenyl-pent-2-enoic acid (2-propylamino-ethyl)-amide;
(S)-2-{3-[4-(4-Fluoro-phenoxy)-phenyl]-ureido}-3-phenyl-N-(2-pyrrolidin-1-yl-ethyl)-propionamide;
(S)-2-{3-[4-(4-Methoxy-phenoxy)-phenyl]-ureido}-3-phenyl-N-(2-pyrrolidin-1-yl-ethyl)-propionamide;
2-(3-Biphenyl-4-yl-ureido)-N-(2-dimethylamino-ethyl)-N-methyl-3-phenyl-propionamide;
(R)-2-(3-Biphenyl-4-yl-1-methyl-ureido)-N-(2-dimethylamino-ethyl)-3-phenyl-propionamide;
(S)-2-(3-Biphenyl-4-yl-1-methyl-ureido)-3-phenyl-N-(2-pyrrolidin-1-yl-ethyl)-propionamide;
(S)-3-Phenyl-N-(2-pyrrolidin-1-yl-ethyl)-2-{3-[4-(5,6,7,8-tetrahydro-naphthalen-2-yloxy)-phenyl]-ureido}-propionamide;
(S)-N-(2-Diisopropylamino-ethyl)-3-phenyl-2-[3-(4-thiophen-2-yl-phenyl)-ureido]-propionamide;
(S)-2-[3-(4-Iodo-phenyl)-ureido]-3-phenyl-N-(2-pyrrolidin-1-yl-ethyl)-propionamide;
(S)-3-Biphenyl-4-yl-2-(3-biphenyl-4-yl-ureido)-N-(3-pyrrolidin-1-yl-propyl)-propionamide;
2-[3-(4-Phenoxy-phenyl)-ureido]-2-propyl-pentanoic acid (2-pyrrolidin-1-yl-ethyl)-amide;
(S)-N-(2-Amino-ethyl)-2-(3-biphenyl-4-yl-ureido)-3-cyclohexyl-propionamide;
(S)-N,N-Bis-(3-amino-propyl)-2-(3-biphenyl-4-yl-ureido)-3-phenyl-propionamide;
1-[3-(4-Phenoxy-phenyl)-ureido]-cyclopentanecarboxylic acid (2-pyrrolidin-1-yl-ethyl)-amide;
(S)-2-[3-(9H-Fluoren-2-yl)-ureido]-3-phenyl-N-(3-pyrrolidin-1-yl-propyl)-propionamide;
(S)-2-[3-(4-Phenoxy-phenyl)-ureido]-N-(2-pyrrolidin-1-yl-ethyl)-3-thiazol-4-yl-propionamide;
(S)-3,3-Dimethyl-2-[3-(4-phenoxy-phenyl)-ureido]-N-(3-pyrrolidin-1-yl-propyl)-butyramide;

(S)-2-[3-(4-Phenoxy-phenyl)-ureido]-3,3-diphenyl-N-(2-pyrrolidin-1-yl-ethyl)-propionamide;
(R)-3-Benzylsulfanyl-2-[3-(4-phenoxy-phenyl)-ureido]-N-(2-pyrrolidin-1-yl-ethyl)-propionamide;
(S)-2-(3-Biphenyl-4-yl-ureido)-3-pyridin-4-yl-N-(3-pyrrolidin-1-yl-propyl)-propionamide;
(S)-3-Methyl-2-[3-(4-phenoxy-phenyl)-ureido]-N-(2-pyrrolidin-1-yl-ethyl)-butyramide;
(S)-2-(3-Biphenyl-4-yl-ureido)-2-phenyl-N-(3-pyrrolidin-1-yl-propyl)-acetamide;
(S)-2-(3-Biphenyl-4-yl-ureido)-4-phenyl-N-(3-pyrrolidin-1-yl-propyl)-butyramide;
(S)-3-Naphthalen-2-yl-2-[3-(4-phenoxy-phenyl)-ureido]-N-(3-pyrrolidin-1-yl-propyl)-propionamide;
2-[3-(4-Phenoxy-phenyl)-ureido]-2,2-diphenyl-N-(2-pyrrolidin-1-yl-ethyl)-acetamide;
2-(3-Biphenyl-4-yl-ureido)-indan-2-carboxylic acid (2-pyrrolidin-1-yl-ethyl)-amide;
(S)-2-{3-[4-(4-Chloro-benzenesulfonyl)-phenyl]-ureido}-3-phenyl-N-(2-pyrrolidin-1-yl-ethyl)-propionamide;
(E)-(S)-4-(3-Biphenyl-4-yl-ureido)-5-phenyl-pent-2-enoic acid (3-diethylamino-propyl)-amide;
(R)-4-(3-Biphenyl-4-yl-ureido)-5-phenyl-pentanoic acid (2-propylamino-ethyl)-amide;
(E)-(S)-4-(3-Biphenyl-4-yl-ureido)-5-(4-methoxy-phenyl)-pent-2-enoic acid (2-pyrrolidin-1-yl-ethyl)-amide;
3-(3-Biphenyl-4-yl-ureido)-N-(2-diethylamino-ethyl)-3-phenyl-propionamide;
(S)-3-[3-(9H-Fluoren-2-yl)-ureido]-5-methyl-hexanoic acid (2-pyrrolidin-1-yl-ethyl)-amide;
N-(2-Amino-ethyl)-2-(3-biphenyl-4-yl-ureido)-3-phenyl-propionamide;
(R)-4-(3-Biphenyl-4-yl-ureido)-5-phenyl-pentanoic acid (2-amino-ethyl)-amide;
(E)-(R)-4-(3-Biphenyl-4-yl-ureido)-5-phenyl-pent-2-enoic acid (2-amino-ethyl)-amide;
(S)-4-(3-Biphenyl-4-yl-ureido)-5-phenyl-pentanoic acid (2-amino-ethyl)-amide;
(R)-4-(3-Biphenyl-4-yl-ureido)-5-phenyl-pentanoic acid (3-amino-propyl)-amide;
(S)-N-(2-Amino-ethyl)-3-phenyl-2-(3-phenyl-ureido)-propionamide;
(S)-N-(2-Amino-ethyl)-2-[3-(4-phenoxy-phenyl)-ureido]-3-phenyl-propionamide;
2-(3-Biphenyl-4-yl-ureido)-3-phenyl-N-(2-pyrrolidin-1-yl-ethyl)-propionamide;
2-(3-Biphenyl-4-yl-ureido)-3-phenyl-N-(2-piperidin-1-yl-ethyl)-propionamide;
(E)-(S)-4-(3-Biphenyl-4-yl-ureido)-5-phenyl-pent-2-enoic acid (2-pyrrolidin-1-yl-ethyl)-amide;
(S)-2-{3-[4-(4-Chloro-phenoxy)-phenyl]-ureido}-3-phenyl-N-(2-pyrrolidin-1-yl-ethyl)-propionamide;
(R)-4-(3-Biphenyl-4-yl-ureido)-5-phenyl-pentanoic acid (2-pyrrolidin-1-yl-ethyl)-amide;
(E)-(S)-4-[3-(4-Phenoxy-phenyl)-ureido]-5-phenyl-pent-2-enoic acid (2-pyrrolidin-1-yl-ethyl)-amide;
(S)-2-[3-(4-tert-Butyl-phenyl)-ureido]-3-phenyl-N-(2-pyrrolidin-1-yl-ethyl)-propionamide;
2-(3-Biphenyl-4-yl-ureido)-N-(2-dimethylamino-ethyl)-3-phenyl-propionamide;
1-(3-Biphenyl-4-yl-ureido)-cyclopentanecarboxylic acid (2-pyrrolidin-1-yl-ethyl)-amide;
(R)-4-[3-(4-Phenoxy-phenyl)-ureido]-5-phenyl-pentanoic acid (2-pyrrolidin-1-yl-ethyl)-amide;
(S)-2-{3-[4-(3,4-Dichloro-phenoxy)-phenyl]-ureido}-3-phenyl-N-(2-pyrrolidin-1-yl-ethyl)-propionamide;
(E)-(S)-4-[3-(4-Phenoxy-phenyl)-ureido]-5-phenyl-pent-2-enoic acid (2-amino-ethyl)-amide;
(R)-4-[3-(4-Phenoxy-phenyl)-ureido]-5-phenyl-pentanoic acid (2-amino-ethyl)-amide;
(E)-(S)-4-[3-(4-Phenoxy-phenyl)-ureido]-5-phenyl-pent-2-enoic acid (3-pyrrolidin-1-yl-propyl)-amide;
(E)-(S)-4-(3-Biphenyl-4-yl-ureido)-5-phenyl-pent-2-enoic acid (3-pyrrolidin-1-yl-propyl)-amide;
(S)-2-[3-(4-Phenoxy-phenyl)-ureido]-3-phenyl-N-(3-pyrrolidin-1-yl-propyl)-propionamide;
(E)-(S)-4-(3-Biphenyl-4-yl-ureido)-5-phenyl-pent-2-enoic acid (2-methylamino-ethyl)-amide;
(E)-(S)-4-(3-Biphenyl-4-yl-ureido)-5-phenyl-pent-2-enoic acid (2-dimethylamino-ethyl)-amide;
(E)-(S)-4-[3-(4-Phenoxy-phenyl)-ureido]-5-phenyl-pent-2-enoic acid (2-dimethylamino-ethyl)-amide;
(E)-(S)-4-(3-Biphenyl-4-yl-ureido)-5-phenyl-pent-2-enoic acid (3-methylamino-propyl)-amide;
(E)-(S)-4-(3-Biphenyl-4-yl-ureido)-5-phenyl-pent-2-enoic acid (3-dimethylamino-propyl)-amide;
(R)-4-(3-Biphenyl-4-yl-ureido)-5-phenyl-pentanoic acid (3-dimethylamino-propyl)-amide;
(Z)-(S)-4-(3-Biphenyl-4-yl-ureido)-5-phenyl-pent-2-enoic acid (2-pyrrolidin-1-yl-ethyl)-amide;
(S)-2-[3-(3-Phenoxy-phenyl)-ureido]-3-phenyl-N-(3-pyrrolidin-1-yl-propyl)-propionamide;
(S)-2-(3-Biphenyl-4-yl-ureido)-N-(2-diethylamino-ethyl)-3-phenyl-propionamide;
2-(3-Biphenyl-4-yl-ureido)-2-propyl-pentanoic acid (2-pyrrolidin-1-yl-ethyl)-amide;
(R)-4-(3-Biphenyl-4-yl-ureido)-5-phenyl-pentanoic acid (2-methylamino-ethyl)-amide;
(S)-3-(3-Biphenyl-4-yl-ureido)-4-phenyl-N-(2-pyrrolidin-1-yl-ethyl)-butyramide;
(S)-3-[3-(4-Phenoxy-phenyl)-ureido]-4-phenyl-N-(2-pyrrolidin-1-yl-ethyl)-butyramide;
(S)-3-(3-Biphenyl-4-yl-ureido)-5-methyl-hexanoic acid (2-pyrrolidin-1-yl-ethyl)-amide;
(S)-5-Methyl-3-[3-(4-phenoxy-phenyl)-ureido]-hexanoic acid (2-pyrrolidin-1-yl-ethyl)-amide;
(S)-2-[3-(2-Phenoxy-phenyl)-ureido]-3-phenyl-N-(3-pyrrolidin-1-yl-propyl)-propionamide;
(S)-3-(3-Biphenyl-4-yl-ureido)-3-phenyl-N-(2-pyrrolidin-1-yl-ethyl)-propionamide;
(R)-3-(3-Biphenyl-4-yl-ureido)-3-phenyl-N-(2-pyrrolidin-1-yl-ethyl)-propionamide;
N-(2-Amino-ethyl)-3-(3-biphenyl-4-yl-ureido)-3-phenyl-propionamide;
(R)-4-(3-Biphenyl-4-yl-ureido)-5-phenyl-pentanoic acid (2-diethylamino-ethyl)-amide;
3-(3-Biphenyl-4-yl-ureido)-N-(2-dimethylamino-ethyl)-3-phenyl-propionamide;
(E)-(R)-4-(3-Biphenyl-4-yl-ureido)-5-phenyl-pent-2-enoic acid (3-pyrrolidin-1-yl-propyl)-amide;
(S)-N-(2-Dimethylamino-ethyl)-2-[3-(4-phenoxy-phenyl)-ureido]-3-phenyl-propionamide;
3-(3-Biphenyl-4-yl-ureido)-3-phenyl-N-(3-pyrrolidin-1-yl-propyl)-propionamide;
(S)-3-(3-Biphenyl-4-yl-ureido)-N-(2-dimethylamino-ethyl)-4-phenyl-butyramide;
(S)-N-(2-Dimethylamino-ethyl)-3-[3-(4-phenoxy-phenyl)-ureido]-4-phenyl-butyramide;
(S)-2-(3-Biphenyl-4-yl-ureido)-N-(2-pyrrolidin-1-yl-ethyl)-3-thiophen-2-yl-propionamide;
(S)-2-(3-Biphenyl-4-yl-ureido)-3-pyridin-3-yl-N-(3-pyrrolidin-1-yl-propyl)-propionamide;

2-(3-Biphenyl-4-yl-ureido)-2,2-diphenyl-N-(2-pyrrolidin-1-yl-ethyl)-acetamide;

3-(3-Biphenyl-4-yl-ureido)-3-(4-chloro-phenyl)-N-(2-pyrrolidin-1-yl-ethyl)-propionamide;

(R)-4-Methyl-3-[3-(4-phenoxy-phenyl)-ureido]-pentanoic acid (2-pyrrolidin-1-yl-ethyl)-amide;

(R)-3-(3-Biphenyl-4-yl-ureido)-4-methyl-pentanoic acid (2-diisopropylamino-ethyl)-amide;

(R)-4-Methyl-3-[3-(4-phenoxy-phenyl)-ureido]-pentanoic acid (2-diisopropylamino-ethyl)-amide;

(E)-(R)-4-(3-Biphenyl-4-yl-ureido)-5-phenyl-pent-2-enoic acid (2-diisopropylamino-ethyl)-amide;

(S)-4-(3-Biphenyl-4-yl-ureido)-5-phenyl-pentanoic acid (2-diisopropylamino-ethyl)-amide;

(S)-2-(3-Biphenyl-3-yl-ureido)-3-phenyl-N-(3-pyrrolidin-1-yl-propyl)-propionamide;

(S)-3-(3-Biphenyl-4-yl-ureido)-N-(2-pyrrolidin-1-yl-ethyl)-3-p-tolyl-propionamide;

(E)-(S)-4-(3-Biphenyl-4-yl-ureido)-5-phenyl-pent-2-enoic acid (3-amino-propyl)-amide;

(E)-(R)-4-(3-Biphenyl-4-yl-ureido)-5-phenyl-pent-2-enoic acid (3-amino-propyl)-amide;

1-[(S)-1-Benzyl-2-(2-pyrrolidin-1-yl-ethylamino)-ethyl]-3-(4-phenoxy-phenyl)-urea; and 1-[(S)-1-Benzyl-4-(2-pyrrolidin-1-yl-ethylamino)-butyl]-3-biphenyl-4-yl-urea;

and stereoisomers, solvates, and pharmaceutically acceptable salts thereof.

22. The compound of claim 1 selected from the group consisting of:

(S)-2-{3-[4-(4-Chloro-phenoxy)-phenyl]-thioureido}-3-phenyl-N-(2-pyrrolidin-1-yl-ethyl)-propionamide;

(S)-N-(2-Diisopropylamino-ethyl)-2-{3-[4-(4-fluoro-phenoxy)-phenyl]-thioureido}-3-phenyl-propionamide;

(R)-4-(3-Biphenyl-4-yl-thioureido)-5-phenyl-pentanoic acid (2-pyrrolidin-1-yl-ethyl)-amide;

(S)-2-(3-Biphenyl-4-yl-thioureido)-3-phenyl-N-(3-pyrrolidin-1-yl-propyl)-propionamide;

(S)-2-{3-[4-(4-Chloro-phenoxy)-phenyl]-thioureido}-N-(2-diisopropylamino-ethyl)-3-phenyl-propionamide; and (S)-N-(2-Diisopropylamino-ethyl)-3-phenyl-2-[3-(4-p-tolyloxy-phenyl)-thioureido]-propionamide;

and stereoisomers, solvates, and pharmaceutically acceptable salts thereof.

23. A pharmaceutical composition comprising a pharmaceutically acceptable carrier and a therapeutically effective dose of a compound of formula (I):

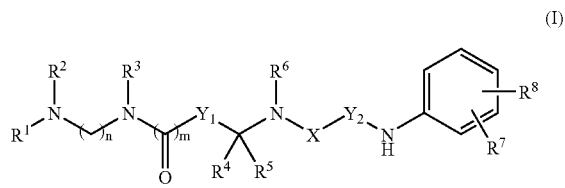

(I)

wherein, $R^1$ and $R^2$ are independently selected from the group consisting of H, $C_{1-6}$ alkyl, $C_{2-6}$ alkenyl, $C_{3-7}$ cycloalkyl and benzyl, or alternatively $R^1$ and $R^2$ taken together with the nitrogen atom to which they are attached form a pyrrolidinyl or piperidinyl optionally substituted with 1–3 independently selected $C_{1-6}$ alkyl substituents;

$R^3$ is H or $C_{1-6}$ alkyl, optionally substituted with $NH_2$;

n is 2, 3, 4 or 5;

m is 0 or 1;

$Y_1$ is a covalent bond, $C_{1-4}$ alkane-diyl, or cis or trans $C_{2-4}$ alkene-diyl, optionally substituted with 1 or 2 independently selected $C_{1-4}$ alkyl substituents;

$R^4$ is H, $C_{1-4}$ alkyl or phenyl;

$R^5$ is selected from the group consisting of $C_{1-6}$ alkyl, $C_{2-6}$ alkenyl, $C_{3-7}$ cycloalkyl, phenyl, thienyl, benzhydryl and —$Y_3$—$R^a$, where $Y_3$ is $C_{1-3}$ alkane-diyl or $C_{2-3}$ alkene-diyl, and $R^a$ is selected from the group consisting of $C_{3-7}$ cycloalkyl, phenyl, naphthyl, biphenyl, benzylsulfanyl, benzyloxy, thienyl, furyl, thiazolyl, oxazolyl, imidazolyl, 1H-indol-2-yl, 1H-indol-3-yl and pyridyl;

or alternatively $R^4$ and $R^5$ taken together with the carbon atom to which they are attached form a 3- to 7-membered monocyclic carbocyclyl, optionally benzofused;

where $R^5$ is substituted at any stable position except $Y_3$ with 0, 1 or 2 substituents independently selected from the group consisting of hydroxy, sulfanyl, halo, $C_{1-4}$ alkyl, $C_{1-4}$ haloalkyl, $C_{1-4}$ alkoxy, $C_{1-4}$ alkylsulfanyl, carboxy, amino and carbamoyl, and $Y_3$ is substituted with 0, 1 or 2 substituents independently selected from the group consisting of fluoro, $C_{1-4}$ alkyl, $C_{1-4}$ haloalkyl, $C_{1-4}$ alkoxy and amino; or alternatively $R^4$ and $R^5$ taken together is substituted with 0, 1 or 2 substituents independently selected from the group consisting of hydroxy, halo, $C_{1-4}$ alkyl, $C_{1-4}$ haloalkyl, $C_{1-4}$ alkoxy and amino;

$R^6$ is H or $C_{1-4}$alkyl;

X is selected from the group consisting of >C=O, >C=S, >C=N—CN and >C=CHNO$_2$;

$Y_2$ is a covalent bond or methylene;

$R^7$ is H, halo or $C_{1-4}$ alkyl;

$R^8$ is selected from the group consisting of H, phenyl, —O-phenyl, —O-tetrahydronaphthyl, —$SO_{0-2}$-phenyl, thienyl and pyridyl;

or alternatively $R^7$ and $R^8$ taken together with the phenyl to which they are attached form fluorenyl or tetrahydronaphthyl;

where $R^8$, or $R^7$ and $R^8$ taken together, is substituted with 0, 1 or 2 substituents independently selected from the group consisting of hydroxy, cyano, nitro, amino, dimethylamino, halo, $C_{1-4}$ alkyl, $C_{1-4}$ haloalkyl, $C_{1-4}$ alkoxy, —(CO)—$C_{1-4}$ alkyl and —(SO$_2$)—$C_{1-4}$ alkyl;

and stereoisomers, solvates, and pharmaceutically acceptable salts thereof.

* * * * *